(12) United States Patent
Oku et al.

(10) Patent No.: US 6,384,080 B1
(45) Date of Patent: May 7, 2002

(54) ANTHRANILIC ACID DERIVATIVES AS INHIBITORS OF THE CGMP-PHOSPHODIESTERASE

(75) Inventors: Teruo Oku, deceased, late of Tokyo, by Noriko Oku, heiress, Chikako Oku, heiress, Tomohito Oku, heir; Kozo Sawada, Tsukuba; Akio Kuroda, Tsukuba; Takayuki Inoue, Tsukuba; Natsuko Kayakiri, Suita; Yuki Sawada, Ushiku; Tsuyoshi Mizutani, Tsukuba, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/509,541
(22) PCT Filed: Apr. 15, 1999
(86) PCT No.: PCT/JP99/02028
§ 371 Date: Apr. 23, 2001
§ 102(e) Date: Apr. 23, 2001
(87) PCT Pub. No.: WO99/54284
PCT Pub. Date: Oct. 28, 1999

(30) Foreign Application Priority Data

Apr. 20, 1998 (AU) .............................................. PP 3085
Sep. 11, 1998 (AU) .............................................. PP 5851
Dec. 18, 1998 (AU) .............................................. PP 7781

(51) Int. Cl.⁷ ........................ A61K 31/18; C07C 235/00
(52) U.S. Cl. ........................ 514/604; 514/603; 564/146; 564/166; 564/185
(58) Field of Search ................................ 514/603, 604; 564/146, 166, 185

(56) References Cited

U.S. PATENT DOCUMENTS 6,069,156 A   5/2000   Oku et al. .................. 514/339

FOREIGN PATENT DOCUMENTS

DE     27 12 023    10/1977
EP     0 686 625    12/1995
JP     9-59236      3/1997

OTHER PUBLICATIONS

H. Luddens, et al., Chemical Abstracts, vol. 129, No. 3, AN 1998:276246, Jul. 20, 1998, "Structure–Activity Relationship of Furosemide–Derived Compounds as Antagonists of Cerebellum–Specific GABAA Receptors", 1998.

*Primary Examiner*—Amelia Owens
(74) *Attorney, Agent, or Firm*—Oblon, Spivak, McClelland, Maier & Neustadt, P.C.

(57) ABSTRACT

Compounds of formula (I)

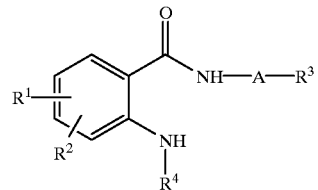

where $R^1$ is hydrogen; $R^2$ is nitro, cyano or halo(lower) alkyl; $R^3$ is phenyl substituted with one or more substituents selected from halogen, cyano and lower alkoxy; A is a lower alkylene group; $R^4$ is a group $CR^6R^7R^8$ wherein $R^6$ and $R^7$ form, together with the carbon atom to which they are attached a cycloalkyl group optionally substituted with hydroxy, lower alkoxy or a lower alkanoylamino; and $R^8$ is hydrogen; its prodrug and a salt thereof.

6 Claims, No Drawings

ANTHRANILIC ACID DERIVATIVES AS INHIBITORS OF THE CGMP-PHOSPHODIESTERASE

This application is a 371 of PCT/JP99/02028 filed Apr. 15, 1999.

TECHNICAL FIELD

This invention relates to novel anthranilic acid derivatives having pharmacological activity, to a process for their production, to a pharmaceutical composition containing the same, and to their use as a medicament.

BACKGROUND ART

It is known that a cyclic guanosine-3',5'-monophosphate (hereinafter referred to as cGMP) derived from a guanosine-5'-triphosphate possesses a relaxant activity of smooth muscle and that a cyclic guanosine-3',5'-monophosphate phosphodiesterase (hereinafter refereed to as cGMP-PDE) acts to catalyze the degradation of cGMP to a guanosine-5'-monophosphate. The compounds having an inhibitory activity of cGMP-PDE are disclosed in European Patent Publication Nos. 579,496; 534,443; 526,004; 636,626; U.S. Pat. Nos. 3,819,631; 5,294,612; 5,488,055; International Patent Publication Nos. 93/07,124; 94/19,351; 95/18,097; 96/32,379; Japan Patent Publication Nos. 05-222,000; 07-330,777; and so on.

DISCLOSURE OF INVENTION

This invention relates to novel anthranilic acid derivatives, which have pharmaceutical activity such as inhibiting activity of cGMP-PDE, to a process for their production, to a pharmaceutical composition containing the same and to a use thereof.

Accordingly, one object of this invention is to provide the novel anthranilic acid derivatives, which have an inhibiting activity of cGMP-PDE.

Another object of this invention is to provide a process for production of the anthranilic acid derivatives.

A further object of this invention is to provide a pharmaceutical composition containing, as an active ingredient, an anthranilic acid derivative.

Still further object of this invention is to provide a use of the anthranilic acid derivatives for treating or preventing various diseases.

The new anthranilic acid derivatives of this invention can be represented by the following formula (I):

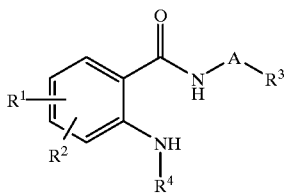

(I)

wherein
$R^1$ is hydrogen atom or a halogen atom;
$R^2$ is an electron withdrawing group;
$R^3$ is hydrogen atom; hydroxy group; a lower alkoxy group; a cycloalkyl group; a substituted or unsubstituted aryl group; or an unsaturated heterocyclic group optionally substituted with lower alkyl;
A is a lower alkylene group;
$R^4$ is a lower alkoxy group,
  a substituted or unsubstituted, saturated or unsaturated heterocyclic group,
  an amino group optionally substituted with halo(lower) alkyl or lower alkyl,
  a group —$CH_2$—$R^5$
    wherein $R^5$ is a cycloalkyl group or an unsaturated heterocyclic group, or
  a group —$CR^6R^7R^8$ wherein
    $R^6$ and $R^7$ are each independently carboxy group,
      a protected carboxy group,
      a carbamoyl group optionally substituted with lower alkyl, or
      a lower alkyl group optionally substituted with one or more substituents selected from the group consisting of halogen atom; hydroxy group; cyano group; azido group; lower alkoxy group; lower alkylthio group; protected carboxy group; lower alkanesulfonyl group; acyloxy group; lower alkanesulfonyloxy group; aryl group; aryloxy group which may be substituted with cyano; unsaturated heterocyclic group which may be substituted with lower alkyl; guanidino group which may be substituted with lower alkyl, cyano and/or halogen; isothioureido group which may be substituted with lower alkyl and/or cyano; and amino group which may be substituted with acyl, protected carboxy, lower alkanesulfonyl, lower alkanesulfonyloxy or aryloxycarbonyl, or
    $R^6$ and $R^7$ together with the carbon atom to which $R^6$ and $R^7$ are attached may form a substituted or unsubstituted, saturated carbocyclic group, or an unsaturated carbocyclic group optionally substituted with hydroxy, and
    $R^8$ is hydrogen atom; a lower alkoxy group; or a lower alkyl group optionally substituted with hydroxy or lower alkoxy;

provided that
  when $R^4$ is the group —$CR^6R^7R^8$ wherein
    $R^6$ is a lower alkyl group optionally substituted with halogen,
    $R^7$ is a lower alkyl group optionally substituted with halogen,
    and $R^8$ is hydrogen atom or a lower alkyl group, or
  when $R^4$ is the group —$CH_2$—$R^5$ wherein $R^5$ is the same as the above, $R^3$ should be hydrogen atom, hydroxy group or a cycloalkyl group; and a pro-drug thereof, and a salt thereof.

The compounds of the formula (I) may contain one or more asymmetric centers and thus they can exist as enantiomers or diastereoisomers.

The compounds of the formula (I) may also exist in tautomeric forms and the invention includes both mixtures and separate individual tautomers.

It is further to be noted that isomerization or rearrangement of the compounds (I) may occur by the effect of light, acid, base or the like, and the compounds obtained as the result of said isomerization or rearrangement are also included within the scope of the present invention.

The compounds of the formula (I) and its salts can be in the form of a solvate, which is included within the scope of the present invention. The solvate preferably include a hydrate and an ethanolate.

Also included in the scope of invention are radiolabelled derivatives of compounds of formula (I) which are suitable for biological studies.

According to this invention, the object compounds (I) or its salts can be prepared by the following process.
Process 1
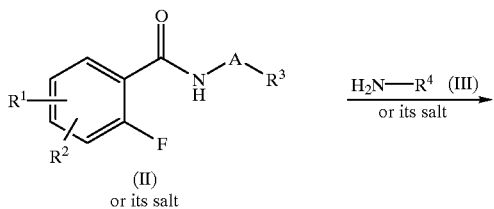
Process 2
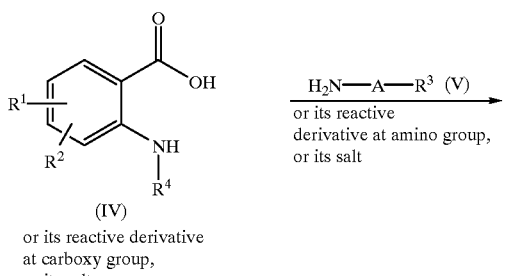
Process 3
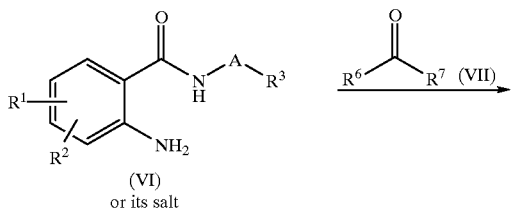
In the above formulae, $R^1$, $R^2$, $R^3$, $R^4$, $R^6$, $R^7$ and A are the same as those defined in the above.
Some of the starting materials are novel and can be prepared by the following processes.
Process A
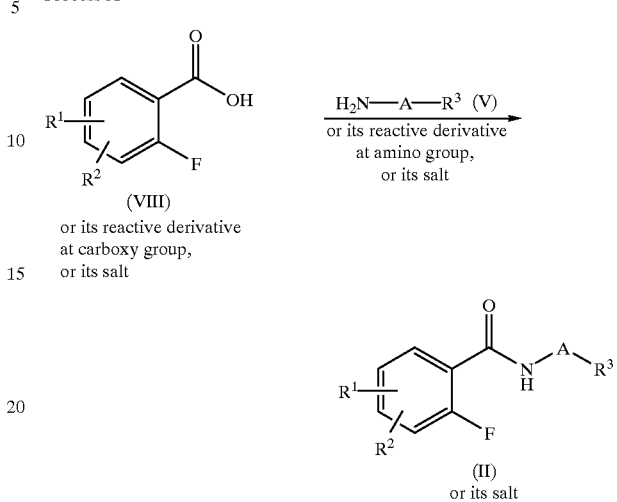
Process B
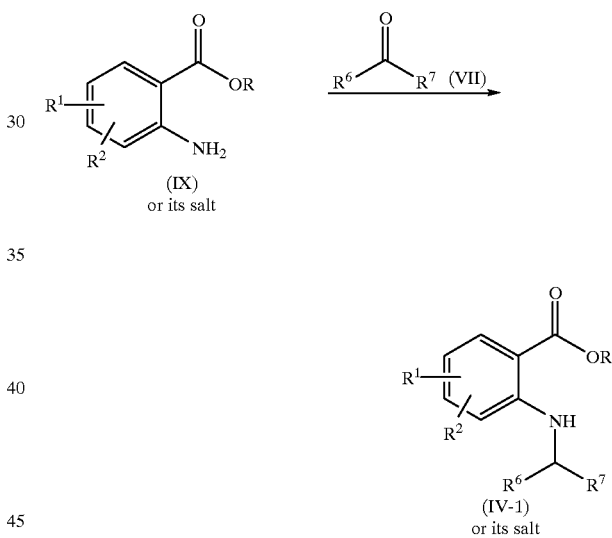
Process C
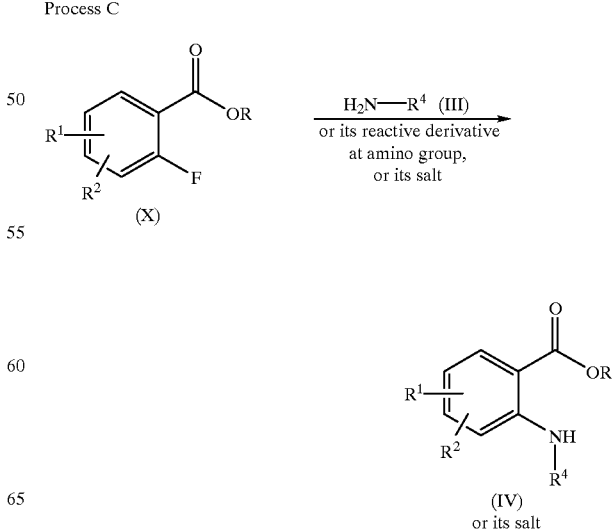

Process D

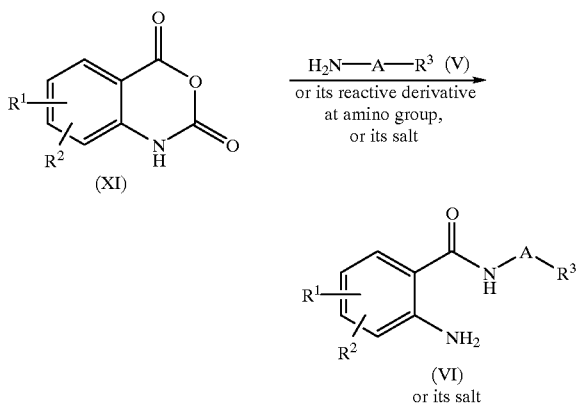

In the above formulae, $R^1$, $R^2$, $R^3$, $R^4$, $R^6$, $R^7$ and A are the same as those defined in the above, R is hydrogen atom or a lower alkyl group.

In the above and subsequent descriptions of the present specification, suitable examples and illustrations of the various definitions which the present invention includes within the scope are explained in detail in the following.

The term "lower" is intended to mean a group having 1 to 6 carbon atom(s), unless otherwise indicated.

Suitably the lower alkyl groups and lower alkyl moieties in the terms of the halo(lower)alkyl, lower akanesulfonyl, lower alkanesulfonyloxy, lower alkoxy, lower alkylthio, hydroxy(lower)alkyl, ar(lower)alkyl, ar(lower)alkoxy and ar(lower)alkoxycarbonyl groups may include straight or branched ones having 1 to 6 carbon atoms, such as methyl, ethyl, propyl, isopropyl, butyl, isobutyl, sec-butyl, tert-butyl, pentyl, isopentyl, hexyl or the like, more suitably the ones having 1 to 4 carbon atoms such as methyl, ethyl, propyl, isopropyl, butyl or isobutyl.

Suitably the examples of the lower alkenyl groups include straight or branched ones having 2 to 6 carbon atoms, such as ethenyl, propenyl (i.e., allyl or 1-propenyl), butenyl, isobutenyl, pentenyl, hexenyl or the like.

Suitable lower alkylene groups and lower alkylene moieties in the lower alkylenedioxy group may include straight or branched ones having 1 to 6 carbon atoms, such as methylene, methylmethylene, ethylene, methylethylene, trimethylene, tetramethylene, 2-methyltrimethylene, pentamethylene, hexamethylene or the like, more suitably the ones having 1 to 3 carbon atoms.

Suitable examples of the acyl groups and acyl moieties in the term of the acyloxy group include aliphatic acyl groups such as lower alkanoyls (e.g., formyl, acetyl, propionyl, butyryl, isobutyryl, valeryl, isovaleryl, oxalyl, succinyl or pivaloyl) and acyl groups containing an aromatic or heterocyclic ring such as aroyls (e.g., benzoyl, toluoyl, xyloyl or naphthoyl), ar(lower)alkanoyls (e.g., phenylacetyl or phenylpropionyl), ar(lower)alkoxycarbonyls (e.g., benzyloxycarbonyl or phenethyloxycarbonyl), heterocyclic carbonyls (e.g., thenoyl or furoyl) and the like.

The cycloalkyl groups may include the ones having 3 to 7 carbon atoms such as cyclopropyl, cyclobutyl, cyclopentyl, cyclohexyl, cycloheptyl or the like.

Suitably the aryl groups and aryl moieties in the terms of the ar(lower)alkyl, ar(lower)alkoxy, aryloxy, aryloxycarbonyl and aroyloxy groups may be an aromatic group having 6 to 12 carbon atoms. Specific examples thereof are phenyl, naphthyl, indenyl, azulenyl, biphenylenyl, fluorenyl and anthracenyl.

Suitable examples of the saturated carbocyclic groups may be the cycloalkyl groups as exemplified in the above.

Suitable examples of unsaturated carbocyclic groups may include cyclopentenyl, cyclohexenyl, cycloheptenyl, 2,3-dihydro-1H-indenyl, benzocyclohexyl and the like.

Suitable examples of the halogen atoms and halo moiety of the halo(lower)alkyl group may be fluorine, chlorine, bromine or iodine.

Suitable examples of the unsaturated heterocyclic group may include mono- or poly-cyclic groups containing at least one hetero atom selected from nitrogen, sulfur and oxygen atoms, such as (1) unsaturated 3 to 7-membered, preferably 5 or 6-membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl or 2H-1,2,3-triazolyl], tetrazolyl [e.g., 1H-tetrazoly or 2H-tetrazolyl] or the like.;

(2) unsaturated 3 to 7-membered, preferably 5 or 6-membered heteromonocyclic groups containing an oxygen atom, for example, pyranyl or furyl;

(3) unsaturated 3 to 7-membered, preferably 5 or 6-membered heteromonocyclic groups containing 1 to 2 sulfur atoms, for example, thienyl or the like (4) unsaturated 3 to 7-membered, preferably 5 or 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl or 1,2,5-oxadiazolyl] or the like;

(5) unsaturated 3 to 7-membered, preferably 5 or 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl or 1,2,5-thiadiazolyl] or the like;

(6) unsaturated condensed heterocyclic groups containing 1 to 2 nitrogen atoms, for example, indolyl, indazolyl, quinolyl, isoquinolyl, quinazolinyl, quinoxalinyl, benzimidazolyl or the like;

(7) unsaturated condensed heterocyclic groups containing 1 to 2 oxygen atoms, for example, benzofuryl or the like;

(8) unsaturated condensed heterocyclic groups containing 1 to 2 sulfur atoms, for example, benzo[b]thienyl or the like;

(9) unsaturated condensed heterocyclic groups containing 1 to 2 oxygen atoms and 1 to 3 nitrogen atoms, for example, benzoxazolyl, benzoxadiazolyl, phenoxazinyl or the like;

(10) unsaturated condensed heterocyclic groups containing 1 to 2 sulfur atoms and 1 to 3 nitrogen atoms, for example, benzothiazolyl, benzoisothiazolyl, phenothiazinyl or the like.

Suitable examples of the saturated heterocyclic group and heterocyclic moiety in the saturated heterocyclic sulfonyl group include monocyclic groups containing at least one hetero atom selected from nitrogen, sulfur and oxygen atoms, such as (1) saturated 3 to 7-membered, preferably 5 or 6-membered heteromonocyclic groups containing 1 to 4 nitrogen atoms [e.g., pyrrolidinyl, imidazolidinyl, piperidyl or piperazinyl];

(2) saturated 3 to 7-membered, preferably 5 or 6-membered heteromonocyclic groups containing 1 to 2 oxygen atoms and 1 to 3 nitrogen atoms [e.g., morpholinyl];

(3) saturated 3 to 7-membered, preferably 5 or 6-membered heteromonocyclic groups containing 1 to 2 sulfur atoms and 1 to 3 nitrogen atoms [e.g., thiazolidinyl or thiomorpholinyl];

(4) saturated 3 to 7-membered, preferably 5 or 6-membered heteromonocyclic groups containing 1 to 2 sulfur atoms and/or 1 to 2 oxygen atoms [e.g., tetrahydrothiophenyl, tetrahydrothiopyranyl, 1-oxotetrahydrothiopyranyl, 1,1-dioxotetrahydrothiopyranyl, dioxacyclohexyl, tetrahydrofuranyl, tetrahydropyranyl or dioxanyl]; or the like.

Suitably carboxy protective groups in the protected carboxy group may include lower alkyl groups (e.g., methyl, ethyl or tert-butyl), halo(lower)alkyl groups (e.g., 2-iodomethyl or 2,2,2-trichloroethyl), ar(lower)alkyl groups (e.g., benzyl, trityl, 4-methoxybenzyl, 4-nitrobenzyl, phenethyl, bis(methoxyphenyl)methyl, 3,4-dimethoxybenzyl or 4-hydroxy-3,5-di-tert-butylbenzyl), aryl groups (e.g., phenyl, naphthyl, tolyl or xylyl), and the like, more suitably the lower alkyl groups such as methyl, ethyl or tert-butyl and ar(lower)alkyl groups such as benzyl.

Specific examples of the each group containing the above-mentioned moiety and having substituent(s) are as follows.

As the halo(lower) alkyl group, fluoromethyl, iodomethyl, chloromethyl, trifluoromethyl, difluoromethyl, trichloromethyl, 2,2,2-trifluoroethyl, 2,2,2-trichloroethyl or the like may be mentioned.

The lower alkanesulfonyl group is methanesulfonyl (mesyl), ethanesulfonyl, propanesulfonyl or the like.

The lower alkanesulfonyloxy group is methanesulfonyloxy(mesyloxy), ethanesulfonyloxy, propanesulfonyloxy or the like.

The lower alkoxy group is methoxy, ethoxy, propoxy, n-butoxy, tert-butoxy of the like.

The lower alkylthio group is methylthio, ethylthio, propylthio, butylthio, isobutylthio or the like.

The acyloxy group is formyloxy, acetyloxy, propionyloxy, benzoyloxy, toluoyloxy, naphthoyloxy, phenylacetyloxy, theonyloxys or the like.

The hydroxy(lower)alkyl group is hydroxymethyl, hydroxyethyl or the like.

The ar(lower)alkyl group is benzyl, 4-methoxybenzyl, 4-nitrobenzyl, phenethyl, trityl, bis(methoxyphenyl)methyl, 3,4-dimethoxybenzyl, 4-hydroxy-3,5-di-tert-butylbenzyl) or the like.

The ar(lower)alkoxy group is benzyloxy, 4-methoxybenzyloxy, 4-nitrobenzyloxy, phenethyloxy, trityloxy, bis(methoxyphenyl)methoxy, 3,4-dimethoxybenzyloxy, 4-hydroxy-3,5-di-tert-butylbenzyloxy or the like.

The lower alkylenedioxy group is methylenedioxy, ethylenedioxy and the like.

The aryloxy group is phenoxy, naphthoxy, tolyloxy, xylyloxy or the like.

The aroyloxy group is benzoyloxy, naphthoyloxy or the like.

The saturated heterocyclic sulfonyl group is piperazinesulfonyl, piperizinesulfonyl, morpholinesulfonyl, pyrazolidinesulfonyl or the like.

Preferred embodiments of the compounds (I) are those represented by the formula (I), wherein $R^1$ is hydrogen atom or a halogen atom;

$R^2$ is an electron withdrawing group;

$R^3$ is hydrogen atom; hydroxy group; a lower alkoxy group; a cycloalkyl group; a substituted or unsubstituted aryl group; or an unsaturated heterocyclic group optionally substituted with lower alkyl;

A is a lower alkylene group;

$R^4$ is a lower alkoxy group,
  a substituted or unsubstituted, saturated or unsaturated heterocyclic group,
  an amino group optionally substituted with halo(lower) alkyl or lower alkyl,
  a group —$CH_2$—$R^5$
    wherein $R^5$ is a cycloalkyl group or an unsaturated heterocyclic group, or
  a group —$CR^6R^7R^8$ wherein
    $R^6$ and $R^7$ are each independently carboxy group,
      a protected carboxy group,
      a carbamoyl group optionally substituted with lower alkyl, or
      a lower alkyl group optionally substituted with one or more substituents selected from the group consisting of halogen atom; hydroxy group; cyano group; azido group; lower alkoxy group; lower alkylthio group; protected carboxy group; lower alkanesulfonyl group; acyloxy group; lower alkanesulfonyloxy group; aryl group; aryloxy group which may be substituted with cyano; unsaturated heterocyclic group which may be substituted with lower alkyl; guanidino group which may be substituted with lower alkyl, cyano and/or halogen; isothioureido group which may be substituted with lower alkyl and/or cyano; and amino group which may be substituted with acyl, protected carboxy, lower alkanesulfonyl, lower alkanesulfonyloxy or aryloxycarbonyl, or
    $R^6$ and $R^7$ together with the carbon atom to which $R^6$ and $R^7$ are attached may form a substituted or unsubstituted,
      saturated carbocyclic group, or
      an unsaturated carbocyclic group optionally substituted with hydroxy, and
    $R^8$ is hydrogen atom; a lower alkoxy group; or a lower alkyl group optionally substituted with hydroxy or a lower alkoxy;

provided that
  when $R^4$ is the group —$CR^6R^7R^8$ wherein
    $R^6$ is a lower alkyl group optionally substituted with halogen,
    $R^7$ is a lower alkyl group optionally substituted with halogen,
    and $R^8$ is hydrogen atom or a lower alkyl group, or
  when $R^4$ is the group —$CH_2$—$R^5$ wherein $R^5$ is the same as the above, $R^3$ should be hydrogen atom, hydroxy group or a cycloalkyl group, the electron withdrawing group for $R^2$ being selected from a group consisting of nitro group; cyano group; acyl group; halo(lower)alkyl group; sulfamoyl group; carbamoyl group optionally substituted with lower alkyl; halogen atom; lower alkenyl group optionally substituted with protected carboxy; lower alkanesulfonyl group; saturated heterocyclic sulfonyl group optionally substituted with protected carboxy; and unsaturated heterocyclic group,
  the substituent(s) on the aryl group for $R^3$ being selected from a group consisting of lower alkyl group; halo(lower)alkyl group; lower alkylthio group; halogen atom; hydroxy group; lower alkylenedioxy group; cyano group; nitro group; carboxy group; protected carboxy group; sulfamoyl group; acyl group; aryl group; ar(lower)alkoxy group; aryloxy group; lower alkoxy group which may be substituted with lower alkoxy or cycloalkyl; amino group which may be substituted with acyl, protected carboxy or lower alkyl; and carbamoyl group which may be substituted with lower alkyl, the substituent(s) on the saturated or unsaturated heterocyclic group for $R^4$ being selected from a group consisting of oxo group; acyl group; protected carboxy group; lower alkanesulfonyl group; sulfamoyl group which may be substituted with protected carboxy; ar(lower)alkyl group; lower alkyl group which may be substituted with hydroxy or aryl; ureido group which may be substituted with lower alkyl; guanidino group which may be substituted with protected carboxy; amidino group which may be substituted with protected carboxyl; and carbamoyl group which may be substituted with lower alkyl, and the substituent(s) on the saturated carbocyclic group formed by combination of $R^6$ and $R^7$ being selected from a group consisting of lower alkyl group; halogen atom; hydroxy group; lower alkoxy group; acyloxy group; carboxy group; protected carboxy group; oxo group; amidino group which may be substituted with protected carboxy; ureido group which may be substituted with lower alkyl or aryl; guanidino group which may be substituted with protected carboxy; amino group which may be substituted with acyl, lower aLkanesulfonyl or protected carboxy; and carbamoyl group which may be substituted with lower alkyl or hydroxy(lower)alkyl;

and a pro-drug thereof, and a salt thereof.

Another preferred embodiments are as follows: compounds of the formula (I),
wherein
$R^1$ is hydrogen atom or a halogen atom;
$R^2$ is an electron withdrawing group;
$R^3$ is a substituted or unsubstituted aryl group;
A is a lower alkylene group; and
$R^4$ is a group —$CR^6R^7R^8$ wherein
$R^6$ and $R^7$ together with the carbon atom to which $R^6$ and $R^7$ are attached may form a substituted or unsubstituted, saturated carbocyclic group, and
$R^8$ is hydrogen atom; and
compounds of the formula (I), wherein
$R^1$ is hydrogen atom or a halogen atom;
$R^2$ is an electron withdrawing group;
$R^3$ is a substituted or unsubstituted aryl group;
A is a lower alkylene group; and
$R^4$ is a group —$CR^6R^7R^8$ wherein
$R^6$ is a lower alkyl group substituted with hydroxy,
$R^7$ is a lower alkyl which may be substituted with hydroxy, and
$R^8$ is hydrogen atom or a lower alkyl group which may be substituted with hydroxy.

Further preferred embodiments are as follows: compounds of the formula (I), wherein
$R^1$ is hydrogen atom or a halogen atom;
$R^2$ is nitro group, cyano group or a halo(lower)alkyl group;
$R^3$ is an aryl group optionally substituted with one or more substituent(s) selected from halogen and lower alkoxy;

A is a lower alkylene group; and
$R^4$ is a group —$CR^6R^7R^8$ wherein
$R^6$ and $R^7$ together with the carbon atom to which $R^6$ and $R^7$ are attached may form a saturated carbocyclic group optionally substituted with hydroxy or amino which may be substituted with acyl; and
$R^8$ is hydrogen atom; and
compounds of the formula (I), wherein
$R^1$ is hydrogen atom or a halogen atom;
$R^2$ is nitro group, cyano group or a halo(lower)alkyl group;
$R^3$ is an aryl group optionally substituted with one or more substituent(s) selected from halogen and lower alkoxy;
A is a lower alkylene group; and
$R^4$ is a group —$CR^6R^7R^8$ wherein
$R^6$ is a lower alkyl group substituted with hydroxy,
$R^7$ is a lower alkyl group which may be substituted with hydroxy, and
$R^8$ is hydrogen atom or a lower alkyl group which may be substituted with hydroxy.

In accordance with the invention, it includes salts of the compounds (I). The salts may be conventional non-toxic pharmaceutically acceptable salts, for example, a salt with an alkali metal (e.g., sodium or potassium) and an alkaline earth metal (e.g., calcium or magnesium), an ammonium, an organic base (e.g., trimethylamine, triethylamine, pyridine, picoline, dicyclohexylamine or dibenzylethylenediamine), an organic acid (e.g., acetic acid, benzoic acid, succinic acid, fumaric acid, maleic acid, lactic acid, citric acid, tartaric acid, gluconic acid, methanesulfonic acid, benzenesulifonic acid, formic acid, p-toluenesulfonic acid or trifluoroacetic acid), inorganic acid (e.g., hydrogen chloride, hydrogen bromide, sulfuric acid or phosphoric acid), an amino acid (e.g., arginine, aspartic acid or glutamic acid) or the like.

The processes for preparing the starting compounds and the object compounds (I) of the present invention are explained in detail in the following.

Process 1

A compound (I) or its salt can be prepared by reacting a compound (II) or its salt with a compound (II) or its salt.

This reaction is usually carried out in the presence of an inorganic or an organic base.

Suitable inorganic base may include an alkali metal [e.g., sodium or potassium], an alkali metal hydroxide [e.g., sodium hydroxide or potassium hydroxide], an alkali metal hydrogen carbonate [e.g., sodium hydrogen carbonate or potassium hydrogen carbonate], an alkali metal carbonate [e.g., sodium carbonate], an alkali earth metal carbonate [e.g., calcium carbonate], an alkali metal hydride [e.g., sodium hydride or potassium hydride] and the like.

Suitable organic base may include tri(lower)alkylamines [e.g., triethylamine or N,N-diisopropylethylamine], alkyl lithiums [e.g., methyl lithium or butyl lithium], lithium diisopropylamide, lithium hexamethyldisilazido and the like.

The reaction is usually carried out in a conventional solvent such as water, alcohols [e.g., methanol, ethanol or isopropyl alcohol], tetrahydrofuran, dioxane, toluene, methylene chloride, chloroform, N,N-dimethylformamide or any other organic solvent which does not adversely affect the reaction, or a mixture thereof.

The reaction is preferably carried out at a temperature under cooling to warming. However, the reaction temperature is not limited.

Process 2

A compound (I) or its salt can be prepared by reacting a compound (IV) or its reactive derivative at the carboxy group, or its salt, with a compound (V) or its reactive derivative at the amino group, or its salt, according to a procedure known in the art.

Suitable reactive derivatives at the carboxy group of the compound (IV) may include the acid chloride, azide, acid anhydride, activated amide, activated ester and the like.

Suitably the acid anhydride may include anhydrides with an acid such as substituted phosphoric acid (e.g., dialkylphosphoric acid, phenylphosphoric acid, diphenylphosphoric acid, dibenzylphosphoric acid or halogenated phosphoric acid), dialkylphosphorous acid, sulfuric acid, thiosulfuric acid, alkanesulfonic acid (e.g., methanesulfonic acid or ethanesulfonic acid), alkanoic acid (e.g., pivalic acid, pentanoic acid or isopentanoic acid), aromatic carboxylic acid (e.g., benzoic acid, chlorobenzoic acid, fluorobenzoic acid or nitrobenzoic acid), or the like.

Suitably the active amide may include the imidazoylylamide, 4-substituted imidazoylylamide, dimethylpyrazolylamide, triazolylamide tetrazolylamide or the like.

Suitably the active ester may include the dimethyliminomethyl [$(CH_3)_2N^+=CH-$] ester, vinyl ester, propargyl ester, 4-nitrophenyl ester, 2,4-dinitrophenyl ester, trichlorophenyl ester, pentachlorophenyl ester, pentafluorophenyl ester, methanesulfonylphenyl ester, phenyl thioester, p-nitrophenyl thioester, carboxymethyl thioester, pyranyl ester, pyridyl ester, 8-quinolyl thioester, an ester with a N-hydroxy compound (e.g., N,N-dimethylhydroxylamine, 1-hydroxy-2H-pyridone, N-hydroxysuccinimide, N-hydroxybenzotriazole or N-hydroxyphthalamide) or the like.

Suitably the reactive derivative at amino group of the compound (V) may include Schiff's base type imino or its tautomeric enamine type isomer formed by the reaction of the compound (V) with a carbonyl compound such as aldehyde, ketone or the like; a silyl derivative formed by the reaction of the compound (V) with a silylating reagent such as trimethylsilylchloride, N,O-bis(trimethylsilyl)acetamide, N-trimethylsilylacetamide or the like.

Each reactive derivative of compounds (IV) and (V) can optionally be selected from the above according to the kinds of the compounds (IV) and (V) to be used, respectively.

When the compound (IV) is used in a free acid form or its salt form in the reaction, the reaction is preferably carried out in the presence of a condensing agent.

Suitable condensing agent may include carbodiimides (e.g., N,N-dicyclohexylcarbodiimide, N-cyclohexyl-N'-(4-diethylaminocyclohexyl)carbodiimide or N-ethyl-N'-(3-dimethylaminopropyl)carbodiimide or its hydrochloride), diphenylphosphinic azide, diphenylphosphinic chloride, diethylphosphoryl cyanide, bis(2-oxo-3-oxazolidinyl) phosphinic chloride, N,N'-carbonyldiimidazole, 2-ethoxy-1-ethoxycarbonyl-1,2-dihydroquinoline, cyanuric chloride or the like.

The reaction may be also carried out in the presence of an organic or inorganic base such as an alkali metal carbonate, tri(lower)alkylamine, pyridine, N-(lower)alylmorphorine or the like.

The reaction is usually carried out in a conventional solvent such as water, acetone, alcohols [e.g., methanol, ethanol or isopropyl alcohol], tetrahydrofuran, dioxane, toluene, methylene chloride, chloroform, N,N'-dimethylformamide or any other organic solvent which does not adversely affect the reaction, or a mixture thereof.

The reaction is preferably carried out at a temperature under cooling to warming. However, the reaction temperature is not limited.

Process 3

A compound (I-1) or its salt can be prepared by reacting a compound (VI) or its salt with a ketone compound (VII) in the presence of an inorganic acid (e.g., sulfuric acid or hydrogen chloride) or an organic acid (e.g., acetic acid) and a reducing agent.

Suitable reducing agent may include sodium cyanoborohydride, sodium triacetoxyborohydride, sodium borohydride, borane-pyridine complex and the like.

The reaction is usually carried out in a conventional solvent such as alcohols (e.g., methanol or ethanol), tetrahydrofuran, dioxane, toluene or any other organic solvent which does not adversely affect the reaction, or a mixture thereof.

The reaction is preferably carried out at a temperature under cooling to ambient temperature. However, the reaction temperature is not limited.

Instead of the ketone compound (VII), its corresponding aldehyde may be used in this reaction.

Process A

The process A can be carried out in a manner similar to Process 2 by using a 2-fluorobenzoic acid derivative (VIII) and an amine compound (V) to obtain the compound (1).

Process B

The process B can be carried out in a manner similar to Process 3 by using an aminobenzoate derivative (IX) and a ketone compound (VII) to obtain the compound (IV-1).

Process C

The process C can be carried out in a manner similar to Process 1 by using a 5-fluorobenzoate derivative (X) and an amine compound (III) to obtain the compound (IV).

Process D

The compound (VI) can be prepared by reacting an isatoic anhydride derivative (XI) with an amine compound (V).

This reaction is usually carried out in a conventional solvent such as acetone, tetrahydrofuran, dioxane, toluene, methylene chloride, chloroform, N,N'-dimethylformamide or any other organic solvent which does not adversely affect the reaction, or a mixture thereof.

The reaction is preferably carried out at a temperature under cooling to ambient temperature. However, the reaction temperature is not limited.

A pharmaceutically acceptable salt of the compound (I) can be prepared by treating a compound (I) with an appropriate base or acid in accordance with the conventional method.

The compounds (I) and pharmaceutically acceptable salts thereof possess inhibitory activity of cGMP-PDE (especially PDE-V), relaxant activity of smooth muscle, bronchodilator activity, vasodilative activity, relaxant activity of the penile corpus cavernosum, inhibitory activity of smooth muscle cells proliferation, inhibitory activity of allergy, and so on.

The compounds (I) and pharmaceutically acceptable salts thereof, therefore, are useful for the treatment and/or prevention of various diseases, such as angina, hypertension, pulmonary hypertension, congestive heart failure, glomerular diseases (e.g., diabetic glomerulosclerosis), renal tubulo-intestitinal diseases (e.g., nephropathy induced by tacrolimus, cyclosporin or the like), renal failure, atherosclerosis, conditions of reduced blood vessel patency (e.g., post-percutaneous transluminal coronary angioplasty), peripheral vascular disease, stroke, chronic reversible obstructive lung diseases (e.g., bronchitis or asthma (chronic asthma, allergic asthma)), allergic rhinitis, urticaria, glaucoma, diseases characterized by disorders of gut motility (e.g., irritable bowel syndrome), erectile dysfunction (e.g., organic erectile dysfunction or psychic erectile dysfunction), female sexual dysfunction, impotence, or diabetic complications (e.g., diabetic gangrene, diabetic arthropathy, diabetic glomerulosclerosis, diabetic dermopathy, diabetic neuropathy, diabetic cataract or diabetic retinopathy).

Further, the compounds (I) and pharmaceutically acceptable salts thereof are also useful for the treatment and/or prevention of micturition disorder, incontinence or storage of urine disorder (such as the ones ascribed to nerve regressive affection, inflammation, injury, neoplasm, diabetes mellitus, cerebral vascular accident, surgery, prostatomegaly, urethra relaxation incompetence, dysuria).

It is to be noted that improvement of sexual performance is also included in the treatment of erectile dysfunction or impotence.

The compounds (I) and their salts of the present invention have much advantages, such as stronger activity, more suitable half-life, decreased adverse effect, or the like, compared to the known anthranilic acid derivatives having an inhibitory activity of cGMP-PDE, which are shown in the prior arts.

In order to exhibit the usefulness of the present invention, the activities of the compounds (I) are shown in the following.

Test Compound

The test compounds are shown in Tables 1 and 2 and test methods 2 and 3.

Test Method 1 cGMP-Phosphodiesterase (PDE) Assay

Human platelet cGMP-PDE was separated from other isozymes in human platelets by a modification of the method of Thompson et. al. (see Cyclic Nucleotide Phosphodiesterase (PDE), in Methods of Enzymatic analysis, Vol 4, p127–234, 1984). In enzyme inhibition assays, the test compounds were dissolved in DMSO and then diluted with assay buffer (50 mM Tris-HCl, 0.077 mg/ml dithiothreitol and 10 mg/ml snake venom, 1 mM EGTA, pH 8.0), at final concentrations ranging from $10^{-10}$ to $10^{-6}$ M. Assays were performed at 0.1 $\mu$M substrate ([$^3$H]-cGMP) concentration, at 30° C. for 10 minutes using enzyme dilutions which gave 10–20% hydrolysis of substrate. Each assay was initiated by addition of substrate and terminated by addition of anion exchange resin (Dowex® 1-X8, 250 mg/mg) followed by centrifugation for 10 minutes (3000 rpm, at 4° C.). Radioactivity of supernatant ($^3$H-GMP) was assayed by liquid scintillation counting.

The obtained results in enzymatic inhibitory test against human platelet PDE-V are shown in Table 1.

TABLE 1

| Test Compounds (nM) | Inhibitory activity $IC_{50}$ (nM) |
|---|---|
| 2-(cyclopentylamino)-N-hexyl-5-nitrobenzamide | <10 |
| N-(2-chlorobenzyl)-2-cyclopentylamino-5-nitrobenzamide | <10 |
| N-(3-chlorobenzyl)-2-(cyclopentylamino)-5-nitrobenzamide | <10 |

TABLE 1-continued

| Test Compounds (nM) | Inhibitory activity $IC_{50}$ (nM) |
|---|---|
| N-(4-chlorobenzyl)-2-(cyclopentylamino)-5-nitrobenzamide | <10 |
| 2-(cyclopentylamino)-N-(2,4-dichlorobenzyl)-5-nitrobenzamide | <10 |
| 2-(cyclopentylamino)-N-(3,4-dichlorobenzyl)-5-nitrobenzamide | <10 |
| 2-(cyclopentylamino)-N-(4-fluorobenzyl)-5-nitrobenzamide | <10 |
| 2-(cyclopentylamino)-N-(4-methylbenzyl)-5-nitrobenzamide | <10 |
| 2-(cyclopentylamino)-N-(4-methoxybenzyl)-5-nitrobenzamide | <10 |
| 2-(cyclopentylamino)-5-nitro-N-[4-(trifluoromethyl)benzyl]-benzamide | <10 |
| N-(4-aminobenzyl)-2-(cyclopentylamino)-5-nitrobenzamide | <10 |
| N-(4-amino-2-chlorobenzyl)-2-(cyclopentylamino)-5-nitrobenzamide | <10 |
| N-(2-chloro-4-methoxybenzyl)-2-(cyclopentylamino)-5-nitrobenzamide | <10 |
| 2-(cyclopentylamino)-5-nitro-N-(4-nitrobenzyl)benzamide | <10 |
| N-(4-bromobenzyl)-2-(cyclopentylamino)-5-nitrobenzamide | <10 |
| 2-(cyclopentylamino)-N-furfuryl-5-nitrobenzamide | <10 |
| 2-(cyclopentylamino)-5-nitro-N-(2-thienyl-methyl)-benzamide | <10 |
| 2-(cyclopentylamino)-N-(4-hydroxy-3-methoxybenzyl)-5-nitrobenzamide | <10 |
| 2-(cyclopentylamino)-5-nitro-N-phenethylbenzamide | <10 |
| 2-(cyclopentylamino)-5-nitro-N-(3-phenyl-propyl)benzamide | <10 |
| N-benzyl-2-(cyclobutylamino)-5-nitrobenzamide | <10 |
| N-benzyl-2-(cyclohexylamino)-5-nitrobenzamide | <10 |
| 2-(cyclopentylamino)-N-(3,4-difluorobenzyl)-5-nitrobenzamide | <10 |
| N-[(2-benzimidazolyl)methyl]-2-(cyclopentylamino)-5-nitrobenzamide | <10 |
| N-benzyl-2-(cyclopropylamino)-5-nitrobenzamide | <10 |
| N-benzyl-2-(trans-2-hydroxycyclopentylamino)-5-nitrobenzamide | <10 |
| 5-nitro-N-(1,3-benzodioxol-5-ylmethyl)-2-(tetrahydro-2H-thiopyran-4-ylamino)benzamide | <10 |
| 2-(tert-butylamino)-5-nitro-N-(1,3-benzodioxol-5-ylmethyl)-benzamide | <10 |
| 2-[1-(ethoxycarbonyl)piperidin-4-ylamino]-5-nitro-N-(1,3-benzodioxol-5-ylmethyl)benzamide | <10 |
| 2-(1-benzylpiperidin-4-ylamino)-5-nitro-N-(1,3-benzodioxol-5-ylmethyl)benzamide | <10 |
| (R)-2-(1-ethyl-2-hydroxyethylamino)-5-nitro-N-(1,3-benzodioxol-5-ylmethyl)benzamide | <10 |
| (R)-5-Nitro-2-(tetrahydro-3-furanylamino)-N-(1,3-benzodioxol-5-ylmethyl)benzamide | <10 |
| 2-(1,1-dioxotetrahydro-2H-thiopyran-4-ylamino)-5-nitro-N-(1,3-benzodioxol-5-ylmethyl)-benzamide | <10 |
| 2-[4-(methoxycarbonyl)cyclohexylamino]-5-nitro-N-(1,3-benzodioxol-5-ylmethyl)benzamide | <10 |
| 2-(4-carboxycyclohexylamino)-5-nitro-N-(1,3-benzodioxol-5-ylmethyl)benzamide | <10 |
| 2-(4-carbamoylcyclohexylamino)-5-nitro-N-(1,3-benzodioxol-5-ylmethyl)benzamide | <10 |
| (R)-2-[1-(methoxycarbonyl)ethylamino]-5-nitro-N-(1,3-benzodioxol-5-ylmethyl)benzamide | <10 |
| N-benzyl-2-(3-hydroxycyclopentylamino)-5-nitrobenzamide | <10 |
| 2-[3-(benzoyloxy)cyclopentylamino]-N-benzyl-5-nitrobenzamide | <10 |
| 2-[1-(hydroxymethyl)cyclopentylamino]-5-nitro-N-(1,3-benzodioxol-5-ylmethyl)benzamide | <10 |
| (S)-2-[1-(hydroxymethyl)-2-methylpropylamino]-5-nitro-N-(1,3-benzodioxol-5-ylmethyl)-benzamide | <10 |
| 5-nitro-2-(4-oxocyclohexylamino)-N-(1,3-benzodioxol-5-ylmethyl)benzamide | <10 |
| 2-[(1R, 2R)-2-hydroxy-1-(hydroxymethyl)propyl-amino]-5-nitro-N-(1,3-benzodioxol-5-yl-methyl)benzamide | <10 |
| 2-[1-(tert-butoxycarbonyl)-4-piperidinylamino]-5-nitro-N-(1,3-benzodioxol-5-ylmethyl)-benzamide | <10 |
| 5-nitro-2-(4-piperidinylamino)-N-(1,3-benzodioxol-5-ylmethyl)benzamide | <10 |
| 2-[1-(hydroxymethyl)pentylamino]-5-nitro-N-(1,3-benzodioxol-5-ylmethyl)benzamide | <10 |
| 2-(1-acetyl-4-piperidinylamino)-5-nitro-N-(1,3-benzodioxol-5-ylmethyl)benzamide | <10 |

TABLE 1-continued

| Test Compounds (nM) | Inhibitory activity IC$_{50}$ (nM) |
|---|---|
| 2-(1-methyl-4-piperidinylamino)-5-nitro-N-(1,3-benzodioxol-5-ylmethyl)benzamide | <10 |
| 2-(1-formyl-4-piperidinylamino)-5-nitro-N-(1,3-benzodioxol-5-ylmethyl)benzamide | <10 |
| N-(3-fluoro-4-methoxybenzyl)-2-[2-hydroxy-1-(hydroxymethyl)ethylamino]-5-nitrobenzamide | <10 |
| 2-(trans-4-hydroxycyclohexyl)amino-N-[4-(methylthio)benzyl]-5-nitrobenzamide | <10 |
| N-(3,5-dichloro-4-methoxybenzyl)-2-(trans-4-hydroxycyclohexylamino)-5-nitrobenzamide | <10 |
| N-(3,4-ethylenedioxybenzyl)-2-(trans-4-hydroxycyclohexylamino)-5-nitrobenzamide | <10 |
| N-(3-chloro-4-fluorobenzyl)-2-[2-hydroxy-1-(hydroxymethyl)ethylamino]-5-nitrobenzamide | <10 |
| (S)-N-(3-chloro-4-methylbenzyl)-2-(2-hydroxy-1-methylethylamino)-5-nitrobenzamide | <10 |
| 2-[2-hydroxy-1-(hydroxymethyl)ethylamino]-N-(3-methoxy-4-methylbenzyl-5-nitrobenzamide | <10 |
| N-cyclohexylmethyl-2-(cis-4-hydroxycyclohexylamino)-5-nitrobenzamide | <10 |
| (S)-2-[1-(chloromethyl)propylamino]-5-nitro-N-(1,3-benzodioxol-5-ylmethyl)benzamide | <10 |
| (R)-N-(4-chloro-3-nitrobenzyl)-2-[1-(hydroxymethyl)propylamino]-5-nitrobenzamide | <10 |
| N-(3,4-dimethylbenzyl)-2-(cis-4-hydroxycyclohexylamino)-5-nitrobenzamide | <10 |
| 2-(cis-4-chlorocyclohexylamino)-5-nitro-N-(1,3-benzodioxol-5-ylmethyl)benzamide | <10 |
| 2-[cis-4-(acetoxy)cyclohexylamino]-N-(3,4-dimethoxybenzyl)-5-nitrobenzamide | <10 |
| 2-[(trans-4-aminocyclohexyl)amino]-N-(3,4-dimethoxybenzyl)-5-nitrobenzamide | <10 |
| 2-[2-chloro-1-(chloromethyl)ethylamino]-5-nitro-N-(1,3-benzodioxol-5-ylmethyl)benzamide | <10 |
| N-(2-chloro-5-methoxybenzyl)-2-(cis-4-hydroxycyclohexylamino)-5-nitrobenzamide | <10 |
| N-(3-chloro-4-methoxybenzyl)-2-[2-hydroxy-1-(hydroxymethyl)ethylamino]-5-(trifluoromethyl)-benzamide | <10 |
| N-(3,4-dimethoxybenzyl)-2-[(1R, 2S)-2-hydroxy-1-methyl-2-phenylethyl]amino-5-nitrobenzamide | <10 |
| N-(3,4-dimethoxybenzyl)-2-(2,2-dimethyl-1,3-dioxan-5-ylamino)-5-nitrobenzamide | <10 |
| N-(3,4-dimethoxybenzyl)-5-nitro-2-[trans-4-(3-propylureido)cyclohexylamino]benzamide | <10 |
| N-(3,4-dimethoxybenzyl)-5-nitro-2-(2-oxo-1,3-dioxan-5-ylamino)benzamide | <10 |
| N-(4-chloro-4-ethoxybenzyl)-2-(cis-4-hydroxycyclohexylamino)-5-nitrobenzamide | <10 |
| N-(4-ethoxy-3-methoxybenzyl)-2-(cis-4-hydroxycyclohexylamino)-5-nitrobenzamide | <10 |
| 2-{trans-4-[2,3-bis(tert-butoxycarbonyl)-guanidino]cyclohexylamino}-N-(3,4-dimethoxybenzyl)-5-nitrobenzamide | <10 |
| 2-[1-(tert-butoxycarbonyl)piperidin-4-ylamino]-N-(3,4-dimethoxybenzyl)-5-nitrobenzamide | <10 |
| (R)-2-(2-hydroxy-1-methylethyl)amino-5-nitro-N-(4-phenoxybenzyl)benzamide | <10 |
| N-(4-ethoxy-3-methoxybenzyl)-2-(trans-4-formamidocyclohexylamino)-5-nitrobenzamide | <10 |
| N-(3,4-dimethoxybenzyl)-5-nitro-2-(4-piperidinyl-amino)benzamide | <10 |
| N-(3,4-dimethoxybenzyl)-2-(trans-4-guanidino-cyclohexylamino)-5-nitrobenzamide hydrochloride | <10 |
| (R)-2-(2-hydroxy-1-methylethyl)amino-5-nitro-N-(4-phenybenzyl)benzamide | <10 |
| N-(benzo[b]thiophen-2-ylmethyl)-2-(cis-4-hydroxycyclohexylamino)-5-nitrobenzamide | <10 |
| 2-(cis-4-hydroxycyclohexylamino)-5-nitro-N-(4-phenylbenzyl)benzamide | <10 |
| N-(3,4-dimethoxybenzyl)-2-[(R)-1-hydroxymethyl-3-(methylthio)propylamino]-5-nitrobenzamide | <10 |
| N-(benzofuran-2-ylmethyl)-2-(cis-4-hydroxy-cyclohexylamino)-5-nitrobenzamide | <10 |
| 2-(cis-4-formamidocyclohexylamino)-N-(3,4-dimethoxybenzyl)-5-nitrobenzamide | <10 |
| 2-[1-[1,3-bis(tert-butoxycarbonyl)amidino]-piperidin-4-ylamino]-N-(3,4-dimethoxybenzyl)-5-nitrobenzamide | <10 |
| 2-(1-amidinopiperidin-4-ylamino)-N-(3,4-dimethoxybenzyl)-5-nitrobenzamide hydrochloride | <10 |
| 5-bromo-N-(3-chloro-4-methoxybenzyl)-2-(cyclopentylamino)benzamide hydrochloride | <10 |
| [(1S, 2R)-1-(carbamoyl)-2-hydroxypropyl-amino]-N-(3,4-dimethoxybenzyl)-5-nitro-benzamide | <10 |
| 2-(cis-4-hydroxycyclohexylamino)-N-[3-methoxy-4-(2-methoxyethoxy)benzyl]-5-nitrobenzamide | <10 |
| N-(4-cyclobutylmethoxy-3-methoxybenzyl)-2-[2-hydroxy-1-(hydroxymethyl)ethylamino]-5-nitrobenzamide | <10 |
| (S)-N-(3,4-dimethoxybenzyl)-2-[1-(formamidomethyl)-2-hydroxyethylamino]-5-nitrobenzamide | <10 |

As shown in the above Table 1, the compounds (I) of the present invention have superior inhibitory activity against cGMP-PDE.

Test method 2
The Effect on Erection Function (a) Effect of Test Compound on Nitroprusside or Ach-induced Relaxation in Isolated Rat Corpora Cavernosa.

Male SD rats were anesthetized with sodium pentobarbital 50 mg/kg intraperitoneally, and the corpora cavernosa was excised. The tunica albuginea was dissected according to the methods described by Italiano et al. (Pharmacological Research, 30, No. 4, 1994) and used for in vitro pharmacological study. The erectile tissue strip was placed in a 25 ml organ bath containing Krebs-Ringer solution. The bath was maintained at 37° C. and bubbled with 95% $O_2$ and 5% $CO_2$. The strip was stretched with a resting force of 0.25 g, and isometric contraction were recorded via force development transducer on a recorder.

The strip was equilibrated in the Krebs-Ringer solution for about 60 minutes, and preconstructed by 0.1 mM norepinephrine to ascertain the responsibility of each preparation. The strip was washed several times, and then constricted by 0.1 mM norepinephrine. After getting stable constrictile response to norepinephrine, the first dose-response curve for sodium nitroprusside or Ach (acetylcholine) was obtained. After washing a few times for 60 minutes, the strip was constricted by norepinephrine again, and the second dose-response curve for sodium nitroprusside or Ach was obtained. The test compound, i.e., (R)-N-(3,4-dimethoxybenzyl)-2-(2-hydroxy-1-methylethylamino)-5-nitrobenzamide which was selected as a representative compound of this invention was added 30 minutes before adding norepinephrine. Relaxant response elicited by 10 $\mu$M nitroprusside was 20% in control preparation, but this relaxant response increased to 32% in the presence of the test compound ($5 \times 10^{-8}$ M).

Said compound at $5 \times 10^{-8}$ M also potentiated Ach-induced relaxation of corpora cavernosa. 100 $\mu$M Ach-induced relaxant response to the contractile response induced by $10^{-4}$ M norepinephrine was only 5.0% in control preparation, but this relaxant response to Ach increased to 18.0% in the presence of said compound ($5 \times 10^{-8}$ M).

(b) Effect of test compounds on the relaxation elicited by electrical field stimulation in rabbit corpora cavernosa.

The rabbit erectile tissue strip prepared according to the method described by Italiano et al. (Pharmacological Research, 30, No 4, 1994) was placed 25 ml organ bath containing Krebs-Ringer solution. The bath was maintained at 37° C. and bubbled with 95% $O_2$ and 5% $CO_2$. The solution also contained atropine (1 μM) and guanethidine (50 μM). The erectile tissue strip was stretched with a resting force of 0.25 g, and isometric contraction were recorded via force development transducer on a recorder. The bipolar platinum electrode connected to the electric stimulator was placed around the strip.

The strip was equilibrated in the Krebs-Ringer solution for about 60 minutes and preconstricted by 0.1 mM norepinephrine to ascertain the responsibility of each preparation. The strip was washed several times, and then constricted by 0.1 mM norepinephrine. After getting stable contractile response to norepinephrine, the first electrical field stimulation (1 to 30 Hz, 20V, 0.5 msec duration, 90 sec interval) was delivered. 30 minutes after adding the tested compound, the second electrical field stimulation was delivered.

The compounds i.e., N-(3,4-dimethoxybenzyl)-2-(cis-4-hydroxycyclohexylamino)-5-nitrobenzamide and (R)-N-(3,4-dimethoxybenzyl)-2-(2-hydroxy-1-methyl-ethylamino)-5-nitrobenzamide which were selected as representative compounds of this invention, at $5 \times 10^{-8}$ M potentiated relaxation of corpora cavernosa elicited by electrical field stimulation in rabbit corpora cavernosa.

Relaxant response elicited by 30 Hz was only 70% in control preparation, but this relaxant response increased to 100% in the presence of $5 \times 10^{-8}$ M said compounds.

(c) Male beagle weighing 8.0–12.0 kg were anesthetized with pentobarbital sodium (35 mg/kg, i.v.). After tracheotomy, the animal was artificially ventilated using a volume-cycled ventilator. The femoral artery was cannulated for continuous blood pressure and heart rate monitoring. The femoral vein was cannulated for maintenance of anesthesia and administration of tested compound.

Either the left or right cavernous nerve was exposed posterolaterally to the prostate and a cuff electrode was placed around the nerve for electrical stimulation. A 21-gauge butterfly needle was placed in the corpus cavernousum and connected to a pressure transducer for intracavernous pressure. After a period of stabilization of all parameters, erection was induced by cavernous nerve electrically stimulation (7 Hz, 10 V) and the following was measured: the duration of detumescence (time (T75) from cessation of stimulation to 75% reduction of intracavernous pressure). The test compounds, i.e., N-(3,4-dimethoxybenzyl)-2-(cis-4-hydroxycyclohexylamino)-5-nitrobenzamide and (R)-N-(3,4-dimethoxybenzyl)-2-(2-hydroxy-1-methyl-ethylamino)-5-nitrobenzamide were each dissolved in 50% PEG400. As shown in Table 2, T75 after the cessation of electrical stimulation was prolonged by the administration of the compounds (0.1 mg/kg, i.v.) which were selected as representative compounds of this invention.

TABLE 2

| test compounds | mean of prolongation of T75 (second) |
|---|---|
| N-(3,4-dimethoxybenzyl)-2-(cis-4-hydroxycyclohexylamino)-5-nitrobenzamide | 52 |
| (R)-N-(3,4-dimethoxybenzyl)-2-(2-hydroxy-1-methylethylamino)-5-nitrobenzamide | 44 |

Test method 3
Toxicities of Compound (I)

Test on the toxicity by repetitive oral administration of the compounds, i.e., N-(3,4-dimethoxybenzyl)-2-(cis-4-hydroxycyclohexylamino)-5-nitrobenzamide and (R)-N-(3,4-dimethoxybenzyl)-2-(2-hydroxy-1-methylethylamino)-5-nitrobenzamide which were selected as representative compounds of this invention, in SD rat was conducted. The dead at dose of 32 mg/kg once a day for 14 consecutive days could not be observed.

The compound (I) or its salt can be administered alone or in a form of a mixture, preferably, with a pharmaceutical vehicle or carrier.

The active ingredient of this invention can be used in a form of a pharmaceutical preparation, for example, in solid, semisolid or liquid form, which contains a compound (I), as an active ingredient, in admixture with an organic or inorganic carrier or excipient suitable for external, enteral, intravenous, intramuscular, parenteral or intramucous applications. The active ingredient may be compounded, for example, with the conventional non-toxic, pharmaceutically acceptable carriers for ointment, cream, plaster, tablets, pellets, capsules, suppositories, solution (saline, for example), emulsion, suspension (olive oil, for example), aerosols, pills, powders, syrups, injections, troches, cataplasms, aromatic waters, lotions, buccal tablets, sublingual tablets, nasal drops and any other form suitable for use. The carriers which can be used are water, wax, glucose, lactose, gum acacia, gelatin, mannitol, starch paster, magnesium trisilicate, talc, corn starch, keratin, paraffin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in a pharmaceutical composition in an effective amount sufficient to produce the desired effect upon the process or condition of the diseases.

The active ingredient may be compounded into, for example, preparations for oral application, preparations for injection, preparations for external application, preparations for inhalation, preparations for application to mucous membranes (oral mucous membrane, fascia penis, facies urethralis penis, etc.).

Mammals which may be treated by the present invention include livestock mammals such as cows, horses, etc., domestic animals such as dogs, cats, rats, etc. and humans, preferably humans.

While the dosage of therapeutically effective amount of a compound (I) varies from and also depends upon the age and condition of each individual patient to be treated, in case of the systemic administration, a daily dose of about 0.01–1000 mg, preferably 0.1–500 mg and more preferably 0.5–100 mg of the active ingredient is generally given for treating the diseases, and an average single dose of about 0.2–0.5 mg, 1 mg, 5 mg, 10 mg, 50 mg, 100 mg, 250 mg and 500 mg is generally administered. Daily doses for chronic administration in humans will be in the range of about 0.3 mg/body to 1,000 mg/body.

The patents, patent applications and publications cited herein above are incorporated by reference.

BEST MODE FOR CARRYING OUT THE INVENTION

The following Examples are given only for the purpose of illustrating the present invention in more detail.

Preparation 1

A mixture of 2-fluoro-5-nitrobenzoic acid (1.00 g), (1,3-benzodioxol-5-ylmethyl)amine (980 mg), 1-[3-(dimethylamino)propyl]-3-ethylcarbodiimide hydrochloride (1.55 g) and 1-hydroxybenzotriazole (1.09 g) in anhydrous dimethylformamide (10 mL) was stirred for 40 hours at ambient temperature. The mixture was partitioned between water and ethyl acetate. The separated organic layer was washed with an aqueous saturated sodium bicarbonate solution, 1N-hydrochloric acid, water and brine. Then, the resultant was dried over magnesium sulfate and evaporated in vacuo. The residue was triturated with diisopropyl ether to give 2-fluoro-5-nitro-N-(1,3-benzodioxol-5-ylmethyl) benzamide as yellow powders (1.48 g).

NMR (DMSO-$d_6$, δ): 4.38 (2H, d, J=7 Hz), 5.99 (2H, s), 6.80–6.98 (3H, m), 7.62 (1H, m), 8.39 (2H, m), 9.12 (1H, br); Mass m/z: 317 ($M^+$).

EXAMPLE 1(1)

To a solution of 2-fluoro-5-nitro-N-(1,3-benzodioxol-5-ylmethyl)benzamide (150 mg) in anhydrous pyridine (3 mL) was added trans-4-aminocyclohexanol (81.4 mg), and the mixture was stirred for 15 hours at ambient temperature, and then for 3 hours at 60° C. The mixture was partitioned between ethyl acetate and water. The separated organic layer was washed with water and brine, dried over magnesium sulfate and evaporated in vacuo. The residue was subjected to a silica gel column chromatography eluting with a mixture of chloroform and methanol (20:1). The eluent was concentrated and the residue was triturated with diisopropyl ether to give 2-(trans-4-hydroxycyclohexylamino)-5-nitro-N-(1,3-benzodioxol-5-ylmethyl)benzamide as yellow powders (164 mg).

NMR (CDCl$_3$, δ): 1.38–1.60 (4H, br), 2.00–2.24 (4H, br), 3.44 (1H, br), 3.76 (1H, br), 4.49 (2H, d, J=7 Hz), 5.97 (2H, s), 6.44 (1H, br), 6.67 (1H, d, J=8 Hz), 6.80 (3H, m), 8.14 (1H, dd, J=4, 8 Hz), 8.29 (1H, d, J=4 Hz), 8.86 (1H br); Mass m/z: 412 ($M^+$).

EXAMPLE 1(2)

To a solution of 2-(trans-4-hydroxycyclohexylamino)-5-nitro-N-(1,3-benzodioxol-5-ylmethyl)benzamide (100 mg) in dichloromethane (3 mL) and acetonitrile (0.4 mL) were added tetrapropylammonium perruthenate (4.25 mg), 4-methylmorpholine N-oxide (42.5 mg) and molecular sieves (4 Å, 0.2 g). The resulting mixture was stirred for 2 hours at ambient temperature. The mixture was subjected to a silica gel chromatography eluting with ethyl acetate to give 5-nitro-2-(4-oxocyclohexylamino)-N-(1,3-benzodioxol-5-ylmethyl)benzamide (92 mg) as a solid substance.

NMR (DMSO-$d_6$, δ): 1.70–1.87 (2H, m), 2.12–2.53 (4H, m), 2.49–2.60 (2H, m), 4.06 (1H, m,), 4.35 (2H, d, J=6 Hz), 5.98 (2H, s), 6.75–6.91 (3H, m), 7.03 (1H, d, J=9 Hz), 8.16 (1H, dd, J=2, 9 Hz), 8.63 (1H, d, J=2 Hz), 9.22 (1H, d, J=8 Hz), 9.36 (1H, t, J=6 Hz); Mass m/z: 410 ($M^+$-1).

EXAMPLE 2(1)

(S)-2-[1-(Hydroxymethyl)propylamino]-5-nitro-N-(1,3-benzodioxol-5-ylmethyl)benzamide (69 mg) was obtained from 2-fluoro-5-nitro-N-(1,3-benzodioxol-5-ylmethyl) benzamide (72 mg) and (S)-2-amino-1-butanol (42.4 mg) in a manner similar to Example 1(1).

mp: 128–130° C. NMR (DMSO-$d_6$, δ): 0.92 (3H, t, J=7 Hz), 1.49 (1H, m), 1.67 (1H, m), 3.4–3.65 (3H, m), 4.36 (2H, d, J=7 Hz), 4.92 (1H, t, J=6 Hz), 5.98 (2H, s), 6.75–6.93 (4H, m), 8.09 (1H, dd, J=2, 8 Hz), 8.59 (1H, d, J=2 Hz), 9.16 (1H, d, J=7 Hz), 9.31 (1H, t, J=6 Hz).

EXAMPLE 2(2)

To a solution of (S)-2-[1-(hydroxymethyl)propylamino]-5-nitro-N-(1,3-benzodioxol-5-ylmethyl)benzamide (127 mg) in 1,2-dichloroethane (4 mL) and carbontetrachloride (2 mL) was added triphenylphosphine (215 mg), and the mixture was stirred for an hour under reflux. The solvent was evaporated in vacuo and the residue was subjected to a silica gel column chromatography eluting with a mixture of chloroform and ethyl acetate (9:1) to give (S)-2-[1-(chloromethyl)propylamino]-5-nitro-N-(1,3-benzodioxol-5-ylmethyl)benzamide (71 mg) as a solid substance.

NMR (DMSO-$d_6$, δ): 0.92 (3H, t, J=7 Hz), 1.52–1.80 (2H, m), 3.82 (2H, m), 3.99 (1H, m), 4.36 (2H, d, J=6 Hz), 5.99 (2H, s), 6.78–6.92 (3H, m), 6.98 (1H, d, J=9 Hz), 8.13 (1H, dd, J=2, 9 Hz), 8.61 (1H, d, J=2 Hz), 9.19 (1H, d, J=8 Hz), 9.36 (1H, t, J=6 Hz); Mass m/z: 404 ($M^+$-1).

EXAMPLE 3(1)

2-[2-Hydroxy-1-(hydroxymethyl)ethylamino]-5-nitro-N-(1,3-benzodioxol-5-ylmethyl)benzamide (108 mg) was obtained as yellow powders from 2-fluoro-5-nitro-N-(1,3-benzodioxol-5-ylmethyl)benzamide (100 mg) and 2-amino-1,3-propanediol (42.9 mg) in a manner similar to Example 1(1).

NMR (DMSO-$d_6$, δ): 3.48–3.68 (5H, br), 4.34 (2H, d, J=7 Hz), 4.93 (2H, t, J=7 Hz), 5.98 (2H, s), 6.78–6.96 (4H, m), 8.12 (1H, dd, J=4 Hz, 8 Hz), 8.58 (1H, d, J=4 Hz), 9.28 (2H, br); Mass m/z: 388 ($M^+$).

EXAMPLE 3(2)

2-[2-Chloro-1-(chloromethyl)ethylamino]-5-nitro-N-(1, 3-benzodioxol-5-ylmethyl)benzamide (36 mg) was obtained from 2-[2-hydroxy-1-(hydroxymethyl)ethylamino]-5-nitro-N-(1,3-benzodioxol-5-ylmethyl)benzamide (101 mg) in a manner similar to Example 2(2).

NMR (DMSO-$d_6$, δ); 3.89 (4H, d, J=6 Hz), 4.36 (2H, d, J=5 Hz), 4.47 (1H, m), 5.99 (2H, s), 6.78–6.93 (3H, m), 7.08 (1H, d, J=9 Hz), 8.16 (1H, dd, J=2, 9 Hz), 8.64 (1H, d, J=2 Hz), 9.39 (1H, t, J=5 Hz), 9.44 (1H, d, J=8 Hz); Mass m/z: 424, 426 ($M^+$-1).

EXAMPLE 3(3)

To a solution of N-(3,4-dimethoxybenzyl)-2-[2-hydroxy-1-(hydroxymethyl)ethylamino]-5-nitrobenzamide (134 mg) in a mixture of dichloromethane (1 mL) and pyridine (1 mL) was added triphosgene (49.1 mg) at −78° C. Then, the resulting mixture was stirred for an hour at ambient temperature. The mixture was diluted with ethyl acetate and washed successively with diluted ammonium chloride, water and brine. The organic layer was dried over sodium sulfate and evaporated in vacuo. The residue was subjected to a silica gel column chromatography eluting with a mixture of chloroform and ethyl acetate (7:3) to give N-(3,4-dimethoxybenzyl)-5-nitro-2-(2-oxo-1,3-dioxan-5-ylamino) benzamide (129 mg) as a solid substance.

NMR (CDCl$_3$, δ): 3.88 (3H, s), 3.90 (3H, s), 4.21 (1H, m), 4.49 (2H, m), 4.53 (2H, d, J=8 Hz), 4.69 (2H, m), 6.60–6.72 (2H, m), 6.84–6.96 (3H, m), 8.23 (1H, dd, J=2, 9 Hz), 8.39 (1H, d, J=2 Hz), 9.44 (1H, m); Mass m/z: 430 ($M^+$-1).

EXAMPLE 3(4)

To a solution of N-(3,4-dimethoxybenzyl)-2-[2-hydroxy-1-(hydroxymethyl)ethylamino]-5-nitrobenzamide (117 mg) in dichloromethane (5.0 mL) were added 2,2-dimethoxypropane (0.36 mL) and 4-toluenesulfonic acid (10 mg), and the mixture was stirred for 30 minutes under reflux. The resulting mixture was diluted with ethyl acetate and washed successively with diluted sodium bicarbonate and brine. The organic layer was dried over sodium sulfate and evaporated in vacuo. The residue was triturated with diethyl ether to give N-(3,4-dimethoxybenzyl)-2-(2,2-dimethyl-1,3-dioxan-5-ylamino)-5-nitrobenzamide (105 mg) as a solid substance.

NMR (CDCl$_3$, δ): 1.50 (3H, s), 1.51 (3H, s), 3.68 (1H, m), 3.83 (2H, dd, J=6, 12 Hz), 3.88 (3H, s), 3.90 (3H, s), 4.15 (2H, dd, J=4, 12 Hz), 4.52–4.57 (2H, m), 6.66 (1H, d, J=9 Hz), 6.83–6.95 (3H, m), 6.94 (1H, m), 8.16 (1H dd, J=2, 9 Hz,), 8.39 (1H, d, J=2 Hz); Mass m/z: 446 (M$^+$+1).

EXAMPLE 4(1)

(S)-2-[1-(tert-Butoxycarbonyl)ethylamino]-5-nitro-N-(1,3-benzodioxol-5-ylmethyl)benzamide (131 mg) was obtained from 2-fluoro-5-nitro-N-(1,3-benzodioxol-5-ylmethyl)benzamide (107 mg) and (S)-alanine tert-butyl ester hydrochloride (85.5 mg) in a manner similar to Example 1(1).

NMR (DMSO-d$_6$, δ); 1.41 (3H, d, J=7 Hz), 1.43 (9H, s), 4.30–4.38 (3H,m), 5.99 (2H, s), 6.71–6.93 (4H, m), 8.17 (1H, dd, J=2, 9 Hz), 8.62 (1H, d, J=2 Hz), 9.34–9.43 (2H, m); Mass m/z: 442 (M$^+$−1).

EXAMPLE 4(2)

To a solution of (S)-2-[1-(tert-butoxycarbonyl)ethylamino]-5-nitro-N-(1,3-benzodioxol-5-ylmethyl)benzamide (104 mg) in dichloromethane (1.5 mL) was added trifluoroacetic acid (0.6 mL), and the mixture was stirred for 2 hour at ambient temperature. The resulting mixture was evaporated in vacuo and the residue was triturated with diethyl ether to give (S)-2-(1-carboxyethylamino)-5-nitro-N-(1,3-benzodioxol-5-ylmethyl)benzamide (76 mg) as a solid substance.

NMR (DMSO-d$_6$, δ); 1.43 (3H, d, J=7 Hz), 4.31–4.42 (3H, m), 5.99 (2H, s), 6.73–6.93 (4H, m), 8.15 (1H, dd, J=2, 9 Hz), 8.61 (1H, d, J=2 Hz), 9.32–9.41 (2H, m); Mass m/z: 386 (M$^+$−1).

EXAMPLE 5

2-(trans-2-Hydroxycyclopentylamino)-5-nitro-N-(1,3-benzodioxol-5-ylmethyl)benzamide (107 mg) was obtained as yellow powders from 2-fluoro-5-nitro-N-(1,3-benzodioxol-5-ylmethyl)benzamide (100 mg) and trans-2-aminocyclopentanol (47.7 mg) in a manner similar to Example 1(1).

NMR (CDCl$_3$, δ): 1.55–1.75 (2H, m), 1.76–1 95 (2H, m), 2.00–2.13 (1H, m), 2.26–2.38 (1H, m), 3.78 (1H, br), 4.16 (1H, br), 4.48 (2H, d, J=7 Hz), 5.96 (2H, s), 6.50 (1H, br) 6.77–6.90 (4H, m), 8.13 (1H, dd, J=4, 8 Hz), 8.30 (1H, d, J=4 Hz), 8.86 (1H, br); Mass m/z: 398 (M$^+$).

EXAMPLE 6

2-(2-Hydroxy-1,1-dimethylethylamino)-5-nitro-N-(1,3-benzodioxol-5-ylmethyl)benzamide (80.0 mg) was obtained from 2-fluoro-5-nitro-N-(1,3-benzodioxol-5-ylmethyl)benzamide (100 mg) and 2-amino-2-methyl-1-propanol (84.0 mg) in a manner similar to Example 1(1).

NMR (CDCl$_3$, δ): 1.47 (6H, s), 1.88 (1H, t, J=7 Hz), 3.70 (2H, d, J=7 Hz), 4.50 (2H, d, J=7 Hz), 5.97 (2H, s), 6.45 (1H, br), 6.76–6.95 (4H, m), 8.10 (1H, dd, J=4, 8 Hz), 8.28 (1H, d, J=4 Hz), 9.13 (1H, br); Mass m/z: 388 (M$^+$).

EXAMPLE 7

(R)-2-(2-Hydroxy-1-methylethylamino)-5-nitro-N-(1,3-benzodioxol-5-ylmethyl)benzamide (65 mg) was obtained from 2-fluoro-5-nitro-N-(1,3-benzodioxol-5-ylmethyl)benzamide (93 mg) and (R)-2-amino-1-propanol(44 mg) in a manner similar to Example 1(1).

mp: 166–168° C.

NMR (DMSO-d$_6$, δ): 1.17 (3H, d, J=7 Hz), 3.46 (2H, m), 3.76 (1H, m), 4.33 (2H, d, J=7 Hz), 4.98 (1H, t, J=6 Hz), 5.98 (2H, s), 6.75–6.93 (4H, m), 8.11 (1H, dd, J=2, 8 Hz), 8.58 (1H, d, J=2 Hz), 9.15 (1H, d, J=7 Hz), 9.29 (1H, t, J=6 Hz).

EXAMPLE 8

5-Nitro-N-(1,3-benzodioxol-5-ylmethyl)-2-(2-thiazolylamino)benzamide (28 mg) was obtained from 2-fluoro-5-nitro-N-(1,3-benzodioxol-5-ylmethyl)benzamide (70 mg) and 2-aminothiazole (26.4 mg) in a manner similar to Example 1(1).

NMR (DMSO-d$_6$, δ): 4.43 (2H, d, J=5 Hz), 5.99 (1H, s), 6.81–6.91 (2H, m), 6.96 (1H, s), 7.27 (1H, d, J=4 Hz), 7.47 (1H, d, J=4 Hz), 8.39 (1H, dd, J=2, 9 Hz), 8.70–8.6 (2H, m), 9.70 (1H, t, J=5 Hz); Mass m/z: 397 (M$^+$−1).

EXAMPLE 9

(R)-2-(1-Ethyl-2-hydroxyethylamino)-5-nitro-N-(1,3-benzodioxol-5-ylmethyl)benzamide (55.8 mg) was obtained from 2-fluoro-5-nitro-N-(1,3-benzodioxol-5-ylmethyl)benzamide (72 mg) and (R)-2-amino-1-butanol (0.045 mL) in a manner similar to Example 1(1).

NMR (DMSO-d$_6$, δ): 0.89 (3H, t, J=7 Hz), 1.49 (1H, m), 1.66 (1H, m), 3.38–3.45 (3H, m), 4.34 (2H, d, J=6 Hz), 4.92 (1H, t, J=5 Hz), 5.98 (2H, s), 6.78–6.92 (4H, m), 8.09 (1H, dd, J=2, 9 Hz), 8.58(1H, d, J=2 Hz), 9.16 (1H, d, J=8 Hz), 9.30 (1H, t, J=6 Hz); Mass m/z: 386 (M$^+$−1).

EXAMPLE 10

(R)-5-Nitro-2-(tetrahydro-3-furanylamino)-N-(1,3-benzodioxol-5-ylmethyl)benzamide (76 mg) was obtained from 2-fluoro-5-nitro-N-(1,3-benzodioxol-5-ylmethyl)benzamide (80 mg) and (R)-3-aminotetrahydrofuran p-toluenesulfonate (78.2 mg) in a manner similar to Example 1(1).

NMR (DMSO-d$_6$, δ): 1.79 (1H, m), 2.31 (1H, m), 3.60 (1H, m), 3.71–3.94 (3H, m), 4.29 (1H, m), 4.37 (2H, d, J=6 Hz), 5.99 (2H, s), 6.81 (1H, d, J=8 Hz), 6.87–6.95 (3H, m), 8.17 (1H, m), 8.63 (1H, d, J=2 Hz), 9.26 (1H, d, J=8 Hz), 9.38 (1H, t, J=6 Hz); Mass m/z: 384 (M$^+$−1).

EXAMPLE 11

(S)-2-[2-Hydroxy-1-(methoxycarbonyl)ethylamino]-5-nitro-N-(1,3-benzodioxol-5-ylmethyl)benzamide (73 mg) was obtained from 2-fluoro-5-nitro-N-(1,3-benzodioxol-5-ylmethyl)benzamide (89 mg) and (S)-serine methyl ester hydrochloride (69.7 mg) in a manner similar to Example 1(1).

NMR (DMSO-d$_6$, δ): 3.67 (3H, s), 3.74 (1H, m), 3.91 (1H, m), 4.36 (2H, d, J=6 Hz), 4.54 (1H, m), 5.34 (1H, t, J=5 Hz), 5.99 (2H, s), 6.76–6.93 (4H, m), 8.11 (1H, dd, J=2, 9 Hz), 8.62 (1H, d, J=2 Hz), 9.34 (1H, t, J=6 Hz), 9.57 (1H, d, J=8 Hz); Mass m/z: 416 (M$^+$−1).

EXAMPLE 12

(R)-2-[1-(Methoxycarbonyl)ethylamino]-5-nitro-N-(1,3-benzodioxol-5-ylmethyl)benzamide (85 mg) was obtained from 2-fluoro-5-nitro-N-(1,3-benzodioxol-5-ylmethyl)benzamide (92 mg) and (R)-alanine methyl ester hydrochloride (64.6 mg) in a manner similar to Example 1(1).

NMR (DMSO-d$_6$, δ): 1.46 (3H, d, J=7 Hz), 3.69 (3H, s), 4.36 (2H, d, J=5 Hz), 4.53 (1H, m), 5.99 (2H, s), 6.75–6.93 (4H, m), 8.14 (1H, dd, J=2, 9 Hz), 8.63 (1H, d, J=2 Hz), 9.34–9.44 (2H, m); Mass m/z: 400 (M$^+$−1).

EXAMPLE 13

2-(2,3-Dihydro-1H-inden-2-ylamino)-5-nitro-N-(1,3-benzodioxol-5-ylmethyl)benzamide (82.7 mg) was obtained from 2-fluoro-5-nitro-N-(1,3-benzodioxol-5-ylmethyl)benzamide (90 mg) and 2-aminoindan hydrochloride (57.6 mg) in a manner similar to Example 1(1).

NMR (DMSO-d$_6$, δ): 2.86 (2H, m), 3.43 (2H, m), 4.32 (2H, d, J=6 Hz), 4.52 (1H, m), 5.99 (2H, s), 6.75–6.79 (3H, m), 6.99 (1H, d, J=9 Hz), 7.15–7.20 (2H, m), 7.21–7.29 (2H, m), 8.17 (1H, dd, J=2, 9 Hz), 8.61 (1H, d, J=2 Hz), 9.26–9.35 (2H, m); Mass m/z: 430 (M$^+$−1).

EXAMPLE 14

2-(trans-2-Aminocyclohexylamino)-5-nitro-N-(1,3-benzodioxol-5-ylmethyl)benzamide (73.5 mg) was obtained from 2-fluoro-5-nitro-N-(1,3-benzodioxol-5-ylmethyl)benzamide (96 mg) and trans-1,2-diaminocyclohexane (0.072 mL) in a manner similar to Example 1(1).

NMR (DMSO-d$_6$, δ): 1.16–1.41 (4H, m), 1.61–1.71 (2H, m), 1.87–2.00 (2H, m), 2.84 (1H, m), 3.46 (1H, m), 4.36 (2H, m), 4.59 (1H, d, J=4 Hz), 5.98 (2H, s), 6.78–6.92 (3H, m), 7.01 (1H, d, J=9 Hz), 8.10 (1H, dd, J=2, 9 Hz), 8.60 (1H, d, J=2 Hz), 9.10 (H, d, J=8 Hz), 9.33 (1H, br); Mass m/z: 413 (M$^+$+1).

EXAMPLE 15

2-[(1R, 2R)-2-Hydroxy-1-(hydroxymethyl)propylamino]-5-nitro-N-(1,3-benzodioxol-5-ylmethyl)benzamide (81.8 mg) was obtained from 2-fluoro-5-nitro-N-(1,3-benzodioxol-5-ylmethyl)benzamide (93 mg) and (R)-threoninol (61.4 mg) in a manner similar to Example 1(1).

NMR (DMSO-d$_6$, δ): 1.07 (3H, d, J=7 Hz), 3.37–3.56 (3H, m), 4.03 (1H, m), 4.34 (2H, d, J=5 Hz), 4.83 (1H, m), 4.97 (1H, d, J=5 Hz), 5.99 (2H, s), 6.75–6.94 (4H, m), 8.09 (1H, dd, J=2, 9 Hz), 8.56 (1H, d, J=2 Hz), 9.23–9.30 (2H, m); Mass m/z: 402 (M$^+$−1).

EXAMPLE 16

2-[2-(Tetrahydro-2-oxo-3-furanyl)amino]-5-nitro-N-(1,3-benzodioxol-5-ylmethyl)benzamide (22.8 mg) was obtained from 2-fluoro-5-nitro-N-(1,3-benzodioxol-5-ylmethyl)benzamide (54.8 mg) and 2-amino-γ-butyrolactone hydrobromide (37.6 mg) in a manner similar to Example 1(1).

NMR (DMSO-d$_6$, δ): 2.15–2.3 (1H, m), 2.7–2.86 (1H, m), 4.29 (1H, m), 4.35 (2H, d, J=5 Hz), 4.42 (1H, t, J=7 Hz), 4.83 (1H, m), 4.97 (1H, d, J=5 Hz), 5.99 (2H, s), 6.75–6.91 (3H, m), 6.97 (1H, d, J=9 Hz), 8.13 (1H, dd, J=2,9 Hz), 8.61 (1H, d, J=2 Hz), 9.24 (1H, d,J=8 Hz), 9.38 (1H, t, J=6 Hz); Mass m/z: 398 (M$^+$−1).

EXAMPLE 17

2-(tert-Butylamino)-5-nitro-N-(1,3-benzodioxol-5-ylmethyl)benzamide (94.3 mg) was obtained from 2-fluoro-5-nitro-N-(1,3-benzodioxol-5-ylmethyl)benzamide (100 mg) and tert-butylamine (115 mg) in a manner similar to Example 1(1).

NMR (CDCl$_3$, δ): 1.48 (9H, s), 4.48 (2H, d, J=7 Hz), 5.96 (2H, s), 6.47 (1H, br), 6.77–6.90 (4H, m), 8.11 (1H, dd, J=4, 8 Hz), 8.29 (1H, d, J=4 Hz), 9.08 (1H, br); Mass m/z: 370(M$^+$).

EXAMPLE 18

2-[1-(Ethoxycarbonyl)piperidin-4-ylamino]-5-nitro-N-(1,3-benzodioxol-5-ylmethyl)benzamide (204 mg) was obtained as yellow powders from 2-fluoro-5-nitro-N-(1,3-benzodioxol-5-ylmethyl)benzamide (150 mg) and ethyl 4-amino-1-piperidinecarboxylate (122 mg) in a manner similar to Example 1(1).

NMR (CDCl$_3$, δ): 1.28 (3H, t, J=7 Hz), 1.50–1.70 (2H, br), 1.97–2.10 (2H, br), 3.06–3.23 (2H, br), 3.58–3.70 (1H, br), 3.95–4.10 (2H, br), 4.16 (2H, q, J=7 Hz), 4.48 (2H, d, J=7 Hz), 5.98 (2H, s), 6.50 (1H, br), 6.69 (1H, d, J=8 Hz), 6.77–6.90 (3H, m), 8.16 (1H, dd, J=4, 8 Hz), 8.32 (1H, d, J=4 Hz), 9.00 (1H, br); Mass m/z: 469(M$^+$).

EXAMPLE 19

2-(1-Benzylpiperidin-4-ylamino)-5-nitro-N-(1,3-benzodioxol-5-ylmethyl)benzamide (123 mg) was obtained as yellow powders from 2-fluoro-5-nitro-N-(1,3-benzodioxol-5-ylmethyl)benzamide (150 mg) and 4-amino-1-benzylpiperidine (122 mg) in a manner similar to Example 1(1).

NMR (CDCl$_3$, δ): 1.63–1.78 (2H, br), 1.96–2.08 (2H, br), 2.17–2.33 (2H, br), 2.75–2.90 (2H, br), 3.48 (1H, br), 3.55 (2H, s), 4.50 (2H, d, J=7 Hz), 5.97 (2H, s), 6.40 (1H, br), 6.65 (1H, d, J=8 Hz), 6.77–6.88 (3H, m), 7.23–7.38 (5H, m), 8.13 (1H, dd, J=4, 8 Hz), 8.28 (1H, d, J=4 Hz), 8.93 (1H, br); Mass m/z: 489(M$^+$).

EXAMPLE 20

2-[2-Hydroxy-1,1-bis(hydroxymethyl)ethylamino]-5-nitro-N-(1,3-benzodioxol-5-ylmethyl)benzamide (14.6 mg) was obtained as brown powders from 2-fluoro-5-nitro-N-(1,3-benzodioxol-5-ylmethyl)benzamide (100 mg) and 2-amino-2-(hydroxymethyl)-1,3-propanediol (114 mg) in a manner similar to Example 1(1).

NMR (DMSO-d$_6$, δ): 3.65 (6H, d, J=7 Hz), 4.33 (2H, d, J=7 Hz), 4.84 (3H, t, J=7 Hz), 5.98 (2H, s), 6.79–6.93 (3H, m), 7.25 (1H, d, J=8 Hz), 8.02 (1H, dd, J=4, 8 Hz), 8.48 (1H, d, J=4 Hz), 9.18 (1H, br), 9.29 (1H, br); Mass m/z: 418(M$^+$).

EXAMPLE 21

2-[2-Hydroxy-1-(hydroxymethyl)-1-methylethylamino]-5-nitro-N-(1,3-benzodioxol-5-ylmethyl)benzamide (115 mg) was obtained from 2-fluoro-5-nitro-N-(1,3-benzodioxol-5-ylmethyl)benzamide (150 mg) and 2-methyl-2-amino-1,3-propanediol (149 mg) in a manner similar to Example 1(1).

NMR (DMSO-d$_6$, δ): 1.26 (3H, s), 3.45–3.60 (4H, m), 4.32 (2H, d, J=7 Hz), 5.00 (2H, t, J=7 Hz), 5.98 (2H, s), 6.78–6.90 (3H, m), 7.08 (1H, d, J=8 Hz), 8.03 (1H, dd, J=4, 8 Hz), 8.51 (1H, d, J=4 Hz), 9.24 (1H, br), 9.33 (1H, br); Mass m/z: 402(M$^+$).

EXAMPLE 22

2-(tert-Butoxyamino)-5-nitro-N-(1,3-benzodioxol-5-ylmethyl)benzamide (56.0 mg) was obtained from 2-fluoro-5-nitro-N-(1,3-benzodioxol-5-ylmethyl)benzamide (150 mg) and 2-tert-butoxyamine (118 mg) in a manner similar to Example 1(1).

NMR (CDCl$_3$, δ): 1.35 (9H, s), 4.51 (2H, d, J=7 Hz), 5.97 (2H, s), 6.48 (1H, br), 6.78–6.86 (3H, m), 7.28 (1H, d, J=8 Hz), 8.19 (1H, dd, J=4, 8 Hz), 8.29 (1H, d, J=4 Hz); Mass m/z: 386(M$^+$).

PREPARATION 23

To a solution of 4-amino-1-cyclohexanecarboxylic acid (500 mg) in dichloromethane (20 mL) and methanol (10 mL) was added 10% hexane solution of trimethylsilyldiazomethane (638 mg), and the mixture was stirred for 21 hours at ambient temperature. The mixture was evaporated in vacuo to give methyl 4-amino-1-cyclohexanecarboxylate as a colorless oil (544 mg).

NMR (CDCl$_3$, δ): 1.27–1.73 (6H, br), 1.88–2.08 (2H, br), 2.48 (1H, m), 2.85 (1H, m), 3.67 and 3.68 (3H, s).

EXAMPLE 23(1)

2-[4-(Methoxycarbonyl)cyclohexylamino]-5-nitro-N-(1,3-benzodioxol-5-ylmethyl)benzamide (381 mg) was obtained from 2-fluoro-5-nitro-N-(1,3-benzodioxol-5-ylmethyl)benzamide (300 mg) and methyl 4-amino-1-cyclohexanecarboxylate (222 mg) in a manner similar to Example 1(1).

NMR (CDCl$_3$, δ): 1.70–2.03 (8H, br), 2.52 (1H, br), 3.63 (1H, br), 3.71 (3H, s), 4.50 (2H, d, J=7 Hz), 5.97 (2H, s), 6.41 (1H, br), 6.66 (1H, m), 6.78–6.87 (3H, m), 8.14 (1H, m), 8.30 (1H, m), 8.86 and 9.08 (1H, br); Mass m/z: 456(M$^+$).

EXAMPLE 23(2)

A mixture of 2-[4-(methoxycarbonyl)cyclohexylamino]-5-nitro-N-(1,3-benzodioxol-5-ylmethyl)benzamide (269 mg), methanol (10 mL), tetrahydrofuran (10 mL) and 1N-sodium hydroxide solution (5 mL) was stirred for an hour at 60° C. The mixture was acidified with 1N-hydrochloric acid to pH 4 and the organic solvent was removed by evaporation. The aqueous layer was diluted with water and extracted with chloroform. The extract was washed with brine, dried over magnesium sulfate and evaporated in vacuo. The residue was triturated with diisopropyl ether to give 2-(4-carboxycyclohexylamino)-5-nitro-N-(1,3-benzodioxol-5-ylmethyl)benzamide as yellow powders (253 mg).

NMR (DMSO-d$_6$, δ): 1.20–2.05 (8H, br), 2.42 (1H, br), 3.77 (1H, br), 4.35 (2H, d, J=7 Hz), 5.96 (2H, s), 6.78–6.95 (4H, m), 8.10 (1H, dd, J=4, 8 Hz), 8.60 (1H, d, J=4 Hz), 9.08 and 9.33 (2H, br); Mass m/z: 440 (M$^+$).

EXAMPLE 23(3)

To a mixture of 2-(4-carboxycyclohexylamino)-5-nitro-N-( 1,3-benzodioxol-5-ylmethyl)benzamide (80.0 mg), 1-[3-(dimethylamino)propyl]-3-ethylcarbodiimide hydrochloride (52.1 mg), 1-hydroxybenzotriazole (36.7 mg) in dimethylformamide (1 mL) was added 28% ammonia solution (10 drops). After stirring for 15 hours at ambient temperature, the mixture was partitioned between water and ethyl acetate. The separated organic layer was washed with an aqueous saturated sodium bicarbonate solution, water and brine. Then, the resultant was dried over magnesium sulfate and evaporated in vacuo. The residue was purified by a silica gel column chromatography eluting with 10% methanol in chloroform. The obtained product was triturated with ciisopropyl ether to give 2-(4-carbamoylcyclohexylamino)-5-nitro-N-(1,3-benzodioxol-5-ylmethyl)benzamide as yellow powders (60.0 mg).

NMR (CDCl$_3$, δ): 1.18–1.85 (8H, br), 2.22 (1H, br), 3.82 (1H, br), 4.37 (2H, d, J=7 Hz), 5.99 (2H, s), 6.70–6.93 (5H, m), 7.23 (1H, br), 8.12 (1H, dd, J=4, 8 Hz), 8.62 (1H, d, J=4 Hz), 9.06 and 9.43 (1H, br), 9.33 (1H, br); Mass m/z: 439(M$^+$).

EXAMPLE 24(1)

2-[1-(tert-Butoxycarbonyl)-4-piperidinylamino]-5-nitro-N-(1,3-benzodioxol-5-ylmethyl)benzamide (539 mg) was obtained from 2-fluoro-5-nitro-N-(1,3-benzodioxol-5-ylmethyl)benzamide (480 mg) and tert-butyl 4-amino-1-piperidinecarboxylate (604 mg) in a manner similar to Example 1(1).

NMR (CDCl$_3$, δ) 1.47 (9H, s), 1.57 (2H, br), 2.00 (2H, br), 3.08 (2H, br), 3.62 (1H, br), 4.00 (2H, br), 4.49 (2H, d, J=7 Hz), 5.97 (2H, s), 6.50 (1H, br), 6.68 (1H, d, J=8 Hz), 6.82 (3H, m), 8.14 (1H, dd, J=4,8 Hz), 8.31 (1H, d, J=4 Hz), 9.00 (1H, d, J=8 Hz); Mass m/z: 497(M$^+$).

EXAMPLE 24(2)

To a solution of 2-[1-(tert-butoxycarbonyl)-4-piperidinylamino]-5-nitro-N-(1,3-benzodioxol-5-ylmethyl)benzamide(469 mg) in dichloromethane (6 mL) was added trifluoroacetic acid (1.07 g), and the mixture was stirred for 4 hours at ambient temperature. The reaction mixture was washed with 1N-sodium hydroxide solution, water and brine. Then, the resultant was dried over magnesium sulfate and evaporated in vacuo. The residue was triturated with diisopropyl ether to give 5-nitro-2-(4-piperidinylamino)-N-(1,3-benzodioxol-5-ylmethyl)benzamide as yellow powders (335 mg).

NMR (DMSO-d$_6$, δ): 1.34 (2H, br), 1.89 (2H, br), 2.10 (1H, br), 2.64 (2H, br), 2.93 (2H, br), 3.65 (1H, br), 4.34 (2H, d, J=7 Hz), 5.98 (2H, s), 6.88 (4H, m), 8.11 (1H, dd, J=4, 8 Hz), 8.61 (1H, d, J=4 Hz), 9.14 (1H, d, J=8 Hz), 9.34 (1H, br); Mass m/z: 399(M$^+$).

EXAMPLE 24(3)

A mixture of 5-nitro-2-(4-piperidinylamino)-N-(1,3-benzodioxol-5-ylmethyl)benzamide (80.0 mg), acetic acid (13.3 mg), 1-[3-(dimethylamino)propyl]-3-ethylcarbodiimide hydrochloride (57.7 mg) and 1-hydroxybenzotriazole (40.7 mg) in anhydrous dimethylformamide (1 mL) was stirred for 3 hours at ambient temperature. The mixture was partitioned between water and ethyl acetate. The organic layer was separated and washed with an aqueous saturated sodium bicarbonate solution, water and brine. Then, the resultant was dried over magnesium sulfate and evaporated in vacuo. The residue was triturated with diisopropyl ether to give 2-(1-acetyl-4-piperidinylamino)-5-nitro-N-(1,3-benzodioxol-5-ylmethyl)benzamide as yellow powders (81.1 mg).

NMR (DMSO-d$_6$, δ): 1.27 (1H, br), 1.46 (1H, br), 1.95 (2H, br), 2.01 (3H, s), 2.90 (1H, br), 3.23 (1H, br), 3.75 (1H, br), 3.82 (1H, br), 4.17 (1H, br), 4.34 (2H, d, J=7 Hz), 5.98 (2H, s), 6.81–6.90 (3H, m), 6.98 (1H, d, J=8 Hz), 8.12 (1H, dd, J=4, 8 Hz), 8.61 (1H, d, J=4 Hz), 9.14 (1H, d, J=8 Hz), 9.35 (1H, br); Mass m/z: 439(M$^+$).

EXAMPLE 24(4)

To a mixture of 5-nitro-2-(4-piperidinylamino)-N-(1,3-benzodioxol-5-ylmethyl)benzamide (80.0 mg) and 37% formaldehyde solution (192 mg) in methanol (4 mL) were added sodium cyanoborohydride (37.9 mg) and acetic acid (4 drops). After stirring for 2 hours at ambient temperature, the mixture was partitioned between an aqueous saturated sodium bicarbonate solution and chloroform. The organic layer was separated and washed with water and brine. Then, the resultant was dried over magnesium sulfate and evaporated in vacuo. The residue was triturated with diisopropyl ether to give 2-(1-methyl-4-piperidinylamino)-5-nitro-N-(1,3-benzodioxol-5-ylmethyl)benzamide as yellow powders (65.0 mg).

NMR (CDCl$_3$, δ): 1.53–1.80 (2H, br), 2.04 (2H, br), 2.19 (2H, br), 2.32 (3H, s), 2.75 (2H, br), 3.48 (1H, br), 4.48 (2H, br), 5.97 (2H, s), 6.41 (1H, br), 6.63 (1H, br), 6.80 (3H, br), 8.13 (1H, br), 8.29 (1H, br), 8.93 (1H, br); Mass m/z: 413(M$^+$).

EXAMPLE 24(5)

2-(1-Formyl-4-piperidinylamino)-5-nitro-N-(1,3-benzodioxol-5-ylmethyl)benzamide (70.0 mg) was obtained from 5-nitro-2-(4-piperidinylamino)-N-(1,3-benzodioxol-5-ylmethyl)benzamide (80.0 mg) and formic acid (10.4 mg) in a manner similar to Example 24(3).

NMR (DMSO-d$_6$, δ): 1.20–1.48 (2H, br), 1.90–2.08 (2H, br), 2.85–2.97 (1H, br), 3.16–3.30 (1H, br), 3.60–3.73 (1H, br), 3.80–3.95 (1H, br), 3.98–4.10 (1H, br), 4.34 (2H, d, J=7 Hz), 5.98 (2H, s), 6.75–6.93 (3H, m), 7.00 (1H, d, J=8 Hz), 7.99 (1H, s), 8.13 (1H, dd, J=4, 8 Hz), 8.62 (1H, d, J=4 Hz), 9.17 (1H, d, J=8 Hz), 9.35 (1H, br); Mass m/z: 425(M$^+$).

EXAMPLE 25

2-[1-(Hydroxymethyl)cyclopentylamino]-5-nitro-N-(1,3-benzodioxol-5-ylmethyl)benzamide (130 mg) was obtained from 2-fluoro-5-nitro-N-(1,3-benzodioxol-5-ylmethyl)benzamide (150 mg) and 1-aminocyclopentanemethanol (81.4 mg) in a manner similar to Example 1(1).

NMR (CDCl$_3$, δ): 1.66–1.86 (5H, m), 1.96 (4H, m), 3.76 (2H, d, J=7 Hz), 4.49 (2H, d, J=7 Hz), 5.97 (2H, s), 6.53 (1H, br), 6.76–6.85 (4H, m), 8.07 (1H, dd, J=4, 8 Hz), 8.29 (1H, d, J=4 Hz), 9.06 (1H, br); Mass m/z: 412(M$^+$).

EXAMPLE 26

(S)-2-[1-(Hydroxymethyl)-2-methylpropylamino]-5-nitro-N-(1,3-benzodioxol-5-ylmethyl)benzamide (127 mg) was obtained from 2-fluoro-5-nitro-N-(1,3-benzodioxol-5-ylmethyl)benzamide (150 mg) and (S)-2-amino-3-methyl-1-butanol (72.9 mg) in a manner similar to Example 1(1).

NMR (CDCl$_3$, δ): 1.03 (6H, t, J=7 Hz), 1.75 (1H, m), 2.02 (1H, m), 3.55 (1H, br), 3.69 (1H, m), 3.83 (1H, m), 4.50 (2H, m), 5.97 (2H, s), 6.57 (1H, br), 6.77–6.85 (4H, m), 8.09 (1H, dd, J=4, 8 Hz), 8.29 (1H, d, J=4 Hz), 8.98 (1H, br); Mass m/z: 400(M$^+$).

EXAMPLE 27

2-[1-(1-Hydroxymethyl)pentylamino]-5-nitro-N-(1,3-benzodioxol-5-ylmethyl)benzamide (203 mg) was prepared from 2-fluoro-5-nitro-N-(1,3-benzodioxol-5-ylmethyl)benzamide (200 mg) and 2-amino-1-hexanol (221 mg) in a similar manner to that of Example 1(1) as yellow crystals. mp 112–115° C.

NMR (DMSO-d$_6$, δ); 0.85 (3H, t, J=8 Hz), 1.20–1.40 (4H, m), 1.45 (1H, m), 1.65 (1H, m), 3.48 (2H, t, J=6 Hz), 3.63 (1H, m), 4.27–4.44 (2H, m), 4.92 (1H, t, J=6 Hz), 5.99 (2H, s), 6.81 (1H, d, J=8 Hz), 6.86–6.91 (3H, m), 8.10 (1H, dd, J=2, 10 Hz), 8.58 (1H, d, J=2 Hz), 9.13 (1H, d, J=8 Hz), 9.30 (1H, t, J=5 Hz).

PREPARATION 28

2-(Cyclopropylamino)-5-nitrobenzoic acid (238 mg) was obtained from 2-fluoro-5-nitrobenzoic acid (275 mg) and cyclopropylamine (255 mg) in a manner similar to Example 1(1).

NMR (DMSO-d$_6$, δ): 0.61 (2H, m), 0.90 (2H, m), 2.69 (1H, m), 7.22 (1H, d, J=9 Hz), 8.26 (1H, dd, J=2, 9 Hz), 8.65 (1H, d, J=2 Hz), 8.79 (1H, br).

EXAMPLE 28

N-Benzyl-2-(cyclopropylamino)-5-nitrobenzamide (151 mg) was obtained from 2-(cyclopropylamino)-5-nitrobenzoic acid (115 mg) and benzylamine (0.073 mL) in a manner similar to Preparation 1.

NMR (DMSO-d$_6$, δ): 0.54 (2H, m), 0.87 (2H, m), 2.62 (1H, m), 4.46 (1H, d, J=6 Hz), 7.18 (1H, d, J=9 Hz), 7.22–7.40 (5H, m), 8.22 (1H, m), 8.64 (1H, d, J=2 Hz), 9.06 (1H, br), 9.44 (1H, t, J=6 Hz); Mass m/z: 310 (M$^+$−1).

PREPARATION 29

2-(2-Hydroxycyclohexylamino)-5-nitrobenzoic acid (291 mg) was obtained from 2-fluoro-5-nitrobenzoic acid (235 mg) and 2-aminocyclohexanol (292 mg) in a manner similar to Example 1(1).

NMR (DMSO-d$_6$, δ): 1.15–1.45 (6H, m), 1.58–1.72 (2H, m), 1.88–2.08 (2H, m), 3.25–3.35 (3H, m), 4.95 (1H, m), 7.02 (1H, d, J=9 Hz) , 8.11 (1H, dd, J=2, 9 Hz), 8.64 (1H, d, J=2 Hz), 8.98 (1H, d, J=6 Hz).

EXAMPLE 29

N-Benzyl-2-(2-hydroxycyclohexylamino)-5-nitrobenzamide (107 mg) was obtained from 2-(2-hydroxycyclohexylamino)-5-nitrobenzoic acid (134 mg) and benzylamine (0.068 mL) in a manner similar to Preparation 1.

NMR (DMSO-d$_6$, δ): 1.38–1.42 (4H, m), 1.55–1.7 (2H, m), 1.8–2.1 (2H, m), 3.3–3.4 (2H, m), 4.43 (2H, d, J=6 Hz), 4.92 (1H, d, J=6 Hz), 6.96 (1H, d, J=9 Hz), 7.2–7.38 (5H, m), 8.09 (1H, dd, J=2, 9 Hz), 8.62 (1H, d, J=2 Hz), 9.28 (1H, d, J=6 Hz), 9.39 (1H, t, J=6 Hz); Mass m/z: 368 (M$^+$−1).

PREPARATION 30(1)

To a solution of ethyl 2-amino-5-nitrobenzoate (5.00 g), cyclopentanone (9.00 g) and sodium borohydride (4.05 g) in anhydrous tetrahydrofuran (100 mL) was added sulfuric acid (6 mL) under ice-water cooling. The mixture was stirred for 9 hours at 0° C. and then for 15 hours at ambient temperature. The mixture was neutralized with an aqueous saturated sodium bicarbonate solution and extracted with ethyl acetate. The extract was washed with water and brine, dried over magnesium sulfate and evaporated in vacuo. The residue was purified by a silica gel column chromatography eluting with a mixture of hexane and ethyl acetate (5:1). The obtained product was triturated with hexane to give ethyl 2-cyclopentylamino-5-nitrobenzoate as yellow powders (5.94 g).

NMR (CDCl$_3$, δ): 1.41 (3H, t, J=7 Hz), 1.58–1.90 (6H, m), 2.10 (2H, m), 3.96 (1H, m), 4.36 (2H, q, J=7 Hz), 6.70 (1H, d, J=8 Hz), 8.18 (1H, dd, J=4, 8 Hz), 8.67 (1H, br), 8.87 (1H, d, J=4 Hz); Mass m/z: 279 (M$^+$).

PREPARATION 30(2)

2-Cyclopentylamino-5-nitrobenzoic acid (5.16 g) was obtained as yellow powders from ethyl 2-cylcopentylamino-5-nitrobenzoate (5.94 g) in a manner similar to Example 23(2).

NMR (DMSO-d$_6$, δ): 1.47 (2H, m), 1.58–1.78 (4H, br), 2.10 (2H br) 4.05 (1H, m) 6.93 (1H, d, J=8 Hz), 8.18 (1H, dd, J=4, 8 Hz), 8.65 (1H, d, J=4 Hz), 8.83 (1H, br); Mass m/z: 249 (M$^+$).

EXAMPLE 30

To a mixture of 2-cyclopentylamino-5-nitrobenzoic acid (1.00 g), 1-[3-(dimethylamino)propyl]-3-ethylcarbodiimide hydrochloride (1.15 g), 1-hydroxybenzotriazole (810 mg) in anhydrous dimethylformamide (10 mL) was added (1,3- benzodioxol-5-ylmethyl)amine (725 mg), and the mixture was stirred for 15 hours at ambient temperature. The mixture was partitioned between ethyl acetate and water. The organic layer was separated and washed with an aqueous saturated sodium bicarbonate solution, water and brine. Then, the resultant was dried over magnesium sulfate and evaporated in vacuo. The residue was purified by a silica gel column chromatography eluting with a mixture of chloroform and methanol (50:1). The obtained product was triturated with diisopropyl ether and recrystallized from a mixture of hexane and ethyl acetate to give 2-cyclopentylamino-5-nitro-N-(1,3-benzodioxol-5-ylmethyl)benzamide as yellow powders (1.51 g).

NMR (CDCl$_3$, δ): 1.58–1.86 (6H, m), 2.08 (2H, m), 3.90 (1H, m), 4.50 (2H, d, J=7 Hz), 5.98 (2H, s), 6.46 (1H, br), 6.68 (1H, d, J=8 Hz), 6.83 (3H, m), 8.15 (1H, dd, J=4, 8 Hz), 8.29 (1H, d, J=4 Hz), 8.86(1H, br); Mass m/z: 382(M$^+$).

EXAMPLE 31

2-(Cyclopentylamino)-N-(4-fluorobenzyl)-5-nitrobenzamide (138 mg) was obtained as yellow powders from 2-(cyclopentylamino)-5-nitrobenzoic acid (100 mg) and 4-fluorobenzylamine (60.0 mg) in a manner similar to Example 30.

NMR (CDCl$_3$, δ): 1.59–1.85 (6H, m), 2.00–2.15 (2H, m), 3.89 (1H, m), 4.58 (2H, d, J=7 Hz), 6.54 (1H, br), 6.68 (1H, d, J=8 Hz), 7.06 (2H, m), 7.33 (2H, m), 8.15 (1H, dd, J=4, 8 Hz), 8.30 (1H, d, J=4 Hz), 8.85 (1H, br); Mass m/z: 356 (M$^+$).

EXAMPLE 32

2-(Cyclopentylamino)-N-(4-methylbenzyl)-5-nitrobenzamide (130 mg) was obtained as yellow powders from 2-(cyclopentylamino)-5-nitrobenzoic acid (100 mg) and 4-methylbenzylamine (58.1 mg) in a manner similar to Example 30.

NMR (CDCl$_3$, δ); 1.59–1.85 (6H, m), 2.03–2.15 (2H, m), 2.37 (3H, s), 3.90 (1H, m), 4.55 (2H, d, J=7 Hz), 6.45 (1H, br), 6.67 (1H, d, J=8 Hz), 7.18 (2H, d, J=8 Hz), 7.25 (2H, d, J=8 Hz), 8.13 (1H, dd, J=4,8 Hz), 8.27 (1H, d, J=4 Hz), 8.87 (1H, br); Mass m/z: 352(M$^+$).

EXAMPLE 33

2-(Cyclopentylamino)-N-(4-methoxybenzyl)-5-nitrobenzamide (138 mg) was obtained as yellow powders from 2-(cyclopentylamino)-5-nitrobenzoic acid (100 mg) and 4-methoxybenzylamine (65.8 mg) in a manner similar to Example 30.

NMR (CDCl$_3$, δ); 1.59–1.85 (6H, m), 2.00–2.15 (2H, m), 3.82 (3H, s), 3.90 (1H, m), 4.52 (2H, d, J=7 Hz), 6.41 (1H, br), 6.67 (1H, d, J=8 Hz), 6.90 (2H, d, J=8 Hz), 7.28 (2H, d, J=8 Hz), 8.12 (1H, dd, J=4,8 Hz), 8.27 (1H, d, J=4 Hz), 8.88 (1H, br); Mass m/z: 368(M$^+$).

EXAMPLE 34

2-(Cyclopentylamino)-5-nitro-N-[4-(trifluoromethyl)benzyl]benzamide (155 mg) was obtained as yellow powders from 2-(cyclopentylamino)-5-nitrobenzoic acid (100 mg) and 4-(trifluoromethyl)benzylamine (84.0 mg) in a manner similar to Example 30.

NMR (CDCl$_3$, δ): 1.59–1.85 (6H, m), 2.02–2.14 (2H, m), 3.92 (1H, m), 4.65 (2H, d, J,=7 Hz), 6.68 (1H, d, J=8 Hz), 6.69 (1H, br), 7.47 (2H, d, J=8 Hz), 7.63 (2H, d, J=8 Hz), 8.16 (1H, dd, J=4,8 Hz), 8.37 (1H, d, J=4 Hz), 8.85 (1H, br); Mass m/z: 406(M$^+$).

EXAMPLE 35

2-(Cyclopentylamino)-5-nitro-N-(4-nitrobenzyl)benzamide (132 mg) was obtained as yellow powders from 2-(cyclopentylamino)-5-nitrobenzoic acid (100 mg) and 4-nitrobenzylamine (90.4 mg) in a manner similar to Example 30.

NMR (CDCl$_3$, δ): 1.59–1.85 (6H, m), 2.03–2.15 (2H, m), 3.90 (1H, m), 4.72 (2H, d, J=7 Hz), 6.69 (1H, d, J=8 Hz), 6.90 (1H, br), 7.52 (2H, d, J=8 Hz), 8.16 (1H, dd, J=4, 8 Hz), 8.23 (2H, d, J=8 Hz), 8.42 (1H, d, J=4 Hz), 8.87 (1H, br); Mass m/z: 385 (M$^+$).

EXAMPLE 36

2-(Cyclopentylamino)-N-[4-(dimethylamino)benzyl]-5-nitrobenzamide (121 mg) was obtained as yellow powders from 2-(cyclopentylamino)-5-nitrobenzoic acid (100 mg) and 4-(dimethylamino)benzylamine hydrochloride (107 mg) in a manner similar to Preparation 1.

NMR (CDCl$_3$, δ): 1.59–1.85 (6H, m), 2.03–2.15 (2H, m), 2.96 (6H, s), 3.91 (1H, m), 4.47 (2H, d, J=7 Hz), 6.32 (1H, br), 6.66 (1H, d, J=8 Hz), 6.73 (2H, d, J=8 Hz), 7.23 (2H, d, J=8 Hz), 8.13 (1H, dd, J=4, 8 Hz), 8.27 (1H, d, J=4 Hz), 8.87 (1H, br); Mass m/z: 383(M$^+$).

EXAMPLE 37

N-(4-Sulfamoylbenzyl)-2-(cyclopentylamino)-5-nitrobenzamide (162 mg) was obtained as yellow powders from 2-(cyclopentylamino)-5-nitrobenzoic acid (100 mg) and 4-sulfamoylbenzylamine hydrochloride (107 mg) in a manner similar to Preparation 1.

NMR (DMSO-d$_6$, δ): 1.38–1.52 (2H, m), 1.56–1.74 (4H, m), 1.96–2.10 (2H, m), 3.96 (1H, m), 4.50 (2H, d, J=7 Hz), 6.86 (1H, d, J=8 Hz), 7.33 (2H, s), 7.50 (2H, d, J=8 Hz), 7.78 (2H, d, J=8 Hz), 8.15 (1H, d, J=8 Hz), 8.67 (1H, d, J=4 Hz), 9.16 (1H, d, J=8 Hz), 9.50 (1H, br); Mass m/z: 417(M$^+$).

EXAMPLE 38

N-(4-Bromobenzyl)-2-(cyclopentylamino)-5-nitrobenzamide (160 mg) was obtained as yellow powders from 2-(cyclopentylamino)-5-nitrobenzoic acid (100 mg) and 4-bromobenzylamine (107 mg) in a manner similar to Preparation 1.

NMR (CDCl$_3$, δ): 1.59–1.85 (6H, m), 2.03–2.15 (2H, m), 3.92 (1H, m), 4.56 (2H, d, J=7 Hz), 6.61 (1H, br), 6.68 (1H, d, J=8 Hz), 7.23 (2H, d, J=8 Hz), 7.48 (2H, d, J=8 Hz), 8.15 (1H, dd, J=4, 8 Hz), 8.32 (1H, d, J=4 Hz), 8.86 (1H, br); Mass m/z: 418(M$^+$).

EXAMPLE 39

2-(Cyclopentylamino)-N-furfuryl-5-nitrobenzamide (120 mg) was obtained as yellow powders from 2-(cyclopentylamino)-5-nitrobenzoic acid (100 mg) and furfurylamine (46.6 mg) in a manner similar to Preparation 1.

NMR (CDCl$_3$, δ): 1.58–1.90 (6H, br), 2.03–2.18 (2H, br), 3.91 (1H, m), 4.61 (2H, d, J=7 Hz), 6.33 (2H, m), 6.51 (1H, br), 6.69 (1H, d, J=8 Hz), 7.40 (1H, s), 8.12 (1H, dd, J=4, 8 Hz), 8.32 (1H, d, J=4 Hz), 8.82 (1H, br); Mass m/z: 328(M$^+$).

EXAMPLE 40

2-(Cyclopentylamino)-5-nitro-N-(2-thienylmethyl)benzamide (130 mg) was obtained as yellow powders from 2-cyclopentylamino-5-nitrobenzoic acid (100 mg) and 2-thiophenemethylamine (54.3 mg) in a manner similar to Preparation 1.

NMR (CDCl₃, δ): 1.59–1.85 (6H, m), 2.01–2.17 (2H, m), 3.90 (1H, m), 4.77 (2H, d, J=7 Hz), 6.55 (1H, br), 6.68 (1H, d, J=8 Hz), 6.98 (1H, m), 7.05 (1H, br), 7.28 (1H, m), 8.15 (1H, dd, J=4, 8 Hz), 8.30 (1H, d, J=4 Hz), 8.81 (1H, br); Mass m/z: 344(M⁺).

EXAMPLE 41

2-(Cyclopentylamino)-5-nitro-N-phenethylbenzamide (141 mg) was obtained as yellow powders from 2-(cyclopentylamino)-5-nitrobenzoic acid (100 mg) and phenethylamine (58.1 mg) in a manner similar to Preparation 1.

NMR (CDCl₃, δ): 1.59–1.85 (6H, m), 2.00–2.15 (2H, m), 2.94 (2H, t, J=7 Hz), 3.68 (2H, m), 3.89 (1H, m), 6.24 (1H, br), 6.65 (1H, d, J=8 Hz), 7.28 (3H, m), 7.35 (2H, m), 8.13 (1H, dd, J=4, 8 Hz), 8.19 (1H, d, J=4 Hz), 8.75 (1H, br); Mass m/z: 352(M⁺).

EXAMPLE 42

2-(Cyclopentylamino)-5-nitro-N-(3-phenylpropyl) benzamide (120 mg) was obtained as yellow powders from 2-(cyclopentylamino)-5-nitrobenzoic acid (100 mg) and 3-phenylpropylamine (64.8 mg) in a manner similar to Preparation 1.

NMR (CDCl₃, δ): 1.59–1.85 (6H, m), 1.94–2.15 (4H, m), 2.74 (2H, t, J=7 Hz), 3.47 (2H, m), 3.89 (1H, m), 6.13 (1H, br), 6.68 (1H, d, J=8 Hz), 7.17–7.33 (5H, m), 8.13 (2H, m), 8.83 (1H, br); Mass m/z: 366(M⁺).

EXAMPLE 43

N-[(2-Benzimidazolyl)methyl]-2-(cyclopentylamino)-5-nitrobenzamide (132 mg) was obtained as yellow powders from 2-(cyclopentylamino)-5-nitrobenzoic acid (100 mg) and 2-(aminomethyl)benzimidazole dihydrochloride hydrate (106 mg) in a manner similar to Preparation 1.

NMR (DMSO-d₆, δ): 1.40–1.54 (2H, br), 1.54–1.75 (4H, br), 1.95–2.13 (2H, br), 3.96 (1H, br), 4.66 (2H, d, J=7 Hz), 6.89 (1H, d, J=8 Hz), 7.14 (2H, br), 7.45 (1H, br), 7.53 (1H, br), 8.14 (1H, dd, J=4, 8 Hz), 8.73 (1H, d, J=4 Hz), 9.14 (1H, br), 9.53 (1H, br), 12.32 (1H, br); Mass m/z: 378(M⁺).

EXAMPLE 44

2-(Cyclopentylamino)-N-(4-hydroxy-3-methoxybenzyl)-5-nitrobenzamide (143 mg) was obtained as yellow powders from 2-(cyclopentylamino)-5-nitrobenzoic acid (100 mg) and 4-hydroxy-3-methoxybenzylamine hydrochloride (90.9 mg) in a manner similar to Preparation 1.

NMR (DMSO-d₆, δ): 1.39–1.53 (2H, m), 1.55–1.75 (4H, m), 1.98–2.10 (2H, m), 3.76 (3H, s), 3.96 (1H, m), 4.35 (2H, d, J=7 Hz), 6.72 (2H, s), 6.85 (2H, m), 8.13 (1H, dd, J=4,8 Hz), 8.59 (1H, d, J=4 Hz), 8.88 (1H, s), 9.12 (1H, d, J=8 Hz), 9.28 (1H, br); Mass m/z: 384(M⁺).

EXAMPLE 45

2-(Cyclopentylamino)-N-(3,4-dihydroxybenzyl)-5-nitrobenzamide (109 mg) was obtained as yellow powders from 2-(cyclopentylamino)-5-nitrobenzoic acid (100 mg) and 3,4-dihydroxybenzylamine hydrobromide (106 mg) in a manner similar to Preparation 1.

NMR (DMSO-d₆, δ): 1.38–1.52 (2H, m), 1.54–1.75 (4H, m), 1.97–2.10 (2H, m), 3.98 (1H, m), 4.28 (2H, br), 6.57 (1H, m), 6.68 (2H, m), 6.87 (1H, d, J=8 Hz), 8.12 (1H, dd, J=4, 8 Hz), 8.59 (1H, d, J=4 Hz), 8.80 (2H, br), 9.20 (1H, d, J=8 Hz), 9.27 (1H, br).

EXAMPLE 46

2-(Cyclopentylamino)-N-(3,4-difluorobenzyl)-5-nitrobenzamide (130 mg) was obtained as yellow powders from 2-(cyclopentylamino)-5-nitrobenzoic acid (100 mg) and 3,4-difluorobenzylamine (68.6 mg) in a manner similar to Preparation 1.

NMR (CDCl₃, δ): 1.58–1.87 (6H, m), 2.03–2.14 (2H, m), 3.90 (1H, m), 4.55 (2H, d, J=7 Hz), 6.68 (1H, br), 6.69 (1H, d, J=8 Hz), 7.04–7.22 (3H, m), 8.16 (1H, dd, J=4, 8 Hz), 8.37 (1H, d, J=4 Hz), 8.88 (1H, br); Mass m/z: 374 (M⁺).

PREPARATION 47(1)

Ethyl 5-nitro-2-(tetrahydro-2H-thiopyran-4-ylamino) benzoate (315 mg) was obtained as yellow powders from ethyl 2-amino-5-nitrobenzoate (300 mg) and tetrahydro-2H-thiopyran-4-one (746 mg) in a manner similar to Preparation 30(1).

NMR (CDCl₃, δ): 1.44 (3H, t, J=7 Hz), 1.75–1.89 (2H, m), 2.28–2.38 (2H, m), 2.70–2.84 (4H, m), 3.49–3.61 (1H, m), 4.38 (2H, q, J=7 Hz), 6.66 (1H, d, J=8 Hz), 8.19 (1H, dd, J=4, 8 Hz), 8.78 (1H, br), 8.87 (1H, d, J=4 Hz); Mass m/z: 309(M⁺).

PREPARATION 47(2)

5-Nitro-2-(tetrahydro-2H-thiopyran-4-ylamino)benzoic acid (280 mg) was obtained as yellow powders from ethyl 5-nitro-2-(tetrahydro-2H-thiopyran-4-ylamino)benzoate (310 mg) in a manner similar to Preparation 30(2).

NMR (DMSO-d₆, δ): 1.55–1.70 (2H, m), 2.17–2.28 (2H, br), 2.62–2.85 (4H, m), 3.66–3.82 (1H, br), 6.98 (1H, d, J=8 Hz), 8.17 (1H, dd, J=4, 8 Hz), 8.66 (1H, d, J=4 Hz), 8.85 (1H, d, J=8 Hz); Mass m/z: 281(M⁺).

EXAMPLE 47(1)

5-Nitro-N-(1,3-benzodioxol-5-ylmethyl)-2-(tetrahydro-2H-thiopyran-4-ylamino)benzamide (170 mg) was obtained as yellow powders from 5-nitro-2-(tetrahydro-2H-thiopyran-4-ylamino)benzoic acid (150 mg) and (1,3-benzodioxol-5-ylmethyl)amine (96.4 mg) in a manner similar to Preparation 1.

NMR (CDCl₃, δ): 1.75–1.90 (2H, m), 2.27–2.36 (2H, m), 2.70–2.82 (4H, m), 3.51 (1H, m), 4.50 (2H, d, J=7 Hz), 5.97 (2H, s), 6.47 (1H, br), 6.64 (1H, d, J=8 Hz), 6.78–6.85 (3H, m), 8.15 (1H, dd, J=4, 8 Hz), 8.31 (1H, d, J=4 Hz), 9.02 (1H, br); Mass m/z: 414(M⁺).

EXAMPLE 47(2)

To a solution of 5-nitro-N-(1,3-benzodioxol-5-ylmethyl)-2-(tetrahydro-2H-thiopyran-4-ylamino)benzamide (50.0 mg) in anhydrous dichloromethane (1 mL) was added m-chloroperbenzoic acid (41.5 mg), and the mixture was stirred for 4 hours at ambient temperature. To the mixture were added an aqueous saturated sodium thiosulfate solution and an aqueous sodium bicarbonate solution. The resulting precipitates were collected by filtration and washed with water, methanol and ethyl acetate to give 2-(1,1-dioxotetrahydro-2H-thiopyran-4-ylamino)-5-nitro-N-(1,3-benzodioxol-5-ylmethyl)benzamide as yellow powders (40.0 mg).

NMR (CDCl₃, δ): 1.88–2.10 (2H, br), 2.20–2.33 (2H, br), 3.04–3.19 (2H, br), 3.29–3.43 (2H, br), 3.98 (1H, br), 4.37 (2H, d, J=7 Hz), 5.98 (2H, s), 6.79–6.98 (4H, m), 8.17 (1H, m), 8.63 (1H, m), 9.18 (1H, br), 9.37 (1H, br); Mass m/z: 4–46(M⁺).

PREPARATION 48(1)

Methyl 5-cyano-2-(cyclopentylamino)benzoate (2.31 g) was obtained as yellow powders from methyl 5-cyano-2-aminobenzoate (2.00 g) and cyclopentanone (3.01 mL) in a manner similar to Preparation 30(1).

NMR (CDCl$_3$, δ); 1.53–1.86 (6H, br), 2.00–2.14 (2H, br), 3.87 (3H, s), 3.90 (1H, br), 6.71 (1H, d, J=8 Hz), 7.49 (1H, dd, J=4, 8 Hz), 8.19 (1H, d, J=4 Hz), 8.34 (1H, br).

PREPARATION 48(2)

A mixture of methyl 5-cyano-2-(cyclopentylamino) benzoate (2.30 g), methanol (100 mL) and 1N-sodium hydroxide solution (20 mL) was heated for 2 hours under reflux. The reaction mixture was acidified with 1N-hydrochloric acid to pH 4 and the organic solvent was removed by evaporation. The aqueous layer was diluted with water and extracted with ethyl acetate. The organic layer was washed with water and brine and dried over magnesium sulfate. Then, the resultant was evaporated in vacuo to give 5-cyano-2-(cyclopentylamino)benzoic acid (2.15 g) as pale yellow powders.

NMR (DMSO-$_6$, δ): 1.43 (2H, m), 1.64 (4H, m), 2.03 (2H, m), 3.96 (1H, m), 6.89 (1H, d, J=8 Hz), 7.68 (1H, dd, J=4, 8 Hz), 8.09 (H, d, J=4 Hz), 8.51 (1H, d, J=8 Hz); Mass m/z; 229(M$^+$).

PREPARATION 48(3)

To a solution of 5-cyano-2-(cyclopentylamino)benzoic acid (40.0 mg) in anhydrous tetrahydrofuran (2 mL) was added 1.5 M diisobutylaluminium hydride hexane solution (0.34 mL) under dry ice-acetone cooling, and the mixture was stirred for an hour at −78° C. and then for 4 hours at ambient temperature. The reaction was quenched by addition of methanol and an aqueous saturated ammonium chloride solution. After stirring at ambient temperature for a half hour, the mixture was partitioned with 5% sulfuric acid and chloroform. The separated organic layer was washed with brine, dried over magnesium sulfate and evaporated in vacuo. The residue was purified by a preparative silica gel chromatography with 10% methanol in chloroform to give 2-(cyclopentylamino)-5-formylbenzoic acid (25.0 mg) as pale orange powders.

NMR (CDCl$_3$, δ): 1.55–1.88 (6H, m), 2.06–2.18 (2H, m), 3.97 (1H, m), 6.81 (1H, d, J=8 Hz), 7.92 (1H, dd, J=4, 8 Hz), 8.41 (1H, br), 8.48 (1H, d, J=4 Hz), 9.73 (1H, s).

EXAMPLE 48

2-(Cyclopentylamino)-5-formyl-N-(1,3-benzodioxol-5-ylmethyl)benzamide (489 mg) was obtained as yellow powders from 2-(cyclopentylamino)-5-formylbenzoic acid (1.00 g) and (1,3-benzodioxol-5-ylmethyl)amine (778 mg) in a manner similar to Example 30.

NMR (CDCl$_3$, δ): 1.55–1.87 (6H, br), 2.02–2.15 (2H, br), 3.88 (1H, br), 4.48 (2H, d, J=7 Hz), 5.95 (2H, s), 6.44 (1H, br), 6.75 (1H, d, J=8 Hz), 6.77–6.84 (3H, m), 7.74 (1H, d, J=8 Hz), 7.87 (1H, s), 8.70 (1H, br), 9.67 (1H, s); Mass m/z: 367(M$^+$).

PREPARATION 49

5-Cyano-2-fluoro-N-(1,3-benzodioxol-5-ylmethyl) benzamide (534 mg) was obtained from 5-cyano-2-fluorobenzoic acid (300 mg) and (1,3-benzodioxol-5-ylmethyl)amine (0.26 mL) in a manner similar to Preparation 1.

NMR (DMSO-d$_6$, δ): 4.37 (2H, d, J=6 Hz), 6.00 (2H, s), 6.80–6.93 (3H, m), 7.56 (1H, t, J=9 Hz), 8.04 (1H, m), 8.13 (1H, dd, J=2,6 Hz), 9.03 (1H, t, J=6 Hz); Mass m/z: 297 (M$^+$−1).

EXAMPLE 49(1)

(R)-5-Cyano-2-(2-hydroxy-1-methylethylamino)-N-(1,3-benzodioxol-5-ylmethyl)benzamide (145 mg) was obtained from 5-cyano-2-fluoro-N-(1,3-benzodioxol-5-ylmethyl) benzamide (150 mg) and (R)-2-amino-1-propanol (0.12 mL) in a manner similar to Example 1(1).

NMR (DMSO-d$_6$, δ): 1.13 (3H, d, J=7 Hz), 3.42 (2H, t, J=5 Hz), 3.67 (1H, m), 4.32 (2H, d, J=6 Hz), 4.92 (1H, t, J=5 Hz), 5.98 (2H, s), 6.77–6.92 (4H, m), 7.60 (1H, dd, J=2, 9 Hz), 8.04 (1H, d, J=2 Hz), 8.73 (1H, d, J=8 Hz), 8.99 (1H, t, J=6 Hz); Mass m/z: 352 (M$^+$−1).

EXAMPLE 49(2)

To a solution of (R)-5-cyano-2-(2-hydroxy-1-methylethylamino)-N-(1,3-benzodioxol-5-ylmethyl) benzamide (76 mg) in ethanol (6 mL) was added 1N-sodium hydroxide (0.65 mL), and the mixture was heated for 6 hours under reflux. The solvent was evaporated in vacuo. The residue was diluted with ethyl acetate and washed successively with water and brine. The organic layer was dried over sodium sulfate and evaporated in vacuo. The residue was subjected to a silica gel column chromatography eluting with a mixture of chloroform and methanol (9:1) to give (R)-5-carbamoyl-2-(2-hydroxy-1-methylethylamino)-N-(1, 3-benzodioxol-5-ylmethyl)benzamide (27 mg) as a solid substance.

NMR (DMSO-d$_6$, δ): 1.13 (3H, d, J=7 Hz), 3.3–3.5 (2H, m), 3.62 (1H, m), 4.33 (2H, d, J=5 Hz), 4.86 (1H, t, J=5 Hz), 5.98 (2H, s), 6.73 (1H, d, J=9 Hz), 6.77–6.90 (3H, m), 7.04 (1H, br), 7.58 (1H, br), 7.77 (1H, dd, J=2, 9 Hz), 8.14 (1H, d, J=2 Hz), 8.30 (1H, d, J=8 Hz), 8.83 (1H, t, J=5 Hz); Mass m/z: 370 (M$^+$−1).

EXAMPLE 50(1)

5-Cyano-2-(trans-4-hydroxycyclohexylamino)-N-(1,3-benzodioxol-5-ylmethyl)benzamide (142 mg) was obtained from 5-cyano-2-fluoro-N-(1,3-benzodioxol-5-ylmethyl) benzamide (120 mg) and trans-4-aminocyclohexanol (139 mg) in a manner similar to Example 1(1).

NMR (DMSO-d$_6$, δ): 1.15–1.40 (4H, m), 1.75–1.86 (2H, m), 1.89–2.00 (2H, m), 3.35–3.53 (2H, m), 4.31 (2H, d, J=6 Hz), 4.60 (1H, d, J=4 Hz), 5.98 (2H, s), 6.79 (1H, dd, J=2, 8 Hz), 6.83–6.92 (3H, m), 7.59 (1H, dd, J=2, 9 Hz), 8.05 (1H, d, J=2 Hz), 8.65 (1H, d, J=7 Hz), 9.01 (1H, t, J=6 Hz); Mass m/z: 392 (M$^+$−1).

EXAMPLES 50(2)

5-Carbamoyl-2-(trans-4-hydroxycyclohexylamino)-N-(1, 3-benzodioxol-5-ylmethyl)benzamide (51 mg) was obtained from 5-cyano-2-(trans-4-hydroxycyclohexylamino)-N-(1,3-benzodioxol-5-ylmethyl)benzamide (71 mg) in a manner similar to Example 49(2).

NMR (DMSO-d$_6$, δ): 1.13–1.40 (4H, m), 1.75–1.87 (2H, m), 1.89–2.00 (2H, m), 3.3–3.53 (2H, m), 4.33 (2H, d, J=6 Hz), 4.59 (1H, d, J=4 Hz), 5.98 (2H, s), 6.74 (1H, d, J=9 Hz), 6.77–6.90 (3H, m), 7.04 (1H, br), 7.58 (1H, br), 7.77 (1H, dd, J=2,9 Hz), 8.13 (1H, d, J=2 Hz), 8.24 (1H, d, J=8 Hz), 8.84 (1H, t, J=6 Hz); Mass m/z: 410 (M$^+$−1).

PREPARATION 51

To a solution of 2-fluoro-5-nitrobenzoic acid (235 mg) in pyridine (1.5 mL) was added trans-4-aminocyclohexanol (292 mg), and the mixture was stirred for 3 hours at 80° C. After evaporation of the solvent, the residue was dissolved in water and neutralized with 1N-hydrochloric acid (1.9 mL). The resulting precipitates were collected by filtration and washed successively with water and methanol to give 2-(trans-4-hydroxycyclohexylamino)-5-nitrobenzoic acid (279 mg) as a solid substance.

NMR (DMSO-$d_6$, δ): 1.21–1.46 (4H, m), 1.7–1.90 (2H, m), 1.90–2.08 (2H, m), 3.3–3.65 (2H, m), 4.67 (1H, br), 6.98 (1H, d, J=8 Hz) 8.14 (1H, dd, J=2, 8 Hz), 8.66 (1H, d, J=2 Hz), 8.74 (1H, d, J=7 Hz).

EXAMPLE 51

To a solution of 2-(trans-4-hydroxycyclohexylamino)-5-nitrobenzoic acid (125 mg) in dimethylformamide (2 mL) were added 1-hydroxybenzotriazole (96.4 mg), benzylamine (0.063 mL) and 1-[3-(dimethylamino)propyl]-3-ethylcarbodiimide hydrochloride (137 mg). The mixture was stirred for 3 hours at 20° C. The resulting mixture was diluted with ethyl acetate and washed successively with diluted hydrochloric acid, aqueous sodium bicarbonate and brine. The organic layer was dried over sodium sulfate and evaporated in vacuo. The resulting residue was triturated with methanol to give N-benzyl-2-(trans-4-hydroxycyclohexylamino)-5-nitrobenzamide (150 mg) as a solid substance.

mp: 233–234° C. NMR (DMSO-$d_6$, δ): 1.17–1.46 (4H, m), 1.72–1.87 (2H, m), 1.92–2.04 (2H, m), 3.4–3.6 (2H, m), 4.42 (2H, d, J=7 Hz), 4.62 (1H, d, J=6 Hz), 6.90 (1H, d, J=8 Hz), 7.22–7.39 (5H, m), 8.13 (1H, dd, J=2, 8 Hz), 8.63(1H, d, J=2 Hz), 9.10 (1H, d, J=7 Hz), 9.41 (1H, t, J=6 Hz).

EXAMPLE 52(1)

2-(trans-4-Hydroxycyclohexylamino)-5-nitro-N-(1,3-benzodioxol-5-ylmethyl)benzamide (173 mg) was obtained as a solid substance from 2-(trans-4-hydroxycyclohexylamino)-5-nitrobenzoic acid (125 mg) and (1,3-benzodioxol-5-ylmethyl)amine (0.072 mL) in a manner similar to Preparation 1.

mp: 205–206° C. NMR (DMSO-$d_6$, δ): 1.20–1.45 (4H, m), 1.75–1.87 (2H, m), 1.92–2.02 (2H, m), 3.4–3.6 (2H, m), 4.34 (2H, d, J=7 Hz), 4.62 (1H, d, J=6 Hz), 5.99 (2H, s), 6.77–6.93 (4H, m), 8.11 (1H, dd, J=2, 8 Hz), 8.60 (1H, d, J=2 Hz), 9.08 (1H, d, J=7 Hz), 9.33 (1H, t, J=6 Hz).

EXAMPLE 52(2)

To a solution of 2-(trans-4-hydroxycyclohexylamino)-5-nitro-N-(1,3-benzodioxol-5-ylmethyl)benzamide (100 mg), benzoic acid (32.5 mg) and diethyl azodicarboxylate (46.3 mg) in anhydrous tetrahydrofuran (2 mL) was added triphenylphosphine (69.8 mg). The mixture was stirred for 4 hours at ambient temperature. The mixture was partitioned between an aqueous saturated sodium bicarbonate solution and ethyl acetate. The separated organic layer was washed with water and brine, dried over magnesium sulfate and evaporated in vacuo. The residue was purified by a silica gel column chromatography eluting with a mixture of hexane and ethyl acetate (5:1 to 3:1). The obtained product was triturated with diisopropyl ether to give 2-[cis-4-(benzoyloxy)cyclohexylamino]-5-nitro-N-(1,3-benzodioxol-5-ylmethyl)benzamide as yellow powders (68.5 mg).

NMR (CDCl$_3$, δ): 1.78–2.17 (8H, m), 3.60 (1H, br), 4 52 (2H, d, J=7 Hz), 5.27 (1H, br), 5 96 (2H, s), 6.48 (1H, br), 6.71 (1H, d, J=8 Hz), 6.78–6.87 (3H, m), 7.46 (2H, m), 7.58 (1H, m), 8.07 (2H, d, J=8 Hz), 8.17 (1H, dd, J=4, 8 Hz), 8.33 (1H, d, J=4 Hz), 9.05 (1H, br); Mass m/z: 516 (M$^+$).

EXAMPLE 52(3)

A mixture of 2-(cis4-benzoyloxycyclohexylamino)-5-nitro-N-(1,3-benzodioxol-5-ylmethyl)benzamide (64.0 mg), methanol (5 mL), tetrahydrofuran (5 mL) and 1N-sodium hydroxide solution (1 mL) was stirred for 2 hours at 60° C. After evaporation of the organic solvent, the aqueous layer was diluted with water and extracted with ethyl acetate. The extract was washed with an aqueous saturated sodium bicarbonate solution, water and brine, dried over magnesium sulfate and evaporated in vacuo. The residue was triturated with diisopropyl ether to give 2-(cis-4-hydroxycyclohexylamino)-5-nitro-N-(1,3-benzodioxol-5-ylmethyl)benzamide as yellow powders (50.5 mg).

NMR (CDCl$_3$, δ): 1.70–1.95 (8H, br), 3.58 (1H, br), 3.93 (1H, br), 4.51 (2H, d, J=7 Hz), 5.97 (2H, s), 6.43 (1H, br), 6.67 (1H, d, J=8 Hz), 6.78–6.87 (3H, m), 8.14 (1H, dd, J=4, 8 Hz), 8.30 (1H, d, J=4 Hz), 9.03 (1H, br); Mass m/z: 412 (M$^+$).

EXAMPLE 53

2-(trans-4-Hydroxycyclohexylamino)-5-nitro-N-(2-pyrazinylmethyl)benzamide (129 mg) was obtained as yellow powders from 2-(trans-4-hydroxycyclohexylamino)-5-nitrobenzoic acid (150 mg) and 2-pyrazinylmethylarnine (70.1 mg) in a manner similar to Example 51.

NMR (DMSO-$d_6$, δ): 1.13–1.40 (4H, br), 1.70–1.88 (2H, br), 1.89–2.02 (2H, br), 3.40–3.60 (2H, br), 4.53–4.68 (3H, br), 6.92 (1H, d, J=8 Hz), 8.12 (1H, dd, J=4, 8 Hz), 8.55 (1H, d, J=4 Hz), 8.58–8.70 (2H, m), 8.98 (1H, d, J=8 Hz), 9.50 (1H, br).

EXAMPLE 54

2-(cis4-Hydroxycyclohexylamino)-5-nitro-N-(3,4,5-trimethoxybenzyl)benzamide (106 mg) was obtained as yellow powders from 2-(cis4-hydroxycyclohexylamino)-5-nitrobenzoic acid (80.0 mg) and 3,4,5-trimethoxybenzylamine (67.6 mg) in a manner similar to Example 51.

NMR (DMSO-d6, δ): 1.46–1.75 (8H, br), 3.63 (3H, s), 3.61–3.72 (2H, br), 3.76 (6H, s), 4.39 (2H, d, J=7 Hz), 4.54 (1H, d, J=4 Hz), 6.67 (2H, s), 6.89 (1H, d, J=8 Hz), 8.12 (1H, dd, J=4, 8 Hz), 8.62 (1H, d, J=4 Hz), 9.22 (1H, br), 9.33 (1H, br).

PREPARATION 55

To a suspension of 2-fluoro-5-nitrobenzoic acid (313 mg) in dichloromethane (4 mL) were added thionyl chloride (0.17 mL) and dimethylformamide (0.05 mL), and the mixture was heated for 36 hours under reflux. After evaporation of the solvent, the residue was dissolved in dichloromethane (4 mL). To this solution were added benzylamine (0.19 mL) and triethylamine (0.47 mL), and the mixture was stirred for 30 minutes at 0° C. After evaporation of the solvent, the residue was dissolved in ethyl acetate and washed successively with diluted hydrochloric acid, an aqueous sodium bicarbonate solution and brine. The organic layer was dried over sodium sulfate and evaporated in vacuo. The resulting residue was triturated with diisopropyl ether to give N-benzyl-2-fluoro-5-nitrobenzamide (436 mg) as a solid substance.

NMR (DMSO-$d_6$, δ): 4.50 (2H, d, J=6 Hz), 7.22–7.40 (5H, m), 7.64 (1H, t, J=8 Hz), 8.38–8.47 (2H, m), 9.19(1H, t, J=6 Hz).

EXAMPLE 55

N-Benzyl-2-[2-hydroxy-1-(hydroxymethyl)ethylamino]-5-nitrobenzamide (54.5 mg) was obtained from N-benzyl-2-fluoro-5-nitrobenzamide (100 mg) and 2-amino-1,3-propanediol (59.8 mg) in a manner similar to Example 1(1).

mp: 171–173° C. NMR (DMSO-$d_6$, δ): 3.45–3.5 (5H, m), 4.43 (2H, d, J=7 Hz), 4.91 (2H, t, J=6 Hz), 6.92 (1H, d, J=8 Hz), 7.2–7.4 (5H, m), 8.13 (1H, dd, J=2, 8 Hz), 8.62 (1H, d, J=2 Hz), 9.28 (1H, d, J=7 Hz), 9.36 (1H, t, J=6 Hz).

EXAMPLE 56

N-Benzyl-2-(trans-4-hydroxycyclohexylamino)-5-nitrobenzamide (346 mg) was obtained from N-benzyl-2-fluoro-5-nitrobenzamide (300 mg) and trans-2-aminocyclohexanol (186 mg) in a manner similar to Example 1(1).

mp: 233–234° C. NMR (DMSO-$d_6$, δ): 1.17–1.46 (4H, m), 1.72–1.87 (2H, m), 1.92–2.04 (2H, m), 3.4–3.6 (2H, m), 4.42 (2H, d, J=7 Hz), 4.62 (1H, d, J=6 Hz), 6.90 (1H, d, J=8 Hz), 7.22–7.39 (5H, m), 8.13 (1H, dd, J=2.8 Hz), 8.63(1H, d, J=2 Hz), 9.10 (1H, d, J=7 Hz), 9.41 (1H, t, J=6 Hz).

EXAMPLE 57

N-Benzyl-2-(morpholinoamino)-5-nitrobenzamide (41 mg) was obtained from N-benzyl-2-fluoro-5-nitrobenzamide (100 mg) and 4-aminomorpholine (40.9 mg) in a manner similar to Example 1(1).

NMR (DMSO-$d_6$, δ): 2.63–2.84 (4H, m), 3.22–3.78 (4H, m), 4.42 (2H, d, J=6 Hz), 7.2–7.4 (5H, m), 8.17 (1H, dd, J=2, 8 Hz), 8.63 (1H, d, J=2 Hz), 9.41 (1I, t, J=6 Hz), 9.55 (1H, s); Mass m/z: 355 ($M^+$–1).

EXAMPLE 58

N-Benzyl-5-nitro-2-(piperidinoamino)benzamide (65 mg) was obtained from N-benzyl-2-fluoro-5-nitrobenzamide (111 mg) and 4-aminopiperidine (44.6 mg) in a manner similar to Example 1(1).

NMR (DMSO-$d_6$, δ): 1.55–1.7 (6H, m), 2.4–3.0 (4H, m), 4.43 (2H, d, J=6 Hz), 7.2–7.4 (5H, m), 8.16 (1H, dd, J=2, 8 Hz), 8.63 (1H, d, J=2 Hz), 9.42 (1H, t, J=6 Hz), 9.56 (1H, s); Mass m/z: 353 ($M^+$–1).

EXAMPLE 59

N-Benzyl-5-nitro-2-(2-thiazolylamino)benzamide (22.7 mg) was obtained from N-benzyl-2-fluoro-5-nitrobenzamide (100 mg) and 2-aminothiazole (49.9 mg) in a manner similar to Example 1(1).

NMR (DMSO-$d_6$, δ): 4.54 (2H, d, J=6 Hz), 7.2–7.5 (6H, m), 7.48 (1H, m), 8.41 (1H, m), 8.73 (1H, d, J=9 Hz), 8.79 (1H, d, J=2 Hz), 9.79 (1H, t, J=6 Hz); Mass m/z: 353 ($M^+$–1).

EXAMPLE 60

N-Benzyl-2-(trans-2-hydroxycyclopentylamino)-5-nitrobenzamide (215 mg) was obtained from N-benzyl-2-fluoro-5-nitrobenzamide (181 mg) and trans-2-aminocyclopentanol (100 mg) in a manner similar to Example 1(1).

NMR (CDCl$_3$, δ): 1.54–1.96 (5H, m), 2.00–2.12 (1H, m), 2.25–2.37 (1H, m), 3.78 (1H, m), 4.16 (1H, m), 4.58 (2H, d, J=7 Hz), 6.60 (1H, br), 6.86 (1H, d, J=8 Hz), 7.28–7.40 (5H, m), 8.15 (1H, dd, J=4, 8 Hz), 8.32 (1H, d, J=4 Hz), 8.85 (1H, br); Mass m/z: 354($M^+$).

PREPARATION 61(1)

To a solution of 1,3-cyclopentanediol (500 mg) in pyridine (10 mL) was added benzoyl chloride (688 mg), and the mixture was stirred for 18 hours at ambient temperature. After evaporation of the solvent, the residue was partitioned between ethyl acetate and water. The separated organic layer was washed with 1N-hydrochloric acid, water and brine, dried over magnesium sulfate and evaporated in vacuo. The residue was purified by a silica gel column chromatography eluting with a mixture of hexane and ethyl acetate (3:1 to 1:1) to give 3-hydroxycyclopentyl benzoate as a colorless oil (630 mg).

NMR (CDCl$_3$, δ): 1.63–1.78 (1H, m), 1.80–2.00 (1H, br), 2.04–2.20 (3H, m), 2.22–2.40 (1H, m), 4.40 and 4.56 (1H, m), 5.40 and 5.54 (1H, br), 7.42 (2H, m), 7.53 (1H, m), 8.00 (2H, d, J=8 Hz).

PREPARATION 61(2)

To a solution of 3-hydroxycyclopentyl benzoate (630 mg) in anhydrous tetrahydrofuran (15 mL) were added diphenylphosphoryl azide (925 mg), diethyl azodicarboxylate (585 mg) and triphenylphosphine (881 mg). After stirring for 2 hours at ambient temperature, the mixture was partitioned between ethyl acetate and water. The separated organic layer was washed with brine, dried over magnesium sulfate and evaporated in vacuo. The residue was purified by a silica gel column chromatography eluting with a mixture of hexane and ethyl acetate (10:1) to give 3-azidocyclopentyl benzoate as pale yellow oil (531 mg).

NMR (CDCl$_3$, δ): 1.74–2.46 (6H, br), 4.12–4.28 (1H, br), 5.28–5.54 (1H, br), 7.37–7.50 (2H, br), 7.51–7.62 (1H, br), 7.94–8.10 (2H, m).

PREPARATION 61(3)

A mixture of 3-azidocyclopentyl benzoate (411 mg) and 10% palladium on activated carbon (41.1 mg) in methanol (15 mL) was stirred under hydrogen atmosphere (4 atm) for 2 hours at ambient temperature. After removal of the catalyst, the filtrate was evaporated in vacuo to give 3-aminocyclopentyl benzoate as a pale yellow oil (354 mg).

NMR (CDCl$_3$, δ): 1.40–2.20 (5H, br), 2.41 (1H, m), 3.43 (1H, m), 5.38 (1H, br), 7.38–7.65 (3H, br), 8.03 (2H, d, J=8 Hz).

EXAMPLE 61(1)

2-[3-(Benzoyloxy)cyclopentylamino]-N-benzyl-5-nitrobenzamide (158 mg) was obtained from N-benzyl-2-fluoro-5-nitrobenzamide (100 mg) and 3-aminocyclopentyl benzoate (112 mg) in a manner similar to Example 1(1).

NMR (CDCl$_3$, δ): 1.88–2.30 (5H, br), 2.57 (1H, m), 4.08 (1H, br), 4.59 (2H, d, J=7 Hz), 5.51 (1H, br), 6.48 (1H, br), 6.68 (1H, d, J=8 Hz), 7.20–7.48 (7H, m), 7.52 (1H, m), 8.10 (2H, d, J=8 Hz), 8.18 (1H, dd, J=4, 8 Hz), 8.32 (1H, d, J=4 Hz), 9.20 (1H, br); Mass m/z: 458($M^+$).

EXAMPLE 61(2)

N-Benzyl-2-(3-hydroxycyclopentylamino)-5-nitrobenzamide (129 mg) was obtained from 2-(3-benzoyloxyccyclopentylamnmo)-N-benzyl-5-nitrobenzamide (189 mg) in a manner similar to Example 52(3).

NMR (CDCl$_3$, δ): 1.62 (1H, d, J=7 Hz), 1.74–1.98 (4H, m), 2.09–2.36 (2H, m), 3.99 (1H, m), 4.47 (1H, br), 4.60 (2H, d, J=7 Hz), 6.47 (1H, br), 6.65 (1H, d, J=8 Hz), 7.28–7.40 (5H, m), 8.16 (1H, dd, J=4,8 Hz), 8.31 (1H, d, J=4 Hz), 9.05 (1H, br); Mass m/z: 356(M⁺).

PREPARATION 62

N-(3-Chloro-4-methoxybenzyl)-2-fluoro-5-nitrobenzamide (320 mg) was obtained as yellow oil from 2-fluoro-5-nitrobenzoic acid (300 mg) and 3-chloro-4-methoxybenzylamine hydrochloride (405 mg) in a manner similar to Preparation 1.

NMR (DMSO-d₆, δ): 3.90 (3H, s), 4.60 (2H, d, J=7 Hz), 6.90 (1H, d, J=8 Hz), 6.88–7.00 (1H, br), 7.20–7.40 (3H, m), 8.38 (1H m), 9.00 (1H, m).

EXAMPLE 62

N-(3-Chloro-4-methoxybenzyl)-2-[2-hydroxy-1-(hydroxy-methyl)ethylamino]-5-nitrobenzamide (85.0 mg) was obtained from N-(3-chloro-4-methoxybenzyl)-2-fluoro-5-nitrobenzamide (105 mg) and 2-amino-1,3-propanediol (42.4 mg) in a manner similar to Example 1(1).

NMR (DMSO-d₆, δ): 3.54 (4H, br), 3.62 (1H,br), 3.83 (3H, s), 4.36 (2H, d, J=7 Hz), 4.92 (2H, t, J=7 Hz), 6.92 (1H, d, J=8 Hz), 7.11 (1H, d, J=8 Hz), 7.26 (1H, dd, J=4, 8 Hz), 7.38 (1H, d, J=4 Hz), 8.10 (1H, dd, J=4, 8 Hz), 8.59 (1H, d, J=4 Hz), 9.30 (2H, br); Mass m/z: 408 (M⁺).

EXAMPLE 63(1)

N-(3-Chloro-4-methoxybenzyl)-2-(trans-4-hydroxycyclohexylamino)-5-nitrobenzamide (200 mg) was obtained from N-(3-chloro-4-methoxybenzyl)-2-fluoro-5-nitrobenzamide (210 mg) and trans-4-aminocyclohexanol (107 mg) in a manner similar to Example 1(1).

NMR (DMSO-d₆, δ): 1.30 (4H, br), 1.80 (2H, br), 1.95 (2H, br), 3.50 (2H, br), 3.82 (3H, s), 4.35 (2H, d, J=7 Hz), 4.60 (1H, d, J=4 Hz), 6.90 (1H, d, J=8 Hz), 7.10 (1H, d, J=8 Hz), 7.25 (1H, dd, J=4, 8 Hz), 7.40 (1H, d, J=4 Hz), 8.10 (1H, dd, J=4, 8 Hz), 8.60 (1H, d, J=4 Hz), 9.04 (1H, d, J=8 Hz), 9.36 (1H, br); Mass m/z: 432 (M⁺).

EXAMPLE 63(2)

2-[cis-4-(Benzoyloxy)cyclohexylamino)-N-(3-chloro-4-methoxybenzyl)-5-nitrobenzamide (155 mg) was obtained from N-(3-choro-4-methoxybenzyl)-2-(trans-4-hydroxycyclohexylamino)-5-nitrobenzamide(197 mg) in a manner similar to Example 52(2).

NMR (CDCl₃, δ): 1.80–2.20 (8H, br), 3.60 (2H, br), 3.91 (3H, s), 4.54 (2H, d, J=7 Hz), 5.25 (4H, br), 6.53 (1H, br), 6.72 (1H, d, J=8 Hz), 6.95 (1H, d, J=8 Hz), 7.25 (1H, m), 7.39–7.50 (3H, m), 7.60 (1H, m), 8.07 (2H, d, J=8 Hz), 8.18 (1H, dd, J=4, 8 Hz), 8.34 (1H, d, J (4 Hz), 9.02 (1H, br).

EXAMPLE 63(3)

N-(3-Chloro-4-methoxybenzyl)-2-(cis-4-hydroxycyclohexylamino)-5-nitrobenzamide (85.0 mg) was obtained from 2-[cis-4-(benzoyloxy)cyclohexylamino]-N-(3-chloro-4-methoxybenzyl)-5-nitrobenzamide (155 m g) in a manner similar to Example 52(3).

NMR (DMSO-d₆, δ): 1.43–1.70 (8H, br), 3.66 (2H, br), 3.83 (3H, s), 4.38 (2H, d, J=7 Hz), 4.54 (1H, d, J=4 Hz), 6.88 (1H, d, J=8 Hz), 7.12 (1H, d, J=8 Hz), 7.28 (1H, dd, J=4, 8 Hz), 7.39 (1H, d, J=4 Hz), 8.11 (1H, dd, J=4, 8 Hz), 8.61 (1H, d, J=4 Hz), 9.26 (1H, d, J=8 Hz), 9.36 (1H, br); Mass m/z: 432 (M⁺).

PREPARATION 64

N-(3,4-Dimethoxybenzyl)-2-fluoro-5-nitrobenzamide (14.2 g) was obtained from 2-fluoro-5-nitrobenzoic acid (10.0 g) and 3,4-dimethoxybenzylamine (9.30 g) in a manner similar to Preparation 55.

NMR (CDCl₃, δ): 3.89 (6H, s), 4.63 (2H, d, J=7 Hz), 6.84–6.93 (4H, m), 7.30 (1H, m), 8.35 (1H, m), 9.03 (1H, m); Mass m/z: 333 (M⁺).

EXAMPLE 64(1)

(R)-N-(3,4-Dimethoxybenzyl)-2-(2-hydroxy-(1-methylethylamino)-5-nitrobenzamide (156 mg) was obtained from N-(3,4-dimethoxybenzyl)-2-fluoro-5-nitrobenzamide (150 mg) and (R)-2-amino-1-propanol (50.6 mg) in a manner similar to Example 1(1). mp: 125–127° C.

NMR (DMSO-d₆, δ): 1.17 (3H, d, J=7 Hz), 3.46 (2H, br), 3.72 (3H, s), 3.74 (3H, s), 3.75 (1H, br), 4.36 (2H, d, J=7 Hz), 4.99 (1H, t, J=7 Hz), 6.83–6.95 (4H, m), 8.09 (1H, dd, J=4, 8 Hz), 8.57 (1H, d, J=4 Hz), 9.09 (1H, d, J=8 Hz), 9.28 (1H, br); Mass m/z: 388 (M⁺).

EXAMPLE 64(2)

To a mixture of (R)-N-(3,4-dimethoxybenzyl)-2-(2-hydroxy-1-methylethylamino)-5-nitrobenzamide (5.00 g), 4-dimethylaminopyridine (1.57 g, 12.8 mmol) and triethylamine (1.79 mL) in dichloromethane (150 mL) was added acetyl chloride (1.83 mL), and the mixture was stirred for 5 hours at ambient temperature. The mixture was washed with 1N-hydrochloric acid, water, an aqueous saturated sodium bicarbonate solution and brine. Then, the resultant was dried over magnesium sulfate and evaporated in vacuo. The residue was triturated with diisopropyl ether. The obtained product was recrystallized from a mixture of ethyl acetate and hexane (1:1) to give (R)-2-(2-acetoxy-1-methylethylamino)-N-(3,4-dimethoxybenzyl)-5-nitrobenzamide as yellow crystals (5.10 g).

NMR (DMSO-d₆, δ): 1.22 (3H, d, J=7 Hz), 1.99 (3H, s), 3.73 (3H, s), 3.74 (3H, s), 4.00–4.12 (1H, br), 4.09 (2H, br), 4.37 (2H, d, J=7 Hz), 6.82–6.98 (4H, m), 8.13 (1H, dd, J=4, 8 Hz), 8.60 (1H, d, J=4 Hz), 9.06 (1H, d, J=8 Hz), 9.33 (1H, br); Mass m/z: 430(M⁺).

EXAMPLE 64(3)

To a solution of (R)-N-(3,4-dimethoxybenzyl)-2-(2-hydroxy-1-methylethylamino)-5-nitrobenzamide (200 mg) in 1,2-dichloroethane (10 mL) were added trimethyloxonium tetrafluoroborate (91.2 mg) and 2,6-di-tert-butyl-4-methylpyridine (158 mg), and the mixture was heated for 3 hours under reflux. The mixture was washed with 1N-hydrochloric acid, water, an aqueous saturated sodium bicarbonate solution and brine. Then, the resultant was dried over magnesium sulfate and evaporated in vacuo. The residue was purified by a silica gel column chromatography eluting with a mixture of hexane and ethyl acetate (3:1 to 1:1). The obtained product was triturated with diisopropyl ether to give (R)-N-(3,4-dimethoxybenzyl)-2-(2-methoxy-1-methylethylamino)-5-nitrobenzamide as yellow powders (145 mg).

NMR (DMSO-d₆, δ): 1.17 (3H, d, J=7 Hz), 3.29 (3H, s), 3.42 (2H, br), 3.73 (3H, s), 3.74 (3H, s), 3.88–4.00 (1H, br), 4.37 (2H, d, J=7 Hz), 6.85–6.96 (4H, m), 8.12 (1H, dd, J=4, 8 Hz), 8.59 (1H, d, J=4 Hz), 9.09 (1H, d, J=8 Hz), 9.29 (1H, br); Mass m/z: 402(M⁺).

EXAMPLE 65

(S)-N-(3,4-Dimethoxybenzyl)-2-[1-(hydroxymethyl)-propylamino]-5-nitrobenzamide (130 mg) was obtained from N-(3,4-dimethoxybenzyl)-2-fluoro-5-nitrobenzamide (150 mg) and (S)-2-amino-1-butanol (60.0 mg) in a manner similar to Example 1(1).

mp: 168–169° C. NMR (DMSO-$d_6$, δ): 0.90 (3H, t, J=7 Hz), 1.40–1.78 (2H, m), 3.48 (2H, br), 3.57 (1H, br), 3.72 (3H, s), 3.74 (3H, s), 4.38 (2H, br), 4.92 (1H, t, J=7 Hz), 6.83–6.95 (4H, m), 8.08 (1H, dd, J=4, 8 Hz), 8.57 (1H, d, J=4 Hz), 9.09 (1H, d, J=8 Hz), 9.29 (1H, br); Mass m/z: 402 ($M^+$).

EXAMPLE 66

N-(3,4-Dimethoxybenzyl)-2-(2-hydroxy-1,1-dimethyl-ethylamino)-5-nitrobenzamide (156 mg) was obtained from N-(3,4-dimethoxybenzyl)-2-fluoro-5-nitrobenzamide (150 mg) and 2-amino-2-methyl-1-propanol (120 mg) in a manner similar to Example 1(1).

mp: 161–162° C. NMR (DMSO-$d_6$, δ): 1.33 (6H, s), 3.43 (2H, d, J=7 Hz), 3.73 (3H, s), 3.74 (3H, s), 4.36 (2H, d, J=7 Hz), 5.19 (1H, t, J=7 Hz), 6.80–6.96 (3H, m), 7.04 (1H, d, J=8 Hz), 8.07 (1H, dd, J=4, 8 Hz), 8.51 (1H, d, J=4 Hz), 9.27 (2H, br); Mass m/z: 402 ($M^+$).

EXAMPLE 67

N-(3,4-Dimethoxybenzyl)-2-(trans-2-hydroxycyclopentylamino)-5-nitrobenzamide (6.18 g) was obtained from N-(3,4-dimethoxybenzyl)-2-fluoro-5-nitrobenzamide (6.00 g) and trans-2-aminocyclopentanol (3.63 g) in a manner similar to Example 1(1).

mp: 154–155° C. NMR (DMSO-$d_6$, δ): 1.60–1.96 (5H, m), 2.00–2.14 (1H, m), 2.27–2.40 (1H, m), 3.78 (1H, br), 3.89 (3H, s), 3.90 (3H, s), 4.16 (1H, br), 4.53 (2H, d, J=7 Hz), 6.50 (1H, br), 6.88 (4H, br), 8.16 (1H, dd, J=4, 8 Hz), 8.31 (1H, d, J=4 Hz), 8.85 (1H, br); Mass m/z: 414 ($M^+$).

EXAMPLE 68

(S)-N-(3,4-Dimethoxybenzyl)-2-(2-hydroxy-1-methyl-ethylamino)-5-nitrobenzamide (188 mg) was obtained from N-(3,4-dimethoxybenzyl)-2-fluoro-5-nitrobenzamide (200 mg) and (S)-2-amino-1-propanol (89.9 mg) in a manner similar to Example 1(1).

mp: 131–132° C. NMR (DMSO-$d_6$, δ): 1.17 (3H, d, J=7 Hz), 3.46 (2H, br), 3.72 (3H, s), 3.74 (3H, s), 3.75 (1H, br), 4.36 (2H, d, J=7 Hz), 4.99 (1H, t, J=7 Hz), 6.83–6.95 (4H, m), 8.09 (1H, dd, J=4, 8 Hz), 8.57 (1H, d, J=4 Hz), 9.09 (1H, d, J=8 Hz), 9.28 (1H, br); Mass m/z: 388 ($M^+$).

EXAMPLE 69

N-(3,4-Dimethoxybenzyl)-5-nitro-2-[2-(2,2,2-trifluoroethyl)hydrazino]benzamide (27 mg) was obtained as a yellow solid substance from N-(3,4-dimethoxybenzyl)-2-fluoro-5-nitrobenzamide (200 mg) and 2,2,2-trifluoroethylhydrazine (116 mg) in a manner similar to Example 1(1).

mp 140–142° C. NMR (DMSO-$d_6$, δ); 3.47–3.65 (2H, m), 3.73 (3H, s), 3.74 (3H, s), 4.38 (2H, d, J=5.5 Hz), 5.81 (1H, t, J=4 Hz), 6.85 (1H, d, J=8.5 Hz), 6.91 (1H, d, J=8.5 Hz), 6.96 (1H, s), 7.39 (1H, d, J=8.5 Hz), 8.18 (1H, dd, J=8.5, 1.5 Hz), 8.57 (1H, d, J=1.5 Hz), 9.31 (1H, t, J=5.5 Hz), 9.84 (1H, s); Mass m/z: 427($M^+$−1).

EXAMPLE 70

N-(3,4-Dimethoxylbenzyl)-2-{[(1R,2S)-cis-2,3-dihydro-2-hydroxy-1H-inden-1-yl]amino}-5-nitrobenzamide (192 mg) was obtained as yellow powders from N-(3,4-dimethoxylbenzyl)-2-fluoro-5-nitrobenzamide (153 mg) and (1R,2S)-cis-1-amino-2-indanol (137 mg) in a manner similar to Example 1(1).

mp. 248–250° C. NMR (DMSO-$d_6$, δ); 2.86 (1H, d, J=16 Hz), 3.11 (1H, dd, J=16, 5 Hz), 3.71 (3H, s), 3.72 (3H, s), 4.30–4.44 (2H, m), 4.58 (1H, m), 5.18 (1H, m), 5.37 (1H, d, J=5 Hz), 6.80–6.97 (3H, m), 7.07–7.34 (5H, m), 8.17 (1H, dd, J=10, 2 Hz), 8.63 (1H, d, J=2 Hz), 9.30 (1H, t, J=6 Hz), 9.55 (1H, d, J=8 Hz); Mass m/z: 462($M^+$).

EXAMPLE 71

N-(3,4-Dimethoxylbenzyl)-2-[(1R, 2S)-2-hydroxy-1-methyl-2-phenylethyl]amino-5-nitrobenzamide (167 mg) was obtained as yellow powders from 2-fluoro-N-(3,4-dimethoxylbenzyl)-5-nitrobenzamide (145 mg) and (1S, 2R)-(+)-Norephedrine (97 mg) in a manner similar to Example 1(1).

m.p. 248–250° C. NMR (DMSO-$d_6$, δ); 2.86 (1H, d, J=16 Hz), 3.11 (1H, dd, J=16,5 Hz), 3.71 (3H, s), 3.72 (3H, s), 4.30–4.44 (2H, m), 4.58 (1H, m), 5.18 (1H, m), 5.37 (1H, d, J=5 Hz), 6.80–6.97 (3H, m), 7.07–7.34 (5H, m), 8.17 (1H, dd, J=10, 2 Hz), 8.63 (1H, d, J=2 Hz), 9.30 (1H, t, J=6 Hz), 9.55 (1H, d, J=8 Hz); Mass m/z: 462($M^+$).

EXAMPLE 72

2-[(1S, 2R)-1-(Carbamoyl)-2-hydroxypropylamino]-N-(3,4-dimethoxybenzyl)-5-nitrobenzamide (151 mg) was obtained as yellow crystals from N-(3,4-dimethoxybenzyl)-2-fluoro-5-nitrobenzamide (200 mg) and L-threoninamide hydrochloride (139 mg) in a manner similar to Example 1(1).

NMR (DMSO-$d_6$, δ): 1.13 (3H, d, J=6 Hz), 3.73 (3H, s), 3.75 (3H, s), 3.91 (1H, m), 4.06 (1H, m), 4.50 (2H, m), 5.23 (1H, d, J=4 Hz), 6.69 (1H, d, J=9 Hz), 6.81 (1H, brd, J=8 Hz), 6.92 (1H, d, J=8 Hz), 6.98 (1H, br), 7.26 (1H, s), 7.44 (1H, s), 8.14 (1H, dd, J=3, 9 Hz), 8.59 (1H, d, J=3 Hz), 9.28 (1H, t, J=5 Hz), 9.38 (1H, d, J=5 Hz); Mass (ESI-): 431 (M-H).

EXAMPLE 73(1)

2-[(trans-4-Aminocyclohexyl)amino]-N-(3,4-dimethoxybenzyl)-5-nitrobenzamide (12.3 g) was obtained from N-(3,4-dimethoxybenzyl)-2-fluoro-5-nitrobenzamide (10.0 g) and trans-1,4-diaminocyclohexane (10.2 g) in a manner similar to Example 1(1).

NMR (DMSO-$d_6$, δ): 1.10–1.38 (4H, br), 1.72–1.82 (2H, br), 1.94–2.05 (2H, br), 2.60 (1H, br), 3.46 (1H, br), 3.73 (3H, s), 3.74 (3H, s), 4.36 (2H, d, J=7 Hz), 6.83–6.95 (4H, m), 8.10 (1H, dd, J=4, 8 Hz), 8.59 (1H, d, J=4 Hz), 9.01 (1H, d, J=8 Hz), 9.31 (1H, br); Mass m/z: 429 ($M^+$).

EXAMPLE 73(2)

To a solution of 2-[(trans-4-aminocyclohexyl)amino]-N-(3,4-dimethoxybenzyl)-5nitrobenzamide (10 g) in dimethylformamide (60 mL) was added ethyl formate (200 mL), and the mixture was heated for 8 hours under reflux. The mixture was partitioned between ethyl acetate and water. The separated organic layer was washed with water and brine, dried over magnesium sulfate and evaporated in vacuo. The residue was purified by a silica gel column chromatography eluting with a mixture of chloroform and methanol (20: 1). The obtained product was recrystallized from ethanol to give N-(3,4-dimethoxybenzyl)-2-[(trans-4-formamidocyclohexyl)amino]-5-nitrobenzamide as yellow crystals (7.21 g).

NMR (DMSO-$d_6$, δ): 1.25–1.55 (4H, br), 1.79–1.92 (2H, br), 1.95–2.10 (2H, br), 3.47–3.59 (1H, br), 3.60–3.72 (1H, br), 3.73 (3H, s), 3.74 (3H, s), 4.37 (2H, d, J=7 Hz), 6.85–6.96 (4H, m), 7.95 (1H, s), 8.04 (1H, br), 8.08 (1H, dd, J=4, 8 Hz), 8.60 (1H, d, J=4 Hz), 9.01 (1H, d, J=8 Hz), 9.32 (1H, br); Mass m/z: 455 (M$^+$).

EXAMPLE 73(3)

Methanesulfonyl chloride (54 mg) and triethylamine (48 mg) were added to a solution of 2-(trans-4-aminocyclohexylamino)-N-(3,4-dimethoxybenzyl)-5-nitrobenzamide (134 mg) in chloroform (2 mL). The mixture was stirred for an hour at ambient temperature. Methanesulfonyl chloride (54 mg) and triethylamine (48 mg) were added to the reaction mixture. After stirring for an hour at ambient temperature, the mixture was concentrated in vacuo. The residue was partitioned between ethyl acetate and 3.6% hydrochloric acid. The separated organic layer was washed with an saturated aqueous sodium bicarbonate solution and brine, dried over magnesium sulfate and concentrated in vacuo. The residual crystals were suspended in hot ethanol and cooled with stirring. The resultant was collected by filtration and washed with ethanol to give N-(3,4-dimethoxybenzyl)-2-[trans-4-(methanesulfonylamino)cyclohexylamino]-5-nitrobenzamide (142 mg) as yellow crystals.

NMR (DMSO-d$_6$, δ): 1.25–1.50 (4H, m), 1.88–2.05 (4H, m), 2.92 (3H, s), 3.18 (1H, m), 3.34–3.54 (1H, m), 3.73(3H, s), 3.74 (3H, s), 4.37 (2H, d, J=6 Hz), 6.84 (1H, dd, J=2, 8 Hz), 6.88–6.97 (3H, m), 7.09 (1H, d, J=7 Hz), 8.10 (1H, dd, J=2, 8 Hz), 8.60 (1H, d, J=2 Hz), 9.00 (1H, dd, J=7 Hz), 9.32 (1H, t, J=6 Hz); Mass (ESI-): 505(M-H).

EXAMPLE 73(4)

2-(trans-4-Acetamidocyclohexylamino)-N-(3,4-dimethoxybenzyl)-5-nitrobenzamide (110 mg) was obtained as yellow powders from 2-(trans-4-aminocyclohexylamino)-N-(3,4-dimethoxybenzyl)-5-nitrobenzamide (100 mg) and acetic acid (15.4 mg) in a manner similar to Example24(3).

NMR (DMSO-d$_6$, δ): 1.22–1.45 (4H, br), 1.79 (3H, s), 1.75–1.90 (2H, br), 1.96–2.09 (2H, br), 3.44–3.63 (2H, br), 3.73 (3H, s), 3.74 (3H, s), 4.36 (2H, d, J=7 Hz), 6.82–6.95 (4H, m), 7.78 (1H, d, J=8 Hz), 8.10 (1H, dd, J=4, 8 Hz), 8.60 (1H, d, J=4 Hz), 9.02 (1H, d, J=8 Hz), 9.32 (1H, br); Mass m/z: 469(M$^+$).

EXAMPLE 73(5)

To a solution of 2-(trans-4-aminocyclohexylamino)-N-(3,4-dimethoxybenzyl)-5-nitrobenzamide (100 mg) in dichloromethane (3 mL) was added propyl isocyanate (21.8 mg), and the mixture was stirred for 2 hours at ambient temperature. After evaporation of the solvent, the residue was triturated with ethyl acetate to give N-(3,4-dimethoxybenzyl)-5-nitro-2-[trans-4-(3-propylureido)cyclohexylamino]benzamide as yellow powders (118 mg).

NMR (DMSO-d$_6$, δ): 0.82 (3H, t, J=7 Hz), 1.20–1.45 (6H, m), 1.79–1.90 (2H, br), 1.96–2.10 (2H, br), 2.92 (2H, q, J=7 Hz), 3.40 (1H, br), 3.51 (1H, br), 3.73 (3H, s), 3.74 (3H, s), 4.37 (2H, d, J=7 Hz), 5.70 (2H, br), 6.82–6.96 (4H, m), 8.11 (1H, dd, J=4, 8 Hz), 8.59 (1H, d, J=4 Hz), 9.02 (1H, d, J=8 Hz), 9.31 (1H, br); Mass m/z: 512(M$^+$).

EXAMPLE 73(6)

N-(3,4-Dimethoxybenzyl)-5-nitro-2-[trans-4-(3-phenylureido)cyclohexylamino]benzamide (158 mg) was obtained as yellow powders from 2-(trans-4-aminocyclohexylamino)-N-(3,4-dimethoxybenzyl)-5-nitrobenzamide (150 mg) and phenyl isocyanate (45.9 mg) in a manner similar to Example 73(5).

NMR (DMSO-d$_6$, δ): 1.28–1.47 (4H, br), 1.87–1.96 (2H, br), 1.96–2.10 (2H, br), 3.45–3.63 (2H, br), 3.73 (3H, s), 3.75 (3H, s), 4.37 (2H, d, J=7 Hz), 6.12 (1H, d, J=8 Hz), 6.83–6.98 (5H, m), 7.21 (2H, m), 7.37 (2H, d, J=8 Hz), 8.12 (1H, dd, J=4, 8 Hz), 8.31 (1H, s), 8.61 (1H, d, J=4 Hz), 9.05 (1H, d, J=8 Hz), 9.33 (1H, br); Mass m/z; 546(M$^+$).

EXAMPLE 73(7)

To a mixture of 2-(trans-4-aminocyclohexylamino)-N-(3,4-dimethoxybenzyl)-5-nitrobenzamide (300 mg) and 1,3-bis(tert-butoxycarbonyl)-2-methyl-2-thiopseudourea (203 mg) in ethanol (20 mL) was added mercury(II) oxide (152 mg). The mixture was stirred for 2 hours at ambient temperature. The resultant precipitates were removed by filtration and the filtrate was evaporated in vacuo. The residue was purified by a silica gel column chromatography eluting with 2% methanol in chloroform. The obtained product was triturated with diisopropyl ether to give 2-{trans-4-[2,3-bis(tert-butoxycarbonyl)guanidino]cyclohexylamino}-N-(3,4-dimethoxybenzyl)-5-nitrobenzamide as yellow powders (432 mg).

NMR (CDCl$_3$, δ): 1.25–1.45 (4H, br), 1.50 (9H, s), 1.52 (9H, s), 1.95–2.10 (4H, br), 3.28–3.40 (1H, br), 3.89 (3H, s), 3.91 (3H, s), 3.85–4.00 (1H, br), 4.54 (2H, d, J=7 Hz), 6.58 (1H, d, J=8 Hz), 6.85–6.98 (4H, m), 8.14 (1H, dd, J=4, 8 Hz), 8.28 (1H, d, J=8 Hz), 8.42 (1H, d, J=4 Hz), 8.89 (1H, d, J=8 Hz); Mass m/z: 671(M$^+$).

EXAMPLE 73(3)

To a solution of 2-{trans-4-[2,3-bis(tert-butoxycarbonyl)guanidino]cyclohexylamino}-N-(3,4-dimethoxybenzyl)-5-nitrobenzamide (200 mg) in ethyl acetate (4 mL) was added 4N-hydrochloric acid in ethyl acetate (8 mL). The mixture was stirred for 15 hours at ambient temperature. After evaporation of the solvent, the residue was triturated with ethyl acetate to give N-(3,4-dimethoxybenzyl)-2-(trans-4-guanidinocyclohexylamino)-5-nitrobenzamide hydrochloride as yellow powders (145 mg).

NMR (DMSO-d$_6$, δ): 1.22–1.53 (4H, br), 1.86–1.97 (2H, br), 2.00–2.11 (2H, br), 3.22–3.62 (2H, br), 3.73 (3H, s), 3.74 (3H, s), 4.37 (2H, d, J=7 Hz), 6.84–6.96 (4H, m), 7.72 (1H, d, J=8 Hz), 8.12 (1H, dd, J=4, 8 Hz), 8.61 (1H, d, J=4 Hz), 9.02 (1H, d, J=8 Hz), 9.35 (1H, br); Mass m/z: 471(M$^+$).

EXAMPLE 73(9)

A mixture of 2-fluoro-N-(3,4-dimethoxybenzyl)-5-nitrobenzamide (200 mg) and trans-4-formamidocyclohexylamine (170 mg) in pyridine (2 mL) was stirred for 4 hours at 50° C. The mixture was partitioned between ethyl acetate and water. The separated organic layer was washed with 1N HCl and brine, dried over magnesium sulfate and evaporated in vacuo. The residue was purified by a silica gel column chromatography eluting with 5% methanol in chloroform. The obtained product was recrystallized from acetone (2 mL) to give N-(3,4-dimethoxybenzyl)-2-[(trans-4-formamidocyclohexyl)amino]-5-nitrobenzamide as yellow crystals (164 mg).

NMR (DMSO-d$_6$, δ): 1.25–1.55 (4H, br), 1.79–1.92 (2H, br), 1.95–2.10 (2H, br), 3.47–3.59 (1H, br), 3.60–3.72 (1H, br), 3.73 (3H, s), 3.74 (3H, s), 4.37 (2H, d, J=7 Hz), 6.85–6.96 (4H, m), 7.95 (1H, s), 8.04 (1H, br), 8.08 (1H, dd,

J=4, 8 Hz), 8.60 (1H, d, J=4 Hz), 9.01 (1H, d, J=8 Hz), 9.32 (1H, br); Mass m/z: 455 (M+).

EXAMPLE 74(1)

2-[1-(tert-Butoxycarbonyl)piperidin-4-ylamino]-N-(3,4-dimethoxybenzyl)-5-nitrobenzamide (1.06 mg) was obtained as yellow powders from N-(3,4-dimethoxybenzyl)-2-fluoro-5-nitrobenzamide (1.00 g) and tert-butyl 4-amino-1-piperidinecarboxylate (899 mg) in a manner similar to Example 1(1).

NMR (CDCl$_3$, δ): 1.48 (9H, s), 1.52–1.65 (2H, br), 1.95–2.10 (2H, br), 3.03–3.17 (2H, br), 3.64 (1H, br), 3.89 (3H, s), 3.90 (3H, s), 3.94–4.06 (2H, br), 4.52 (2H, d, J=7 Hz), 6.49 (1H, br), 6.69 (1H, d, J=8 Hz), 6.84–6.95 (3H, m), 8.15 (1H, dd, J=4, 8 Hz), 8.33 (1H, d, J=4 Hz), 8.98 (1H, br); Mass m/z: 513(M+).

EXAMPLE 74(2)

N-(3,4-Dimethoxybenzyl)-5-nitro-2-(4-piperidinylamino)benzamide (713 mg) was obtained as yellow powders from 2-[1-(tert-butoxycarbonyl)piperidin-4-ylamino]-N-(3,4-dimethoxybenzyl)-5-nitrobenzamide (950 mg) in a manner similar to Example 24(2).

NMR (DMSO-d$_6$, δ): 1.20–1.40 (2H, br), 1.83–1.96 (2H, br), 2.55–2.65 (2H, br), 2.85–2.98 (2H, br), 3.56–3.68 (1H, br), 3.73 (3H, s), 3.74 (3H, s), 4.37 (2H, d, J=7 Hz), 6.85–6.96 (4H, m), 8.11 (1H, dd, J=4, 8 Hz), 8.60 (1H, d, J=4 Hz), 9.10 (1H, d, J=8 Hz), 9.32 (1H, br); Mass m/z: 415(M+).

EXAMPLE 74(3)

2-[1-[1,3-Bis(tert-butoxycarbonyl)amidino]piperidin-4-ylamino]-N-(3,4-dimethoxybenzyl)-5-nitrobenzamide (299 mg) was obtained as yellow powders from N-(3,4-dimethoxybenzyl)-5-nitro-2-(4-piperidinylamino) benzamide (200 mg) in a manner similar to Example 73(7).

NMR (CDCl$_3$, δ): 1.49 (9H, s), 1.51 (9H, s), 1.70–1.85 (2H, br), 2.05–2.18 (2H, br), 3.19–3.34 (2H, br), 3.67–3.78 (1H, br), 3.89 (3H, s), 3.90 (3H, s), 3.95–4.15 (2H, br), 4.53 (2H, d, J=7 Hz), 6.59 (1H, br), 6.69 (1H, d, J=8 Hz), 6.84–6.91 (3H, m), 8.16 (1H, dd, J=4, 8 Hz), 8.34 (1H, d, J=4 Hz), 9.01 (1H, d, J=8 Hz). Mass m/z: 655(M+).

EXAMPLE 74(4)

2-(1-Amidinopiperidin-4-ylamino)-N-(3,4-dimethoxybenzyl)-5-nitrobenzamide hydrochloride (150 mg) was obtained as yellow powders from 2-[1-[1,3-bis(tert-butoxycarbonyl)amidino]piperidin-4-ylamino]-N-(3,4-dimethoxybenzyl)-5-nitrobenzamide (200 mg) in a manner similar to Example 73(8).

NMR (DMSO-d$_6$, δ): 1.40–1.58 (2H, br), 2.00–2.11 (2H, br), 3.17–3.30 (2H, br), 3.73 (3H, s), 3.74 (3H, s), 3.77–3.97 (3H, br), 4.37 (2H, d, J=7 Hz), 6.82–7.04 (4H, m), 7.52 (4H, br), 8.14 (1H, dd, J=4, 8 Hz), 8.63 (1H, d, J=4 Hz), 9.09 (1H, d, J=8 Hz), 9.38 (1H, br); Mass m/z: 457(M+).

EXAMPLE 75(1)

N-(3,4-Dimethoxybenzyl)-2-(trans-4-hydroxycyclohexylamino)-5-nitrobenzamide (11.8 g) was obtained from N-(3,4-dimethoxybenzyl)-2-fluoro-5-nitrobenzamide (10.0 g) and trans-4-aminocyclohexanol (6.89 g) in a manner similar to Example 1(1).

NMR (DMSO-d$_6$, δ): 1.23–1.41 (4H, m), 1.78–1.88 (2H, br), 1.91–2.01 (2H, br), 3.50 (2H, br), 3.73 (3H, s), 3.74 (3H, s), 4.37 (2H, d, J=7 Hz), 4.62 (1H, d, J=4 Hz), 6.82–6.96 (4H, m), 8.11 (1H, m), 8.60 (1H, m), 9.04 (1H, br), 9.32 (1H, br); Mass m/z: 428 (M+).

EXAMPLE 75(2)

2-[cis4-(Benzoyloxy)cyclohexylamino]-N-(3,4-dimethoxybenzyl)-5-nitrobenzamide (9.00 g) was obtained from N-(3,4-dimethoxybenzyl)-2-(trans-4-hydroxycyclohexylamino)-5-nitrobenzamide (10.0 g) in a manner similar to Example 52(2).

NMR (CDCl$_3$, δ): 1.78–2.15 (8H, br), 3.61 (1H, br), 3.88 (3H, s), 3.89 (3H, s), 4.56 (2H, d, J=7 Hz), 5.26 (1H, br), 6.48 (1H, br), 6.71 (1H, d, J=8 Hz), 6.85–6.93 (3H, m), 7.42–7.50 (2H, m), 7.58 (1H, m), 8.06 (2H, d, J=8 Hz), 8.18 (1H, dd, J=4, 8 Hz), 8.33 (1H, d, J=4 Hz), 9.05 (1H, br); Mass m/z: 532 (M+).

EXAMPLE 75(3)

N-(3,4-Dimethoxybenzyl)-2-(cis-4-hydroxycyclohexylamino)-5-nitrobenzamide (4.56 g) was obtained from 2-[cis-4-(benzoyloxy)cyclohexylamino]-N-(3,4-dimethoxybenzyl)-5-nitrobenzamide (9.00 g) and in a manner similar to Example 52(3).

NMR (DMSO-d$_6$, δ): 1.45–1.72 (8H, br), 3.66 (2H, br), 3.73 (3H, s), 3.75 (3H, s), 4.38 (2H, d, J=7 Hz), 4.55 (1H, d, J=4 Hz), 6.83–6.97 (4H, m), 8.12 (1H, dd, J=4, 8 Hz), 8.61 (1H, d, J=4 Hz), 9.26 (1H, br), 9.32 (1H, br); Mass m/z: 428 (M+).

EXAMPLE 75(4)

To a suspension of N-(3,4-dimethoxybenzyl)-2-(cis-4-hydroxycyclohexylamino)-5-nitrobenzamide (1.0 g) in dichloromethane (20 mL) were added triethylamine (0.49 mL) and 4-dimethylaminopyridine (284 mg), and then acetyl chloride (0.20 mL) at 20° C. The reaction mixture was stirred for 2 hours at 20° C. and then, acetyl chloride (0.05 mL) was added. After stirring for an hour at 20° C., the reaction mixture was partitioned between chloroform and 1N-hydrochloric acid. The separated organic layer was washed with water and brine, dried over magnesium sulfate and evaporated in vacuo. The residue was purified by a silica gel column chromatography eluting with a mixture of ethyl acetate and hexane (1:2). The residual solid was recrystallized from ethyl acetate to give 2-[cis-4-(acetoxy) cyclohexylamino]-N-(3,4-dimethoxybenzyl)-5-nitrobenzamide (429 mg) as yellow crystals.

mp 147–148° C. NMR (DMSO-d$_6$, δ); 1.55–1.90 (8H, br), 2.03 (3H, s), 3.73 (3H, s), 3.74 (1H, m), 3.75 (3H, s), 4.39 (2H, d, J=8 Hz), 4.82 (1H, m), 6.85 (1H, dd, J=2, 8 Hz), 6.92 (1H, d, J=8 Hz), 6.93 (1H, d, J=10 Hz), 6.97 (1H, d, J=2 Hz), 8.12 (1H, dd, J=3, 10 Hz), 8.63 (1H, d, J=3 Hz), 9.26 (1H, d, J=10 Hz), 9.36 (1H, t, J=6 Hz).

EXAMPLE 76(1)

N-(3,4-Dimethoxylbenzyl)-2-[(R)-1-methoxycarbonyl-3-(methylthio)propylamino]-5-nitrobenzamide (245 mg) was obtained from 2-fluoro-N-(3,4-dimethoxylbenzyl)-5-nitrobenzamide (210 mg) and (R)-methionine methyl ester (205 mg) in a manner similar to Example 1(1).

NMR (DMSO-d$_6$, δ): 2.00–2.22 (2H, m), 2.03 (3H, s), 2.44–2.60 (2H, m), 3.70 (3H, s), 3.73 (3H, s), 3.75 (3H, s), 4.40 (2H, d, J=5 Hz), 4.61 (1H, dt, J=8, 6 Hz), 6.79–7.00 (4H, m), 8.15 (1H, dd, J=9, 3 Hz), 8.63 (1H, d, J=3 Hz), 9.32–9.43 (2H, m); Mass m/z: 476(M+).

EXAMPLE 76(2)

To a solution of N-(3,4-dimethoxylbenzyl)-2-[(R)-1-methoxycarbonyl-3-(methylthio)propylamino]-5- nitrobenzamide (175 mg) in anhydrous tetrahydrofuran (3 mL) were added lithium chloride (31 mg), and then sodium borohydride (28 mg) in ethanol (3 mL) at ambient temperature. The mixture was stirred for one day. After evaporation of the solvent, the residue was partitioned between ethyl acetate and 10% citric acid aqueous solution. The separated organic layer was washed with water and brine and dried over magnesium sulfate. The residual solid was recrystallized from ethyl acetate-hexane to give N-(3,4-dimethoxybenzyl)-2-[(R)-1-hydroxymethyl-3-(methylthio) propylamino]-5-nitrobenzamide (122 mg).

m.p. 150–152° C. NMR (DMSO-$d_6$, δ): 1.73 (1H, m), 1.92 (1H, m), 2.03 (3H, s), 2.40–2.62 (2H, m), 3.50 (2H, m), 3.73 (3H, s), 3.74 (3H, s), 3.78 (1H, m), 4.35 (1H, dd, J=15, 6 Hz), 4.40 (1H, dd, J=15,6 Hz), 4.99 (1H, t, J=5 Hz), 6.80–6.99 (4H, m), 8.12 (1H, dd, J=9, 3 Hz), 8.58 (1H, d, J=3 Hz), 8.58 (1H, d, J=3 Hz), 9.10 (1H, d, J=8 Hz), 9.30 (1H, dd, J=6, 6 Hz); Mass m/z: 448($M^+$).

PREPARATION 77(1)

cis-4-(N-tert-Butoxycarbonylamino)cyclohexylazide (266 mg) was obtained as an oil from trans-4-(N-tert-butoxycarbonylamino)cyclohexanol (200 mg) in a manner similar to Preparation 61(2).

NMR (CDCl$_3$, δ): 1.44 (9H, s), 1.4–1.85 (8H, m), 3.51 (1H, br), 3.71 (1H, br), 4.48 (1H, br).

PREPARATION 77(2)

cis-4-(N-tert-Butoxycarbonylamino)cyclohexylamine (77 mg) was obtained as an oil from cis-4-(N-tert-butoxycarbonylamino)cyclohexylazide (252 mg) in a manner similar to Preparation 61(3).

NMR (CDCl$_3$, δ): 1.44 (9H, s), 1.5–1.8 (4H, m), 1.8–2.2 (4H, m), 2.91 (1H, br), 3.65 (1H, br), 4.66 (1H, br); Mass (ESI+): 215(M+H).

EXAMPLE 77(1)

2-[cis-4-(N-tert-Butoxycarbonylamino) cyclohexylamino]-N-(3,4-dimethoxybenzyl)-5-nitrobenzamide (282 mg) was obtained as amorphous powders from N-(3,4-dimethoxybenzyl)-2-fluoro-5-nitrobenzamide (200 mg) and cis-4-(N-tert-butoxycarbonylamino)cyclohexylamine (256 mg) in a manner similar to Example 1(1).

NMR (CDCl$_3$, δ): 1.45 (9H, s), 1.51–1.70 (2H, m), 1.75–1.94 (6H, m), 3.55–3.80 (2H, m), 3.89 (3H, s), 3.90 (3H, s), 4.54 (2H, d, J=5 Hz), 4.59 (1H, m), 6.49 (1H, m), 6.66 (1H, d, J=9 Hz), 6.82–6.95 (3H, m), 8.15 (1H, d, J=9 Hz), 8.33 (1H, d, J=2 Hz), 9.17 (1H, d, J=7 Hz); Mass (ESI−): 527(M−H).

EXAMPLE 77(2)

4N-Hydrogen chloride solution in ethyl acetate (2 mL) was added to a solution of 2-[cis-4-(N-tert-butoxycarbonylamino)cyclohexylamino]-N-(3,4-dimethoxybenzyl)-5-nitrobenzamide (270 mg) in ethyl acetate (1 mL). The mixture was stirred for 2 hours at ambient temperature. The reaction mixture was concentrated in vacuo. To the residue were added an aqueous saturated sodium bicarbonate solution and ethyl acetate. The appeared precipitates were collected by filtration and washed with ethyl acetate and water successively to give 2-(Cis-4-aminocyclohexylamino)-N-(3,4-dimethoxybenzyl)-5-nitrobenzamide (77 mg) as yellow powders. The filtrate was separated, and the aqueous layer was extracted with chloroform. The combined organic layer was dried over magnesium sulfate and concentrated in vacuo to give a second crop (137.8 mg).

NMR (DMSO-$d_6$, δ): 1.50–1.90 (8H, m), 3.16 (1H, m), 3.73 (3H, s), 3.75 (3H, s), 3.80 (1H, m), 4.40 (2H, d, J=5 Hz), 6.83–6.99 (4H, m), 8.14 (1H, dd, J=2, 9 Hz), 8.13 (1H, dd, J=2, 9 Hz), 8.66 (1H, d, J=3 Hz), 9.35–9.44 (2H, m); Mass: (ESI+) 429(M+H), (ESI−) 427(M−H).

EXAMPLE 77(3)

2-(cis-4-Formamidocyclohexylamino)-N-(3,4-dimethoxybenzyl)-5-nitrobenzamide(129 mg) was obtained as yellow crystals from 2-(cis-4-aminocyclohexylamino)-N-(3,4-dimethoxybenzyl)-5-nitrobenzamide (180 mg) in a manner similar to Example 73(2).

NMR (DMSO-$d_6$, δ): 1.42–1.60 (2H, m), 1.60–1.83 (6H, m), 3.65–3.78 (1H, m), 3.73 (3H, s), 3.85 (1H, m), 4.39 (2H, d, J=6 Hz), 6.82–6.98 (4H, m), 7.95 and 8.03 (1H, s), 8.12 (1H, dd, J=2, 9 Hz), 8.20 (1H, d, J=7 Hz), 8.63 (1H, d, J=2 Hz), 9.27–9.41 (2H, m); Mass: (ESI+) 457(M+H), (ESI−) 455(M−H).

PREPARATION 78(1)

Iodomethane (554 mg) was added to a suspension of (S)-2-(benzyloxycarbonylamino)-3-(tert-butoxycarbonylamino)propionoic acid (1.1 g) and potassium carbonate (539 mg) in N,N-dimethylformamide (7 mL). The mixture was stirred for 2 hours at ambient temperature and partitioned between ethyl acetate and water. The organic layer was washed with brine, dried over magnesium sulfate and concentrated in vacuo to give methyl (S)-2-(benzyloxycarbonylamino)-3-(tert-butoxycarbonylamino)propionate (1.2 g) as an oil.

NMR (CDCl$_3$, δ): 1.42 (9H, s), 3.45–3.60 (2H, m), 3.76 (3H, s), 4.41 (1H, m), 4.83 (1H, m), 5.12 (2H, s), 5.79 (1H, m), 7.30–7.40 (5H, m).

PREPARATION 78(2)

Sodium borohydride (251 mg) was added to a solution of methyl (S)-2-(benzyloxycarbonylamino)-3-(tert-butoxycarbonylamino)propionate (1.17 g) in methanol (10 mL) at 0° C. The mixture was stirred for an hour at the same temperature and then for an hour at ambient temperature. After addition of 3.6% hydrochloric acid, the mixture was concentrated in vacuo and the residue was partitioned between ethyl acetate and an aqueous saturated sodium bicarbonate solution. The organic layer was washed with brine, dried over magnesium sulfate and concentrated in vacuo. The residual crystals were suspended in hot diisopropyl ether and cooled to ambient temperature with stirring. The residual crystals were collected by filtration and washed with diisopropyl ether to give (S)-2-(benzyloxycarbonylamino)-3-(tert-butoxycarbonylamino) propanol (945 mg) as white crystals.

NMR (CDCl$_3$, δ): 1.44 (9H, s), 3.18–3.40 (2H, m), 3.46–3.75 (4H, m), 4.90 (1H, m), 5.09 (2H, s), 5.35 (1H, d, J=5 Hz), 7.30–7.40 (5H, m); Mass: (ESI−) 323 (M−H).

PREPARATION 78(3)

10% Palladium on activated carbon (10 mg) was added to a solution of (S)-2-(benzyloxycarbonylamino)-3-(tert-butoxycarbonylamino)propanol (920 mg) in methanol (10 mL) and dioxane (1 mL). The mixture was stirred under hydrogen atmosphere (3.5 atm) for one and a half days at ambient temperature. The catalyst was removed by filtration and the filtrate was concentrated in vacuo. The residue was dissolved in ethyl acetate, dried over magnesium sulfate, and concentrated in vacuo to give (S)-2-amino-3-(tert-butoxycarbonylamino)propanol (571 mg) as a white solid substance.

NMR (CDCl$_3$, δ): 1.45(9H, s), 2.90(1H, m), 3.18(2H, m), 3.49(2H, m), 4.90(1H, br); Mass: (ESI+) 191(M+H), (ESI−) 189(M−H).

EXAMPLE 78(1)

(S)-2-{1-[tert-(Butoxycarbonyl)aminomethyl]-2-hydroxyethylamino}-N-(3,4-dimethoxybenzyl)-5-nitrobenzamide (719 mg) was obtained as yellow crystals from N-(3,4-dimethoxybenzyl)-2-fluoro-5-nitrobenzamide (930 mg) and (S)-2-amino-3-(tert-butoxycarbonylamino) propanol (556 mg) in a manner similar to Example 1(1).

NMR (DMSO-d$_6$, δ): 1.36 (9H, s), 3.08 (2H, m), 3.53 (1H, m), 3.73 (3H, s), 3.74 (3H, s), 4.36 (2H, d, J=6 Hz), 4.99 (1H, t, J=6 Hz), 6.84 (1H, brd, J=8 Hz), 6.90–7.06 (4H, m), 8.09(1H, dd, J=2,9 Hz), 8.58 (1H, d, J=2 Hz), 9.20(1H, d, J=9 Hz), 9.26 (1H, t, J=6 Hz); Mass: (ESI−) 503 (M−H).

EXAMPLE 78(2)

(S)-2-{1-[tert-(Butoxycarbonyl)aminomethyl]-2-hydroxyethylamino}-N-(3,4-dimethoxybenzyl)-5-nitrobenzamide (618 mg) was dissolved in pyridine (5 mL) and acetic anhydride (2 mL). The mixture was stirred at ambient temperature overnight, then concentrated in vacuo. The residue was partitioned between ethyl acetate and 3.6% hydrochloric acid. The organic layer was washed with an aqueous saturated sodium bicarbonate solution and brine, dried over magnesium sulfate and concentrated in vacuo. 4N-Hydrogen chloride solution in ethyl acetate (5 mL) was added to the residue and the mixture was stirred at ambient temperature for 2 hours. The mixture was concentrated in vacuo, and the residue was partitioned between ethyl acetate and an aqueous saturated sodium bicarbonate solution. The organic layer was washed with brine, dried over magnesium sulfate and concentrated in vacuo. The residue was purified by a silica gel column chromatography eluting with 5% methanol in chloroform and then a mixture of 28% ammonium hydroxide, methanol and chloroform (1:10:100) to give (S)-2-[1-(acetylaminomethyl)-2-hydroxyethylamino]-N-(3,4-dimethoxybenzyl)-5-nitrobenzamide (171 mg) as yellow crystals;

NMR (DMSO-d$_6$, δ): 1.80 (3H, s), 3.09–3.30 (2H, m), 3.48–3.60 (2H, m), 3.66–3.78 (1H, m), 3.73 (3H, s), 3.75 (3H, s), 4.37 (2H, d, J=6 Hz), 5.04 (1H, t, J=5 Hz), 6.85 (1H, dd, J=2,8 Hz), 6.91 (1H, d, J=8 Hz), 6.96 (1H, d, J=2 Hz), 7.08(1H, d, J=9 Hz), 8.07–8.15 (2H, m), 8.58 (1H, d, J=3 Hz), 9.20 (1H, d, J=8 Hz), 9.28 (1H, t, J=6 Hz); Mass: (ESI+) 447 (M+H), (ESI−) 445 (M−H), and (S)-2-[1-(aminomethyl)-2-hydroxyethylamino]-N-(3,4-dimethoxybenzyl)-5-nitrobenzamide (178 mg) as amorphous powders.

NMR (DMSO-d$_6$, δ): 2.73(2H, m), 3.47–3.64(3H, m), 3.73(3H, s), 3.74(3H, s), 4.36(2H, s), 6.85(1H, dd, J=2, 8 Hz), 6.90–7.00(3H, m), 8.09(1H, dd, J=3, 9 Hz), 8.56(1H, d, J=3 Hz), 9.15–9.33(2H, m); Mass: (ESI+) 405(M+H).

EXAMPLE 78(3)

(S)-N-(3,4-Dimethoxybenzyl)-2-[1-(formamidomethyl)-2-hydroxyethylamino]-5-nitrobenzamide (112 mg) was obtained as yellow crystals from (S)-2-[1-(aminomethyl)-2-hydroxyethylamino]-N-(3,4-dimethoxybenzyl)-5-nitrobenzamide (147 mg) in a manner similar to Example 73(2).

NMR (DMSO-d$_6$, δ): 3.26 (2H, m), 3.54 (2H, m), 3.65–3.84 (1H, m), 3.73 (3H, s), 3.74 (3H, s), 4.37 (2H, d, J=6 Hz), 5.06 (1H, t, J=5 Hz), 6.85 (1H, brd, J=8 Hz), 6.91 (1H, d, J8 Hz), 6.96 (1H, br), 7.06 (1H, d, J=9 Hz), 8.05 (1H, s), 8.11 (1H, dd, J=3, 9 Hz), 8.25 (1H, t, J=5 Hz), 8.60 (1H, d, J=3 Hz), 9.21 (1H, d, J=7 Hz), 9.29(1H, t, J=6 Hz); Mass: (ESI+) 433 (M+H), (ESI−) 431 (M−H).

PREPARATION 79(1)

Diphenylphosphorylazide (2.60 g) was added dropwise to a mixture of N-(tert-butoxycarbonyl)nipecotic acid (2.06 g) and triethylamine (1.00 g) in toluene (20 mL). The reaction mixture was warmed in an oil bath over 10 minutes at 100° C. Stirring was continued for 2 hours at 100° C., then the reaction vessel was taken out from the oil bath. After reflux was ceased, benzyl alcohol (1.07 g) was added to the reaction mixture. The mixture was stirred for 3 hours at 100° C., and then poured into a mixture of 3.6% hydrochloric acid, ice and ethyl acetate. The separated organic layer was washed with brine, an aqueous saturated sodium bicarbonate solution and brine, successively. The resultant was dried over magnesium sulfate and concentrated in vacuo. The residue was purified by a silica gel column chromatography eluting with 30% ethyl acetate in hexane to give 3-(benzyloxycarbonylamino)-1-tert-butoxycarbonylpiperidine (2.66 g) as an oil.

NMR (CDCl$_3$, δ): 1.44(9H, s), 1.40–2.00(4H, m), 3.09–3.45(3H, m), 3.59(1H, brd, J=13 Hz), 3.70(1H, br), 4.70 and 4.88(1H, m), 5.10(2H, s), 7.27–7.40(5H, m); Mass: (ESI+) 335(M+H), (ESI−) 333(M−H).

PREPARATION 79(2)

3-Amino-1-tert-butoxycarbonylpiperidine (1.48 g) was obtained as syrup from 3-(benzyloxycarbonylamino)-1-tert-butoxycarbonylpiperidine (2.54 g) in a manner similar to Preparation 78(3).

NMR (CDCl$_3$, δ): 1.30(1H, m), 1.40–1.60(1H, m), 1.46 (9H, s), 1.70(1H, m), 1.96(1H, m), 2.66(1H, m), 2.75–2.95 (2H, m), 3.80(1H, m), 3.94(1H, m).

EXAMPLE 79(1)

2-[1-(tert-Butoxycarbonyl)piperidin-3-ylamino]-N-(3,4-dimethoxybenzyl)-5-nitrobenzamide (900 mg) was obtained as amorphous powders from N-(3,4-dimethoxybenzyl)-2-fluoro-5-nitrobenzamide (700 mg) and 3-amino-1-tert-butoxycarbonylpiperidine (503 mg) in a manner similar to Example 1(1).

NMR (DMSO-d$_6$, δ): 1.20–2.00(13H, m), 3.10–3.65(4H, m), 3.65–3.80(1H, m), 3.73(3H, s), 3.74(3H, s), 4.37(2H, d, J=6 Hz), 6.83(1H, d, J=8 Hz), 6.84–6.96(3H, m), 8.15(1H, dd, J=2, 9 Hz), 8.65(1H, s), 9.15–9.45(1H, m), 9.34(1H, t, J=6 Hz); Mass: (ESI+) 515(M+H), (ESI−) 513(M−H).

EXAMPLE 79(2)

A mixture of 2-[1-(tert-butoxycarbonyl)piperidin-3-ylamino]-N-(3,4-dimethoxybenzyl)-5-nitrobenzamide (190 mg) and 4 N hydrogenchloride solution in ethyl acetate (5 mL) was stirred for 2 hours at ambient temperature. The reaction mixture was concentrated in vacuo. The residual crystals were collected by filtration and washed with ethyl acetate to give N-(3,4-dimethoxybenzyl)-5-nitro-2-(piperidin-3-ylamino)benzamide hydrochloride (138 mg) as yellow crystals.

NMR (DMSO-d$_6$, δ): 1.55–1.96(3H, m), 2.04(1H, m), 2.78–2.92(2H, m), 3.18–3.40(2H, m), 3.73(3H, s), 3.75(3H, s), 3.98(1H, m), 4.39(2H, d, J=6 Hz), 6.85(1H, d, J=8 Hz), 6.90–7.00(3H, m), 8.19(1H, dd, J=3, 9 Hz), 8.65(1H, d, J=3 Hz), 9.08(1H, d, J=8 Hz), 9.41(1H, t, J=6 Hz); Mass: (ESI−) 413(M−H).

EXAMPLE 79(3)

N-(3,4-Dimethoxybenzyl)-2-[1-(methanesulfonyl) piperidin-3-ylamino]-5-nitrobenzamide (100 mg) was obtained as yellow crystals from N-(3,4-dimethoxybenzyl)-5-nitro-2-(piperidin-3-ylamino)benzamide hydrochloride (100 mg) in a manner similar to Example 73(3).

NMR (DMSO-$d_6$, δ): 1.50–1.83(3H, m), 1.87(1H, m), 2.89(3H, s), 2.95–3.15(1H, m), 3.01(1H, dd, J=7, 10 Hz), 3.21(1H, m), 3.41(1H, dd, J=4, 10 Hz), 3.73(3H, s), 3.74 (3H, s), 3.91(1H, m), 4.38(2H, d, J=6 Hz), 6.85(1H, dd, J=2, 8 Hz), 6.90–7.00(3H, m), 8.16(1H, dd, J=3, 9 Hz), 8.63(1H, d, J=3 Hz), 9.25(1H, d, J=8 Hz), 9.35(1H, t, J=6 Hz); Mass: (ESI+) 493(M+H), (ESI−) 491(M−H).

EXAMPLE 79(4)

N-(3,4-Dimethoxybenzyl)-5-nitro-2-(piperidin-3-ylamino)benzamide (550 mg) was obtained as yellow crystals from 2-[1-(tert-butoxycarbonyl)piperidin-3-ylamino]-N-(3,4-dimethoxybenzyl)-5-nitrobenzamide (802 mg) in a manner similar to Example 77(2).

NMR (DMSO-d6, δ): 1.36–1.64(2H, m), 1.82(1H, m), 2.40–2.65(2H, m), 2.70(1H, m), 2.96(1H, dd, J=4, 10 Hz), 3.63(1H, m), 3.73(3H, s), 3.74(3H, s), 4.38(2H, d, J=6 Hz), 6.84–6.93(3H, m), 6.96(1H, d, J=2 Hz), 8.11(1H, dd, J=3,9 Hz), 8.58(1H, d, J=3 Hz), 9.20(1H, d, J=8 Hz), 9.29(1H, t, J=6 Hz); Mass: (ESI+) 415(M+H), (ESI−) 413(M−H).

EXAMPLE 79(5)

N-(3,4-Dimethoxybenzyl)-2-(1-formylpiperidin-3-ylamino)-5-nitrobenzamide (102 mg) was obtained as yellow crystals from N-(3,4-dimethoxybenzyl)-5-nitro-2-(piperidin-3-ylamino)benzamide (126 mg) in a manner similar to Example 73(2).

NMR (DMSO-$d_6$, δ): 1.40–1.76(3H, m), 1.93–2.05(1H, m), 3.14–3.86(5H, m), 3.73(3H, s), 3.75(3H, s), 4.37(2H, d, J=5 Hz), 6.84(1H, d, J=2.8 Hz), 6.90–7.04(3H, m), 7.96 and 8.06(1H, s), 8.13 and 8.16(1H, d, J=3.9 Hz), 8.63 and 8.64(1H, d, J=3 Hz), 9.19 and 9.23(1H, d, J=8 Hz), 9.34 and 9.35(1H, t, J=5 Hz); Mass: (ESI+) 443 (M+H), (ESI−) 441 (M−H).

EXAMPLE 80

2-(1H-Benzimidazol-5-ylamino)-N-(3,4-dimethoxybenzyl)-5-nitrobenzamide (130.9 mg) was obtained as a yellow solid substance from N-(3,4-dimethoxybenzyl)-2-fluoro-5-nitrobenzamide (200 mg) and 5-amino-1H-benzimidazole (159 mg) in a manner similar to Example 1(1).

mp. 226.5–227° C. NMR (DMSO-$d_6$, δ): 3.73(3H, s), 3.75(3H, s), 4.45(2H, br), 6.90(1H, d, J=8.0 Hz), 6.94(1H, d, J=8.0 Hz), 7.00(1H, s), 7.04(1H, br), 7.11(1H, brd, J=8.5 Hz), 7.51(1H, br), 7.64(1H, br), 8.10(1H, dd, J=8.5, 2.5 Hz), 8.26(1H, s), 8.69(1H, d, J=2.5 Hz), 9.50(1H, br), 10.71(1H, br), 12.53(1H, br); Mass m/z: 448(M$^+$+1).

EXAMPLE 81(1)

2-[(3S, 5S)-1-(tert-Butoxycarbonyl)-5-(methoxycarbonyl)pyrrolidin-3-ylamino]-N-(3,4-dimnethoxylbenzyl)-5-nitrobenzamide (814 mg) was obtained from N-(3,4-dimethoxylbenzyl)-2-fluoro-5-nitrobenzamide (513 mg) and methyl (2S,4S)-4-amino-1-(tert-butoxycarbonyl)pyrroridine-2-carboxylate (750 mg) in a manner similar to Example 1(1).

NMR (DMSO-$d_6$, δ): 1.35 (9×3/5H, s), 1.41 (9×2/5H, s), 1.94 (1H, m), 2.70 (1H, m), 3.21 (1H, dd, J=11, 4 Hz), 3.56 (3×2/5H, s), 3.58 (3×3/5H, s), 3.72 (3H, s), 3.74 (3H, s), 3.85 (1H, m), 4.25–4.45 (3H, m), 6.83–6.98 (4H, m), 8.15 (1H, dd, J=9,2 Hz), 8.61 (1H, d, J=2 Hz), 9.06 (1H, m), 9.34 (1H, t, J=6 Hz); Mass m/z: 558(M$^+$).

EXAMPLE 81(2)

A mixture of 2-[(3S,5S)-1-(tert-butoxycarbonyl)-5-(methoxycarbonyl)pyrrolidin-3-ylamino]-N-(3,4-dimethoxylbenzyl)-5-nitrobenzamide (143 mg) and 30% methanol solution of methylamine (4 mL) was stirred for one day at ambient temperature. After evaporation of the solvent, the residue was partitioned between ethyl acetate and water. The organic layer was separated, washed with brine and dried over magnesium sulfate. The residue was subjected to a silica gel column chromatography eluting with ethyl acetate to give 2-[(3S,5S)-1-(tert-butoxycarbonyl)-5-(methylcarbamoyl)pyrrolidin-3-ylamino]-N-( 3,4-dimethoxylbenzyl)-5-nitrobenzamide (149 mg).

NMR (DMSO-$d_6$, δ): 1.48 (9H, s), 2.33–2.70 (2H, m), 2.79 (3H, d, J=5 Hz), 3.47 (1H, m), 3.88 (3H, s), 3.90 (3H, s), 4.15 (1H, m), 4.40 (1I, m), 4.50 (1H, dd, J=16, 7 Hz), 4.57 (1H, dd, J=16, 7 Hz), 6.58 (1H, m), 6.62 (1H, d, J=9 Hz), 6.83–6.93 (3H, m), 8.16 (1H, dd, J=9, 3 Hz), 8.33 (1H, d, J=3 Hz), 8.98 (1H, m); Mass m/z: 558(M$^+$).

EXAMPLE 81(3)

To a solution of 2-[(3S, 5S)-1-(tert-butoxycarbonyl)-5-(methoxycarbonyl)pyrrolidin-3-ylamino]-N-(3,4-dimethoxylbenzyl)-5-nitrobenzamide (492 mg) in tetrahydrofuran (5 mL) was added lithium chloride (75 mg), and then a solution of sodium borohydride (67 mg) in ethanol (10 mL) at ambient temperature. After stirring for one day, the mixture was evaporated and the residue was partitioned between ethyl acetate and 10% citric acid aqueous solution. The organic layer was separated, washed with water and brine and dried over magnesium sulfate. The residue was subjected to a silica gel column chromatography eluting with a mixture of ethyl acetate and hexane (1:1 to 2:1) to give 2-[(3S,5S)-1-(tert-butoxycarbonyl)-5-(hydroxymethyl) pyrrolidin-3-ylamino]-N-(3,4-dimethoxylbenzyl)-5-nitrobenzamide (399 mg) as pale yellow foams.

NMR (DMSO-$d_6$, δ): 1.41 (9H, s), 1.93 (1H, m), 2.44 (1H, m), 3.04 (1H, m), 3.51–3.62 (2H, m), 3.70–3.95 (2H, m), 3.73 (3H, s), 3.74 (3H, s), 4.21 (1H, m), 4.38 (2H, d, J=6 Hz), 4.84 (1H, t, J=5 Hz), 6.81–6.97 (4H, m), 8.15 (1H, dd, J=10, 3 Hz), 8.60 (1H, d, J=3 Hz), 9.18 (1H, d, J=8 Hz), 9.33 (1H, t, J=6 Hz).

EXAMPLE 81(4)

A mixture of 2-[(3S,5S)-1-(tert-butoxycarbonyl)-5-(hydroxymethyl)pyrrolidin-3-ylamino]-N-(3,4-dimethoxylbenzyl)-5-nitrobenzamide (326 mg) and 4N-hydrogen chloride solution in ethyl acetate (5 mL) was stirred for one day at ambient temperature. After evaporation of the solvent, the residue was partitioned between chloroform and an aqueous saturated sodium bicarbonate solution. The organic layer was separated, washed with brine and dried over magnesium sulfate. The filtrate was evaporated to give N-(3,4-dimethoxylbenzyl)-2-[(3S,5S)-5-(hydroxymethyl)pyrrolidin-3-ylamino]-5-nitrobenzamide (242 mg) as pale yellow foams.

NMR (DMSO-d$_6$, δ): 1.32 (1H, m), 2.35 (1H, m), 2.72 (1H, m), 3.13 (1H, m), 3.20–3.41 (2H, m), 3.53 (1H, m), 3.73 (3H, s), 3.74 (3H, s), 4.05 (1H, m), 4.38 (2H, d, J=6 Hz), 4.61 (1H, brt, J=5 Hz), 6.80–6.99 (4H, m), 8.13 (1H, dd, J=9, 3 Hz), 8.60 (1H, m), 9.13 (1H, m), 9.32 (1H, m); Mass (ES) m/z: 431(M$^+$).

EXAMPLE 81(5)

N-(3,4-Dimethoxylbenzyl)-2-[(3S,5S)-5-(methylcarbamoyl)pyrrolidin-3-ylamino]-5-nitrobenzamide (75 mg) was obtained as pale yellow foams from 2-[1(3S, 5S)-1-(tert-butoxycarbonyl)-5-(methylcarbamoyl) pyrrolidin-3-ylamino]-N-(3,4-dimethoxylbenzyl)-5-nitrobenzamide (111 mg) in a manner similar to Example 81(4).

NMR (DMSO-d$_6$, δ): 1.70 (1H, ddd, J=13, 5, 5 Hz), 2.43 (1H, m), 2.53 (3H, d, J=5 Hz), 2.72 (1H, dd, J=10, 4 Hz), 3.26 (1H, dd, J=10, 5 Hz), 3.60 (1H, m), 3.72 (3H, s), 3.74 (3H, s), 4.07 (1H, m), 4.34 (1H, dd, J=15, 6 Hz), 4.40 (1H, dd, J=15, 6 Hz), 6.81–6.97 (4H, m), 7.85 (1H, q, J=5 Hz), 8.14 (1H, dd, J=9, 2 Hz), 8.59 (1I, d, J=2 Hz), 9.07 (1H, d, J=8 Hz), 9.30 (1H, t, J=6 Hz); Mass m/z: 458(M$^+$).

PREPARATION 82

To a suspension of cis-4-aminocyclohexanecarboxylic acid (1.04 g) in methanol (25 mL) was added thionyl chloride (0.583 mL) under ice-water cooling. The mixture was stirred for an hour at 0° C. and for 17 hours at ambient temperature. After evaporation of the solvent, the residue was triturated with diethyl ether to give methyl cis-4-aminocyclohexanecarboxylate hydrochloride as white powders (1.37 g).

NMR (DMSO-d$_6$, δ): 1.40–1.68 (4H, m), 1.73–1.85 (2H, br), 1.93–2.07 (2H, br), 2.62 (1H, m), 3.02–3.14 (1H, br), 3.63 (3H, s), 8.00 (3H, br).

EXAMPLE 82(1)

N-(3,4-Dimethoxybenzyl)-2-[cis-4-(methoxycarbonyl) cyclohexylamino-5-nitrobenzamide (1.38 g) was obtained as yellow powders from N-(3,4-dimethoxybenzyl)-2-fluoro-5-nitrobenzamide (1.00 g) and methyl cis-4-aminocyclohexanecarboxylate hydrochloride (985 mg) in a manner similar to Example 1(1).

NMR (DMSO-d$_6$, δ): 1.55–1.85 (8H, br), 2.50–2.60 (1H, br), 3.62 (3H, s), 3.73 (3H, s), 3.74 (3H, s), 3.75–3.85 (1H, br), 4.38 (2H, d, J=7 Hz), 6.82–6.98 (4H, m), 8.12 (1H, dd, J=4, 8 Hz), 8.62 (1H, d, J=4 Hz), 9.28–9.38 (2H, br).

EXAMPLE 82(2)

2-(cis-4-Carboxycyclohexylamino)-N-(3,4-dimethoxybenzyl)-5-nitrobenzamide (1.12 g) was obtained as yellow powders from N-(3,4-dimethoxybenzyl)-2-cis-4-(methoxycarbonyl)cyclohexylamino]-5-nitrobenzamide (1.27 g) in a manner similar to Example 23(2).

NMR (DMSO-d$_6$, δ): 1.55–1.85 (8H, br), 2.39–2.49 (1H, br), 3.73 (3H, s), 3.74 (3H, s), 3.75–3.85 (1H, br), 4.38 (2H, d, J=7 Hz), 6.80–7.00 (4H, m), 8.12 (1H, dd, J=4 Hz, 8 Hz), 8.61 (1H, d, J=4 Hz), 9.33 (2H, br).

EXAMPLE 82(3)

N-(3,4-Dimethoxybenzyl)-2-cis-4-(dimethylcarbamoyl) cyclohexylamino]-5-nitrobenzamide (81.8 mg) was obtained as yellow powders from 2-(cis-4-carboxycyclohexylamino)-N-(3,4-dimethoxybenzyl)-5-nitrobenzamide (100 mg) and dimethylamine hydrochloride (21.4 mg) in a manner similar to Example 23(3).

NMR (DMSO-d$_6$, δ): 1.52–1.90 (8H, br), 2.66–2.76 (1H, br), 2.80 (3H, s), 3.02 (3H, s), 3.73 (3H, s), 3.74 (3H, s), 3.85–3.95 (1H, br), 4.40 (2H, 7 Hz), 6.83–6.98 (4H, m), 8.12 (1H, dd, J=4, 8 Hz), 8.63 (1H, d, J=4 Hz), 9.33 (1H, br), 9.50 (1H, d, J=8 Hz); Mass m/z: 483(M$^+$).

EXAMPLE 82(4)

N-(3,4-Dimethoxybenzyl)-2-[cis-4-(2-hydroxyethylcarbamoyl)cyclohexylamino]-5-nitrobenzamide (100 mg) was obtained as yellow powders from 2-(cis-4-carboxycyclohexylamino)-N-(3,4-dimethoxybenzyl)- 5-nitrobenzamide (100 mg) and 2-aminoethanol (16.0 mg) in a manner similar to Example 23(3).

NMR (DMSO-d$_6$, δ): 1.55–1.72 (8H, br), 2.20–2.30 (1H, br), 3.06–3.16 (2H, m), 3.35–3.41 (2H, m), 3.73 (3H, s), 3.74 (3H, s), 3.78–3.88 (1H, br), 4.39 (2H, d, J=7 Hz), 4.65 (1H, t, J=7 Hz), 6.83–6.98 (4H, m), 7.74 (1H, br), 8.12 (1H, dd, J=4, 8 Hz), 8.63 (1H, d, J=4 Hz), 9.33 (1H, br), 9.43 (1H, d, J=8 Hz); Mass m/z: 499(M$^+$).

PREPARATION 83(1)

4-(Benzyloxycarbonylamino)-1-tert-butoxycarbonylpiperidine (5.44 g) was obtained as a solid substance from N-tert-butoxycarbonylisonipecotic acid (4.5 g) in a manner similar to Preparation 79(1).

NMR (CDCl$_3$, δ): 1.30 (2H, dq, J=4, 10 Hz), 1.45 (9H, s), 1.94 (2H, br d, J=10 Hz), 2.85 (2H, t, J=10 Hz), 3.66 (1H, m), 4.01 (2H, br), 4.65 (1H, m), 5.09 (2H, s), 7.27–7.40 (5H, m).

PREPARATION 83(2)

4-Amino-1-tert-butoxycarbonylpiperidine (3.83 g) was obtained as syrup from 4-(benzyloxycarbonylamino)-1-tert-butoxycarbonylpiperidine (5.11 g) in a manner similar to Preparation 78(3).

NMR (CDCl$_3$, δ): 1.30(2H, m), 1.83(2H, m), 2.56(2H, m), 2.60–2.95(3H, m), 4.06(2H, m); Mass: (ESI+) 201(M$^+$+ 1).

EXAMPLE 83(1)

2-[1-(tert-Butoxycarbonyl)piperidin-4-ylamino]-5-cyano-N-(3,4-dimethoxybenzyl)benzamide (360 mg) was obtained as amorphous powders from 5-cyano-N-(3,4-dimethoxybenzyl)-2-fluorobenzamide (300 mg) and 4-amino-1-tert-butoxycarbonylpiperidine (287mg) in a manner similar to Example 1(1).

NMR (DMSO-d$_6$, δ): 1.28(2H, m), 1.90(2H, m), 3.00(2H, m), 3.61–3.75(1H, m), 3.72(3H, s), 3.74(3H, s), 3.80(2H, m), 4.35(2H, d, J=6 Hz), 6.83(1H, dd, J=2, 8 Hz), 6.88–6.94 (3H, m), 7.63(1H, dd, J=2, 9 Hz), 8.07(1H, d, J=2 Hz), 8.71(1H, d, J=8 Hz), 9.03(1H, t, J=6 Hz); Mass: (ESI−) 493(M−H).

EXAMPLE 83(2)

5-Cyano-N-(3,4-dimethoxybenzyl)-2-(piperidin-4-ylamino)benzamide hydrochloride (254 mg) was obtained as white crystals from 2-[1-(tert-butoxycarbonyl)piperidin-4-ylamino]-5-cyano-N-(3,4-dimethoxybenzyl)benzamide (297 mg) in a manner similar to Example 79(2).

NMR (DMSO-d$_6$, δ): 1.60(2H, m), 2.10(2H, m), 3.01(2H, m), 3.26(2H, m), 3.64–3.87(1H, m), 3.73(3H, s), 3.74(3H, s), 4.36(2H, d, J=6 Hz), 6.84(1H, dd, J=2, 8 Hz), 6.89–7.00 (3H, m), 7.67(1H, dd, J=2, 8 Hz), 8.12(1H, d, J=2 Hz), 8.70–9.05(2H, m), 9.11(1H, t, J=6 Hz); Mass: (ESI+) 395 (M+H), (ESI–) 393(M–H).

EXAMPLE 83(3)

5-Cyano-N-(3,4-dimethoxybenzyl)-2-(piperidin-4-ylamino)benzamide hydrochloride (100 mg) was partitioned between ethyl acetate and an aqueous saturated sodium bicarbonate solution. The organic layer was separated, dried over magnesium sulfate and concentrated in uacuo. The residue was dissolved in N,N-dimethylformamide (1 mL), and ethyl formate (5 mL) was added to the solution. The mixture was refluxed under heating overnight and partitioned between ethyl acetate and water. The organic layer was washed with brine, dried over magnesium sulfate and concentrated in vacuo. The residue was crystallized from ethyl acetate to give 5-cyano-N-(3,4-dimethoxybenzyl)-2-(1-formylpiperidin-4-ylamino)benzamide (52 mg) as white crystals.

NMR (DMSO-d$_6$, δ): 1.15–1.44(2H, m), 1.88–2.03(2H, m), 2.91(1H, m), 3.16–3.35(2H, m), 3.60–3.85(2H, m), 3.72(3H, s), 3.74(3H, s), 4.01(1H, m), 4.35(2H, d, J=5Hz), 6.83(1H, dd, J=2, 8Hz), 6.84–6.97(3H, m), 7.64(1H, dd, J=2, 9Hz), 7.99(1H, s), 8.07(1H, d, J=2Hz), 8.74(1H, d, J=8 Hz), 9.03(1H, t, J=5 Hz); Mass: (ESI–) 421(M–H).

EXAMPLE 83(4)

5-Cyano-N-(3,4-dimethoxybenzyl)-2-[1-(methanesulfonyl)piperidin-4-ylamino]benzamide (78 mg) was obtained as white crystals from 5-cyano-N-(3,4-dimethoxybenzyl)-2-(piperidin-4-ylamino)benzmaide hydrochloride (100 mg) in a manner similar to Example 73(3).

NMR (DMSO-d$_6$, δ): 1.48(2H, m), 2,02(2H, m), 2.89(3H, s), 2.96(2H, m), 3.50(2H, m), 3.64(1H, m), 3.72(3H, s), 3.74(3H, s), 4.35(2H, d, J=5 Hz), 6.84(1H, dd, J=2, 8 Hz), 6.88–6.96(3H, m), 7.65(1H, d, J=2, 9 Hz), 8.08(1H, d, J=2 Hz), 8.73(1H, d, J=8 Hz), 9.04(1H, t, J=5 Hz); Mass: (ESI–) 471(M–H).

EXAMPLE 84(1)

2-[1-(tert-Butoxycarbonyl)piperidin-3-ylamino]-5-cyano-N-(3,4-dimethoxybenzyl)benzamide (368 mg) was obtained as amorphous powders from 5-cyano-N-(3,4-dimethoxybenzyl)-2-fluorobenzamide (300 mg) and 3-amino-1-tert-butoxycarbonylpiperidine (249mg) in a manner similar to Example 1(1).

NMR (DMSO-d$_6$, δ): 1.10–1.75(12H, m), 1.88(1H, m), 2.95–3.65(5H, m3, 3.72(3H, s), 3.74(3H, s), 4.35(2H, d, J=6 Hz), 6.80–6.96(4H, m), 7.65(1H, d, J=9 Hz), 8.10(1H, s), 8.75–9.10(1H, m), 9.03(1H, t, J=6 Hz); Mass: (ESI–) 493 (M–H).

EXAMPLE 84(2)

5-Cyano-N-(3,4-dimethoxybenzyl)-2-(piperidin-3-ylamino)benzamide (283 mg) was obtained as an oil from 2-[1-(tert-butoxycarbonyl)piperidin-3-ylamino]-5-cyano-N-(3,4-dimethoxybenzyl)benzamide (311 mg) in a manner similar to Example 77(2).

NMR (DMSO-d$_6$, δ): 1.44(2H, m), 1.58(1H, m), 1.82(1H, m), 2.45(1H, dd, J=7, 10 Hz), 2.56(1H, m), 2.71(1H, m), 2.97(1H, dd, J=4, 10 Hz), 3.52(1H, m), 3.72(3H, s), 3.74 (3H, s), 4.36(2H, d, J=6 Hz), 6.80–6.95(4H, m), 7.60(1H, dd, J=3, 9 Hz), 8.04(1H, d, J=3 Hz), 8.78(1H, d, J=8 Hz), 8.98(1H, t, J=6 Hz); Mass: (ESI+) 395(M+H), (ESI–) 393 (M–H).

EXAMPLE 84(3)

5-Cyano-N-(3,4-dimethoxybenzyl)-2-(1-formylpiperidin-3-ylamino)benzamide (61 mg) was obtained as amorphous powders from 5-cyano-N-(3,4-dimethoxybenzyl)-2-(piperidin-3-ylamino)benzamide (94 mg) in a manner similar to Example 73(2).

NMR (DMSO-d$_6$, δ): 1.40–1.75(3H, m), 3.06–3.84(5H, m), 3.72(3H, s), 3.74(3H, s), 4.36(2H, d, J=6 Hz), 6.80–7.01 (4H, m), 7.63 and 7.67(1H, d, J=9 Hz), 7.95 and 8.05(1H, s), 8.08(1H, br), 8.80 and 8.84(1H, d, J=8 Hz), 9.04(1H, t, J=6 Hz); Mass: (ESI+) 423(M+H), (ESI–) 421(M–H).

EXAMPLE 84(4)

5-Cyano-N-(3,4-dimethoxybenzyl)-2-[1-(methanesulfonyl)piperidin-3-ylamino]benzamide (83 mg) was obtained as white crystals from 5-cyano-N-(3,4-dimethoxybenzyl)-2-(piperidin-3-ylamino)benzamide (82 mg) in a manner similar to Example 73(3).

NMR (DMSO-d$_6$, δ): 1.44–1.94(4H, m), 2.8–2.96(1H, m), 2.88(3H, s), 3.04(1H, m), 3.22(1H, m), 3.42(1H, m), 3.72(3H, s), 3.74(3H, s), 3.80(1H, m), 4.36(2H, d, J=5 Hz), 6.84(1H, d, J=2, 8 Hz), 6.88–6.92(2H, m), 6.94(1H, d, J=2 Hz), 7.66(1H, dd, J=2, 9 Hz), 8.08(1H, d, J=2 Hz), 8.85(1H, d, J=8 Hz), 9.04(1H, t, J=5 Hz); Mass: (ESI+) 473(M+H), 495(M+Na), (ESI–) 471(M–H).

PREPARATION 85(1)

A solution of di-tert-butyl dicarbonate (5.44 g) in dioxane (10 mL) was added dropwise to a solution of (S)-3-benzyloxycarbonylaminopyrrolidine (3.66 g) in dioxane (10 mL) under cooling on an ice bath. The reaction mixture was stirred at ambient temperature overnight, then the reaction was quenched by addition of 3-(N,N-dimethylamino)propylamine (5 mL). The mixture was concentrated in vacuo and the residue was partitioned between ethyl acetate and 3.6% hydrochloric acid. The organic layer was washed with an aqueous saturated sodium bicarbonate solution and brine, dried over magnesium sulfate and concentrated in vacuo. The residue was purified by a silica gel column chromatography eluting with 30% ethyl acetate in hexane to give (S)-3-benzyloxycarbonylamino-1-tert-butoxycarbonylpyrrolidine (1.26 g) as an oil.

NMR (CDCl$_3$, δ): 1.45(9H, s), 1.84(1H, m), 2.14(1H, m), 3.20(1H, m), 3.33–3.50(2H, m), 3.61(1H, dd, J=2, 10 Hz), 4.25(1H, m), 4.85(1H, m), 5.10(2H, s), 7.27–7.41(5H, m); Mass: (ESI+) 321(M+H).

PREPARATION 85(2)

(S)-3-Amino-1-tert-butoxycarbonylpyrrolidine (2.49 g) was obtained as syrup from (S)-3-benzyloxycarbonylamino-1-tert-butoxycarbonylpyrrolidine (4.10 g) in a manner similar to Preparation 78(3).

NMR (DMSO-d$_6$, δ): 1.39(9H, s), 1.57(1H, m), 1.88(1H, m), 2.89(1H, dd, J=5, 11 Hz), 3.00–3.40(3H, m), 3.42(1H, m); Mass: (ESI+) 187(M+H).

EXAMPLE 85(1)

(S)-2-[1-(tert-Butoxycarbonyl)pyrrolidin-3-ylamino]-5-cyano-N-(3,4-dimethoxybenzyl)benzamide (368 mg) was obtained as amorphous powders from 5-cyano-N-(3,4-dimethoxybenzyl)-2-fluorobenzamide (500 mg) and (S)-3-amino-1-tert-butoxycarbonylpyrrolidine (593 mg) in a manner similar to Example 1(1).

NMR(DMSO-d$_6$, δ): 1.82(1H, m), 2.20(1H, m), 3.10(1H, m), 3.25–3.45(2H, m), 3.61(1H, m), 3.72(3H, s), 3.74(3H, s), 4.18(1H, m), 4.35(2H, d, J=6 Hz), 6.84(1H, dd, J=2, 8 Hz), 6.80–6.94(3H, m), 7.66(1H, dd, J=2, 8 Hz), 8.09(1H, d, J=2 Hz), 8.82(1H, d, J=7 Hz), 9.05(1H, t, J=6 Hz).

EXAMPLE 85(2)

(S)-5-Cyano-N-(3,4-dimethoxybenzyl)-2-(3-pyrrolidinylamino)benzamide (201 mg) was obtained as amorphous powders from (S)-2-[1-(tert-butoxycarbonyl)pyrrolidin-3-ylamino]-5-cyano-N-(3,4-dimethoxybenzyl)benzamide (277 mg) in a manner similar to Example 77(2).

NMR (DMSO-d$_6$, δ): 1.50(1H, m), 2.11(1H, m), 2.57(1H, dd, J=4, 10 Hz), 2.70–2.95(2H, m), 3.13(1H, dd, J=6, 10 Hz), 3.72(3H, s), 3.74(3H, s), 3.96(1H, m), 4.34(2H, d, J=6 Hz), 6.78–6.94(4H, m), 7.64(1H, dd, J=2, 8 Hz), 8.06(1H, d, J=2 Hz), 8.72(1H, d, J=7 Hz), 9.02(1H, t, J=6 Hz); Mass: (ESI+) 381(M+H), (ESI–) 379(M–H).

EXAMPLE 85(3)

(S)-5-Cyano-N-(3,4-dimethoxybenzyl)-2-[1-(methanesulfonyl)pyrrolidin-3-ylamino]benzamide (81 mg) was obtained as white crystals from (S)-5-cyano-N-(3,4-dimethoxybenzyl)-2-(3-pyrrolidinylamino)benzamide (100 mg) in a manner similar to Example 73(3).

NMR PDMSO-d$_6$, δ): 1.89(1H, m), 2.30(1H, m), 2.90 (3H, s), 3.09(1H, dd, J=4, 10 Hz), 3.28–3.45(2H, m), 3.62 (1H, dd, J=6, 10 Hz), 3.72(3H, s), 3.74(3H, s), 4.25(1H, m), 4.36(2H, d, J=6 Hz), 6.84(1H, dd, J=2, 8 Hz), 6.85–6.94(3H, m), 7.68(1H, d, J=2, 8 Hz), 8.09(1H, d, J=2 Hz), 8.84(1H, d, J=7 Hz), 9.07(1H, t, J=6 Hz); Mass: (ESI+) 459(M+H), (ESI–) 457(M–H).

EXAMPLE 85(4)

(S)-5-Cyano-N-(3,4-dimethoxybenyl)-2-(1-formylpyrrolidin-3-ylamino)benzamide (89 mg) was obtained as amorphous powders from (S)-5-cyano-N-(3,4-dimethoxybenzyl)-2-(3-pyrrolidinylamino)benzamide (100 mg) in a manner similar to Example 73(2).

NMR (DMSO-d$_6$, δ): 1.86(1H, m), 2.25(1H, m), 3.15 (ca.0.5H, dd, J=4, 10 Hz), 3.25–3.75(3H, m), 3.72(3H, s), 3.74(3H, s), 3.84(ca.0.5H, dd, J=6, 10 Hz), 4.13–4.29(1H, m), 4.35(1H, d, J=6 Hz), 6.83(1H, d, J=8 Hz), 6.88–6.96(3H, m), 7.68(1H, dd, J=2, 8 Hz), 8.10(1H, d, J=2 Hz), 8.17 and 8.19(1H, s), 8.82(1H, d, J=7 Hz), 9.06(1H, t, J=6 Hz); Mass: (ESI+) 409(M+H), (ESI–) 407(M–H).

EXAMPLE 85(5)

A solution of methyl chloroformate (26 mg) in chloroform (2 mL) was added dropwise to a mixture of (S)-5-cyano-N-(3,4-dimethoxybenzyl)-2-(3-pyrrolidinylamino)benzamide (80 mg) and triethylamine (43 mg) in a mixture of chloroform (2 mL) and 1,3-dimethyl-2-imidazolidinone (1 mL) under cooling on an ice bath. The reaction mixture was stirred for 2 hours at same temperature and the reaction was quenched by addition of 3-(N,N-dimethylamino)propylamine (0.1 mL). The mixture was concentrated in vacuo, and the residue was partitioned between ethyl acetate and 3.6% hydrochloric acid. The organic layer was washed with an aqueous saturated sodium bicarbonate solution and brine, dried over magnesium sulfate and concentrated in vacuo. The residue was purified by a silica gel column chromatography eluting with 70% ethyl acetate in hexane. The obtained crystals were recrystallized from a mixture of 2-propanol and diisopropyl ether to give (S)-5-cyano-N-(3,4-dimethoxybenzyl)-2-[1-(methoxycarbonyl)pyrrolidin-3-ylamino]benzamide (55 mg) as white crystals.

NMR (DMSO-d$_6$, δ): 1.86(1H, m), 2.21(1H, m), 3.16(1H, m), 3.30–3.50(2H, m), 3.55–3.80(1H, m), 3.57 and 3.59(3H, s), 3.72(3H, s), 3.74(3H, s), 4.20(1H, m), 4.35(2H, d, J=6 Hz), 6.83(1H, d, J=2, 8 Hz), 6.88–6.94(3H, m), 7.66(1H, dd, J=2, 8 Hz), 8.09(1H, d, J=2 Hz), 8.83(1H, d, J=7 Hz), 9.06(1H, t, J=6 Hz); Mass: (ESI–) 437(M–H).

EXAMPLE 85(6)

Acetic anhydride (64 mg) was added to a solution of (S)-5-cyano-N-(3,4-dimethoxybenzyl)-2-(3-pyrrolidinylamino)benzamide (80 mg) in pyridine (1 mL). The mixture was stirred for an hour at ambient temperature. The mixture was partitioned between ethyl acetate and 1% hydrochloric acid. The organic layer was washed with an aqueous saturated sodiunn bicarbonate solution and brine. The resultant was dried over magnesium sulfate and concentrated in vacuo. The residue was purified by a thin layer chromatography developed with 5% methanol in chloroform to give (S)-2-(1-acetylpyrrolidin-3-ylamino)-5-cyano-N-(3,4-dimethoxybenzyl)benzamide (62mg) as amorphous powders.

NMR (DMSO-d$_6$, δ): 1.72–1.88(1H, m), 1.92 and 1.95 (3H, s), 2.13–2.36(1H, m), 3.20(ca.0.5H, dd, J=3, 12 Hz), 3.27(ca.0.5H, dd, J=5, 10 Hz), 3.35–3.60(4H, m), 3.63 (ca.0.5H, dd, J=6, 12 Hz), 3.72(3H, s), 3.74(3H, s), 3.85 (ca.0.5H, dd, J=4, 10 Hz), 4.18 and 4.26(1H, m), 4.35(2H, d, J=6 Hz), 6.83(1H, dd, J=2, 8 Hz), 6.80–6.96(3H, m), 7.67(1H, dd, J=2, 8 Hz), 8.09(1H, d, J=2 Hz), 8.81 and 8.86(1H, d, J=6 Hz), 9.06(1H, t, J=6 Hz); Mass: (ESI+) 423(M+H), (ESI–) 421(M–H).

EXAMPLE 86

(R)-5-Cyano-N-(3,4-dimethoxybenzyl)-2-(tetrahydrofuran-3-ylamino)benzamide (96 mg) was obtained from 5-cyano-N-(3,4-dimethoxybenzyl)-2-fluorobenzamide (126 mg) and (R)-3-aminotetrahydrofuran toluene-4-sulfonate (135 mg) in a manner similar to Example 1(1).

NMR (DMSO-d$_6$, δ): 1.74 (1H, m), 2.27 (1H, m), 3.54 (1H, dd, J=3,9 Hz), 3.70–3.92 (3H, m), 3.72 (3H, s), 3.74 (3H, s), 4.20 (1H, m), 4.35 (2H, d, J=6 Hz), 6.81–6.95 (4H, m), 7.66 (1H, dd, J=2, 9 Hz), 8.08 (1H, d, J=2 Hz), 8.81(1H, d, J=7 Hz), 9.05 (1H, t, J=6 Hz); Mass m/z: 380 (M$^+$–1).

EXAMPLE 87(1)

(R)-2-[1-(tert-Butoxycarbonyl)pyrrolidin-3-ylamino]-5-cyano-N-(3,4-dimethoxybenzyl)benzamide (918 mg) was obtained as amorphous powders from 5-cyano-N-(3,4-dimethoxybenzyl)-2-fluorobenzamide (700 mg) and (R)-3-amino-1-tert-butoxycarbonylpyrrolidine (830 mg) in a manner similar to Example 1(1).

NMR (DMSO-d$_6$, δ): 1.82(1H, m), 2.20(1H, m), 3.10(1H, m), 3.25–3.45(2H, m), 3.61(1H, m), 3.72(3H, s), 3.74(3H, s), 4.18(1H, m), 4.35(2H, d, J=6 Hz), 6.84(1H, dd, J=2, 8 Hz), 6.80–6.94(3H, m), 7.66(1H, dd, J=2, 8 Hz), 8.09(1H, d, J=2 Hz), 8.82(1H, d, J=7 Hz), 9.05(1H, t, J=6 Hz).

EXAMPLE 87(2)

Trifluoroacetic acid (5 mL) was added to a solution of (R)-2-[1-(tert-butoxycarbonyl)pyrrolidin-3-ylamino]-5- cyano-N-(3,4-dimethoxybenzyl)benzamide (918 mg) in chloroform (5 mL). The mixture was stirred for 4 hours at ambient temperature and concentrated in vacuo. The residue was partitioned between chloroform and an aqueous saturated sodium bicarbonate solution. The organic layer was dried over magnesium sulfate and concentrated in vacuo to give (R)-5-cyano-N-(3,4-dimethoxybenzyl)-2-(3-pyrrolidinylamino)benzamide (610 mg) as amorphous powders.

NMR (DMSO-$d_6$, δ): 1.50(1H, m), 2.11(1H, m), 2.57(1H, dd, J=4, 10 Hz), 2.7–2.95(2H, m), 3.13(1H, dd, J=6, 10 Hz), 3.72(3H, s), 3.74(3H, s), 3.96(1H, m), 4.34(2H, d, J=6 Hz), 6.78–6.94(4H, m), 7.64(1H, dd, J=2, 8 Hz), 8.06(1H, d, J=2 Hz), 8.72(1H, d, J=7 Hz), 9.02(1H, t, J=6 Hz).

EXAMPLE 87(3)

(R)-5-Cyano-N-(3,4-dimethoxybenzyl)-2-[1-(methanesulfonyl)pyrrolidin-3-ylamino]benzamide (93 mg) was obtained as white crystals from (R)-5-cyano-N-(3,4-dimethoxybenzyl)-2-(3-pyrrolidinylamino)benzamide (114 mg) in a manner similar to Example 73(3).

NMR (DMSO-$d_6$, δ): 1.89(1H, m), 2.30(1H, m), 2.90(3H, s), 3.09(1H, dd, J=4, 10 Hz), 3.28–3.45(2H, m), 3.62(1H, dd, J=6, 10 Hz), 3.72(3H, s), 3.74(3H, s), 4.25(1H, m), 4.36(2H, d, J=6 Hz), 6.84(1H, dd, J=2, 8 Hz), 6.85–6.94(3H, m), 7.68(1H, d, J=2, 8 Hz), 8.09(1H, d, J=2 Hz), 8.84(1H, d, J=7 Hz), 9.07(1H, t, J=6 Hz).

EXAMPLE 87(4)

(R)-5-Cyano-N-(3,4-dimethoxybenzyl)-2-[1-(methoxycarbonyl)pyrrolidin-3-ylamino]benzamide (94 mg) was obtained as powders from (R)-5-cyano-N-(3,4-dimethoxybenzyl)-2-(3-pyrrolidinylamino)benzamide (116 mg) in a manner similar to Example 85(5).

NMR (DMSO-$d_6$, δ): 1.86(1H, m), 2.21(1H, m), 3.16(1H, m), 3.30–3.50(2H, m), 3.55–3.80(1H, m), 3.57 and 3.59(3H, s), 3.72(3H, s), 3.74(3H, s), 4.20(1H, m), 4.35(2H, d, J=6 Hz), 6.83(1H, d, J=2, 8 Hz), 6.88–6.94(3H, m), 7.66(1H, dd, J=2, 8 Hz), 8.09(1H, d, J=2 Hz), 8.83(1H, d, J=7 Hz), 9.06(1H, t, J=6 Hz).

EXAMPLE 87(5)

(R)-2-(1-Acetylpyrrolidin-3-ylamino)-5-cyano-N-(3,4-dimethoxybenzyl)benzamide (66 mg) was obtained as amorphous powders from (R)-5-cyano-N-(3,4-dimethoxybenzyl)-2-(3-pyrrolidinylamino)benzamide (100 mg) in a manner similar to Example 85(6).

NMR (DMSO-$d_6$, δ): 1.72–1.88(1H, m), 1.92 and 1.95 (3H, s), 2.13–2.36(1H, m), 3.20(ca.0.5H, dd, J=3, 12 Hz), 3.27(ca.0.5H, dd, J=5, 10 Hz), 3.35–3.60(4H, m), 3.63 (ca.0.5H, dd, J=6, 12 Hz), 3.72(3H, s), 3.74(3H, s), 3.85 (ca.0.5H, dd, J=4, 10 Hz), 4.18 and 4.26(1H, m), 4.35(2H, d, J=6 Hz), 6.83(1H, dd, J=2, 8 Hz), 6.80–6.96(3H, m), 7.67(1H, dd, J=2, 8 Hz), 8.09(1H, d, J=2 Hz), 8.81 and 8.86(1H, d, J=6 Hz), 9.06(1H, t, J=6 Hz).

EXAMPLE 87(6)

(R)-5-Cyano-N-(3,4-dimethoxybenzyl)-2-(1-formylpyrrolidin-3-ylamino)benzamide (52 mg) was obtained as amorphous powders from (R)-5-cyano-N-(3,4-dimethoxybenzyl)-2-(3-pyrrolidinylamino)benzamide (100 mg) in a manner similar to Example 73(2).

NMR (DMSO-$d_6$, δ): 1.86(1H, m), 2.25(1H, m), 3.15 (ca.0.5H, dd, J=4, 10 Hz), 3–25–3.75(3H, m), 3.72(3H, s), 3.74(3H, s), 3.84(ca.0.5H, dd, J=6, 10 Hz), 4.13–4.29(1H, m), 4.35(1H, d, J=6 Hz), 6.83(1H, d, J=8 Hz), 6.88–6.96(3H, m), 7.68(1H, dd, J=2, 8 Hz), 8.10(1H, d, J=2 Hz), 8.17 and 8.19(1H, s), 8.82(1H, d, J=7 Hz), 9.06(1H, t, J=6 Hz).

EXAMPLE 87(7)

A solution of potassium cyanate (53 mg) in water (1.5 mL) was added to a solution of (R)-5-cyano-N-(3,4-dimethoxybenzyl)-2-(3-pyrrolidinylamino)benzamide (100 mg) in acetic acid (1.5 mL). The mixture was stirred for 3 hours at 60° C. and then for 2 hours at 90° C. The reaction mixture was concentrated in vacuo and the residue was partitioned between chloroform and an aqueous saturated sodium bicarbonate solution. The organic layer was dried over magnesium sulfate and concentrated in vacuo. The residue was purified by thin layer chromatography developed with 5% methanol in chloroform. The obtained product was triturated with diethyl ether to give (R)-2-(1-carbamoylpyrrolidin-3-ylamino)-5-cyano-N-(3,4-dimethoxybenzyl)benzamide (22 mg) as a powders.

NMR (DMSO-$d_6$, δ): 1.83(1H, m), 2.20(1H, m), 3.12(1H, dd, J=4, 10 Hz), 3.20–3.45(2H, m), 3.57(1H, dd, J=6, 10 Hz), 3.72(3H, s), 3.74(3H, s), 4.19(1H, m), 4.35(2H, d, J=6 Hz), 5.80(2H, s), 6.84(1H, dd, J=2, 8 Hz), 6.87–6.95(3H, m), 7.66(1H, dd, J=2, 8 Hz), 8.09(1H, d, J=2 Hz), 8.83(1H, d, J=7 Hz), 9.05(1H, t, J=6 Hz); Mass: (ESI+) 424(M+H).

EXAMPLE 87(8)

A solution of benzyl alcohol (28 mg) in 1,2-dichloroethane (1 mL) was added dropwise to a solution of chlorosulfonyl isocyanate (37 mg) in 1,2-dichloroethane (2 mL) under 5° C. on an ice-salt bath. The mixture was stirred for one and a half hours at 4° C. To the mixture was added dropwise a mixture of (R)-5-cyano-N-(3,4-dimethoxybenzyl)-2-(3-pyrrolidinylamino)benzamide (100 mg) and triethylamine (40 mg) in 1,2-dichloroethane (3 mL) under 5° C. After addition, the reaction mixture was allowed to warm to ambient temperature and stirred overnight. The reaction mixture was washed with brine, dried over magnesium sulfate and concentrated in vacuo. The residue was purified by a thin layer chromatography developed with 5% methanol in chloroform. The obtained product was triturated with diethyl ether to give (R)-2-[1-(N-benzyloxycarbonylsulfamoyl)pyrrolidin-3-ylamino]-5-cyano-N-(3,4-dimethoxybenzyl)benzamide (65 mg) as a syrup.

NMR (DMSO-$d_6$, δ): 1.84(1H, m), 2.22(1H, m), 3.21(1H, dd, J=4, 10H 3.40–3.55(2H, m), 3.65–3.80(1H, m), 3.71(3H, s), 3.72(3H, s), 4.20(1H, m), 4.36(2H, d, J=6 Hz), 5.08(2H, s), 6.83(1H, dd, J=2, 8 Hz), 6.89(1H, d, J=8 Hz), 6.93(1H, d, J=2 Hz), 7.25–7.45(6H, m), 7.68(1H, dd, J=2, 8 Hz), 8.11(1H, d, J=2 Hz), 8.85(1H, d, J=7 Hz), 9.06(1H, t, J=6 Hz); Mass: (ESI+) 594(M+H), (ESI−) 593(M−H).

EXAMPLE 87(9)

(R)-2-(1-Sulfamoylpyrrolidin-3-ylamino)-5-cyano- N-(3,4-dimethoxybenzyl)benzamide (26 mg) was obtained as white crystals from (R)-2-[1-(N-benzyloxycarbonylsulfamoyl)pyrrolidin-3-ylamino]-5-cyano-N-(3,4-dimethoxybenzyl)benzamide (60 mg) in a manner similar to Preparation 78(3).

NMR (DMSO-$d_6$, δ): 1.79(1H, m), 2.29(1H, m), 2.94(1H, dd, J=5, 10 Hz), 3.15–3.30(2H, m), 3.51(1H, dd, J=7, 10 Hz), 3.72(3H, s), 3.74(3H, s), 4.22(1H, m), 4.36(2H, d, J=6 Hz), 6.80–6.95(6H, m), 7.67(1H, dd, J=2, 9 Hz), 8.10(1H, d, J=2 Hz), 8.85(1H, d, J=7 Hz), 9.07(1H, t, J=6 Hz).

PREPARATION 88(1)

To a solution of 5-bromo-2-fluorobenzaldehyde (10 g) in dimethylformamide (60 mL) were added zinc cyanide (6.92 g) and tetrakis(triphenylphosphine)palladium(O) (2.28 g), and the mixture was stirred at 80° C. for 6 hours. The resulting mixture was diluted with ethyl acetate and washed successively with water and brine. The organic layer was dried over sodium sulfate and evaporated in vacuo. The residue was subjected to a silica gel column chromatography eluting with a mixture of hexane and ethyl acetate (3:1) to give 5-cyano-2-fluorobenzaldehyde (5.3 g) as a solid substance.

NMR (DMSO-$d_6$, $\delta$): 7.35 (1H, t, J=9 Hz), 7.91 (1H, m), 8.22 (1H, dd, J=2, 7 Hz), 10.36 (1H, s); Mass m/z: 150 ($M^+$+1).

PREPARATION 88(2)

To a solution of 5-cyano-2-fluorobenzaldehyde (145 mg) in acetonitrile (2 mL) were added a sodium dihydrogenphosphate aqueous solution (23 mg in 1 mL water) and 30% hydrogen peroxide (0.09 mL). To the resulting mixture was added dropwise a sodium chlorite aqueous solution (126mg in 1 mL water) for an hour at 0° C. The mixture was stirred for an hour at ambient temperature, then a small amount of sodium sulfite was added. The mixture was diluted with ethyl acetate and washed successively with 1N-hydrochloric acid and brine. The organic layer was dried over sodium sulfate and evaporated in vacuo. The residue was triturated with diisopropyl ether to give 5-cyano-2-fluorobenzoic acid (137 mg) as a solid substance.

NMR (DMSO-$d_6$, $\delta$): 7.29 (1H, t, J=9 Hz), 7.83 (1H, m), 8.32 (1H, dd, J=2, 7 Hz); Mass m/z: 164 ($M^+$−1).

PREPARATION 88(3)

5-Cyano-N-(3,4-dimethoxybenzyl)-2-fluorobenzamide (228 mg) was obtained from 5-cyano-2-fluorobenzoic acid (130 mg) and veratrylamine (0.14 mL) in a manner similar to Preparation 1.

NMR (DMSO-$d_6$, $\delta$): 3.73 (3H, s), 3.75 (3H, s), 4.40 (2H, d, J=6 Hz), 6.82–6.96 (3H, m), 7.56 (1H, t, J=9 Hz), 8.04 (1H, m), 8.11 (1H, dd, J=2, 6 Hz), 9.02 (1H, t, J=6 Hz); Mass m/z: 313 ($M^+$−1).

EXAMPLE 88(1)

(S)-5-Cyano-N-(3,4-dimethoxybenzyl)-2-(2-hydroxy-1-methylethylamino)benzamide (112 mg) was obtained from 5-cyano-N-(3,4-dimethoxybenzyl)-2-fluorobenzamide (120 mg) and (S)-2-amino-1-propanol (0.09 mL) in a manner similar to Example 1(1).

mp 142–143.5° C.; NMR (DMSO-$d_6$, $\delta$); 1.13(3H, d, J=6 Hz), 3.42 (2H, t, J=5 Hz), 3.67 (1H, m), 3.72 (3H, s), 3.74 (3H, s), 4.34 (2H, d, J=5 Hz), 4.92 (1H, t, J=5 Hz), 6.81–6.95 (4H, m), 7.60 (1H, dd, J=2, 9 Hz), 8.03 (1H, d, J=2 Hz), 8.69 (1H, d, J=8 Hz), 8.97 (1H, t, J=5 Hz); Mass m/z: 368 ($M^+$−1).

EXAMPLE 88(2)

To a solution of (S)-5-cyano-N-(3,4-dimethoxybenzyl)-2-(2-hydroxy-1-methylethylamino)benzamide (177 mg) in dimethylformamide (4 mL) was added sodium hydride (19.2 mg) at ambient temperature. After stirring for 20 minutes, 4-fluorobenzonitrile (63.8 mg) was added to the mixture. After stirring for an hour at 60° C., the mixture was diluted with ethyl acetate and washed successively with water and brine. The organic layer was dried over sodium sulfate and evaporated in vacuo. The residue was subjected to a silica gel column chromatography eluting with the mixture of chloroform and ethyl acetate (9:1) to give (S)-5-cyano-2-[2-(4-cyanophenoxy)-1-methylethylamino]-N-(3,4-dimethoxybenzyl)benzamide (76 mg) as a solid substance.

NMR (DMSO-$d_6$, $\delta$): 1.28 (3H, d, J=7 Hz), 3.49 (2H, m), 3.72 (3H, s), 3.73 (3H, s), 4.13 (3H, m), 4.34 (2H, d, J=6 Hz), 6.80–6.95 (4H, m), 7.09 (2H, d, J=9 Hz), 7.63 (1H, dd, J=2, 9 Hz), 7.76 (2H, d, J=9 Hz), 8.06 (1H, d, J=2 Hz), 8.83 (1H, d, J=8 Hz), 9.02 (1H, t, J=6 Hz); Mass m/z: 469 ($M^+$−1).

EXAMPLE 88(3)

To a solution of (S)-5-cyano-N-(3,4-dimethoxybenzyl)-2-(2-hydroxy-1-methylethylamino)benzamide (4 g) in pyridine (20 mL) was added methanesulfonyl chloride (1.36 g), and the mixture was stirred for an hour at 0° C. The resulting mixture was diluted with ethyl acetate and washed successively with water and brine. The organic layer was dried over sodium sulfate and evaporated in vacuo. The residue was triturated with diisopropyl ether to give (S)-5-cyano-N-(3,4-dimethoxybenzyl)-2-[2-(methanesulfonyloxy)-1-methylethylamino]benzamide (5.43 g) as an oil.

NMR (DMSO-$d_6$, $\delta$): 1.22 (3H, d, J=7 Hz), 3.17 (3H, s), 3.72 (3H, s), 3.74 (3H, s), 4.08 (1H, m), 4.23 (2H, d, J=5 Hz), 4.36 (2H, d, J=6 Hz), 6.81–6.96 (4H, m), 7.66 (1H, dd, J=2, 9 Hz), 8.08 (1H, d, J=2 Hz), 8.74 (1H, d, J=8 Hz), 9.05 (1H, t, J=6 Hz); Mass m/z: 448 ($M^+$+1).

EXAMPLE 88(4)

Triphenylphosphine (156 mg) was added to a mixture of (S)-5-cyano-N-(3,4-dimethoxybenzyl)-2-(2-hydroxy-1-methylethylamino)benzamide (200 mg) and carbontetrabromide (215 mg) in dichloromethane (4 mL), and the mixture was stirred for an hour at ambient temperature. After evaporation of the solvent, the residue was subjected to a silica gel column chromatography eluting with a mixture of chloroform and ethyl acetate (9:1) to give (S)-2-(2-bromo-1-methylethylamino)-5-cyano-N-(3,4-dimethoxybenzyl) benzamide (161 mg) as a solid substance.

NMR (DMSO-$d_6$, $\delta$):1.25 (3H, d, J=7 Hz), 3.67 (2H, m), 3.72 (3H, s), 3.74 (3H, s), 4.04 (1H, m), 4.36 (2H, d, J=6 Hz), 6.82–6.95 (4H, m), 7.65 (1H, dd, J=2, 9 Hz), 8.07 (1H, d, J=2 Hz), 8.79 (1H, d, J=8 Hz), 9.04 (1H, t, J=6 Hz).

EXAMPLE 88(5)

To a solution of (S)-2-(2-bromo-1-methylethylamino)-5-cyano-N-(3,4-dimethoxybenzyl)benzamide (117 mg) in dimethylsulfoxide (2 mL) was added sodium cyanide (26.5 mg), and the mixture was stirred for an hour at 90° C. The resulting mixture was diluted with ethyl acetate and washed successively with water and brine. The organic layer was dried over sodium sulfate and evaporated in vacuo. The residue was subjected to a silica gel column chromatography eluting with a mixture of chloroform and ethyl acetate (9:1) to give (S)-5-cyano-2-(2-cyano-1-methylethylamino)-N-(3,4-dimethoxybenzyl)benzamide (73 mg) as a solid substance.

NMR (DMSO-$d_6$, $\delta$): 1.29 (3H, d, J=7 Hz), 2.83 (2H, d, J=5 Hz), 3.72 (3H, s), 3.74 (3H, s), 4.08 (1H, m), 4.36 (2H, d, J=6 Hz), 6.82–6.95 (4H, m), 7.66 (1H, dd, J=2, 9 Hz), 8.09 (1H, d, J=2 Hz), 8.78 (1H, d, J=8 Hz), 9.07 (1H, t, J=6 Hz); Mass m/z: 377 ($M^+$−1).

EXAMPLE 88(6)

To a solution of (S)-2-(2-bromo-1-methylethylamino)-5-cyano-N-(3,4-dimethoxybenzyl)benzamide (61 mg) in dimethylsulfoxide (2 mL) was added imidazole (28.8 mg), and the mixture was stirred for 2 hours at 100° C. The resulting mixture was diluted with ethyl acetate and washed successively with sodium bicarbonate solution, water and brine. The organic layer was dried over sodium sulfate and evaporated in vacuo. The residue was subjected to a silica gel column chromatography eluting with 10% methanol in chloroform. The obtained product was treated with hydrochloric acid to give (S)-5-cyano-N-(3,4-dimethoxybenzyl)-2-[2-(1-imidazolyl)-1-methylethylamino]benzamide hydrochloride (24 mg) as a solid substance.

NMR (DMSO-$d_6$, δ): 1.17 (3H, d, J=7 Hz), 3.73 (3H, s), 3.75 (3H, s), 4.20–4.45 (5H, m), 6.80–6.97 (4H, m), 7.61 (1H, dd, J=2, 9 Hz), 7.64 (1H, s), 7.72 (1H, s), 8.08 (1H, d, J=2 Hz), 8.63 (1H, d, J=8 Hz), 9.09 (2H, m) Mass m/z: 454 ($M^+$–1).

EXAMPLE 88(7)

(S)-5-Cyano-N-(3,4-dimethoxybenzyl)-2-[2-(2-methylimidazol-1-yl)-1-methylethylamino]benzamide hydrochloride (68 mg) was obtained from (S)-2-(2-bromo-1-methylethylamino)-5-cyano-N-(3,4-dimethoxybenzyl) benzamide (153 mg) and 2-methylimidazole (87.1 mg) in a manner similar to Example 88 (6).

NMR (DMSO-$d_6$, δ): 1.23 (3H, d, J=7 Hz), 3.70 (1H, m), 3.73 (3H, s), 3.75 (3H, s), 4.29 (2H, m), 4.36 (1H, d, J=6 Hz), 6.70–6.95 (4H, m), 7.49 (1H, d, J=2 Hz), 7.56 (1H, dd, J=2, 9 Hz), 7.62 (1H, d, J=2 Hz), 8.04 (1H, d, J=2 Hz), 8.57 (1H, d, J=8 Hz), 9.11 (1H, t, J=6 Hz); Mass m/z: 468 ($M^+$–1).

EXAMPLE 88(8)

To a solution of (S)-2-(2-bromo-1-methylethylamino)-5-cyano-N-(3,4-dimethoxybenzyl)benzamide (147 mg) in dimethylsulfoxide (2 mL) was added benzenesulfonic acid sodium salt (81.6 mg), and the mixture was stirred for 3 hours at 90° C. The resulting mixture was diluted with ethyl acetate and washed successively with water and brine. The organic layer was dried over sodium sulfate and evaporated in vacuo. The residue was subjected to a silica gel column chromatography eluting with a mixture of chloroform and ethyl acetate (9:1) to give (S)-5-cyano-N-(3,4-dimethoxybenzyl)-2-(2-phenylsulfonyl-1-methylethylamino)benzamide (94 mg) as a solid substance.

NMR (DMSO-$d_6$, δ): 1.27 (3H, d, J=7 Hz), 3.65 (2H, m), 3.72 (3H, s), 3.74 (3H, s), 4.07 (1H, m), 4.30 (2H, m), 6.62 (1H, d, J=9 Hz), 6.83 (1H, dd, J=2, 9 Hz), 6.91 (1H, d, J=9 Hz), 6.92 (1H, d, J=2 Hz), 7.48–7.69 (4H, m), 7.79 (1H, d, J=8 Hz), 7.99 (1H, d, J=2 Hz), 8.55 (1H, d, J=8 Hz), 8.93 (1H, t, J=6 Hz); Mass m/z: 492 ($M^+$–1).

EXAMPLE 88(9)

To a solution of (S)-2-(2-bromo-1-methylethylamino)-5-cyano-N-(3,4-dimethoxybenzyl)benzamide (101 mg) in a mixture of dimethylformamide (1.5 mL) and water (0.2 mL) was added sodium acide (45.6 mg), and the mixture was stirred for 2 hours at 80° C. The resulting mitre was diluted with ethyl acetate and washed successively with water and brine. The organic layer was dried over sodium sulfate and evaporated in vacuo The residue was triturated with diethyl ether to give (S)-2-(2-azido-1-methylethylamino)-5-cyano-N-(3,4-dimethoxybenzyl)benzamide (75 mg) as a solid substance.

NMR (DMSO-$d_6$, δ): 1.18 (3H, d, J=7 Hz), 3.49 (2H, m), 3.72 (3H, s), 3.74 (3H, s), 3.96 (1H, m), 4.36 (2H, d, J=6 Hz), 6.81–6.95 (4H, m), 7.64 (1H, dd, J=2,9 Hz), 8.07 (1H, d, J=2 Hz), 8.74 (1H, d, J=8 Hz), 9.03 (1H, t, J=6 Hz); Mass m1/; 393 ($M^+$–1).

EXAMPLE 88(10)

To a solution of (S)-2-(2-azido-1-methylethylamino)-5-cyano-N-(3,4-dimethoxybenzyl)benzamide (505 mg) in a mixture of ethanol (5 mL) and dichloromethane (3 mL) was added 10% palladium on activated carbon (60 mg), and the mixture was stirred under hydrogen atmosphere (1 atm) for 3 hours at ambient temperature. The resulting mixture was filtered through celite and washed with ethanol. The filtrate and the washings were combined and evaporated in vacuo. The residue was subjected to a silica gel column chromatography eluting with 10% methanol in chloroform to give (S)-2-(2-amino-1-methylethylamino)-5-cyano-N-(3,4-dimethoxybenzyl)benzamide (393 mg) as a solid substance.

NMR (DMSO-$d_6$, δ): 1.13 (3H, d, J=7 Hz), 1.58 (2H, br), 2.55 (1H, m), 2.57 (1H, m), 3.54 (1H, m), 3.72 (3H, s), 3.74 (3H, s), 4.35 (2H, d, J=6 Hz), 6.81–6.95 (4H, m), 7.59 (1H, dd, J=2, 9 Hz), 8.02 (1H, d, J=2 H), 8.66 (1H, d, J=8 Hz), 8.98 (1H, t, J=6 Hz); Mass m/z: 367 ($M^+$–1).

EXAMPLE 88(11)

(S)-5- Oyano-N-(3,4-dimethoxybenzyl)-2-[2-(formamido)-1-methylethylamino]benzamide (73 mg) was obtained from (S)-2-(2-amino-1-methylethylamino)-5-cyano-N-(3,4-dimethoxybenzyl)benzamide (100 mg) and ethyl formate (2.0 g) in a manner similar to Example 73(2).

NMR (DMSO-$d_6$, δ): 1.16 (3H, d, J=7 Hz), 3.05 (1H, m), 3.28 (1H, m), 3.70 (1H, m), 3.72 (3H, s), 3.74 (3H, s), 4.35 (2H, d, J=6 Hz), 6.81–6.98 4H, m), 7.63 (1H, dd, J=2, 9 Hz), 8.03–8.07 (2H, m), 8.26 (1H, m), 8.63 (1H, d, J=8 Hz), 9.01 (1H, t, J=6 Hz). Mass m/z: 395 ($M^+$–1).

EXAMPLE 88(12)

To a solution of (S)-2-(2-amino-1-methylethylamino)-5-cyano-N-(3,4-dimethoxybenzyl)benzamide (99 mg) in dichloromethane (3 mL) was added acetic anhydride (38 mg), and the mixture was stirred for an hour at ambient temperature. The resulting mixture was evaporated in vacuo. The residue was triturated with diisopropyl ether to give (S)-2-[2-(acetamido)-1-methylethylamino]-5-cyano-N-(3,4-dimethoxybenzyl)benzamide (107 mg) as a solid substance.

NMR (DMSO-$d_6$, δ): 1.15 (3H, d, J=7 Hz), 1.80 (3H, s), 3.04 (1H, m), 3.23 (1H, m), 3.68 (1H, m), 3.72 (3H, s), 3.74 (3H, s), 4.35 (2H, d, J=6 Hz), 6.81–7.02 (4H, m), 7.63 (1H, dd, J=2, 9 Hz), 8.05 (1H, d, J=8 Hz), 8.10 (1H, t, J=6 Hz, 8.59 (1H, d, J=8 Hz), 9.01 (1H, t, J=6 Hz); Mass m/z: 409 ($M^+$–1).

EXAMPLE 88(13)

To a mixture of (S)-2-(2-amino-1-methylethylamino)-5-cyano-N-(3,4-dimethoxybenzyl)benzamide (98 mg) and triethylamine (0.074 mL) in dichloromethane (3 mL) was added methanesulfonyl chloride (0.029 mL), and the mixture was stirred for an hour at ambient temperature. The resulting mixture was diluted with ethyl acetate and washed successively with water and brine. The organic layer was dried over sodium sulfate and evaporated in vacuo. The residue was triturated with diisopropyl ether to give (S)-5-cyano-N-(3,4-dimethoxybenyl1)-2-[2-(methanesulfonylamino)-1-methylethylamino]benzamide (110 mg) as a solid substance.

NMR (DMSO-$d_6$, δ): 1.19 (3H, d, J=7 Hz), 2.88 (3H, s), 2.94 (1H, m), 3.07 (1H, m), 3.68 (1H, m), 3.72 (3H, s), 3.74

(3H, s), 4.35(2H, d, J=6 Hz), 6.81–6.94 (4H, m), 7.27 (1H, t, J=6 Hz), 7.64 (1H, dd, J=2, 9 Hz), 8.05 (1H, d, J=8 Hz), 8.63 (1H, a, J=8 Hz), 9.02 (1H, t, J=6 Hz); Mass m/z: 445 ($M^+$–1).

EXAMPLE 88(14)

(S)-5-Cyano-2-[2-(ethoxycabonylamino)-1-methylethylamino]-N-(3,4-dimethoxybenzyl)benzamide (60 mg) was obtained from (S)-2-(2-amino-1-methylethylamino)-5-cyano-N-(3,4-dimethoxybenzyl) benzamide (110 mg) and ethyl chloroformate (0.04 mL) in a manner similar to Example 88(13).

NMR (DMSO-$d_6$, δ): 1.14 (3H, t, J=7 Hz), 1.15 (3H, d, J=7 Hz), 2.87 (1H, m), 3.15 (1H, m), 3.67 (1H, m), 3.72 (3H, s), 3.74 (3H, s), 3.98 (2H, q, J=7 Hz), 4.35 (2H, d, J=6 Hz), 6.82–6.99 (4H, m), 7.37 (1H, t, J=6 Hz), 7.63 (1H, dd, J=2, 9 Hz), 8.05 (1H, d, J=8 Hz), 8.59 (1H, d, J=8 Hz), 9.00 (1H, t, J=6 Hz); Mass m/z: 439 ($M^+$–1).

EXAMPLE 88(15)

To a solution of (S)-2-(2-amino-1-methylethylamino)-5-cyano-N-(3,4-dimethoxybenzyl)benzamide (52 mg) in ethanol (3 mL) was added dimethyl N-cyanodithioiminocarbonate (22.7 mg), and the mixture was stirred for 6 hours at ambient temperature. The solvent of the reaction mixture was evaporated in vacuo. The residue was subjected to a silica gel column chromatography eluting with a mixture of chloroform and ethyl acetate (2:1) to give (S)-5-cyano-2-[2-(N-cyano-S-methylisothioureido)-1-methylethylamino]-N-(3,4-dimethoxybenzyl)benzamide (52 mg) as a solid substance.

NMR (DMSO-$d_6$, δ): 1.18 (3H, d, J=7 Hz), 3.29 (1H, m), 3.34 (3H, s), 3.44 (1H, m), 3.72 (3H, s), 3.75 (3H, s), 3.93 (1H, m), 4.36 (2H, m), 6.81–6.97 (4H, m), 7.62 (1H, dd, J=2, 9 Hz), 8.06 (1H, d, J=8 Hz), 8.49 (1H, br), 8.64 (1H, d, J=8 Hz), 9.02 (1H, t, J=6H); Mass m/z: 465 ($M^+$–1).

EXAMPLE 88(16)

To a solution of (S)-5-cyano-2-[2-(N-cyano-S-methylisothioureido)-1-methylethylamino]-N-(3,4-dimethoxybenzyl)benzamide (48 mg) in ethanol (2 mL) was added methylamine in methanol (30%, 0.3 mL), and the mixture was stirred in a sealed tube for 6 hours at 60° C. The resulting mixture was evaporated in vacuo and the residue was triturated with diethyl ether to give (S)-5-cyano-2-[2-(2-cyano-3-methylguanidino)-1-methylethylamino]-N-(3,4-dimethoxybenzyl)benzamide (32 mg) as a solid substance.

NMR (DMSO-$d_6$, δ): 1.17 (3H, d, J=7 Hz), 2.63 (3H, d, J=5 Hz), 3.07 (1H, m), 3.27 (1H, m), 3.72 (3H, s), 3.74 (3H, s), 3.83 (1H, m), 4.35 (2H, m), 6.82–7.00 (4H, m), 7.07 (1H, q, J=5 Hz), 7.14 (1H, t, J=5 Hz), 7.60 (1H, dd, J=2, 9 Hz), 8.05 (1H, d, J=8 Hz), 8.59 (1H, d, J=8 Hz), 9.02 (1H, t, J=6 Hz); Mass m/z: 448 ($M^+$–1).

EXAMPLE 88(17)

(R)-5-Cyano-N-(3,4-dimethoxybenzyl)-2-(2-hydroxy-1-methylethylamino)benzamide (103 mg) was prepared from 5-cyano-N-(3,4-dirnethoxrbenzyl)-2-fluorobenzamide (115 mg) and (R)-2-amino-1-propanol (0.085 mL) in a similar manner to Example 1(1).

NMR (DMSO-$d_6$, δ): 1.13(3H, d, J=6 Hz), 3.42(2H, t, J=5 Hz), 3.67(1H, m), 3.72(3H, s), 3.74(3H, s), 4.34(2H, d, J=5 Hz), 4.92(1H, t, J=5 Hz), 6.81–6.95(4H, m), 7.60(1H, dd, J=2, 9 Hz), 8.03(1H, d, J=2 Hz), 8.69(1H, d, J=8 Hz), 8.97(1H, t, J=5 Hz); Mass m/z: 168 ($M^+$–1).

PREPARATION 89(1)

5-Bromo-N-(3,4-dimethoxybenzyl)-2-fluorobenzamide (4.01 g) was obtained from 5-bromo-2-fluorobenzoic acid (3.0 g) and veratrylamine (2.27 mL) in a in a manner similar to Preparation 1.

NMR (DMSO-$d_6$, δ): 3.73 (3H, s), 3.74 (3H, s), 4.38 (2H, d, J=6 Hz), 6.82–6.96 (3H, m), 7.31 (1H, t, J=9 Hz), 7.68–7.76 (2H, m), 8.94 (1H, t, J=6 Hz); Mass m/z: 366, 368 ($M^+$–1).

PREPARATION 89(2)

To a solution of 5-bromo-N-(3,4-dimethoxybenzyl)-2-fluorobenzamide (200 mg) in dimethylformamide (2 mL) were added methyl acrylate (0.068 mL), triethylamine (0.09 mL) and dichlorobis(triphenylphosphine)pailadium(II) (13.4 mg), and the mixture was stirred for 6 hours at 120° C. in a sealed tube. The resulting mixture was diluted with ethyl acetate and washed successively with water and brine. The organic layer was dried over sodium sulfate and evaporated in vacuo. The residue was subjected to a silica gel column chromatography eluting with a mixture of chloroform and ethyl acetate (9:1) to give N-(3,4-dimethoxybenzyl)-2-fluoro-5-[trans-2-(methoxycarbonyl)ethenyl]benzamide (117 mg) as a solid substance.

NMR (DMSO-$d_6$, δ): 3.73 (3H, s), 3.74 (3H, s), 3.75 (3H, s), 4.40 (2H, d, J=6 Hz), 6.68 (1H, d, J=16 Hz), 6.82–6.96 (3H, m), 7.36 (1H, t, J=9 Hz), 7.70 (1H, d, J=16 Hz), 7.87–7.96 (2H, m), 8.91 (1H, t, J=6 Hz). Mass m/z: 372 ($M^+$+1).

EXAMPLE 89(1)

N-(3,4-Dimethoxybenzyl)-2-(trans-4-hydroxycyclohexylamino)-5-(trans-2-methoxycarbonylethenyl)benzamide (121 mg) was obtained from N-(3,4-dimethoxybenzyl)-2-fluoro-5-[trans-2-(methoxycarbonyl)ethenyl]benzamide and trans-4-aminocyclohexanol (118 mg) in a manner similar to Example 1(1).

NMR (DMSO-$d_6$, δ): 1.14–1.40 (4H, m), 1.76–1.86 (2H, m), 1.91–2.00 (2H, m), 3.35–3.53 (2H, m), 3.68 (3H, s), 3.72 (3H, s), 3.74 (3H, s), 4.37 (2H, d, J=6 Hz), 4.59 (1H, d, J=4 Hz), 6.41 (1H, d, J=16 Hz), 6.77 (1H, d, J=9 Hz), 6.83 (1H, dd, J=2, 9 Hz), 6.91 (1H, d, J=9Hz), 6.93 (1H, d, J=2 Hz), 7.52 (1H, d, J=16 Hz), 7.61 (1H, dd, J=2, 9 Hz), 8.02 (1H, d, J=2 Hz), 8.49 (1H, d, J=8 Hz), 8.91 (1H, t, J=6 Hz).

EXAMPLE 89(2)

To a solution of N-(3,4-dimethoxybenzyl)-2-(trans-4-hydroxycyclohexylamino)-5-(trans-2-methoxycarbonylethenyl)benzamide (82 mg) in a mixture of tetrahydrofuran (2 mL) and water (0.1 mL) were added 4-methylmorpholine N-oxide (53.2 mg) and 4% aqueous solution of osmium tetroxide (0.1 mL). The mixture was stirred for 2 hours under reflux. To the mixture were added 50% aqueous methanol (2 mL) and sodium periodate (161 mg). After siring for 20 minutes, the mixture was diluted with ethyl acetate and washed successively with water and brine. The organic layer was dried over sodium sulfate and evaporated in vacuo. The residue was subjected to a silica gel column chromatography eluting with a mixture of chloroform and ethyl acetate (1:1) to give N-(3,4-diimethoxybenzyl)-5-formyl-2-(trans-4-hydroxycyclohexylamino)benzamide (117 mg) as a solid substance.

NMR (DMSO-$d_6$, δ): 1.16–1.42 (4H, m), 1.77–1.87 (2H, m), 1.92–2.02 (2H, m), 3.38–3.54 (2H, m), 3.72 (3H, s), 3.74

(3H, s), 4.36 (2H, d, J=6 Hz), 4.61 (1H, d, J=4 Hz), 6.80–6.95 (4H, m), 7.75 (1H, dd, J=2,9 Hz), 8.17 (1H, d, J=2 Hz), 8.79 (1H, d, J=8 Hz), 9.10 (1H, t, J=6 Hz), 9.65 (1H, s) Mass m/z: 411 (M$^+$–1).

PREPARATION 90(1)

N-(3,4-Dimethoxybenzyl)-2-fluoro-5-formylbenzamide (915.8 mg) was obtained from N-(3,4-dimethoxybenzyl)-2-fluoro-5-vinylbenzamide (1.1 g) in a manner similar to Example 89(2) as a colorless solid substance.

mp. 132–133° C.; NMR (CDCl$_3$, δ): 3.86(3H, s), 3.89(3H, s), 4.64(2H, d, J=5.5 Hz), 6.85(1H, d, J=8.0 Hz), 6.91(1H, s), 6.92(1H, d, J=8.0 Hz), 6.89–7.01(1H, m), 7.29(1H, dd, J=11.0, 8.5 Hz), 8.06(1H, m), 8.66(1H, dd, J=7.0, 2.0 Hz), 10.04(1H, s); Mass m/z: 316(M$^+$–1).

PREPARATION 90(2)

N-(3,4-Dimethoxybenzyl)-2-fluoro-5-formylbenzamide (900 mg) and glyoxal trimeric dihydrate (596 mg) were stirred in methanol (9 mL) at –10° C. Ammonia was bubbled through the solution for 5 minutes and the mixture was stirred for an hour at –10° C. The mixture was allowed to warm to ambient temperature over 16 hours, then poured into water and extracted twice with chloroform. The combined extracts were dried over anlydrous magnesium sulfate and concenfrated in vacuo. The residue was purified by a flash column chromatography over silica gel with 5% methanol in chloroform as eluent to give N-(3,4-dimethoxybenzyl)-2-fluoro-5-(1H-imidazol-2-yl)benzamide (323.1 mg) as a pale brown solid substance.

mp. 164–166° C. NMR (DMSO-d$_6$, δ): 3.73(3H, s), 3.75(3H, s), 4.42(2H, d, J=5.5 Hz), 6.87(1H, d, J=8.0 Hz), 6.93(1H, d, J=8.0 Hz), 6.98(1H, s), 7.03(1H, s), 7.26(1H, s), 7.39(1H, t, J=8.0 Hz), 8.05(1H, m), 8.17(1H, dd, J=7.0, 1.5 Hz), 8.92(1H, t, J=5.5 Hz), 12.61(1H, s); Mass m/z: 354 (M$^+$–1).

EXAMPLE 90

N-(3,4-Dimethoxybenzyl)-2-(trans-4-hydroxycyclohexylamino)-5-(1H-imidazol-2-yl)benzamide (18.5 mg) was obtained as a pale gray solid substance from N-(3,4-dimethoxybenzyl)-2-fluoro-5-(1H-imidazol-2-yl) benzamide (70 mg) and trans-4-aminocyclohexanol (90.8 mg) in a manner similar to Example 1(1).

mp. 189–190° C. NMR (DMSO-d$_6$, δ): 1.10–1.42(4H, m), 1.76–1.88(2H, m), 1.93–2.05(2H, m), 3.27–3.54(2H, m), 3.73(3H, s), 3.74(3H, s), 4.36(2H, d, J=5.5 Hz), 4.58(1H, d, J=4.5 Hz), 6.80(1H, d, J=8.5 Hz), 6.85(1H, d, J=8.0 Hz), 6.92(1H, d, J=8.0 Hz), 6.97(1H, s), 7.04(2H, s), 7.77(2H, d, J=8.0 Hz), 8.13(1H, s), 8.83(1H, t, J=5.5 Hz), 12.18(1H, s); Mass m/z: 451(M$^+$+1).

PREPARATION 91(1)

To a solution of 2-chloro-5-methylphenol (5.00 g) and potassium carbonate (7.27 g) in anhydrous dimethylformamide (30 mL) was added methyl iodide (3.27 mL), and the mixture was stirred for 3 hours at ambient temperature. The mixture was partitioned between water and ethyl acetate. The separated organic layer was washed with water and brine and dried over magnesium sulfate. The resultant was evaporated in vacuo to give 4-chloro-3-methoxytoluene as a colorless oil (5.65 g).

NMR (CDCl$_3$, δ): 2.34 (3H, s), 3.89 (3H, s), 6.72 (2H, m), 7.22 (1H, d, J=8 Hz).

PREPARATION 91(2)

To a solution of 4-chloro-3-methoxytoluene (5.65 g) and N-bromosuccinimide (6.74 g) in anhydrous dichloromethane (60 mL) was added 2,2'-azolbis(4-methoxy-2,4-diaethylvaleronitrile) (674 mg). After stirring for 3 hours under reflux, the mixture was washed with water and brine, dried over magnesium sulfate and evaporated in vacuo. The residue was triturated with hexane to give 4-chloro-3-methoxybenzyl bromide as white powders (2.00 g).

NMR (CDCl$_3$, δ): 3.92 (3H, s), 4.46 (2H, s), 6.91–6.96 (2H, m), 7.32 (1H, d, J=8 Hz).

PREPARATION 91(3)

To a solution of 4-chloro-3-methoxybenzyl bromide (7.00 g) in anhydrous dimethylformamide (50 mL) was added potassium phthalimide (6.03 g), and the mixture was stirred for 2 hours at ambient temperature. The mixture was partitioned between ethyl acetate and water. The separated organic layer was washed with water and brine, dried over magnesium sulfate and evaporated in vacuo. The residue was triturated with diisopropyl ether to give N-(4-chloro-3-methoxybenzyl)phthalimide as white powders (5.88 g).

NMR (CDCl$_3$, δ): 3.90 (3H, s), 4.80 (2H, s), 6.96 (1H, d, J=8 Hz), 7.05 (1H, s), 7.25–7.31 (1H, m), 7.68–7.75 (2H, m), 7.82–7.90 (214, m).

PREPARATION 91(4)

To a solution of N-(4-chloro-3-methoxybenzyl) phthalimide (3.00 g) in ethanol (60 mL) was added hydrazine hydrate (2.62 mL), and the mixture was heated for an hour under reflux. The resulting precipitates were faltered off and the filtrate was evaporated in vacuo. The residue was partitioned between chloroform and an aqueous saturated sodium bicarbonate solution. The separated organic layer was washed with water and brine, dried over magnesium sulfate and evaporated in vacuo to give 4-chloro-3-methoxybenzylamine as a yellow oil (1.64 g).

NMR (CDCl$_3$, δ): 3.86 (2H, s), 3.92 (3H, s), 6.85 (1H, d, J=8 Hz), 6.93 (1H, s), 7.25–7.34 (1H, d, J=8 Hz).

PREPARATION 91(5)

N-(4-Chloro-3-methoxybenzyl)-2-fluoro-5-nitrobenzamide (1.97 g) was obtained from 2-fluoro5-nitrobenzoic acid (1.72 g) and 4-chloro-3-methoxybenzylamine (1.64 g) in a manner similar to Preparation 55.

NMR (CDCl$_3$, δ): 3.85 (3H, s), 4.50 (2H, d, J=7 Hz), 6.94 (1H, d, J=8 Hz), 7.15 (1H, s), 7.39 (1H, d, J=8 Hz), 7.64 (1H, m), 8.40–8.47 (2H, m), 9.21 (1H, br); Mass m/z: 337 (M$^+$).

EXAMPLE 91

N-(4-Chloro-3-methoxybenzyl)-2-[2-hydroxy-1-(hydroxymethyl)ethylamino]-5-nitrobenzamide (165 mg) was obtained from N-(4-chloro-3-methoxybenzyl)-2-fluoro-5-nitrobenzamide (150 mg) and 2-amino-1,3-propanediol (60.5 mg) in a manner similar to Example 1(1).

mp: 176–177° C. NMR (DMSO-d$_6$, δ): 3.50 (4H, br), 3.55–3.68 (1H, br), 3.82 (3H, s), 4.40 (2H, d, J=7 Hz), 4.90 (2H, t, J=7 Hz), 6.86–6.93 (2H, m), 7.11 (1H, s), 7.35 (1H, d, J=8 Hz), 8.10 (1H, dd, J=4, 8 Hz), 8.58(1H, d, J=4 Hz), 9.19 (1H, d, J=8 Hz), 9.32 (1H, br); Mass m/z: 408 (M$^+$).

PREPARATION 92(1)

To a mixture of 4-(methylthio)benzyl alcohol (2.00 g) and carbon tetrabromide (6.45 g) in dichloromethane (40 mL) was added triphenylphosphine (4.08 g), and the mixture was stirred for an hour at ambient temperature. After evaporation of the solvent, the residue was purified by a silica gel column chromatography eluting with a mixture of hexane and ethyl acetate (20:1) to give 4-(methylthio)benzyl bromide (2.00 g) as a colorless oil.

NMR (CDCl$_3$, δ) 2.49 (3H, s), 4.48 (2H, s), 7.20 (2H, d, J=8 Hz), 7.32 (2H, d, J=8 Hz).

PREPARATION 92(2)

N-[4-(Methylthio)benzyl]phthalimide (2.40 g) was obtained as colorless powders from 4-(methylthio)benzyl bromide (1.99 g) and potassium phthalimide (1.87 g) in a manner similar to Preparation 91(3).

NMR (CDCl$_3$, δ): 2.45 (3H, s), 4.80 (2H, s), 7.19 (2H, d, J=8 Hz), 7.36 (2H, d, J=8 Hz), 7.69 (2H, m), 7.84 (2H, m).

PREPARATION 92(3)

4-(Methylthio)benzylamine (1.17 g) was obtained as a pale yellow oil from N-[4-(methylthio)benzyl]phthalimide (2.04 g) in a manner similar to Preparation 91(4).

NMR (CDCl$_3$, δ); 2.48 (3H, s), 3.83 (2H, s), 7.24 (4H, s).

PREPARATION 92(4)

2-Fluoro-N-[4-(methylthio)benzyl]-5-nitrobenzamide (1.45 g) was obtained as yellow powders from 2-fluoro-5-nitrobenzoic acid (1.35 g) and 4-(methylthio)benzylamine (1.15 g) in a manner similar to Preparation 55.

NMR (CDCl$_3$, δ): 3.89 (6H, s), 4.63 (2H, d, J=7 Hz), 6.84–6.93 (4H, m), 7.30 (1H, m), 8.35 (1H, m), 9.03 (1H, m); Mass m/z: 333(M$^+$).

EXAMPLE 92

2-(trans-4-Hydroxycyclohexyl)amino-N-[4-(methylthio) benzyl]-5-nitrobenzamide (456 mg) was obtained as yellow powders from 2-fluoro-N-[4-(methylthio)benzyl]-5-nitrobenzamide (400 mg) and trans-4-aminocyclohexanol (288 mg) in a manner similar to Example 1(1).

NMR(DMSO-d$_6$, δ): 1.20–1.44 (4H, br), 1.75–1.88 (2H, br), 1.90–2.05 (2H, br), 2.45 (3H, s), 3.42–3.59 (2H, br), 4.39 (2H, d, J=7 Hz), 4.61 (1H, d, J=4 Hz), 6.91 (1H, d, J=8 Hz), 7.20–7.30 (4H, m), 8.11 (1H, dd, J=4, 8 Hz), 8.62 (1H, d, J=4 Hz), 9.10 (1H, d, J=8 Hz), 9.38 (1H, br); Mass m/z: 414(M$^+$).

PREPARATION 93(1)

3,5-Dichloro-4-methoxytoluene (5.39 g) was obtained as yellow oil from 2,6-dichloro-4-methylphenol (5.00 g) and methyl iodide (2.64 mL) in a manner similar to preparation 91(1).

NMR (CDCl$_3$, δ): 2.27 (3H, s), 3.87 (3H, s), 7.10 (2H, s).

PREPARATION 93(2)

3,5-Dichloro-4-methoxybenzyl bromide (9.10 g) was obtained as yellow oil from 3,5-dichloro-4-methoxytoluene (5.39 g) in a manner similar to preparation 91(2).

NMR (CDCl$_3$, δ): 3.90 (3H, s), 4.36 (2H, s), 7.33 (2H, s).

PREPARATION 93(3)

N-(3,5-Dichloro-4-methoxybenzyl)phthalimide (6.34 g) was obtained as colorless powders from 3,5-dichloro-4-methoxybenzyl bromide (8.00 g) and potassium phthaimide (6.04 g) in a manner similar to Preparation 91(3).

NMR (CDCl$_3$, δ): 3.86 (3H, s), 4.74 (2H, s), 7.37 (2H, s), 7.70–7.78 (2H, m), 7.83–7.90 (2H, m).

PREPARATION 93(4)

3,5-Dichloro-4-methoxybenzylamine (1.50 g) was obtained as yellow oil from N-(3,5-dichloro-4-methoxybenzyl)phthalimide (3.00 g) in a manner similar to Preparation 91(4).

NMR (CDCl$_3$, δ): 3.82 (2H, s), 3.90 (3H, s), 7.28 (2H, br).

PREPARATION 93(5)

N-(3,5-Dichloro-4-methoxybenzyl)-2-fluoro-5-nitrobenzamide (2.20 g) was obtained as colorless powders from 2-fluoro-5-nitrobenzoic acid (1.31 g) and 3,5-dichloro-4-methoxybenzylamine (1.50 g) in a manner similar to Preparation 55.

NMR (DMSO-d$_6$, δ): 3.81 (3H, s), 4.46 (2H, d, J=7 Hz), 7.48 (2H, s), 7.66 (1H, t, J=8 Hz), 8.38–8.45 (1H, m), 8.46–8.53 (1H, m), 9.20 (1H, br).

EXAMPLE 93

N-(3,5-Dichloro-4-methoxybenzyl)-2-(trans-4-hydroxycyclohexylamino)-5-nitrobenzamide (365 mg) was obtained as yellow powders from N-(3,5-dichloro-4-methoxybenzyl)-2-fluoro-5-nitrobenzamide (400 mg) and trans-4-aminocyclohexanol (185 mg) in a manner similar to Example 1(1).

NMR (DMSO-d$_6$, δ): 1.20–1.43 (4H, m), 1.76–1.89 (2H, br), 1.91–2.01 (2H, br), 3.48 (2H, br), 3.81 (3H, s), 4.39 (2H, d, J=7 Hz), 4.61 (1H, d, J=4 Hz), 6.92 (1H, d, J=8 Hz), 7.45 (2H, s), 8.12 (1H, dd, J=4, 8 Hz), 8.63 (1H, d, J=4 Hz), 9.03 (1H, d, J=8 Hz), 9.37 (1H, br).

PREPARATION 94(1)

4-Chloro-3-nitrobenzyl bromide (7.90 g) was obtained as orange oil from 4-chloro-3-nitrotoluene (5.00 g) in a manner similar to Preparation 9 1 (2).

NMR (CDCl$_3$, δ): 4.47 (2H, s), 7.54 (2H, s), 7.92 (1H, s).

PREPARATION 94(2)

N-(4-Chloro-3-nitrobenzyl)phthalimide (5.49 g) was obtained as colorless powders from 4-chloro-3-nitrobenzyl bromide (7.00 g) and potassium phthalimide (5.69 g) in a manner similar to Preparation 91(3).

NMR (CDCl$_3$, δ): 4.88 (2H, s), 7.50 (1H, d, J=8 Hz), 7.60 (1H, dd, J=4, 8 Hz), 7.75 (2H, m), 7.88 (2H, m), 7.90 (1H, d, J=4 Hz).

PREPARATION 94(3)

4-Chloro-3-nitrobenzylamine (1.27 g) was obtained as brown oil from N-(4-chloro-3-nitrobenzyl)phthalimide (3.00 g) in a manner similar to Preparation 91(4).

NMR (CDCl$_3$, δ): 3.96 (2H, s), 7.50 (2H, s), 7.89 (1H, s).

PREPARATION 94(4)

N-(4-Chloro-3-nitrobenzyl)-2-fluoro-5-nitrobenzamide (1.72 g) was obtained as pale yellow powders from 2-fluoro-5-nitrobenzoic acid (1.20 g) and 4-chloro-3-nitrobenzylamne(1.25 g) in a manner similar to Preparation 55.

NMR (DMSO-d$_6$, δ): 4.58 (2H, d, J=7 Hz), 7.62–7.73 (2H, m), 7.78 (1H, d, J=8 Hz), 8.06 (1H, s), 8.44 (1H, m), 8.50 (1H, m), 9.29 (1H, br) Mass m/z: 352(M$^+$).

EXAMPLE 94

(R)-N-(4-Chloro-3-nitrobenzyl)-2-[1-(hydroxymethyl) propylamino]-5-nitrobenzamide (150 mg) was obtained as yellow powders from N-(4-chloro-3-nitrobenzyl)-2-fluoro-5-nitrobenzamide (150 mg) and (R)-2-amino-1-butanol (56.7 mg) in a manner similar to Example 1(1).

NMR (DMSO-d$_6$, δ): 0.89 (3H, t, J=7 Hz), 1.40–1.56 (1H, m), 1.60–1.77 (1H, m), 3.47 (2H, br), 3.60 (1H, br), 4.51 (2H, d, J=7 Hz), 4.91 (1H, t, J=7 Hz), 6.92 (1H, d, J=8 Hz), 7.67 (1H, dd, J=4, 8 Hz), 7.76 (1H, d, J=8 Hz), 8.04 (1H, d, J=4 Hz), 8.12 (1H, dd, J=4, 8 Hz), 8.65 (1H, d, J=4 Hz), 9.14 (1H, d, J=8 Hz), 9.46 (1H, br); Mass m/z: 421 (M$^+$).

PREPARATION 95(1)

To a mixture of 4-cyanobenzaldehyde (5.00 g) in ethanol (50 mL) and tetrahydrofuran (20 mL) was added sodium borohydride (2.16 g) under ice-water cooling, and the mixture was stirred for an hour at 0° C. After evaporation of the solvent, the residue was partitioned between ethyl acetate and water. The separated organic layer was washed with water and brine, dried over magnesium sulfate and evaporated in vacuo to give 4-cyanobenzyl alcohol (4.76 g) as a colorless oil.

NMR (CDCl$_3$, δ): 1.98 (1H, t, J=7 Hz), 4.78 (2H, d, J=7 Hz), 7.48 (2H, d, J=8 Hz), 7.66 (2H, d, J=8 Hz).

PREPARATION 95(2)

4-Cyanobenzyl bromide (3.16 g) was obtained as colorless powders from 4-cyanobenzyl alcohol (2.35 g) in a manner similar to Preparation 921(1).

NMR (CDCl$_3$, δ): 4.48 (2H, s), 7.50 (2H, d, J=8 Hz), 7.64 (2H, d, J=8 Hz).

PREPARATION 95(3)

N-(4-Cyanobenzyl)phthalimide (3.75 g) was obtained as colorless powders from 4-cyanobenzyl bromide (3.00 g) and potassium phthalimide (3.12 g) in a manner similar to Preparation 91(3).

NMR (CDCl$_3$, δ):4.89 (2H, s), 7.52 (2H, d, J=8 Hz), 7.63 (2H, d, J=8 Hz), 7.75 (2H, m), 7.86 (2H, m).

PREPARATION 95(4)

4-Cyanobenzylamine (1.61 g) was obtained as pale yellow oil from N-(4-cyanobenzyl)phthalimide (3.70 g) in a manner similar to Preparation 91(4).

NMR (CDCl$_3$, δ): 3.96 (2H, s), 7.45 (2H, d, J=8 Hz), 7.63 (2H, d, J=8 Hz).

PREPARATION 95(5)

N-(4-Cyanobenzyl)-2-fluoro-5-nitrobenzamide (3.07 g) was obtained as colorless powders from 2-fluoro-5-nitrobenzoic acid (2.19 g) and 4-cyanobenzylamine (1.61 g) in a manner similar to Preparation 55.

NMR (DMSO-d$_6$, δ): 4.58 (2H, d, J=7 Hz), 7.55 (2H, d, J=8 Hz), 7.65 (1H, t, J=7 Hz), 7.84 (2H, d, J=8 Hz), 8.39–8.51 (2H, m), 9.29 (1H, br); Mass m/z: 298(M$^+$).

EXAMPLE 95

N-(4-Cyanobenzyl)-2-(trans-4-hydroxycyclohexylamino)-5-nitrobenzamide (428 mg) was obtained as yellow powders from N-(4-cyanobenzyl)-2-fluoro-5-nitrobenzamide (400 mg) and trans-4-aminocyclohexanol (308 mg) in a manner similar to Example 1(1).

NMR (DMSO-d$_6$, δ): 1.18–1.45 (4H, br), 1.75–1.88 (2H, br), 1.90–2.00 (2H, br), 3.40–3.58 (2H, br), 4.50 (2H, d, J=7 Hz), 4.62 (1H, d, J=4 Hz), 6.92 (1H, d, J=8 Hz), 7.51 (2H, d, J=8 Hz), 7.82(2H, d, J=8 Hz),8.12(1H, dd, J=4, 8 Hz), 8.67 (1H, d, J=4 Hz), 9.07 (1H, d, J=8 Hz), 9.50 (1H, br); Mass m/z: 393(M$^+$).

PREPARATION 96

2-Fluoro-5-nitro-N-(2-pyridylmethyl)benzamide (468 mg) was obtained as yellow powders from 2-fluoro-5-nitrobenzoic acid (500 mg) and 2-(aminomethyl)pyridine (307 mg) in a manner similar to Preparation 55.

NMR (DMSO-d$_6$, δ): 4.60 (2H, d, J=5 Hz), 7.30 (1H, t, J=5 Hz), 7.40 (1H, d, J=8 Hz), 7.66 (1H, t, J=8 Hz), 7.80 (1H, t, J=7.5 Hz), 8.39–8.49 (1H, m), 8.49–8.57 (2H, m), 9.24 (1H, br); Mass m/z: 276.1 (M$^+$+1).

EXAMPLE 96

2-(trans-4-Hydroxycyclohexylamino)-5-nitro-N-(2-pyridylmethyl)benzamide (580 mg) was obtained as yellow powders from 2-fluoro-5-nitro-N-(2-pyridyhnethyl)benzamide (450 mg) and trans-4-aminocyclohexanol (282 mg) in a manner similar to Example 1(1).

NMR (DMSO-d$_6$, δ): 1.18–1.43 (4H, m), 1.70–1.88 (2H, m), 1.88–2.04 (2H, m), 3.38–3.59 (2H, m), 4.54 (2H, d, J=5 Hz), 4.61 (1H, d, J=4 Hz), 6.92 (1H, d, J=8 Hz), 7.28 (1H, dd, J=5, 7.5 Hz), 7.33 (1H, d, J=8 Hz), 7.77 (1H, t d, J=8, 2 Hz), 8.12 (1H, dd, J=8, 2 Hz), 8.51 (1H, d, J=5 Hz), 8.68 (1H, d, J=2 Hz), 9.05 (1H, d, J 8 Hz), 9.48 (1H, m); Mass m/z: 369.2 (M$^+$−1).

PREPARATION 97

2-Fluoro-5-nitro-N-(3-pyridylmethyl)benzamide (510 mg) was obtained as yellow powders from 2-fluoro-5-nitrobenzoic acid (500 mg) and 3-(aminomethyl)pyridine (307 mg) in a manner similar to Preparation 55.

NMR (DMSO-d$_6$, δ): 4.52 (2H, d, J=5 Hz), 7.40 (1H, dd, J=5, 7.5 Hz), 7.64 (1H, t, J=8 Hz), 7.76 (1H, d, J=7.5 Hz), 8.36–8.51 (3H, m), 8.59 (1H, d, J=2 Hz), 9.25 (1H, br); Mass m/z: 274.0 (M$^+$−1).

EXAMPLE 97

2-(trans-4-Hydroxycyclohexylamino)-5-nitro-N-(3-pyridylmethyl)benzamide (625 mg) was obtained as yellow powders from 2-fluoro-5-nitro-N-(3-pyridylmethyl)benzamide (550 mg) and trans-4-aminocyclohexanol (345 mg) in a manner similar to Example 1(1). NMR (DMSO-d$_6$, δ): 1.19–1.44 (4H, m), 1.71–1.88 (2H, m), 1.88–2.07 (2H, m), 3.40–3.61 (2H, m), 4.45 (2H, d, J=5 Hz), 4.62 (1H, d, J=4 Hz), 6.92 (1H, d, J=8 Hz), 7.37 (1H, dd, J=5, 7.5 Hz), 7.43 (1H, d, J=7.5 Hz), 8.12 (1H, dd, J=8, 2 Hz), 8.47 (1H, d, J=5 Hz), 8.56 (1H, d, J=2 Hz), 8.63 (1H, d, J=2 Hz), 9.06 (1H, d, J=8 Hz), 9.43 (1H, m); Mass m/z: 369.3 (M$^+$−1).

PREPARATION 98

2-Fluoro-5-nitro-N-(4-pyridylmethyl)benzamide (534 mg) was obtained as yellow powders from 2-fluoro-5-nitrobenzoic acid (500 mg) and 4-(aminomethyl)pyridine (307 mg) in a manner similar to Preparation 55.

NMR (DMSO-d$_6$, δ): 4.53 (2H, d, J=5 Hz), 7.35 (2H, d, J=5 Hz), 7.66 (1H, t, J=8 Hz), 8.38–8.65 (4H, m), 9.28 (1H); Mass m/z: 274.1 (M$^+$−1).

EXAMPLE 98

2-(trans-4-Hydroxycyclohexylamino)-5-nitro-N-(4-pyridylmethyl)benzamide (548 mg) was obtained as yellow powders from 2-fluoro-5-nitro-N-(4-pyridylmethyl) benzamide (500 mg) and trans-4-aminocyclohexanol (314 mg) in a manner similar to Example 1(1).

NMR (DMSO-d$_6$, δ): 1.14–1.43 (4H, m), 1.69–1.88 (2H, m), 1.88–2.05 (2H, m), 3.36–3.60 (2H, m), 4.45 (2H, d, J=5 Hz), 4.61 (1H, d, J=4 Hz), 6.93 (1H, d, J=8 Hz), 7.31 (2H, d, J=5 Hz), 8.13 (1H, dd, J=8, 2 Hz), 8.51 (2H, d, J=5 Hz), 8.69 (1H, d, J=2 Hz), 9.06 (1H, d, J=8 Hz), 9.48 (1H, m); Mass m/z: 369.2 (M$^+$–1).

PREPARATION 99(1)

2-Naphthalenemethylamine hydrochloride (1.36 g) was obtained as white powders from N-(2-naphthylmethyl) phthanmide (2.80 g) in a manner similar to Preparation 91(4).

NMR (DMSO-d$_6$, δ): 4.19 (2H, s), 7.51–7.60 (2H, m), 7.63 (1H, dd, J=8, 2 Hz), 7.87–8.05 (4H, m), 8.46 (3H, br).

PREPARATION 99(2)

2-Fluoro-N-(2-naphthylmethyl)-5-nitrobenzamide (1.73 g) was obtained as yellow powders from $^2$-fluoro-5-nitrobenzoic acid (1.00 g) and 2-Naphthalenemethylamine hydrochloride (1.10 g) in a manner similar to Preparation 55.

NMR (DMSO-d$_6$, δ): 4.67 (2H, d, J=5 Hz), 7.44–7.57 (3H, m), 7.64 (1H, t, J=8 Hz), 7.80–7.98 (4H, m), 8.37–8.47 (1H, m), 8.47–8.55 (1H, m), 9.28 (1H, m).

EXAMPLE 99

2-[2-Hydroxy-1-(hydroxymethyl)ethylamino]-N-(2-naphthylmethyl)-5-nitrobenzamide (156 mg) was obtained as yellow powders from 2-fluoro-N-(2-naphthylmethyl)-5-nitrobenzamide (200 mg) and 2-amino-1,3-propanediol (84.3 mg) in a manner similar to Example 1(1).

NMR (DMSO-d$_6$, δ): 3.45–3.72 (5H, m), 4.61 (2H, d, J=5 Hz), 4.92 (1H, t, J=5 Hz), 6.93 (1H, d, J=8 Hz), 7.42–7.57 (3H, m), 7.82 (1H, s), 7.85–7.98 (3H, m), 8.13 (1H, dd, J=8, 2 Hz), 8.67 (1H, d, J=2 Hz), 9.33 (1H, d, J=8 Hz), 9.46 (1H, m); Mass m/z: 394.2 (M$^+$–1).

PREPARATION 100

2-Fluoro-N-[2-(2-methoxyphenyl)ethyl]-5-nitrobenzamide (1.03 g) was obtained as yellow powders from 2-fluoro-5-nitrobenzoic acid (1.00 g) and (2-methoxyphenyl)ethylamine(613 mg) in a manner similar to Preparation 55.

NMR (DMSO-d$_6$, δ): 2.81 (2H, t, J=7.5 Hz), 3.44 (2H, q, J=7.5 Hz), 3.77 (3H, s), 6.86 (1H, t, J=8 Hz), 6.95 (1H, d, J=8 Hz), 7.11–7.24 (2H, m), 7.57 (1H, t, J=8 Hz), 8.27–8.41 (2H, m), 8.65 (1H, br).

EXAMPLE 100

2-[2-Hydroxy-1-(hydroxymethyl)ethylamino]-N-[2-(2-methoxyphenyl)ethyl]-5-nitrobenzamide (198 mg) was obtained as yellow powders from 2-fluoro-N-[2-(2-methoxyphenyl)ethyl]-5-nitrobenzamide (200 mg) and 2-amino-1,3-propanediol (85.9 mg) in a manner similar to Example 1(1).

NMR (DMSO-d$_6$, δ): 2.83 (2H, t, J=7.5 Hz), 3.42 (2H, q, J=7.5 Hz), 3.48–3.68 (5H, m), 3.79 (3H, s), 4.92 (2H, t, J=5 Hz), 6.84–6.95 (2H, m), 6.97 (1H, d, J=8 Hz), 7.12–7.27 (2H, m), 8.10 (1H, dd, J=8, 2 Hz), 8.47 (1H, d, J=2 Hz), 8.83 (1H, m), 9.17 (1H, d, J=8 Hz); Mass m/z: 388.3 (M$^+$–1).

PREPARATION 101

N-(4-Ethoxy-3-methoxybenzyl)-2-fluoro-5-nitrobenzamide (2.51 g) was obtained as pale yellow powders from 2-fluoro-5-nitrobenzoic acid (1.50 g) and 4-ethoxy-3-methoxybenzylamine(1.51 g) in a manner similar to Preparation 55.

NMR (DMSO-d$_6$, δ); 1.31 (3H, t, J=7 Hz), 3.75 (3H, s), 3.98 (2H, q, J=7 Hz), 4.42 (2H, d, J=7 Hz), 6.82–6.97 (3H, m), 7.62 (1H, m), 8.39–8.44 (2H, m), 9.11 (1H, br).

EXAMPLE 101(1)

2-(trans-4-Aminocyclohexylamino)-N-(4-ethoxy-3-methoxybenzyl)-5-nitrobenzamide (314 mg) was obtained as yellow powders from N-(4-ethoxy-3-methoxybenzyl)-2-fluoro-5-nitrobenzamide (300 mg) and trans-1,4-cyclohexanediamine (295 mg) in a manner similar to Example 1(1).

NMR (DMSO-d$_6$, δ); 1.15–1.35 (4H, br), 1.30 (3H, t, J=7 Hz), 1.73–1.85 (2H, br), 1.94–2.05 (2H, br), 2.56–2.70 (1H, br), 3.40–3.50 (1H, br), 3.74 (3H, s), 3.97 (2H, q, J=7 Hz), 4.36 (2H, d, J=7 Hz), 6.80–6.96 (4H, m), 8.11 (1H, dd, J=4, 8 Hz), 8.60 (1H, d, J=4 Hz), 9.02 (1H, d, J=8 Hz), 9.31 (1H, br); Mass m/z: 441(M$^+$).

EXAMPLE 101(2)

N-(4-Ethoxy-3-methoxybenzyl)-2-(trans-4-formamidocyclohexylamino)-5-nitrobenzamide (115 mg) was obtained as yellow powders from 2-(trans-4-aminocyclohexylamino)-N-(4-ethoxy-3-methoxybenzyl)-5-nitrobenzamide (150 mg) in a manner similar to Example 73(2).

NMR (DMSO-d$_6$, δ); 1.31 (3H, t, J=7 Hz), 1.25–1.45 (4H, br), 1.75–1.90 (2H, br), 1.94–2.10 (2H, br), 3.48–3.55 (1H, br), 3.52–3.62 (1H, br), 3.75 (3H, s), 3.97 (2H, q, J=7 Hz), 4.36 (2H, d, J=7 Hz), 6.80–6.96 (4H, m), 7.95 (1H, s), 8.03 (1H, br), 8.10 (1H, dd, J=4, 8 Hz), 8.60 (1H, d, J=4 Hz), 9.03 (1H, d, J=8 Hz), 9.32 (1H, br); Mass m/z: 469(M$^+$).

PREPARATION 102(1)

A solution of sodium sulphite (10.6 g) in water (20 mL) was warmed to 80° C. and slowly added with stirring to a solution of 5-chlorosulfonyl-2-fluorobenzoic acid (10 g) in acetone (10 mL), saturated aqueous sodium carbonate being added simultaneously for keeping the liquid in alkaline. The mixture was stirred at 60° C. for one and a half hours, and concentrated in vacuo. The residue was suspended in a mixture of ethanol (20 mL) and water (20 mL), then iodomethane (2.61 mL) was added to the mixture. The reaction mixture was stirred for 2 hours at 60° C. and for an hour at 100° C. After cooling to ambient temperature, ethanol was removed in vacuo. The resultant aqueous solution was acidified with concentrated hydrochloric acid. The aqueous solution was extracted with chloroform (3 times), and the combined organic layer was dried over magnesium sulfate. After evaporation of the solvent, the residual oil was crystallized from ethanol to give 2-fluoro-5-methanesulfonylbenzoic acid (563.6 mg) as a colorless solid.

mp 194–195° C. NMR (DMSO-d$_6$, δ); 3.29 (3H, s), 7.63 (1H, dd, J=10.5, 8.5 Hz), 8.19 (1H, ddd, J=8.5, 7.0, 2.5 Hz), 8.37 (1H, dd, J=7.0, 2.5 Hz). Mass m/z: 217(M$^+$–1)

PREPARATION 102(2)

N-(4-Chloro-3-methoxybenzyl)-2-fluoro-5-methanesulfonylbenzamide (313.9 mg) was obtained as an off-white solid substance from 2-fluoro-5-methanesulfonylbenzoic acid (250 mg) and 4-chloro-3-methoxybenzylamine (203 mg) in a manner similar to Preparation 55.

mp. 121–123° C. NMR (DMSO-d$_6$, δ); 3.28 (3H, s), 3.85(3H, s), 4.49 (2H, d, J=6.0 Hz), 6.94 (1H, dd, J=8.0, 2.0 Hz), 7.15 (1H, d, J=2.0 Hz), 7.40 (1H, d, J=8.0 Hz), 7.63 (1H, dd, J=10.0, 8.5 Hz), 8.10 (1H, m), 8.16 (1H, dd, J=6.5, 2.5 Hz), 9.17 (1H, brt, J=6.0 Hz); Mass m/z: 370(M$^+$–1).

EXAMPLE 102

N-(4-Chloro-3-methoxybenzyl)-2-(trans-4-hydroxycyclohexylamino)-5-methanesulfonylbenzamide (57.2 mg) was obtained as an off-white solid substance from N-(4-chloro-3-nmethoxybenzyl)-2-fluoro-5-methanesulfonylbenzamide (80 mg) and trans-4-aminocyclohexanol (49.6 mg) in a manner similar to Example 1(1).

mp. 234–235.5° C. NMR (DMSO-d$_6$, δ); 1.15–1.41 (4H, m), 1.76–1.86 (2H, m), 1.90–2.02(2H, m), 3.10 (3H, s), 3.38–3.53 (2H, m), 3.84 (3H, s), 4.43 (2H, d, J=6 Hz), 4.60 (1H, d, J=4 Hz), 6.89 (1H, dd, J=9, 2 Hz), 6.91 (1H, d, J=9 Hz), 7.12(1H, d, J=2 Hz), 7.38 (1H, d, J=8.5 Hz), 7.70 (1H, dd, J 8.5, 2.5 Hz), 8.11 (1H, d, J=2.5 Hz), 8.49 (1H, d, J=8 Hz), 9.20 (1H, t, J=6 Hz); Mass m/z: 465(M$^+$–1).

PREPARATION 103

2-Fluoro-N-(3-fluoro-4-methoxybenzyl)-5-nitrobenzamide (1.34 g) was obtained as pale yellow powders from 2-fluoro-5-nitrobenzoic acid (1.16 g) and 3-fluoro-4-methoxybenzylamine hydrochloride (1.00 g) in a manner similar to Preparation 55.

m.p. 112° C. NMR (DMSO-d$_6$, δ): 3.82 (3H, s), 4.42 (1H, d, J=6 Hz), 7.06–7.23 (3H, m), 7.62 (1H, dd, J=9, 9 Hz), 8.37–8.47 (2H, m), 9.15 (1H, t, J=6 Hz); Mass m/z: 321 (M$^+$).

EXAMPLE 103

N-(3-Fluoro-4-methoxybenzyl)-2-[2-hydroxy-1-(hydroxynethyl)ethylamino]-5-nitrobenzamide (230 mg) was obtained as yellow powders from 2-fluoro-N-(3-fluoro-4-methoxybenzyl)-5-nitrobenzamide (263 mg) and 2-amino-1,3-propanediol (112 mg) in a manner similar to Example 1(1).

m.p. 130–132° C. NMR (DMSO-d$_6$, δ): 3.45–3.70 (5H, m), 3.81 (3H, s), 4.36 (1H, d, J=6 Hz), 4.91 (2H, t, J=5 Hz), 6.92 (1H, d, J=10 Hz), 7.06–7.21 (3H, m), 8.12 (1H, dd, J=10, 2 Hz), 8.59 (1H, d, J=3 Hz), 9.23–9.35 (2H, m); Mass m/z: 392(M$^+$).

PREPARATION 104

N-(3-Chloro-4-fluorobenzyl)-2-fluoro-5-nitrobenzainide (976 mg) was obtained as pale yellow powders from 2-fluoro-5-nitrobenzoic acid (1000 mg) and 3-chloro-4-fluorobenzylamine (948 mg) in a manner similar to Preparation 55.

NMR (DMSO-d$_6$, δ): 4.49 (2H, d, J=6 Hz), 7.32–7.46 (2H, m), 5.57 (1H, d, J=8 Hz), 7.64 (1H, dd, J=9, 9 Hz), 8.37–8.53 (2H, m), 9.21 (1H, t, J=6 Hz); Mass m/z: 325 (M$^+$).

EXAMPLE 104

N-(3-Chloro-4-fluorobenzyl)-2-[2-hydroxy-1-(hydroxymethyl)ethylamino]-5-nitrobenzamide (211 mg) was obtained as yellow powders from 2-fluoro-N-(3-chloro-4-fluorobenzyl)-5-nitrobenzamide (207 mg) and 2-amino-1,3-propanediol (115 mg) in a manner similar to Example 1(1).

m.p. 235–238° C. NMR (DMSO-d$_6$, δ): 3.28–3.70 (5H, m), 4.42 (2H, d, J=6 Hz), 4.93 (2H, t, J=5 Hz), 6.93 (1H, d, J=10 Hz), 7.30–7.44 (3H, m), 7.54 (1H, dd, J=6, 2 Hz), 8.13 (1H, dd, J=10, 3 Hz), 8.62 (1H, d, J=3 Hz), 9.28 (1H, d, J=8 Hz), 9.37 (1H, t, J=5 Hz); Mass m/z: 396(M$^+$).

PREPARATION 105

N-(3-Chloro-4-methylbenzyl)-2-fluoro-5-nitrobenzamide (2.25 g) was obtained as pale yellow powders from 2-fluoro-5-nitrobenzoic acid (1.65 g) and 3-chloro-4-methylbenzylamine (1.46 g) in a manner similar to Preparation 55.

NMR (DMSO-d$_6$, δ): 2.31 (3H, s), 4.46 (2H, d, J=6 Hz), 7.23 (1H, dd, J=8, 1 Hz), 7.33 (1H, d, J=8 Hz), 7.39 (1H, d, J=1 Hz), 7.64 (1H, dd, J=9, 9 Hz), 8.37–8.50 (2H, m), 9.19 (1H, t, J=6 Hz); Mass m/z: 321(M$^+$).

EXAMPLE 105

(S)-N-(3-Chloro-4-methylbenzyl)-2-(2-hydroxy-1-methylethylamino)-5-nitrobenzamide (131 mg) was obtained as yellow powders from N-(3-chloro-4-methylbenzyl)-2-fluoro-5-nimtrbenzamide (184 mg) and (S)-2-amino-1-propanol (64 mg) in a manner similar to Example 1 (1).

m.p. 178–179° C. NMR (DMSO-d$_6$, δ): 1.16 (3H, d, J=6 Hz), 2.30 (3H, s), 3.45 (2H, m), 3.76 (1H, m), 4.40 (2H, d, J=5 Hz), 4.99 (1H, t, J=5 Hz), 6.90 (1H, d, J=9 Hz), 7.21 (1H, dd, J=8, 1 Hz), 7.32 (1H, d, J=8 Hz), 8.12 (1H, dd, J=9, 3 Hz), 8.61 (1H, d, J=3 Hz), 9.16 (1H, d, J=8 Hz), 9.36 (1H, t, J=5 Hz); Mass m/z: 376(M$^+$).

PREPARATION 106

2-Fluoro-N-(3-methoxy-4-methylbenzyl)-5-nitrobenzamide (3.31 g) was obtained as yellow powders from 2-fluoro-5-nitrobenzoic acid (2.60 g) and 3-methoxy-4-methylbenzylamine (2.30 g) in a manner similar to Preparation 55.

NMR (DMSO-d$_6$, δ): 2.12 (3H, s), 3.78 (3H, s), 4.46 (2H, d, J=6 Hz), 6.83 (1H, d, J=7.5 Hz), 6.94 (1H, s), 7.10 (1H, d, J=7.5 Hz), 7.63 (1H, dd, J=10, 9 Hz), 8.37–8.47 (2H, m), 9.15 (1H, t, J=6 Hz); Mass m/z: 317(M$^+$).

EXAMPLE 106

2-[2-Hydroxy-1-hydroxymethyl)ethylamino]-N-(3-methoxy-4-methylbenzyl)-5-nitrobenzamide (173 mg) was obtained as yellow powders from 2-fluoro-N-(3-methoxy-4-methylbenzyl)-5-nitrobenzamide (171 mg) 2-amino-1,3-propanediol (98 mg) in a manner similar to Example 1(1).

m.p. 160–162° C. NMR (DMSO-d$_6$, δ): 2.11 (3H, s), 3.46–3.60 (4H, m), 3.63 (1H, m), 3.77 (3H, s), 4.40 (2H, d, J=6 Hz), 4.92 (2H, t, J=5 Hz), 6.80 (1H, br d, J=8 Hz), 6.92 (1H, s), 6.92 (1H, d, J=10 Hz), 7.08 (1H, d, J=8 Hz), 8.12 (1H, dd, J=10, 3 Hz), 8.59 (1H, d, J=3 Hz), 9.21 (1H, d, J=8 Hz), 9.30 (1H, t, J=6 Hz); Mass m/z: 388(M$^+$).

PREPARATION 107

N-(3,5-Dimethoxybenzyl)-2-fluoro-5-nitrobenzamide (3.08 g) was obtained as pale yellow powders from 2-fluoro-5-nitrobenzoic acid (2.12 g) and 3,5-dimethoxybenzylamine (2.01 g) in a manner similar to Preparation 55.

NMR (DMSO-d$_6$, δ): 3.73 (6H, s), 4.44 (2H, d, J=6 Hz), 6.40 (1H, dd, J=2, 2 Hz), 6.52 (2H, d, J=2 Hz), 7.64 (1H, dd, J=9, 9 Hz), 8.37–8.48 (2H, m), 9.16 (1H, t, J=6 Hz); Mass m/z: 333(M$^+$).

EXAMPLE 107

(S)-N-(3,5-Dimethoxybenzyl)-2-(2-hydroxy-1-methylethyl)amino-5-nitrobenzamide (178 mg) was obtained as yellow powders from N-(3,5-dimethoxybenzyl)-2-fluoro-5-nitrobenzamide (169 mg) and (S)-2-amino-1-propanol (57 mg) in a manner similar to Example 1(1).

m.p. 98–101° C.

NMR (DMSO-$d_6$, δ): 1.16 (3H, d, J=7 Hz), 3.46 (2H, m), 3.73 (6H, s), 3.75 (1H, m), 4.37 (2H, d, J=6 Hz), 4.99 (1H, t, J=5 Hz), 6.39 (1H, dd, J=2, 2 Hz), 6.49 (2H, d, J=2 Hz), 6.90 (1H, d, J=10 Hz), 8.12 (1H, dd, J=10, 2 Hz), 8.61 (1H, d, J=2 Hz), 9.11 (1H, d, J=8 Hz), 9.32 (1H, t, J=6 Hz); Mass m/z: 388($M^+$).

PREPARATION 108

2-Fluoro-5-nitro-N-(4-phenoxybenzyl)benzamide (1.22 g) was obtained as yellow powders from 2-fluoro-5-nitrobenzoic acid (1.00 g) and 4-phenoxybenzylamine (1.13 g) in a manner similar to Preparation 55.

NMR (DMSO-$d_6$, δ): 4.49 (2H, d, J=6 Hz), 6.95–7.05 (4H, m), 7.13 (1H, dd, J=7.5, 7.5 Hz), 7.32–7.45 (4H, m), 7.63 (1H, dd, J=9, 9 Hz), 8.37–8.50 (2H, m),9.18 (1H, t, J=6 Hz); Mass m/z: 365($M^+$).

EXAMPLE 108

(R)-2-(2-Hydroxy-1-methylethyl)amino-5-nitro-N-(4-phenoxybenzyl)benzamide (197 mg) was obtained as yellow powders from 2-fluoro-5-nitro-N-(4-phenoxybenzyl)benzamide (207 mg) and (R)-2-amino-1-propanol (85 mg) in a manner similar to Example 1(1).

m.p. 127–129° C. NMR (DMSO-$d_6$, δ): 1.16 (3H, d, J=7 Hz), 3.46 (2H, m), 3.76 (1H, m), 4.43 (2H, d, J=6 Hz), 4.99 (1H, t, J=5 Hz), 6.90 (1H, d, J=7 Hz), 6.99 (4H, d, J=9 Hz), 7.13 (1H, t, J=8 Hz), 7.30–7.45 (4H, m), 8.12 (1H, dd, J=10, 3 Hz), 8.62 (1H, d, J=3 Hz), 9.20 (1H, d, J=8 Hz), 9.37 (1H, t, J=6 Hz); Mass m/z: 420($M^+$).

PREPARATION 109

2-Fluoro-5-nitro-N-(4-phenylbenzyl)benzamide (1.44 g) was obtained from 2-fluoro-5-nitrobenzoic acid (827 mg) and 4-phenylbenzylamine (860 mg) in a manner similar to Preparation 55.

NMR (DMSO-$d_6$, δ): 4.55 (2H, d, J=6 Hz), 7.36 (1H, dd, J=7.5, 7.5 Hz), 7.40–7.51 (4H, m), 7.57–7.72 (5H, m), 8.37–8.52 (2H, m), 9.23 (1H, t, J=6 Hz); Mass m/z: 349 ($M^+$).

EXAMPLE 109

(R)-2-(2-Hydroxy-1-methylethyl)amino-5-nitro-N-(4-phenybenzyl)benzamide (167 mg) was obtained as yellow powders from 2-fluoro-5-nitro-N-(4-phenybenzyl)benzamide (178 mg) and (R)-2-amino-1-propanol (76 mg) in a manner similar to Example 1(1).

m.p. 168.5–170.5° C. NMR (DMSO-$d_6$, δ): 1.17 (3H, d, J=6 Hz), 3.46 (2H, m), 3.77 (1H, m), 4.49 (2H, d, J=6 Hz), 4.99 (1H, t, J=5 Hz), 6.90 (1H, d, J=10 Hz), 7.30–7.52 (5H, m), 7.60–7.71 (4H, m), 8.13 (1H, dd, J=10, 2 Hz), 8.65 (1H, d, J=2 Hz), 9.21 (1H, d, J=8 Hz), 9.42 (1H, t, J=6 Hz); Mass m/z: 404($M^+$).

EXAMPLE 110(1)

2-(Cyclopentylamino)-N-(4-ethoxycarbonylbenzyl)-5-nitrobenzainide (760 mg) was obtained as yellow powders from 2-(cyclopentylamino)-5-nitrobenzoic acid (500 mg) and 4-ethoxycarbonyibenzylamine (430 mg) in a manner similar to Example 30.

NMR (CDCl$_3$, δ): 1.38 (3H, t, J=7 Hz), 1.59–1.85 (6H, m), 2.00–2.15 (2H, m), 3.91 (1H, m), 4.37 (2H, q, J=7 Hz), 4.66 (2H, d, J=7 Hz), 6.64 (1H, br), 6.69 (1H, d, J=8 Hz), 7.40 (2H, d, J=8 Hz), 8.03 (2H, d, J=8 Hz), 8.16 (1H, dd, J=4, 8 Hz), 8.37 (1H, d, J=4 Hz), 8.84 (1H, br); Mass m/z: 410($M^+$).

EXAMPLE 110(2)

A mixture of 2-(cyclopentylamino)-N-(4-ethoxycarbonylbenzyl)-5-nitrobenzamide (645 mg), ethanol (30 mL) and 1N-sodium hydroxide solution (5 mL) was heated for 2 hours under reflux. The mixture was acidified with 1 N-hydrochloric acid to pH 4 and the organic solvent was removed by evaporation. The resulting precipitates were collected by filtration and washed with water and diethyl ether to give N-(4-carboxybenzyl)-2-(cyclopentylamino)-5-nitrobenzamide as yellow powders (541 mg).

NMR (DMSO-$d_6$, δ): 1.38–1.50 (2H, m), 1.56–1.70 (4H, m), 2.04 (2H, m), 3.97 (1H, m), 4.52 (2H, d, J=7 Hz), 6.87 (1H, d, J=8 Hz), 7.42 (2H, d, J=8 Hz), 7.90 (2H, d, J=8 Hz), 8.13 (1H, dd, J=4, 8 Hz), 8.66 (1H, d, J=4 Hz), 9.16 (1H, d, J=8 Hz), 9.46 (1H, br); Mass m/z: 382($M^+$).

EXAMPLE 110(3)

A mixture of N-(4-carboxybenzyl)-2-(cyclopentylamino)-5-nitrobenzamide (120 mg), 1-[3-(dimethylamino)propyl]-3-ethylcarbodiimide hydrochloride (90.0 mg) and 1-hydroxybenzotriazole (63.4 mg) in anhydrous dimethylformamide (2 mL) was stirred for an hour at ambient temperature. After addition of 28% ammonia solution (10 drops), the mixture was stirred for 15 hours at ambient temperature and poured into water. The resulting precipitates were collected by filtration, washed with water and purified by a silica gel column chromatography eluting with 10% methanol in chloroform. The obtained product was triturated with diisopropyl ether to give N-(4-carbamoylbenzyl)-2-(cyclopentylamino)-5-nitrobenzamide (107 mg) as yellow powders.

NMR (DMSO-$d_6$, δ): 1.39–1.52 (2H, m), 1.56–1.73 (4H, m), 1.98–2.10 (2H, m), 3.98 (1H, m), 4.48 (2H, d, J=7 Hz), 6.87 (1H, d, J=8 Hz), 7.31 (1H, br), 7.38 (2H, d, J=8 Hz), 7.85 (2H, d, J=8 Hz), 7.91 (1H, br), 8.13 (1H, dd, J=4, 8 Hz), 8.67 (1H, d, J=4 Hz), 9.15 (1H, d, J=8 Hz), 9.44 (1H, br); Mass m/z: 383($M^+$).

EXAMPLE 111(1)

N-(4-Aminobenzyl)-2-(cyclopentylamino)-5-nitrobenzamide (270 mg) was obtained as yellow powders from 2-(Cyclopentylamino)-5-nitrobenzoic acid (300 mg) and 4-aminobenzylamine (176 mg) in a manner similar to Example 30.

NMR (DMSO-$d_6$, δ): 1.40–1.51 (2H, m), 1.55–1.75 (4H, m), 1.98–2.10 (2H, m), 3.97 (1H, m), 4.24 (2H, d, J=7 Hz), 4.97 (2H, br), 6.52 (2H, d, J=8 Hz), 6.86 (1H, d, J=8 Hz), 6.97 (2H, d, J=8 Hz), 8.12 (1H, dd, J=4, 8 Hz), 8.57 (1H, d, J=4 Hz), 9.10–9.25 (2H, m); Mass m/z: 355($M^+$).

EXAMPLE 111(2)

To a mixture of N-(4-aminobenzyl)-2-(cyclopentylamino)-5-nitrobenzamide (126 mg) and triethylamine (0.119 mL) in anhydrous dichloromethane (20 mL)

was added acetyl chloride (33.5 mg). After stirring for 2 hours at ambient temperature, the mixture was washed with an aqueous saturated sodium bicarbonate solution, water and brine. The resultant was dried over magnesium sulfate and evaporated in vacuo. The residue was purified by a silica gel column chromatography eluting with 10% methanol in chloroform. The obtained product was triturated with diisopropyl ether to give N-(4-acetamidobenzyl)-2-(cyclopentylamino)-5-nitrobenzamide as yellow powders (135 mg).

NMR (DMSO-$d_6$, δ): 1.38–1.54 (2H, m), 1.60–1.75 (4H, m), 1.98–2.10 (5H, br), 3.96 (1H, m), 4.38 (2H, d, J=7 Hz), 6.86 (1H, d, J=8 Hz), 7.25 (2H, d, J=8 Hz), 7.54 (2H, d, J=8 Hz), 8.13 (1H, d, J=8 Hz), 8.62 (1H, s), 9.17 (1H, d, J=8 Hz), 9.35 (1H, br), 9.92 (1H, s); Mass m/z: 395($M^+$).

PREPARATION 112(1)

N-[4-[Bis(tert-butoxycarbonyl)amino]-2-chlorobenzyl]phthalimide (2.14 g) was obtained as colorless powders from 4-[bis(tert-butoxycarbonyl)amino]-2-chlorobenzyl bromide (2.00 g) and potassium plithmide (969 mg) in a manner similar to Preparation 91(3).

NMR (CDCl$_3$, δ): 1.42 (18H, s), 4.99 (2H, s), 7.00 (1H, dd, J=4, 8 Hz), 7.22 (2H, m), 7.75 (2H, m), 7.87 (2H, m).

PREPARATION 112(2)

4-(tert-Butoxycarbonylamino)-2-chlorobenzylamine (950 mg) was obtained as colorless oil from N-[4-[bis(tert-butoxycarbonyl)amino]-2-chlorobenzyl]phthalimide (2.00 g) in a manner similar to Preparation 91(4).

NMR (CDCl$_3$, δ): 1.50 (9H, s), 3.87 (2H, s), 7.14 (1H, m), 7.25 (2H, m); Mass m/z: 257($M^+$).

EXAMPLE 112(1)

N-[4-(tert-Butoxycarbonyl)amino-2-chlorobenzyl]-2-(cyclopentylamino)-5-nitrobenzamide (206 mg) was obtained as yellow powders from 2-(Cyclopentylamino)-5-nitrobenzoic acid (200 mg) and 4-(tert-butoxycarbonyamino)-2-chlorobenzylamine (246 mg) in a manner similar to Example 51.

NMR (CDCl$_3$, δ): 1.50 (9H, s), 1.59–1.85 (6H, m), 2.06 (2H, m), 3.90 (1H, m), 4.61 (2H, d, J=7 Hz), 6.48 (1H, br), 6.54 (1H, br), 6.67 (1H, d, J=8 Hz), 7.14 (1H, dd, J=4, 8 Hz), 7.32 (1H, d, J=8 Hz), 7.61 (1H, d, J=4 Hz), 8.13 (1H, dd, J=4, 8 Hz), 8.28 (1H, d, J=4 Hz), 8.77 (1H, br); Mass m/z: 487($M^+$).

EXAMPLE 112(2)

To a solution of N-[4-(tert-butoxycarbonyl)amino-2-chlorobenzyl]-2-(cyclopentylamino)-5-nitrobenzamide (141 mg) in anhydrous ethyl acetate (2 mL) was added 4N-hydrochloric acid ethyl acetate solution. (4 mL). After stirring for 2 hours at ambient temperature, the mixture was partitioned between 1N-sodium hydroxide solution and chloroform. The separated organic layer was washed with water and brine, dried over magnesium sulfate and evaporated in vacuo. The residue was triturated with diisopropyl ether to give N-(4-amino-2-chlorobenzyl)-2-(cyclopentylamino)-5-nitrobenzamide as yellow powders (102 mg).

NMR (DMSO-$d_6$, δ): 1.39–1.52 (2H, m), 1.55–1.74 (4H, m), 1.96–2.10 (2H, m), 3.97 (1H, m), 4.33 (2H, d, J=7 Hz), 5.32 (2H, s), 6.49 (1H, dd, J=4, 8 Hz), 6.62 (1H, d, J=4 Hz), 6.85 (1H, d, J=8 Hz), 7.03 (1H, d, J=8 Hz), 8.13 (1H, dd, J=4, 8 Hz), 8.59 (1H, d, J=4 Hz), 9.07 (1H, d, J=8 Hz), 9.14 (1H,br); Mass m/z: 389($M^+$).

PREPARATION 113(1)

N-(2-Chloro-4-methoxybenzyl)phthalimide (2.40 g) was obtained as colorless powders from 2-chloro-4-methoxybenzyl bromide (2.00 g) and potassium phthalimide (1.86 g) in a manner similar to Preparation 91(3).

NMR (CDCl$_3$, δ): 3.77 (3H, s), 4.93 (2H, s), 6.74 (1H, dd, J=4, 8 Hz), 6.92 (1H, d, J=4 Hz), 7.22 (1H, d, J=8 Hz), 7.73 (2H, m), 7.86 (2H, m).

PREPARATION 113(2)

2-Chloro-4-methoxybenzylamine (630 mg) was obtained as pale yellow oil from N-(2-Chloro-4-methoxybenzyl)phthanmide (1.00 g) in a manner similar to Preparation 91(4).

NMR (CDCl$_3$, δ): 3.79 (3H, s), 3.86 (2H, s), 6.78 (1H, dd, J=4, 8 Hz), 6.92 (1H, d, J=4 Hz), 7.27 (1H, m); Mass m/z: 154($M^+$).

EXAMPLE 113

N-(2- Chloro-4-methoxybenzyl)-2-(cyclopentyrlamino)-5-nitrobenzamide (146 mg) was obtained as yellow powders from 2-(cyclopentylamino)-5-nitrobenzoic acid (100 mg) and 2-chloro-4-methoxybenzylamine (82.3 mg) in a manner similar to Preparation 1.

NMR (CDCl$_3$, δ): 1.59–1.85 (6H, m), 2.00–2.13 (2H, m), 3.80 (3H, s), 3.90 (1H, m), 4.62 (2H, d, J=7 Hz), 6.52 (1H, br), 6.67 (1H, d, J=8 Hz), 6.80 (1H, dd, J=4, 8 Hz), 6.97 (1H, d, J=4 Hz), 7.34 (1H, d, J=8 Hz), 8.13 (1H, dd, J=4, 8 Hz), 8.29 (1H, d, J=4 Hz), 8.78 (1H, br); Mass m/z: 404($M^+$).

PREPARATION 114

A solution of 3-chloro-4-methoxybenzylamine (234 mg) in N,N-dimethylformamide (5 mL) was added dropwise to a solution of 5-bromoisatoic anhydride (300 mg) in N,N-dimethylformamide (3 mL). The reaction mixture was stirred for an hour at ambient temperature. The mixture was poured into a mixture of water and ethyl acetate. The precipitates were collected by filtration and washed with 2-propanol to give 2-amino-5-bromo-N-(3-chloro-4-methoxybenyl)benzamide (245 mg) as white powders.

NMR (DMSO-$d_6$, δ): 3.83 (3H, s), 4.32 (2H, d, J=6 Hz), 6.61 (2H, s), 6.68 (1H, d, J=9 Hz), 7.11 (1H, d, J=9 Hz), 7.25 (1H, dd, J=2, 9 Hz), 7.27 (1H, dd, J=2, 9 Hz), 7.35 (1H, d, J=2 Hz), 7.69 (1H, d, J=2 Hz), 8.88 (1H, t, J=6 Hz).

EXAMPLE 114

A solution of 97% sulfuric acid (79 mg) in tetrahydrofuran (0.5 mL) was added to a mixture of 2-amino-5-bromo-N-(3-chloro-4-methoxybenzyl)benzamide (199 mg), cyclopentanone (68 mg) and sodium borohydride (31 mg) in tetrahydrofuran (3 mL). The mixture was stirred for an hour at ambient temperature. Then cyclopentanone (68 mg), sodium borohydride (31 mg) and a solution of 97% sulfuric acid (80 mg) in tetrahydrofuran (0.5 mL) were added to the reaction mixture. After stirring for additional 2 hours at ambient temperature, the reaction mixture was diluted with water. The resultant was made alkaline with an aqueous saturated sodium bicarbonate solution and extracted with ethyl acetate. The extract was washed with brine, dried over magnesium sulfate and concentrated in vacuo. The residue was purified by a preparative silica gel thin layer chromatography developed by 25% ethyl acetate in hexane. The obtained substance was dissolved in diethyl ether, and 4 N-hydrogen chloride solution in ethyl acetate (0.3 mL) was added thereto. The mixture was concentrated in vacuo and the residue was triturated with diethyl ether to give 5-bromo-N-(3-chloro-4-methoxybenzyl)-2-(cycloperitylamino) benzamide hydrochloride (198 mg) as white powders.

NMR (DMSO-$d_6$, δ): 1.38 (2H, m), 1.50–1.70 (4H, m), 1.95 (2H, m), 3.77(1H, m), 3.83 (3H, s), 4.32 (1H, d, J=6 Hz), 6.87 (1H, d, J=9 Hz), 7.11 (1H, d, J=9 Hz), 7.25 (1H, dd, J=2, 9 Hz), 7.35 (1H, d, J=2 Hz), 7.40 (1H, dd, J=2, 9 Hz), 7.77 (1H, d, J=2 Hz), 8.99 (1H, t, J=6 Hz); Mass: (ESI+) 437,439 (M+H), (ESI−) 435,437 (M−H).

PREPARATION 115

2-Amino-5-chloro-N-(1,3-benzodioxol-5-ylmethyl) benzamide (321 mg) was obtained as white powders from 5-chloroisatoic anhydride (300 mg) and (1,3-benzodioxol-5-ylmethyl)amine (275 mg) in a manner similar to Preparation 114.

NMR (DMSO-$d_6$, δ): 4.30 (2H, d, J=6 Hz), 5.98 (2H, s), 6.58 (2H, s), 6.72 (1H, d, J=9 Hz), 6.78 (1H, dd, J=1, 8 Hz), 6.86 (1H, d, J=8 Hz), 6.87 (1H, d, J=1 Hz), 7.17 (1H, dd, J=2, 9 Hz), 7.58 (1H, d, J=2 Hz), 8.84 (1H, t, J=6 Hz); Mass: (ESI+) 305, 307 (M+H), (ESI−) 303, 305 (M−H).

EXAMPLE 115

5-Chloro-2-(cyclopentylamino)-N-(1,3-benzodioxol-5-ylmethyl)benzamide hydrochloride (140 mg) was obtained as white crystals from 2-amino-5-chloro-N-(1,3-benzodioxol-5-ylmethyl)benzamide (135 mg) and cyclopentanone (110 mg) in a manner similar to Example 114.

NMR (DMSO-$d_6$, δ): 1.32–1.45 (2H, m), 1.50–1.73 (4H, m), 1.90–2.03 (2H, m), 4.30 (2H, d, J=6 Hz), 5.98 (2H, s), 6.73 (1H, d, J=9 Hz), 6.77 (1H, d, J=8 Hz), 6.86 (1H, d, J=8 Hz), 6.88 (1H, s), 7.29 (1H, brd, J=9 Hz), 7.67 (1H, br), 8.95 (1H, t, J=6 Hz); Mass: (ESI+) 373, 375 (M+H), (ESI−) 371, 373 (M−H).

PREPARATION 116

To a suspension of 5-nitroisatoic anhydride (300 mg) in dimethylformamide (4 mL) was added 2-chlorobenzylamine (245 mg), and the mixture was stirred for 15 hours at ambient temperature. The mixture was partitioned between ethyl acetate and water. The separated organic layer was washed with water and brine, dried over magnesium sulfate and evaporated in vacuo. The residue was triturated with diisopropyl ether to give 2-amino-N-(2-chlorobenzyl)-5-nitrobenzamide as yellow powders (397 mg).

NMR (DMSO-$d_6$, δ): 4.50 (2H, d, J=7 Hz), 6.82 (1H, d, J=8 Hz), 7.27–7.41 (3H, m), 7.47 (1H, d, J=8 Hz), 7.80 (2H, br), 8.05 (1H, dd, J=4, 8 Hz), 8.65 (1H, d, J=4 Hz), 9.28 (1H, br); Mass m/z: 304 (M+).

EXAMPLE 116

N-(2-Chlorobenzyl)-2-cyclopentylamino-5-nitrobenzamide (152 mg) was obtained as yellow powders from 2-amino-N-(2-chlorobenzyl)-5-nitrobenzamide (150 mg) and cyclopentanone (61.9 mg) in a manner similar to Preparation 30(1).

NMR (CDCl$_3$, δ): 1.58–1.84 (6H, m), 2.00–2.15 (2H, m), 3.88 (1H, m), 4.68 (2H, d, J=7 Hz), 6.60 (1H, br), 6.68 (1H, d, J=8 Hz), 7.27 (2H, m), 7.42 (2H, m), 8.15 (1H, dd, J=4, 8 Hz), 8.32 (1H, d, J=4 Hz), 8.78 (1H, br). Mass m/z: 372 (M+).

PREPARATION 117

2-Amino-N-(3-chlorobenzyl)-5-nitrobenzamide (400 mg) was obtained as yellow powders from 5-nitroisatoic anhydride (300 mg) and 3-chlotobenzylamine (245 mg) in a manner similar to Preparation 114.

NMR (DMSO-$d_6$, δ): 4.42 (2H, d, J=7 Hz), 6.80 (1H, d, J=8 Hz), 7.28–7.40 (4H, m), 7.82 (2H, br), 8.03 (1H, dd, J=4, 8 Hz), 8.59 (1H, d, J=4 Hz), 9.28 (1H, br); Mass m/z: 304(M+).

EXAMPLE 117

N-(3-Chlorobenzyl)-2-(cyclopentylamino)-5-nitrobenzamide (136 mg) was obtained as yellow powders from 2-amino-N-(3-chlorobenzyl)-5-nitrobenzanmiie (1S0 mg) and cyclopentanone (61.9 mg) in a manner similar to Preparation 30(1).

NMR (CDCl$_3$, δ): 1.58–1.84 (6H, m), 2.00–2.15 (2H, m), 3.88 (1H, m), 4.58 (2H, d, J=7 Hz), 6.60 (1H, br), 6.68 (1H, d, J=8 Hz), 7.20–7.35 (4H, m), 8.15 (1H, dd, J=4, 8 Hz), 8.32 (1H, d, J=4 Hz), 8.85 (1H, br); Mass m/z: 372(M+).

PREPARATION 118

2-Amino-N-(4-chlorobenzyl)-5-nitrobenzamide (407 mg) was obtained as yellow powders from 5-nitroisatoic anhydride (300 mg) and 4-chlorobenzylamine (245 mg) in a manner similar to Preparation 114.

NMR (DMSO-$d_6$, δ): 4.42 (2H, d, J=7 Hz), 6.80 (1H, d, J=8 Hz), 7.32–7.44 (4H, m), 7.82 (2H, br), 8.03 (1H, dd, J=4, 8 Hz), 8.58 (1H, d, J=4 Hz), 9.30 (1H, br); Mass m/z: 304(M+).

EXAMPLE 118

N-(4-Chlorobenzyl)-2-(cyclopentylamino)-5-nitrobenzamide (97.7 mg) was obtained as yellow powders from 2-amino-N-(4-chlorobenzyl)-5-nitrobenzamide (150 mg) and cyclopentanone (61.9 mg) in a manner similar to Preparation 30(1).

NMR (CDCl$_3$, δ): 1.58–1.84 (6H, m), 2.00–2.15 (2H, m), 3.88 (1H, m), 4.57 (2H, d, J=7 Hz), 6.54 (1H, br), 6.68 (1H, d, J=8 Hz), 7.27–7.36 (4H, m), 8.15 (1H, dd, J=4, 8 Hz), 8.32 (1H, d, J=4 Hz), 8.78 (1H, br); Mass m/z: 372(M+).

PREPARATION 119

2-Amino-N-hexyl-5-nitrobenzamide (1.09 g) was obtained as yellow powders from 5-nitroisatoic anhydride (1.00 g) and hexylamine (583 mg) in a manner similar to Preparation 114.

NMR (DMSO-$d_6$, δ): 0.85 (3H, br), 1.30 (6H, br), 1.52 (2H, br), 3.20 (2H, m), 6.78(1H, dd, J=8 Hz), 7.75(2H, br), 8.02(1H, dd, J=4, 8 Hz), 8.48(1H, d, J=4 Hz), 8.67 (1H, br); Mass m/z: 264(M+).

EXAMPLE 119

2-(Cyclopentylamino)-N-hexyl-5-nitrobenzamide (98.0 mg) was obtained as yellow powders from 2-amino-N-hexyl-5-nitrobenzamide (100 mg) and cyclopentanone (47.6 mg) in a manner similar to Preparation 30(1).

NMR (CDCl$_3$, δ): 0.90 (3H, br), 1.28–1.48 (6H, br), 1.58–1.83 (8H, br), 2.07 (2H, br), 3.38 (2H, m), 3.89 (1H, br), 6.20 (1H, br), 6.63 (1H, d, J=8 Hz), 8.12 (1H, dd, J=4, 8 Hz), 8.29 (1H, d, J=4 Hz), 8.82 (1H, br); Mass m/z: 332(M+).

EXAMPLE 120

N-Hexyl-5-nitro-2-[(2-thienylmethyl)amino]benzamide (124 mg) was obtained as yellow powders from 2-amino- N-hexyl-5-nitrobenzamide (200 mg) and 2-thiophenecarboxaldehyde (93.0 mg) in a manner similar to Preparation 30(1).

NMR (CDCl$_3$, δ): 0.90 (3H, br), 1.28–1.48 (6H, br), 1.60–1.70 (2H, br), 3.41 (2H, m), 4.66 (2H, d, J=7 Hz), 6.28 (1H, br), 6.72 (1H, d, J=8 Hz), 6.98 (1H, m), 7.03 (1H, m), 7.24 (1H, m), 8.15 (1H, dd, J=4, 8 Hz), 8.33 (1H, d, J=4 Hz), 9.17 (1H, br); Mass m/z: 360(M$^+$).

EXAMPLE 121

2-(Cycloheptylamino)-N-hexyl-5-nitrobenzamide (225 mg) was obtained as yellow powders from 2-amino-N-hexyl-5-nitrobenzamide (200 mg) and cycloheptanone (211 mg) in a manner similar to Preparation 30(1).

NMR (CDCl$_3$, δ): 0.89 (3H, br), 1.28–1.45 (6H, br), 1.48–1.78 (12H, br), 1.93–2.06 (2H, br), 3.40 (2H, m), 3.60 (1H, m), 6.20 (1H, br), 6.57 (1H, d, J=8 Hz), 8.13 (1H, dd, J=4, 8 Hz), 8.30 (1H, d, J=4 Hz), 8.88 (1H, br); Mass m/z: 360(M$^+$).

PREPARATION 122

2-Amino-N-(5-hydroxypentyl)-5-nitrobenzamide (167 mg) was obtained as yellow powders from 5-nitroisatoic anhydride (200 mg) and 5-amino-1-pentanol (119 mg) in a manner similar to Preparation 114.

NMR (DMSO-d$_6$, δ): 1.25–1.60 (6H, m), 3.22 (2H, m), 3.40 (2H, m), 4.37 (1H, t, J=7 Hz), 6.78 (1H, d, J=8 Hz), 7.75 (2H, br), 8.02 (1H, dd, J=4, 8 Hz), 8.49 (1H, d, J=4 Hz), 8.68 (1H, br); Mass m/z: 266(M$^+$).

EXAMPLE 122

2-(Cyclopentylamino)-N-(5-hydroxypentyl)-5-nitrobenzamide (83.5 mg) was obtained as yellow powders from 2-amino-N-(5-hydroxypentyl)-5-nitrobenzamide (150 mg) and cyclopentanone (142 mg) in a manner similar to Preparation 30(1).

NMR (CDCl$_3$, δ): 1.43–1.88 (12H, br), 2.00–2.15 (2H, br), 3.43 (2H, m), 3.69 (2H, t, J=7 Hz), 3.83–3.96 (1H, m), 6.55 (1H, br), 6.65 (1H, m), 8.13 (1H, dd, J=4, 8 Hz), 8.36 (1H, d, J=4 Hz), 8.86 (1H, br); Mass m/z: 334(M$^+$).

PREPARATION 123

2-Amino-N-(3-ethoxypropyl)-5-nitrobenzamide (332 mg) was obtained as yellow powders from 5-nitroisatoic anhydride (300 mg) and 3-ethoxypropylamine (178 mg) in a manner similar to Preparation 114.

NMR (DMSO-d$_6$, δ): 1.10 (3H, t, J=7 Hz), 1.25 (2H, m), 3.29 (2H, m), 3.42 (4H, m), 6.78 (1H, d, J=8 Hz), 7.76 (2H, br), 8.01 (1H, dd, J=4, 8 Hz), 8.48 (1H, d, J=4 Hz), 8.68 (1H, br); Mass m/z: 266(M$^+$).

EXAMPLE 123

2-(Cyclopentylamino)-N-(3-ethoxypropyl)-5-nitrobenzamide (150 mg) was obtained as yellow powders from 2-amino-N-(3-ethoxypropyl)-5-nitrobenzamide (150 mg) and cyclopentanone (165 mg) in a manner similar to Preparation 30(1).

NMR (CDCl$_3$, δ): 1.28 (3H, t, J=7 Hz), 1.61–1.84 (6H, br), 1.93 (2H, m), 2.03–2.12 (2H, m), 3.57 (4H, m), 3.68 (2H, t, J=7 Hz), 3.91 (1H, m), 6.67 (1H, d, J=8 Hz), 7.45 (1H, br), 8.15 (1H, dd, J=4, 8 Hz), 8.32 (1H, d, J=4 Hz), 9.01 (1H, br); Mass m/z: 334(M$^+$).

PREPARATION 124

2-Amino-N-benzyl-5-nitrobenzamide (1.66 g) was obtained as yellow powders from 5-nitroisatoic anhydride (1.50 g) and benzylamine (850 mg) in a manner similar to Preparation 114.

NMR (DMSO-d$_6$, δ): 4.45 (2H, d, J=7 Hz), 6.80 (1H, d, J=8 Hz), 7.26 (1H, m), 7.33 (4H, m), 7.80 (2H, br), 8.01 (1H, dd, J=4, 8 Hz), 8.58 (1H, d, J=4 Hz), 9.28 (1H, br); Mass m/z: 270(M$^+$).

EXAMPLE 124

N-Benzyl-2-(cyclobutylamino)-5-nitrobenzamide (210 mg) was obtained as yellow powders from 2-amino-N-benzyl-5-nitrobenzamide (200 mg) and cyclobutanone (77.5 mg) in a manner similar to preparation 30(1).

NMR (CDCl$_3$, δ): 1.80–2.10 (4H, m), 2.44–2.55 (2H, m), 4.00 (1H, m), 4.61 (2H, d, J=7 Hz), 6.52 (1H, br), 6.53 (1H, d, J=8 Hz), 7.28–7.42 (5H, m), 8.12 (1H, dd, J=4, 8 Hz), 8.31 (1H, d, J=4 Hz), 8.89 (1H, br); Mass m/z: 324(M$^+$).

EXAMPLE 125

N-Benzyl-2-cycloheptylamino-5-nitrobenzamide (165 mg) was obtained as yellow powders from 2-amino-N-benzyl-5-nitrobenzamide (200 mg) and cycloheptanone (372 mg) in a manner similar to Preparation 30(1).

NMR (CDCl$_3$, δ): 1.44–1.80 (10H, br), 1.95–2.07 (2H, br), 3.63 (1H, m), 4.61 (2H, d, J=7 Hz), 6.47 (1H, br), 6.58 (1H, d, J=8 Hz), 7.29–7.42 (5H, m), 8.15 (1H, dd, J=4, 8 Hz), 8.30 (1H, d, J=4 Hz), 8.90 (1H, br); Mass m/z: 366(M$^+$).

EXAMPLE 126

N-Benzyl-2-(cyclohexylamino)-5-nitrobenzamide (135 mg) was obtained as yellow powders from 2-amino-N-benzyl-5-nitrobenzamide (200 mg) and cyclohexanone (217 mg) in a manner similar to Preparation 30(1).

NMR (CDCl$_3$, δ): 1.27–1.70 (6H, br), 1.80 (2H, br), 2.03 (2H, br), 3.46 (1H, br), 4.59 (2H, d, J=7 Hz), 6.46 (1H, br), 6.66 (1H, d, J=8 Hz), 7.28–7.40 (5H, m), 8.13 (1H, dd, J=4, 8 Hz), 8.32 (1H, d, J=4 Hz), 8.88 (1H, br); Mass m/z: 352(M$^+$).

PREPARATION 127

2-Amino-N-(2,4-dichlorobenzyl)-5-nitrobenzamide (437 mg) was obtained as yellow powders from 5-nitroisatoic anhydride (300 mg) and 2,4-dichlorobenzylamine (305 mg) in a manner similar to Preparation 116.

NMR (DMSO-d$_6$, δ): 4.48 (2H, d, J=7 Hz), 6.83 (1H, d, J=8 Hz), 7.42 (2H, m), 7.63 (1H, s), 7.81 (2H, br), 8.05 (1H, dd, J=4, 8 Hz), 8.64 (1H, d, J=4 Hz), 9.29 (1H, br).

EXAMPLE 127

2-(Cyclopentylamino)-N-(2,4-dichlorobenzyl)-5-nitrobenzamide (151 mg) was obtained as yellow powders from 2-amino-N-(2,4-dichlorobenzyl)-5-nitrobenzamide (150 mg) and cyclopentanone (111 mg) in a manner similar to Preparation 30(1).

NMR (CDCl$_3$, δ): 1.58–1.88 (6H, m), 2.08 (2H, m), 3.89 (1H, m), 4.65 (2H, d, J=7 Hz), 6.67 (1H, d, J=8 Hz), 6.65–6.75 (1H, br), 7.25 (1H, m), 7.36 (1H, d, J=8 Hz), 7.43 (1H, d, J=4 Hz), 8.13 (1H, dd, J=4, 8 Hz), 8.33 (1H, d, J=4 Hz), 8.75 (1H, br).

PREPARATION 128

2-Amino-N-(3,4-dichlorobenzyl)-5-nitrobenzamide (444 mg) was obtained as yellow powders from 5-nitroisatoic anhydride (300 mg) and 3,4-dichlorobenzylamine (305 mg) in a manner similar to Preparation 116.

NMR (DMSO-d$_6$, δ): 4.43 (2H, d, J=7 Hz), 6.83 (1H, d, J=8 Hz), 7.33 (1H, d, J=8 Hz), 7.59 (2H, m), 7.83 (2H, br), 8.04 (1H, dd, J=4, 8 Hz), 8.58 (1H, d, J=4 Hz), 9.32 (1H,br).

EXAMPLE 128

2-(Cyclopentylamino)-N-(3,4-dichlorobenzyl)-5-nitrobenzamide (81.8 mg) was obtained as yellow powders from 2-amino-N-(3,4-dichlorobenzyl)-5-nitrobenzamide (150 mg) and cyclopentanone (111 mg) in a manner similar to Preparation 30(1).

NMR (CDCl$_3$, δ): 1.58–1.86 (6H, m), 2.07 (2H, m), 3.90 (1H, m), 4.56 (2H, d, J=7 Hz), 6.63 (1H, br), 6.69 (1H, d, J=8 Hz), 7.18 (1H, d, J=8 Hz), 7.43 (2H, m), 8.17 (1H, dd, J=4, 8 Hz), 8.35 (1H, d, J=4 Hz), 8.85 (1H, br).

PREPARATION 129(1)

Methyl 2-(trans-4-hydroxycyclohexylamino)-5-nitrobenzoate(20.4 g) was obtained as yellow powders from methyl 2-fluoro-5-nitrobenzoate (15.0 g) and trans-4-aminocyclohexanol (13.0 g) in a manner similar to Example 1(1).

NMR (CDCl$_3$, δ): 1.36–1.57 (4H, m), 1.97–2.25 (4H, m), 3.43–3.56 (1H, m), 3.70–3.84 (1H, m), 3.90 (3H, s), 6.69 (1H, d, J=8 Hz), 8.19 (1H, dd, J=2, 8 Hz), 8.60 (1H, br d, J=8 Hz), 8.87 (1H, d, J=2 Hz); Mass m/z: 294(EI+).

PREPARATION 129(2)

Methyl 2-(cis-4-acetoxycyclohexylamino)-5-nitrobenzoate (14.6 g) was obtained as yellow powders from methyl 2-(trans-4-hydroxycyclohexylamino)-5-nitrobenzoate (20.0 g) in a manner similar to Example 52(2).

NMR (DMSO-d$_6$, δ): 1.56–1.92 (8H, m), 2.04 (3H, s), 3.74–3.86 (1H, m), 3.89 (3H, s) 4.85 (1H, br), 7.05 (1H, d, J=8 Hz), 8.20 (1H, dd, J=2, 8 Hz), 8.64–8.73 (2H, m).

PREPARATION 129(3)

2-(cis-4-Hydroxycyclohexylamino)-5-nitrobenzoic acid (11.7 g) was obtained as yellow powders from methyl 2-(cis-4-acetoxycyclohexylamino)-5-nitrobenzoate (14.4 g) in a manner similar to Example 52(3).

NMR (DMSO-d$_6$, δ): 1.45–1.84 (8H, m), 3.62–3.81 (2H, m), 4.57 (1H, br), 6.95 (1H, d, J=8 Hz), 8.15 (1H, dd, J=2, 8 Hz), 8.66 (1H, d, J=2 Hz), 8.99 (1H, d, J=8 Hz); Mass m/z: 279.1 (M$^+$–1).

PREPARATION 129(4)

To a mitre of 3-methoxy-4-nitrobenzyl alcohol (3.00 g) and carbon tetrabromide (8.15 g) in dichloromethane (60 mL) was added triphenylphosphine (5.16 g) under ice-water cooling, and the mixture was stirred for an hour at ambient temperature. After evaporation of the solvent, the residue was purified by a silica gel column chromatography eluting with a mixture of hexane and ethyl acetate (5:1) to give 3-methoxy-4-nitrobenzyl bromide as pale yellow powders (4.87 g).

NMR (CDCl$_3$, δ): 3.99 (3H, s), 4.47 (2H, s), 7.04 (1H, d, J=8 Hz), 7.10 (1H, s), 7.83 (1H, d, J=8 Hz).

PREPARATION 129(5)

N-(3-Methoxy-4-nitrobenzyl)phthalimide (4.49 g) was obtained as colorless powders from 3-methoxy-4-nitrobenzylbromide (4.00 g) and potassium phthalimide (3.31 g) in a manner similar to Preparation 91(3).

NMR (CDCl$_3$, δ): 3.97 (3H, s), 4.87 (2H, s), 7.07 (1H, d, J=8 Hz), 7.18 (1H, s), 7.72–7.80 (2H, m), 7.81 (1H, d, J=8 Hz), 7.83–7.91 (2H, m).

PREPARATION 129(6)

3-Methoxy-4-nitrobenzylamine (1.28 g) was obtained as yellow oil from N-(3-methoxy-4-nitrobenzyl)phthalimide (3.00 g) in a manner similar to Preparation 91(4).

NMR (CDCl$_3$, δ): 3.97 (2H, s), 3.98 (3H, s), 6.95 (1H, d, J=8 Hz), 7.10 (1H, s), 7.84 (1H, d, J=8 Hz).

EXAMPLE 129

2-(cis-4-Hydroxycyclohexylamino)-N-(3-methoxy-4-nitrobenzyl)-5-nitrobenzamide (110 mg) was obtained as yellow powders from 2-(cis-4-hydroxycyclohexylamino)-5-nitrobenzoic acid (100 mg) and 3-methoxy-4-nitrobenzylamine (78.0 mg) in a manner similar to Preparation 1.

NMR (DMSO-d$_6$, δ): 1.44–1.75 (8H, br), 3.66 (2H, br), 3.93 (3H, s), 4.54 (3H, br), 6.90 (1H, d, J=8 Hz), 7.06 (1H, d, J=8 Hz), 7.34 (1H, s), 7.88 (1H, d, J=8 Hz), 8.13 (1H, dd, J=4, 8 Hz), 8.69 (1H, d, J=4 Hz), 9.27 (1H, br), 9.49 (1H, br); Mass m/z: 443(M$^+$).

PREPARATION 130(1)

N-(2-Chloro-5-methoxybenzyl)phthalimide (7.69 g) was obtained as colorless powders from 2-chloro-5-methoxybenzyl bromide (8.30 g) and potassium phthalimide (6.85 g) in a manner similar to Preparation 91(3).

NMR (CDCl$_3$, δ): 3.73 (3H, s), 4.95 (2H, s), 6.75 (2H, m), 7.27 (1H, m), 7.75 (2H, m), 7.88 (2H, m).

PREPARATION 130(2)

2-Chloro-5-methoxybenzylamine (1.67 g) was obtained as yellow oil from N-(2-chloro-5-methoxybenzyl)phthalimide (3.00 g) in a manner similar to Preparation 91(4).

NMR (CDCl$_3$, δ): 3.80 (3H, s), 3.89 (2H, s), 6.73 (1H, dd, J=4, 8 Hz), 6.94 (1H, d, J=4 Hz), 7.25 (1H, d, J=8 Hz).

EXAMPLE 130

N-(2-Chloro-5-methoxybenzyl)-2-(cis-4-hydroxycyclohexylamino)-5-nitrobenzamide (125 mg) was obtained as yellow powders from 2-(cis-4-hydroxycyclohexylamino)-5-nitrobenzoic acid (100 mg) and 2-chloro-5-methoxybenzylamine (73.5 mg) in a manner similar to Preparation 1.

NMR (DMSO-d$_6$, δ): 1.45–1.75 (8H, br), 3.61–3.72 (2H, br), 3.74 (3H, s), 4.48 (2H, d, J=7 Hz), 4.53 (1H, d, J=4 Hz), 6.88–6.93 (3H, m), 7.39 (1H, d, J=8 Hz), 8.13 (1H, dd, J=4, 8 Hz), 8.67 (1H, d, J=4 Hz), 9.17 (1H, d, J=8 Hz), 9.36 (1H, br); Mass m/z: 432(M$^+$).

PREPARATION 131(1)

To a solution of 3-hydroxy-4-methoxybenzoic acid (10.0 g) in methanol (100 mL) was added conc. sulfuric acid (10 mL) under ice-water cooling, and the mixture was heated for 15 hours under reflux. After evaporation of the solvent, the residue was partitioned between ethyl acetate and water. The separated organic layer was washed with an aqueous saturated sodium bicarbonate solution, water and brine. The resultant was dried over magnesium sulfate and evaporated in vacuo to give methyl 3-hydroxy-4-methoxybenzoate as a brown oil (9.43 g).

NMR (CDCl$_3$, δ): 3.88 (3H, s), 3.95 (3H, s), 5.69 (1H, s), 6.87 (1H, d, J=8 Hz), 7.57–7.64 (2H, m).

PREPARATION 131(2)

To a mixture of methyl 3-hydroxy-4-methoxybenzoate (4.00 g) and potassium carbonate (4.55 g) in dimethylformamide (20 mL) was added ethyl iodide (2.63 mL) under water-cooling and the mixture was stirred for 2 hours at ambient temperature. The mixture was partitioned between water and ethyl acetate. The separated organic layer was washed with water and brine, dried over magnesium sulfate and evaporated in vacuo to give methyl 3-ethoxy-4-methoxybenzoate as pale brown powders (4.55 g).

NMR (CDCl$_3$, δ): 1.49 (3H, t, J=7 Hz), 3.89 (3H, s), 3.93 (3H, s), 4.16 (2H, q, J=7 Hz), 6.89 (1H, d, J=8 Hz), 7.54 (1H, d, J=4 Hz), 7.66 (1H, dd, J=4, 8 Hz).

PREPARATION 131(3)

A mixture of methyl 3-ethoxy-4-methoxybenzoate (4.42 g), methanol (160 mL) and 1N-sodium hydroxide solution (40 mL) was heated for 2 hours under reflux. The reaction mixture was acidified with 1N-hydrochloric acid to pH 4, and the organic solvent was removed by evaporation. The aqueous layer was diluted with water and extracted with ethyl acetate. The extract was washed with brine, dried over magnesium sulfate and evaporated in vacuo. The residue was triturated with hexane to give 3-ethoxy-4-methoxybenzoic acid as colorless powders (3.76 g). NMR (CDCl$_3$, δ): 1.50 (3H, t, J=7 Hz), 3.95 (3H, s), 4.17 (2H, q, J=7 Hz), 6.92 (1H, d, J=8 Hz), 7.60 (1H, d, J=4 Hz), 7.76 (1H, dd, J=4, 8 Hz); Mass m/z: 195(M$^+$).

PREPARATION 131(4)

To a mixture of 3-ethoxy-4-methoxybenzoic acid (3.66 g) and oxalyl chloride (2.12 mL) in dichloromethane (40 mL) was added dimethylformamide (5 drops), and the mixture was stirred for 2 hours at ambient temperature. After evaporation of the solvent, the residue was redissolved in dichloromethane (40 mL). The solution was added to a mixture of 28% animonia solution (40 mL) and dichloromethane (40 mL) under ice-water cooling. The mixture was stirred for an hour at ambient temperature. The resulting precipitates were collected by filtration and washed with water and diethyl ether to give 3-ethoxy-4-methoxybenzamide as colorless powders (3.40 g).

NMR (DMSO-d$_6$, δ): 1.34 (3H, t, J=7 Hz), 3.80 (3H, s), 4.04 (2H, q, J=7 Hz), 7.00 (1H, d, J=8 Hz), 7.18 (1H, br), 7.39–7.51 (2H, m), 7.83 (1H, br).

PREPARATION 131(5)

To a solution of 3-ethoxy-4-methoxybenzamide (3.30 g) in pyridine (33 mL) was added phosphorus oxychloride (1.73 mL) under ice-water cooling, and the mixture was stirred for 2 hours at ambient temperature. After evaporation of the solvent, the residue was partitioned between ethyl acetate and water under ice-water cooling. The separated organic layer was washed with 1N-hydrochloric acid, water and brine, dried over magnesium sulfate and evaporated in vacuo. The residue was purified by a silica gel column chromatography eluting with a mixture of hexane and ethyl acetate (5:1 to 4:1) to give 3-ethoxy-4-methoxybenzonitrile as colorless powders (2.83 g).

NMR (CDCl$_3$, δ): 1.49 (3H, t, J=7 Hz), 3.93 (3H, s), 4.10 (2H, q, J=7 Hz), 6.90 (1H, d, J=8 Hz), 7.08 (1H, d, J=4 Hz), 7.27 (1H, dd, J=4, 8 Hz).

PREPARATION 131(6)

To a suspension of lithium aluminum hydride (1.17 g) in anhydrous tetrahydrofuran (15 mL) was added a solution of 3-ethoxy-4-methoxybenzonitrile (2.73 g) in tetrahydrofuran (15 mL). The mixture was stirred for an hour under water cooling and then for an hour at ambient temperature. Potassium sodium (+)-tartrate aqueous solution was added to the mixture under ice-water cooling. The mixture was diluted with ethyl acetate and the insolubles were filtered off. After evaporation of the filtrate, ethyl acetate was added. The solution was dried over magnesium sulfate and evaporated in vacuo to give 3-ethoxy-4-methoxybenzylamine as yellow oil (2.81 g).

NMR (CDCl$_3$, δ): 1.47 (3H, t, J=7 Hz), 3.80 (2H, s), 3.87 (3H, s), 4.12 (2H, q, J=7 Hz), 6.80–6.90 (3H, m).

EXAMPLE 131

N-(3-Ethoxy-4-methoxybenzyl)-2-(cis-4-hydroxycyclohexylamino)-5-nitrobenzamide (130 mg) was obtained as yellow powders from 2-(cis-4-hydroxycyclohexylamino)-5-nitrobenzoic acid (100 mg) and 3-ethoxy-4-methoxybenzylamine (77.6 mg) in a manner similar to Preparation 1.

NMR (DMSO-d$_6$, δ): 1.32 (3H, t, J=7 Hz), 1.45–1.80 (8H, br), 3.60–3.75 (2H, br), 3.73 (3H, s), 3.99 (2H, q, J=7 Hz), 4.37 (2H, d, J=7 Hz), 4.55 (1H, d, J=4 Hz), 6.82–6.96 (4H, m), 8.10 (1H, dd, J=4, 8 Hz), 8.60 (1H, d, J=4 Hz), 9.24 (1H, d, J=8 Hz), 9.32 (1H, br); Mass m/z: 442(M$^+$).

PREPARATION 132(1)

4-Chloro-3-ethoxytoluene (6.08 g) was obtained as pale yellow oil from 2-chloro-5-methylphenol (5.00 g) and ethyl iodide (4.21 mL) in a manner similar to Preparation 91(1).

NMR (CDCl$_3$, δ): 1.46 (3H, t, J=7 Hz), 2.32 (3H, s), 4.09 (2H, q, J=7 Hz), 6.66–6.73 (2H, m), 7.22 (1H, d, J=8 Hz).

PREPARATION 132(2)

4-Chloro-3-ethoxybenzyl bromide (8.75 g) was obtained as yellow oil from 4-chloro-3-ethoxytoluene (6.00 g) in a manner similar to Preparation 91(2).

NMR (CDCl$_3$, δ): 1.48 (3H, t, J=7 Hz), 4.11 (2H, q, J=7 Hz), 4.44 (2H, s), 6.84–6.95 (2H, m), 7.30 (1H, d, J=8 Hz).

PREPARATION 132(3)

N-(4-Chloro-3-ethoxybenzyl)phthalimide (7.88 g) was obtained as colorless powders from 4-chloro-3-ethoxybenzyl bromide (8.75 g) and potassium phthalimirde (6.82 g) in a manner similar to Preparation 91(3).

NMR (CDCl$_3$, δ): 1.46 (3H, t, J=7 Hz), 4.11 (2H, q, J=7 Hz), 4.78 (2H, s), 6.95 (1H, d, J=8 Hz), 7.04 (1H, s), 7.27 (1H, d, J=8 Hz), 7.72 (2H, m), 7.85 (2H, m).

PREPARATION 132(4)

4-Chloro-3-ethoxybenzylamine (2.25 g) was obtained as yellow oil from N-(4-chloro-3-ethoxybenzyl)phthaiimide (4.00 g) in a manner similar to Preparation 91(4).

NMR (CDCl$_3$, δ): 1.48 (3H, t, J=7 Hz), 3.82 (2H, s), 4.12 (2H, q, J=7 Hz), 6.79 (1H, d, J=8 Hz), 6.90 (1H, s), 7.25 (1H, d, J=8 Hz).

EXAMPLE 132

N-(4-Chloro-3-ethoxybenzyl)-2-(cis-4-hydroxycyclohexylamino)-5-nitrobenzaride (130 mg) was obtained as yellow powders from 2-(cis-4-hydroxycyclohexylamino)-5-nitrobenzoic acid (100 mg) and 4-chloro-3-ethoxybenzylamine (79.5 mg) in a manner similar to Preparation 1.

NMR (DMSO-$d_6$, δ): 1.36 (3H, t, J=7 Hz), 1.45–1.80 (8H, br), 3.58–3.65 (2H, br), 4.11 (2H, q, J=7 Hz), 4.44 (2H, d, J=7 Hz), 4.56 (1H, d, J=4 Hz), 6.86–6.92 (2H, m), 7.12 (1H, s), 7.38 (1H, d, J=8 Hz), 8.12 (1H, dd, J=4, 8 Hz), 8.64 (1H, d, J=4 Hz), 9.25 (1H, d, J=8 Hz), 9.40 (1H, br); Mass m/z: 446($M^+$).

PREPARATION 133(1)

Methyl 4-hydroxy-3-methoxybenzoate (25.2 g) was obtained as colorless powders from 4-hydroxy-3-methoxybenzoic acid (25.9 g) in a manner similar to Preparation 131 (1).

NMR (CDCl$_3$, δ): 3.89 (3H, s), 3.94 (3H, s), 6.07 (1H, s), 6.94 (1H, d, J=8 Hz), 7.55 (1H, s), 7.64 (1H, d, J=8 Hz).

PREPARATION 133(2)

Methyl 4-ethoxy-3-methoxybenzoate (4.10 g) was obtained as colorless powders from methyl 4-hydroxy-3-methoxybenzoate (4.00 g) and ethyl iodide (2.63 mL) in a manner similar to Preparation 131(2).

NMR (CDCl$_3$, δ): 1.50 (3H, t, J=7 Hz), 3.89 (3H, s), 3.93 (3H, s), 4.14 (2H, q, J=7 Hz), 6.88 (1H, d, J=8 Hz), 7.54 (1H, d, J=4 Hz), 7.65 (1H, dd, J=4, 8 Hz).

PREPARATION 133(3)

4-Ethoxy-3-methoxybenzoic acid (3.46 g) was obtained as colorless powders from methyl 4-ethoxy-3-methoxybenzoate (3.97 g) in a manner similar to Preparation 131(3).

NMR (CDCl$_3$, δ): 1.52 (3H, t, J=7 Hz), 3.92 (3H, s), 4.18 (2H, q, J=7 Hz), 6.89 (1H, d, J=8 Hz), 7.58 (1H, s), 7.73 (1H, d, J=8 Hz); Mass m/z: 195($M^+$).

PREPARATION 133(4)

4-Ethoxy-3-methoxybenzamide (1.74 g) was obtained as colorless powders from 4-ethoxy-3-methoxybenzoic acid (3.36 g) in a manner similar to Preparation 131(4).

NMR (DMSO-$d_6$, δ): 1.34 (3H, t, J=7 Hz), 3.79 (3H, s), 4.05 (2H, q, J=7 Hz), 6.97 (1H, d, J=8 Hz), 7.19 (1H, br), 7.44–7.49 (2H, m), 7.85 (1H, br).

PREPARATION 133(5)

4-Ethoxy-3-methoxybenzonitrile (1.88 g) was obtained as colorless powders from 4-ethoxy-3-methoxybenzamide (2.21 g) in a manner similar to Preparation 131(5).

NMR (CDCl$_3$, δ): 1.52 (3H, t, J=7 Hz), 3.89 (3H, s), 4.17 (2H, q, J=7 Hz), 6.88 (1H, d, J=8 Hz), 7.07 (1H, d, J=4 Hz), 7.25 (1H, dd, J=4, 8 Hz); Mass m/z: 178($M^+$).

PREPARATION 133(6)

4-Ethoxy-3-methoxybenzylamine (1.77 g) was obtained as colorless oil from 4-ethoxy-3-methoxybenzonitrile (1.78 g) in a manner similar to Preparation 131(6).

NMR (CDCl$_3$, δ): 1.46 (3H, t, J=7 Hz), 3.81 (2H, s), 3.89 (3H, s), 4.09 (2H, q, J=7 Hz), 6.80–6.90 (3H, m).

EXAMPLE 133

N-(4-Ethoxy-3-methoxybenzyl)-2-(cis-4-hydroxycyclohexylamino)-5-nitrobenzamide (120 mg) was obtained as yellow powders from 2-(cis-4-hydroxycyclohexylamino)-5-nitrobenzoic acid (100 mg) and 4-ethoxy-3-methoxybenlamine (77.6 mg) in a manner similar to Preparation 1.

NMR (DMSO-$d_6$, δ): 1.31 (3H, t, J=7 Hz), 1.43–1.75 (8H, br), 3.62–3.72 (2H, br), 3.75 (3H, s), 3.97 (2H, q, J=7 Hz), 4.38 (2H, d, J=7 Hz), 4.55 (1H, d, J=4 Hz), 6.81–6.97 (4H, m), 8.11 (1H, dd, J=4, 8 Hz), 8.61 (1H, d, J=4 Hz), 9.27 (1H, d, J=8 Hz), 9.32 (1H, br); Mass m/z: 442($M^+$).

PREPARATION 134(1)

Ethyl 3-methoxy-4-(2-methoxyethoxy)benzoate (5.69 g) was obtained as colorless powders from ethyl 4-hydroxy-3-methoxybenzoate (5.00 g) and 2-methoxyethyl bromide (3.59 mL) in a manner similar to Preparation 131(2).

NMR (CDCl$_3$, δ): 1.39 (3H, t, J=7 Hz), 3.46 (3H, s), 3.81 (2H, t, J=4 Hz), 3.91 (3H, s), 4.23 (2H, t, J=4 Hz), 4.35 (2H, q, J=7 Hz), 6.91 (1H, d, J=8 Hz), 7.55 (1H, d, J=4 Hz), 7.65 (1H, dd, J=4, 8 Hz).

PREPARATION 134(2)

3-Methoxy-4-(2-methoxyethoxy)benzoic acid (4.57 g) was obtained as colorless powders from ethyl 3-methoxy-4-(2-methoxyethoxy)benzoate (5.68 g) in a manner similar to Preparation 131(3).

NMR (DMSO-$d_6$, δ): 3.31 (3H, s), 3.68 (2H, t, J=4 Hz), 3.80 (3H, s), 4.15 (2H, t, J=4 Hz), 7.05 (1H, d, J=8 Hz), 7.44 (1H, d, J=4 Hz), 7.53 (1H, dd, J=4, 8 Hz); Mass m/z: 225($M^+$).

PREPARATION 134(3)

3-Methoxy-4-(2-methoxyethoxy)benzamide (3.86 g) was obtained as colorless powders from 3-methoxy-4-(2-methoxyethoxy)benzoic acid (4.56 g) in a manner similar to Preparation 131(4).

NMR (DMSO-$d_6$, δ): 3.31 (3H, s), 3.67 (2H, t, J=4 Hz), 3.80 (3H, s), 4.12 (2H, t, J=4 Hz), 7.00 (1H, d, J=8 Hz), 7.21 (1H, br), 7.46 (2H, m), 7.86 (1H, br).

PREPARATION 134(4)

3-Methoxy-4-(2-methoxyethoxy)benzonitrile (3.21 g) was obtained as colorless powders from 3-methoxy-4-(2-methoxyethoxy)benzamide (3.66 g) in a manner similar to Preparation 131(5).

NMR (CDCl$_3$, δ): 3.45 (3H, s), 3.81 (2H, t, J=4 Hz), 3.88 (3H, s), 4.20 (2H, t, J=4 Hz), 6.93 (1H, d, J=8 Hz), 7.08 (1H, d, J=4 Hz), 7.25 (1H, dd, J=4, 8 Hz).

PREPARATION 134(5)

3-Methoxy-4-(2-methoxyethoxy)benzylamine (3.26 g) was obtained as pale yellow oil from 3-methoxy-4-(2-methoxyethoxy)benzonitrile (3.11 g) in a manner similar to Preparation 131(6).

NMR (CDCl$_3$, δ): 3.45 (3H, s), 3.77 (2H, t, J=4 Hz), 3.79 (2H, s), 3.87 (3H, s), 4.16 (2H, t, J=4 Hz), 6.78–6.92 (3H, m).

EXAMPLE 134

2-(cis-4-Hydroxycyclohexylamino)-N-[3-methoxy-4-(2-methoxyethoxy)benzyl]-5-nitrobenzamide (150 mg) was obtained as yellow powders from 2-(cis-4-hydroxycyclohexylamino)-5-nitrobenzoic acid (120 mg) and 3-methoxy-4-(2-methoxyethoxy)benzylamine (109 mg) in a manner similar to Preparation 1.

NMR (DMSO-d$_6$, δ): 1.45–1.75 (8H, br), 3.30 (3H, s), 3.62 (2H, m), 3.60–3.70 (2H, br), 3.75 (3H, s), 4.03 (2H, m), 4.38 (2H, d, J=7 Hz), 4.56 (1H, d, J=4 Hz), 6.83–6.98 (4H, m), 8.11 (1H, dd, J=4, 8 Hz), 8.61 (1H, d, J=4 Hz), 9.26 (1H, br), 9.32 (1H, br).

PREPARATION 135(1)

Ethyl 4-cyclobutylmethoxy-3-methoxybenzoate (6.32 g) was obtained as colorless oil from ethyl 4-hydroxy-3-methoxybenzoate (5.00 g) and cyclobutylmethyl bromide (4.30 mL) in a manner similar to Preparation 131(2).

NMR (CDCl$_3$, δ): 1.41 (3H, t, J=7 Hz), 1.80–2.05 (4H, m), 2.13–2.28 (2H, m), 2.78–2.96 (1H, m), 3.91 (3H, s), 4.04 (2H, d, J=7 Hz), 4.35 (2H, q, J=7 Hz), 6.87 (1H, d, J=8 Hz), 7.54 (1H, d, J=4 Hz), 7.65 (1H, dd, J=4, 8 Hz).

PREPARATION 135(2)

4-Cyclobutylmethoxy-3-methoxybenzoic acid (5.10 g) was obtained as colorless powders from ethyl 4-cyclobutylmethoxy-3-methoxybenzoate (6.20 g) in a manner similar to Preparation 131(3).

NMR (DMSO-d$_6$, δ): 1.76–1.98 (4H, m), 2.00–2.17 (2H, m), 2.65–2.83 (1H, m), 3.80 (3H, s), 4.00 (2H, d, J=7 Hz), 7.04 (1H, d, J=8 Hz), 7.43 (1H, d, J=4 Hz), 7.54 (1H, dd, J=4, 8 Hz); Mass m/z: 235(M$^+$).

PREPARATION 135(3)

4-Cyclobutylnethoxy-3-methoxybenzamide (4.50 g) was obtained as colorless powders from 4-cyclobutylmethoxy-3-methoxybenzoic acid (4.90 g) in a manner similar to Preparation 131(4).

NMR (DMSO-d$_6$, δ): 1.75–2.00 (4H, m), 2.03–2.17 (2H, m), 2.67–2.80 (1H, m), 3.79 (3H, s), 3.98 (2H, d, J=7 Hz), 6.99 (1H, d, J=8 Hz), 7.19 (1H, br), 7.43–7.50 (2H, m), 7.85 (1H, br).

PREPARATION 135(4)

4-Cyclobutylmethoxy-3-methoxybenzonitrile (3.21 g) was obtained as colorless powders from 4-cyclobutylmethoxy-3-methoxybenzaraide (4.35 g) in a manner similar to Preparation 131(5).

NMR (DMSO-d$_6$, δ): 1.80–2.06 (4H, m), 2.12–2.27 (2H, m), 2.78–2.94 (1H, m), 3.87 (3H, s), 4.03 (2H, d, J=7 Hz), 6.88 (1H, d, J=8 Hz), 7.07 (1H, d, J=4 Hz), 7.25 (1H, dd, J=4, 8 Hz).

PREPARATION 135(5)

4-Cyclobutylmethoxy-3-methoxybenzylamine (3.61 g) was obtained as pale yellow oil from 4-cyclobutylmethoxy-3-methoxybenzonitrile (3.54 g) in a manner similar to Preparation 131(6).

NMR (CDCl$_3$, δ):1.80–2.00 (4H, m), 2.10–2.25 (2H, m), 2.76–2.92 (1H, m), 3.81 (2H, s), 3.87 (3H, s), 3.98 (2H, d, J=7 Hz), 6.78–6.86 (3H, m).

PREPARATION 135(6)

N-(4-Cyclobutylmethoxy-3-methoxybenzyl)-2-fluoro-5-nitrobenzamide (3.17 g) was obtained as yellow powders from 2-fluoro-5-nitrobenzoic acid (2.33 g) and 4-cyclobutylmethoxy- 3-methoxybenzylamine(2.87 g) in a manner similar to Preparation 55.

NMR (DMSO-d$_6$, δ): 1.75–1.98 (4H, m), 2.02–2.14 (2H, m), 2.63–2.78 (1H, m), 3.75 (3H, s), 3.90 (2H, d, J=7 Hz), 4.42 (2H, d, J=7 Hz), 6.83–6.98 (3H, m), 7.63 (1H, t, J=7 Hz), 8.37–8.44 (2H, m), 9.12 (1H, br); Mass m/z: 387(M$^+$).

EXAMPLE 135

N-(4-Cyclobutylmethoxy-3-methoxybenzyl)-2-[2-hydroxy-1-(hydroxymethyl)ethylamino]-5-nitrobenzamide (123 mg) was obtained as yellow powders from N-(4-cyclobutylmethoxy-3-methoxybenzyl)-2-fluoro-5-nitrobenzamide (150 mg) and 2-amino-1,3-propanediol (52.8 mg) in a manner similar to Example 1(1).

NMR (DMSO-d$_6$, δ): 1.75–1.98 (4H, m), 2.00–2.15 (2H, m), 2.65–2.79 (1H, m), 3.50–3.60 (4H, br), 3.60–3.70 (1H, br), 3.74 (3H, s), 3.89 (2H, d, J=7 Hz), 4.36 (2H, d, J=7 Hz), 4.93 (2H, t, J=7 Hz), 6.83 (1H, dd, J=4, 8 Hz), 6.89–7.00 (3H, m), 8.12 (1H, dd, J=4, 8 Hz), 8.57 (1H, d, J=4 Hz), 9.21 (1H, d, J=8 Hz), 9.27 (1H, br).

EXAMPLE 136

A mixture of 2-(cis-4-hydroxycyclohexylamino)-5-nitrobenzoic acid (120 mg), cyclohexanemethylamine (53.3 mg), 1-[3-(dimethylamino)propyl]-3-ethylcarbodiimde hydrochloride (107 mg) and 1-hydroxybenzotriazole (81.0 mg) in anhydrous dimethylformamide (3 mL) was stirred for 18 hours at ambient temperature. The mixture was partitioned between water and ethyl acetate. The separated organic layer was washed with 1N-hydrochloric acid, water, an aqueous saturated sodium bicarbonate solution and brine, successively, and dried over magnesium sulfate. After evaporation of the solvent, the residue was triturated with diisopropyl ether to give N-cyclohexylmethyl-2-(cis-4-hydroxycyclohexylamino)-5-nitrobenzamide (157 mg) as yellow powders.

NMR (DMSO-d$_6$, δ): 0.83–1.04 (2H, m), 1.04–1.31 (3H, m), 1.40–1.82 (14H, m), 3.09 (2H, t, J=7 Hz), 3.65 (2H, br), 4.55 (1H, d, J=4 Hz), 6.86 (1H, d, J=8 Hz), 8.10 (1H, dd, J=2, 8 Hz), 8.55 (1H, d, J=2 Hz), 8.83 (1H, m),9.25 (1H, d, J=8 Hz); Mass m/z: 374.3 (M$^+$−1).

EXAMPLE 137

2-(cis-4-Hydroxycyclohexylamino)-N-(1-naphthylmethyl)-5-nitrobenzamide (165 mg) was obtained as yellow powders from 2-(cis-4-hydroxycyclohexylamino)-5-nitrobenzoic acid (120 mg) and 1-naphthalenemethylamine (74.0 mg) in a manner similar to Example 136.

NMR (DMSO-d$_6$, δ): 1.45–1.80 (8H, m), 3.67 (2H, br), 4.58 (1H, d, J=4 Hz), 4.94 (2H, d, J=5 Hz), 6.89 (1H, d, J=8 Hz), 7.45–7.66 (4H, m), 7.84–7.93 (1H, m), 7.97 (1H, dd, J=2, 8 Hz), 8.11 (1H, dd, J=2, 9 Hz), 8.17 (1H, d, J=8 Hz), 8.61 (1H, d, J=2 Hz), 9.26 (1H, d, J=8 Hz), 9.43 (1H, m); Mass m/z: 418.2 (M$^+$−1).

EXAMPLE 138

2-(cis-4-Hydroxycyclohexylamino)-5-nitro-N-(2-quinolinylmethyl)benzamide (53.0 mg) was obtained as yellow powders from 2-(cis-4-hydroxycyclohexylamino)-5-nitrobenzoic acid (100 mg) and 2-aminomethylqunoline (62.1 mg) in a manner similar to Example 136.

NMR (DMSO-d$_6$, δ): 1.39–1.76 (8H, m), 3.65 (2H, br), 4.51 (1H, d, J=4 Hz), 4.74 (2H, d, J=5 Hz), 6.93 (1H, d, J=8

Hz), 7.52–7.64 (2H, m), 7.76 (1H, t, J=8 Hz), 7.95–8.04 (2H, m), 8.14 (1H, dd, J=2, 8 Hz), 8.37 (1H, d, J=8 Hz), 8.78 (1H, d, J=2 Hz), 9.25 (1H, d, J=8 Hz), 9.63 (1H, m); Mass m/z: 419.2 ($M^+$–1).

EXAMPLE 139

2-(cis-4-Hydroxycyclohexylamino)-5-nitro-N-[(1S)-1-phenylethyl]benzamide (123 mg) was obtained as yellow powders from 2-(cis-4-hydroxycyclohexylamino)-5-nitrobenzoic acid (120 mg) and (S)-1-phenylethylamine (62.3 mg) in a manner similar to Example 136.

NMR (DMSO-$d_6$, δ): 1.41–1.72 (11H, m), 3.65 (2H, br), 4.53 (1H, d, J=4 Hz), 5.10–5.24 (1H, m), 6.87 (1H, d, J=8 Hz), 7.19–7.30 (1H, m), 7.30–7.45 (4H, m), 8.12 (1H, dd, J=2, 8 Hz), 8.71 (1H, d, J=2 Hz), 9.10–9.23 (2H, m); Mass m/z: 382.2 ($M^+$–1).

PREPARATION 140(1)

To a solution of 2-(trifluoromethyl)benzyl bromide (1.50 g) in ethanol (15 mL) was added a solution of sodium cyanide (461 mg) in water (15 mL) at ambient temperature, and the mixture was heated for 3 hours under reflux. After evaporation of the organic solvent, the aqueous layer was extracted with ethyl acetate. The extract was washed with water and brine, dried over magnesium sulfate and evaporated in vacuo to give [2-(trifluoromethyl)phenyl]acetonitrile (1.08 g) as an oil.

NMR (CDCl$_3$, δ): 3.97 (2H, s), 7.48 (1H, t, J=8 Hz), 7.62 (1H, t, J=8 Hz), 7.66–7.75 (2H, m).

PREPARATION 140(2)

2-[2-(Trifluoromethyl)phenyl]ethylamine hydrochloride (187 mg) was obtained as pale yellow powders from [2-(trifluoromethyl)phenyl]acetonitrile (1.08 g) in a manner similar to Preparation 131(6).

NMR (DMSO-$d_6$, δ): 2.94–3.15 (4H, m), 7.44–7.59 (2H, m), 7.62–7.79 (2H, m), 8.16 (2H, br).

EXAMPLE 140

A mixture of 2-(cis-4-hydroxycyclohexylamino)-5-nitrobenzoic acid (120 mg), [2-(trifluoromethyl)phenyl]ethylamine hydrochloride (111 mg), 1-[3-(dimethylamino)propyl]-3-ethylcarbodiimide (86.4 mg) and 1-hydroxybenzotriazole (81.0 mg) in anhydrous dimethylformamide (3 mL) was stirred for 18 hours at ambient temperature. The mixture was partitioned between water and ethyl acetate. The separated organic layer was washed with IN-hydrochloric acid, water, an aqueous saturated sodium bicarbonate solution and brine, successively, and dried over magnesium sulfate. After evaporation of the solvent, the residue was purified by a preparative silica gel thin layer chromatography with a mixture of hexane and ethyl acetate (2:1). The obtained product was recrystallized from a mixture of petroleum ether and diethyl ether to give 2-(cis-4-hydroxycyclohexylamino)-5-nitro-N-{[2-(trifluoromethyl)phenyl]ethyl}benzamide (157 mg) as yellow powders.

NMR (DMSO-$d_6$, δ): 1.44–1.75(8H, m), 3.03(2H, t, J=7.5 Hz), 3.51(2H, q, J=7.5 Hz), 3.66(2H, br), 4.56(1H, d, J=4 Hz), 6.87(1H, d, J=8 Hz), 7.41–7.55(2H, m), 7.64(1H, t, J=8 Hz), 7.71(1H, d, J=8 Hz), 8.11(1H, d, J=2 Hz), 8.53(1H, d, J=2 Hz), 9.00(1H, m), 9.14(1H, d, J=8 Hz); Mass m/z: 450.2 ($M^+$–H).

PREPARATION 141(1)

4-Bromomethylthiazole (1.80 g) was obtained as an oil from 4-methylthiazole (1.00 g) and N-bromosuccinimide (1.97 g) in a manner similar to Preparation 91(2).

NMR (DMSO-$d_6$, δ): 4.65 (2H, s), 7.37 (1H, d, J=2 Hz), 8.82 (1H, d, J=2 Hz).

PREPARATION 141(2)

N-(Thiazol-4-ylmethyl)phthalimide (1.20 g) was obtained as white powders from 4-bromomethylthiazole (1.80 g) and potassium phthalimde (1.87 g) in a manner similar to Preparation 91(3).

NMR (DMSO-$d_6$, δ): 5.06 (2H, s), 7.30 (1H, d, J=2 Hz), 7.68–7.80 (2H, m), 7.84–7.92 (2H, m), 8.76 (1H, d, J=2 Hz).

PREPARATION 141(3)

4-Aminomethylthiazole hydrochloride (305 mg) was obtained as white powders from N-(thiazol-4-ylmethyl) phthalimide (1.15 g) in a manner similar to Preparation 91(4).

NMR (DMSO-$d_6$, δ): 4.18 (2H, q, J=5 Hz), 7.83 (1H, d, J=2 Hz), 8.52 (3H, br), 9.20 (1H, d, J=2 Hz).

EXAMPLE 141

2-(cis-4-Hydroxycyclohexylamino)-5-nitro-N-(4-thiazolylmethyl)benzamide (92 mg) was obtained as yellow powders from 2-(cis-4-hydroxycyclohexylamino)-5-nitrobenzoic acid (120 mg) and 4-aminomethylthiazole hydrochloride (70.9 mg) in a manner similar to Preparation 1.

NMR (DMSO-$d_6$, δ): 1.42–1.–76 (8H, m), 3.65 (2H, br), 4.54 (1H, d, J=4 Hz), 4.59 (1H, d, J=5 Hz), 6.89 (1H, d, J=8 Hz), 7.52 (1H, d, J=2 Hz), 8.12 (1H, dd, J=2, 8 Hz), 8.66 (1H, d, J=2 Hz), 9.07 (1H, d, J=2 Hz), 9.28 (1H, d, J=8 Hz), 9.45 (1H, m); Mass m/z: 375.2 ($M^+$–H).

PREPARATION 142(1)

2-Cyanobenzo[b]thiophene (250 mg) was obtained as an oil from benzo[b]thiophene-2-carboxamide (500 mg) in a manner similar to Preparation 131(5).

NMR (CDCl$_3$, δ): 7.48 (1H, t, J=8 Hz), 7.54 (1H, t, J=8 Hz), 7.84–7.94 (3H, m).

PREPARATION 142(2)

2-(Aminomethyl)benzo[b]thiophene hydrochloride (281 mg) was obtained as pale yellow powders from 2-cyanobenzo[b]thiophene (250 mg) in a manner similar to Preparation 131(6).

NMR (DMSO-$d_6$, δ): 4.35 (2H, s), 7.34–7.45 (2H, m), 7.57 (1H, s), 7.83–7.90 (1H, m), 7.96–8.04 (1H, m), 8.67 (3H, br).

EXAMPLE 142

N-(Benzo[b]thiophen-2-ylmethyl)-2-(cis-4-hydroxycyclohexylamino)-5-nitrobenzamide (104 mg) was obtained as yellow powders from 2-(cis-4-hydroxycyclohexylamino)-5-nitrobenzoic acid (100 mg) and 2-(aminomethyl)benzo[b]thiophene hydrochloride (78.4 mg) in a manner similar to Example 140.

NMR (DMSO-$d_6$, δ): 1.44–1.80 (8H, m), 3.66 (2H, br), 4.57 (1H, d, J=4 Hz), 4.72 (2H, d, J=5 Hz), 6.91 (1H, d, J=8 Hz), 7.24–7.28 (3H,m), 7.79 (1H, d, J=8 Hz), 7.91 (1H, d, J=8 Hz), 8.13 (1H, dd, J=2, 8 Hz), 8.64 (1H, d, J=2 Hz), 9.26 (1H, d, J=8 Hz), 9.62 (1H, m).

PREPARATION 143(1)

2-Cyanobenzofuran (402 mg) was obtained as an oil from benzofuran-2-carboxamide (500 mg) in a manner similar to Preparation 131(5).

NMR (CDCl$_3$, δ): 7.37 (1H, t, J=8 Hz), 7.43–7.60 (3H, m), 7.69 (1H, d, J=8 Hz).

PREPARATION 143(2)

2-(Aminomethyl)benzofuran hydrochloride (333 mg) was obtained as pale yellow powders from 2-cyanobenzofuran (400 mg) in a manner similar to Preparation 131(6).

NMR (DMSO-d$_6$, δ): 4.23 (2H, s), 7.03 (1H, s), 7.28 (1H, t, J=8 Hz), 7.35 (1H, t, J=8 Hz), 7.60 (1H, d, J=8 Hz), 7.69 (1H, d, J=8 Hz), 8.62 (3H, br).

EXAMPLE 143

N-(Benzofuran-2-ylmethyl)-2-(cis-4-hydroxycyclohexylamino)-5-nitrobenzamide (154 mg) was obtained as yellow powders from 2-(cis-4-hydroxycyclohexylamino)-5-nitrobenzoic acid (120 mg) and 2-(aminomethyl)benzofuran hydrochloride (86.5 mg) in a manner similar to Example 140.

NMR (DMSO-d$_6$, δ): 1.43–1.77 (8H, m), 3.67 (2H, br), 4.55 (1H, d, J=4 Hz), 4.63 (2H, d, J=5 Hz), 6.81 (1H, s), 6.90 (1H, d, J=8 Hz), 7.22 (1H, t, J=8 Hz), 7.27 (1H, t, J=8 Hz), 7.56 (1H, d, J=8 Hz), 7.60 (1H, d, J=8 Hz), 8.11 (1H, dd, J=2, 8 Hz), 8.67 (1H, d, J=2 Hz), 9.30 (1H, d, J=8 Hz), 9.49 (1H, m).

EXAMPLE 144

N-(3,4-Dimethylbenzyl)-2-(cis-4-hydroxycyclohexylamino)-5-nitrobenzamide (185 mg) was obtained as yellow powders from 2-(cis-4-hydroxycyclohexyl)amino-5-nitrobenzoic acid (200 mg) and 3,4-dimethylbenzylamine (116 mg) in a manner similar to Preparation 1.

m.p. 157–158° C. NMR (DMSO-d$_6$, δ): 1.34–1.74 (8H, m), 2.19 (3H, s), 2.21 (3H, s), 3.60–3.72 (2H, m), 4.38 (2H, d, J=5 Hz), 4.55 (1H, d, J=4 Hz), 6.88 (1H, d, J=10 Hz), 7.04 (1H, br d, J=8 Hz), 7.07–7.14 (2H, m), 8.11 (1H, dd, J=10, 3 Hz), 8.62 (1H, d, J=3 Hz), 9.30 (1H, d, J=8 Hz), 9.34 (1H, t, J=5 Hz); Mass m/z: 396(M$^+$).

EXAMPLE 145

2-(cis-4-Hydroxycyclohexylamino)-5-nitro-N-(4-phenylbenzyl)benzamide (113 mg) was obtained as yellow powders from 2-(cis-4-hydromycyclohexyl)amino-5-nitrobenzoic acid (78 mg) and 4-phenylbenzylamine (61 mg) in a manner similar to Preparation 1.

m.p. 168–170° C. NMR (DMSO-d$_6$, δ): 1.43–1.80 (8H, m), 3.59–3.75 (2H, m), 4.50 (2H, d, J=6 Hz), 4.55 (1H, d, J=5 Hz), 6.90 (1H, d, J=10 Hz), 7.35 (1H, dd, J=7.5, 7.5 Hz), 7.39–7.52 (4H, m), 7.65 (4H, m), 8.12 (1H, dd, J=10, 2 Hz), 8.67 (1H, d, J=2 Hz), 9.33 (1H, d, J=8 Hz), 9.45 (1H, t, J=6 Hz).

PREPARATION 146(1)

Methyl 3-benzyloxy-4-methoxybenzoate (5.70 g) was obtained as colorless powders from methyl 3-hydroxy-4-methoxybenzoate (4.00 g) and benzyl bromide (3.13 mL) in a manner similar to Preparation 131(2).

NMR (CDCl$_3$, δ): 3.87 (3H, s), 3.93 (3H, s), 5.18 (2H, s), 6.90 (1H, d, J=8 Hz), 7.28–7.40 (3H, m), 7.46 (2H, m), 7.61 (1H, d, J=4 Hz), 7.68 (1H, dd, J=4, 8 Hz).

PREPARATION 146(2)

3-Benzyloxy-4-methoxybenzoic acid (5.06 g) was obtained as colorless powders from methyl 3-benzyloxy-4-methoxybenzoate (5.60 g) in a manner similar to Preparation 131(3).

NMR (DMSO-d$_6$, δ): 3.84 (3H, s), 5.13 (2H, s), 7.07 (1H, d, J=8 Hz), 7.30–7.50 (5H, m), 7.53 (1H, d, J=4 Hz), 7.58 (1H, dd, J=4, 8 Hz).

PREPARATION 146(3)

3-Benzyloxy-4-methoxybenzanmide (4.03 g) was obtained as colorless powders from 3-benzyloxy-4-methoxybenzoic acid (4.96 g) in a manner similar to Preparation 131(4).

NMR (DMSO-d$_6$, δ): 3.81 (3H, s), 5.11 (2H, s), 7.02 (1H, d, J=8 Hz), 7.21 (1H, br), 7.32–7.47 (5H, m), 7.51 (1H, dd, J=4, 8 Hz), 7.58 (1H, d, J=4 Hz), 7.85 (1H, br).

PREPARATION 146(4)

3-Benzyloxy-4-methoxybenzonitrile (3.35 g) was obtained as colorless powders from 3-benzyloxy-4-methoxybenzamide (3.93 g) in a manner similar to Preparation 131(5).

NMR (CDCl$_3$, δ): 3.94 (3H, s), 5.15 (2H, s), 6.91 (1H, d, J=8 Hz), 7.10 (1H, d, J=4 Hz), 7.25–7.45 (6H, m).

PREPARATION 146(5)

3-Benzyloxy-4-methoxybenzylamine (3.51 g) was obtained as pale yellow oil from 3-benzyloxy-4-methoxybenzonitrile (3.30 g) in a manner similar to Preparation 131(6).

NMR (CDCl$_3$, δ):3.76 (2H, s), 3.88 (3H, s), 5.16 (2H, s), 6.83–6.90 (3H, m), 7.24–7.45 (5H, m).

EXAMPLE 146

N-(3-Benzyloxy-4-methoxybenzyl)-2-(cis-4-hydroxycyclohexylamino)-5-nitrobenzamide (152 mg) was obtained as yellow powders from 2-(cis-4-hydroxycyclohexylamino)-5-nitrobenzoic acid (100 mg) and 3-benzyloxy-4-methoxybenzylamine (104 mg) in a manner similar to Preparation 1.

NMR (DMSO-d$_6$, δ): 1.45–1.77 (8H, br), 3.62–3.72 (2H, br), 3.75 (3H, s), 4.37 (2H, d, J=7 Hz), 4.56 (1H, d, J=4 Hz), 5.06 (2H, s), 6.85–6.97 (3H, m), 7.05 (1H, d, J=2 Hz), 7.24–7.37 (3H, m), 7.40–7.47 (2H, m), 8.12 (1H, dd, J=4, 8 Hz), 8.61 (1H, d, J=4 Hz), 9.30 (2H, br); Mass m/z: 504(M$^+$).

PREPARATION 147(1)

3,4-Ethylenedioxybenzyl bromide (2.31 g) was obtained as colorless oil from 3,4-ethylenedioxybenzyl alcohol (2.00 g) and carbon tetrabromide (5.99 g) in a manner similar to Preparation 129(4).

NMR (CDCl$_3$, δ): 4.25 (4H, s), 4.44 (2H, s), 6.78–6.94 (3H, m).

PREPARATION 147(2)

N-(3,4-Ethylenedioxybenzyl)phthalimide (2.65 g) was obtained as white powders from 3,4-ethylenedioxybenzyl bromide (2.31 g) and potassium phthalimide (1.92 g) in a manner similar to preparation 91(3). NMR (CDCl$_3$, δ): 4.20 (4H, s), 4.64 (2H, s), 6.72–6.81 (3H, m), 7.80–7.93 (4H, m); Mass m/z: 296.1 (M$^+$+1).

PREPARATION 147(3)

3,4-Ethylenedioxybenzylamine hydrochloride (1.70 g) was obtained as white powders from N-(3,4-ethylenedioxybenzyl)phthalimide(2.60 g) in a manner similar to Preparation 91(4).

NMR (DMSO-d$_6$, δ): 3.88 (2H, q-like), 4.24 (4H, s), 6.84–6.97 (2H, m), 7.03 (1H, d, J=2 Hz), 8.29 (3H, br).

PREPARATION 147(4)

N-(3,4-Ethylenedioxybenzyl)-2-fluoro-5-nitrobenzamide (1.39 g) was obtained as yellow powders from 2-fluoro-5-nitrobenzoic acid (1.00 g) and 3,4-ethylenedioxybenzylamine hydrochloride (1.14 g) in a manner similar to Preparation 55.

NMR (DMSO-d$_6$, δ): 4.19 (4H, s), 4.34 (1H, d, J=5 Hz), 6.73–6.84 (3H, m), 7.59 (1H, t, J=8 Hz), 8.34–8.44 (2H, m), 9.07 (1H, m); Mass m/z: 331.4 (M$^+$–1).

EXAMPLE 147

N-(3,4-Ethylenedioxybenzyl)-2-(trans-4-hydroxycyclohexylamino)-5-nitrobenzamide (496 mg) was obtained as yellow powders from N-(3,4-ethylenedioxybenzyl)-2-fluoro-5-nitrobenzamide (400 mg) and trans-4-arninocyclohexanol (208 mg) in a manner similar to Example 1(1).

NMR (DMSO-d$_6$, δ): 1.20–1.43 (4H, m), 1.73–1.88 (2H, m), 1.88–2.05 (2H, m), 3.40–3.59 (2H, m), 4.21 (4H, s), 4.30 (2H, d, J=5 Hz), 4.62 (1H, d, J=4 Hz), 6.74–6.84 (3H, m), 6.90 (1H, d, J=8 Hz), 8.11 (1H, dd, J=8, 2 Hz), 8.59 (1H, d, J=2 Hz), 9.08 (1H, d, J=8 Hz), 9.30 (1H, m); Mass m/z: 426.2 (M$^+$–1).

PREPARATION 148

N-(3-Chloro-4-methoxybenzyl)-2-fluoro-5-(trifluoromethyl)benzamide (2.92 g) was obtained from 2-fluoro-5-(trifluoromethyl)benzoic acid (1.76 g) and 3-chloro-4-methoxybenzylamine (1.45 g) in a in a manner similar to Preparation 1.

NMR (DMSO-d$_6$, δ): 3.83 (3H, s), 4.41 (2H, d, J=6 Hz), 7.13 (1H, d, J=9 Hz), 7.29 (1H, dd, J=2, 8 Hz), 7.41 (1H, d, J=2 Hz), 7.58 (1H, t, J=9 Hz), 7.93 (1H, m), 7.97 (1H, d, J=8 Hz), 9.08 (1H, t, J=6 Hz).

EXAMPLE 148

N-(3-Chloro-4-methoxybenzyl)-2-[2-hydroxy-1-(hydroxymethyl)ethylamino]-5-(trifluoromethyl)benzamide (91 mg) was obtained from N-(3-chloro-4-methoxybenzyl)-2-fluoro-5-(trifluoromethyl)benzamide (194 mg) and 2-amino-1,3-propanediol (147 mg) in a manner similar to Example 1(1).

NMR (DMSO-d$_6$, δ): 3.4–3.6 (5H, m), 3.83 (3H, s), 4.35 (2H, d, J=6 Hz), 4.83 (2H, m), 6.91 (1H, d, J=9 Hz), 7.11 (1H, d, J=9 Hz), 7.26 (1H, dd, J=2, 9 Hz), 7.37 (1H, d, J=2 Hz), 7.53 (1H, dd, J=2, 9 Hz), 7.93 (1H, d, J=2 Hz), 8.63 (1H, m), 9.07 (1H, t, J=6 Hz); Mass m/z : 431 (M$^+$–1).

EXAMPLE 149(1)

(R)-2-[1-tert-Butoxycarbonyl)pyrrolidin-3-ylamino]-N-(3-chloro-4-methoxybenzyl)-5-(trifluoromethyl)benzamide (696 mg) was obtained as amorphous powders from N-(3-chloro-4-methoxybenzyl)-2-fluoro-5-trifluoromethylbenzamide (700 mg) and (R)-3-amino-1-tert-butoxycarbonylpyrrolidine (721 mg) in a manner similar to Example 1(1).

NMR (DMSO-d$_6$, δ): 1.39(9H, s), 1.83(1H, m), 2.20(1H, m), 3.09(1H, m), 3.25–3.45(2H, m), 3.61(1H, m), 3.83(3H, s), 4.15(1H, m), 4.36(2H, d, J=6 Hz), 6.93(1H, d, J=8 Hz), 7.10(1H, d, J=8 Hz), 7.25(1H, dd, J=2, 8 Hz), 7.36(1H, d, J=2 Hz), 7.59(1H, brd, J=8 Hz), 7.98(1H, br), 8.61(1H, d, J=7 Hz), 9.17(1H, t, J=6 Hz); Mass: (ESI+) 528(M+H), (ESI–) 526(M–H).

EXAMPLE 149(2)

(R)-N-(3-Chloro-4-methoxybenzyl)-2-(3-pyrrolidinylamino)-5-(trifluoromethyl)benzamide (448 mg) was obtained as amorphous powders from (R)-2-[1-(tert-butoxycarbonyl)pyrrolidin-3-ylamino]-N-(3-chloro-4-methoxybenzyl)-5-(trifluoromethyl)benzamide (596 mg) in a manner similar to Example 87(2).

NMR (DMSO-d$_6$, δ): 1.49(1H, m), 2.10(1H, m), 2.55(1H, dd, J=4, 10 Hz), 2.7–2.95(2H, m), 3.13(1H, dd, J=6, 10Hz), 3.83(3H, s), 3.93(1H, m), 4.35(2H, d, J=6 Hz), 6.83(1H, d, J=8 Hz), 7.11(1H, d, J=8 Hz), 7.26(1H, dd, J=2, 8 Hz), 7.37(1H, d, J=2 Hz), 7.56(1H, dd, J=2, 8 Hz), 7.95(1H, d, J=2 Hz), 8.52(1H, d, J=7 Hz), 9.13(1H, t, J=6 Hz); Mass: (ESI+) 428(M+H), (ESI–) 426(M–H).

EXAMPLE 149(3)

(R)-N-(3-Chloro-4-methoxybenzyl)-2-[1-(methoxycarbonyl)pyrroldin-3-ylamino]-5-trifluoromethylbenzamide (119 mg) was obtained as amorphous powders from (R)-N-(3-chloro-4-methoxybenzyl)-2-(3-pyrrolidinylamino)-5-(trifluoromethyl)benzamide (109 mg) in a manner similar to Example 85(5).

NMR (DMSO-d$_6$, δ): 1.86(1H, m), 2.21(1H, m), 3.16(1H, m), 3.30–3.50(2H, m), 3.58 and 3.59(3H, s), 3.66(1H, m), 3.83(3H, s), 4.18(1H, m), 4.36(2H, d, J=6 Hz), 6.93(1H, d, J=9 Hz), 7.11(1H, d, J=9 Hz), 7.25(1H, dd, J=2, 9 Hz), 7.36(1H, d, J=2 Hz), 7.59(1H, brd, J=9 Hz), 7.99(1H, br), 8.62(1H, d, J=7 Hz), 9.18(1H, t, J=6 Hz).

EXAMPLE 150(1)

(S)-2-[1-(tert-Butoxycarbonyl)pyrrolidin-3-ylamino]-N-(3-chloro-4-methoxybenzyl)-5-(trifluoromethyl)benzamide (516 mg) was obtained as amorphous powders from N-(3-chloro-4-methoxybenzyl)-2-fluoro-5-trifluoromethylbenzamide (700 mg) and (S)-3-amino-1-tert-butoxycarbonylpyrrolidine (721 mg) in a manner similar to Example 1(1).

NMR (DMSO-d$_6$, δ): 1.39(9H, s), 1.83(1H, m), 2.20(1H, m), 3.09(1H, m), 3.25–3.45(2H, m), 3.61(1H, m), 3.83(3H, s), 4.15(1H, m), 4.36(2H, d, J=6 Hz), 6.93(1H, d, J=8 Hz), 7.10(1H, d, J=8 Hz), 7.25(1H, dd, J=2, 8 Hz), 7.36(1H, d, J=2 Hz), 7.59(1H, brd, J=8 Hz), 7.98(1H, brs), 8.61(1H, d, J=7 Hz), 9.17(1H, t, J=6 Hz).

EXAMPLE 150(2)

(S)-N-(3-Chloro-4-methoxybenzyl)-2-(3-pyrrolidinylamino)-5-(trifluoromethyl)benzamide (262 mg) was obtained as amorphous powders from (S)-2-[1-(tert-butoxycarbonyl)pyrrolidin-3-ylamino]-N-(3-chloro-4-methoxybenzyl)-5-(trifluoromethyl)benzamide (430 mg) in a manner similar to Example 87(2).

NMR (DMSO-d$_6$, δ): 1.49(1H, m), 2.10(1H, m), 2.55(1H, dd, J=4, 10 Hz), 2.7–2.95(2H, m), 3.13(1H, dd, J=6, 10 Hz), 3.83(3H, s), 3.93(1H, m), 4.35(2H, d, J=6 Hz), 6.83(1H, d, J=8 Hz), 7.11(1H, d, J=8 Hz), 7.26(1H, dd, J=2, 8 Hz), 7.37(1H, d, J=2 Hz), 7.56(1H, dd, J=2, 8 Hz), 7.95(1H, d, J=2 Hz), 8.52(1H, d, J=7 Hz), 9.13(1H, t, J=6 Hz); Mass (ESI+) 428(M+H), (ESI–) 426(M–H).

EXAMPLE 150(3)

(S)-N-(3-Chloro-4-methoxybenzyl)-2-[1-(methoxycarbonyl)pyrrolidin-3-ylamino]-5-

(trifluoromethyl)benzamide (105 mg) was obtained as amorphous powders from (S)-N-(3-chloro-4-methoxybenzyl)-2-(3-pyrrolidinylamino)-5-(trifluoromethyl)benzamide (115 mg) in a manner similar to Example 85(5).

NMR (DMSO-d$_6$, δ): 1.86(1H, m), 2.21(1H, m), 3.16(1H, m), 3.30–3.50(2H, m), 3.58 and 3.59(3H, s), 3.66(1H, m), 3.83(3H, s), 4.18(1H, m), 4.36(2H, d, J=6 Hz), 6.93(1H, d, J=9 Hz), 7.11(1H, d, J=9 Hz), 7.25(1H, dd, J=2, 9 Hz), 7.36(1H, d, J=2 Hz), 7.59(1H, brd, J=9 Hz), 7.99(1H, br), 8.62(1H, d, J=7 Hz), 9.18(1H, t, J=6 Hz).

PREPARATION 151

4-Chloro-2,5-difluoro-N-(3,4-dimethoxybenzyl) benzamide (1.66 g) was obtained from 4-chloro-2,5-difluorobenzoic acid (1.05 g) and veratrylamine (0.91 mL) in a in a manner similar to preparation 1.

NMR (DMSO-d$_6$, δ): 3.73 (3H, s), 3.74 (3H, s), 4.39 (2H, d, J=6 Hz), 6.81–6.97 (3H, m), 7.67 (1H, dd, J=6, 9 Hz), 7.79 (1H, dd, J=6, 9 Hz), 8.96 (1H, t, J=6 Hz).

EXAMPLE 151

4-Chloro-N-(3,4-dimethoxybenzyl)-5-fluoro-2-(trans-4-hydroxycyclohexylamino)benzamide (27 mg) was obtained from 4-chloro-2,5-chloro-N-(3,4-dimethoxybenzyl) benzamide (102 mg) and trans-4-aminocyclohexanol (103 mg) in a manner similar to Example NMR (DMSO-d$_6$, δ): 1.06–1.39 (4H, m), 1.74–1.84 (2H, m), 1.88–1.97 (2H, m), 3.38–3.53 (2H, m), 3.72 (3H, s), 3.73 (3H, s), 4.33 (2H, d, J=6 Hz), 4.57 (1H, d, J=4 Hz), 6.80–6.93 (4H, m), 7.66 (1H, d, J=11 Hz), 7.83 (1H, d, J=8 Hz), 8.89 (1H, t, J=6 Hz).

PREPARATION 152(1)

5-Bromo-N-(4-chloro-3-methoxybenzyl)-2-fluorobenzamide (3.07 g) was obtained as colorless powders from 5-bromo-2-fluorobenzoic acid (2.00 g) and 4-chloro-3-methoxybenzylamine (1.72 g) in a manner similar to Preparation 1.

NMR (DMSO-d$_6$, δ): 3.85 (3H, s), 4.45 (2H, d, J=7 Hz), 6.91 (1H, dd, J=4, 8 Hz), 7.13 (1H, d, J=4 Hz), 7.32 (1H, t, J=8 Hz), 7.38 (1H, d, J=8 Hz), 7.69–7.80 (2H, m), 9.05 (1H, br).

PREPARATION 152(2)

To a solution of 5-bromo-N-(4-chloro-3-methoxybenzyl)-2-fluorobenzamide (2.00 g) in toluene (40 mL) were added tetrakis(triphenylphosphine)palladium (217 mg) and tributylvinyltin (1.87 g), and the mixture was heated for 4 hours under reflux. After evaporation of the solvent, the residue was partitioned between ethyl acetate and saturated potassium fluoride solution. The remaining precipitates were removed by filtration. The separated organic layer was washed with water and brine, dried over magnesium sulfate and evaporated in vacuo. The residue was purified by a silica gel column chromatography eluting with a mixture of hexane and ethyl acetate (3:1) to give N-(4-chloro-3-methoxybenzyl)-2-fluoro-5-vinylbenzamide as pale yellow powders (1.51 g).

NMR (CDCl$_3$, δ): 3.90 (3H, s), 4.65 (2H, br), 5.31 (1H, d, J=10 Hz), 5.77 (1H, d, J=15 Hz), 6.65–6.78 (1H, dd, J=10, 15 Hz), 6.84–6.94 (2H, br), 6.96–7.10 (2H, m), 7.33 (1H, d, J=8 Hz), 7.50 (1H, m), 8.12 (1H, dd, J=4, 8 Hz); Mass m/z: 318(M$^+$).

PREPARATION 152(3)

A mixture of copper(I) chloride (464 mg) and palladium (II) chloride (83.2 mg) in a mixture of dimethylformamide (42 mL) and water (6 mL) was stirred for an hour under oxygen atmosphere (1 atm) at ambient temperature. To the mixture was added N-(4-chloro-3-methoxybenzyl)-2-fluoro-5-vinylbenzamide (1.50 g). After stirring for 6 hours at 60° C., the mixture was partitioned between ethyl acetate and 1N-hydrochoric, acid. The separated organic layer was washed with water, an aqueous saturated sodium bicarbonate solution and brine, dried over magnesium sulfate and evaporated in vacuo. The residue was purified by a silica gel column chromatography eluting with a mixture of hexane and ethyl acetate (2:1 to 1:1) to give 5-acetyl-2-fluoro-N-(4-chloro-3-methoxybenzyl)benzamide as colorless powders (719 mg).

NMR PMSO-d$_6$, δ): 2.61 (3H, s), 3.85 (3H, s), 4.48 (2H, d, J=7 Hz), 6.94 (1H, dd, J=4, 8 Hz), 7.15 (1H, d, J=4 Hz), 7.39 (1H, d, J=8 Hz), 7.47 (1H, t, J=8 Hz), 8.12 (1H, m), 8.19 (1H, dd, J=4, 8 Hz), 9.09 (1H, br); Mass m/z :334(M$^+$).

EXAMPLE 152

(R)-5-Acetyl-N-(4-chloro-3-methoxybenzyl)-2-(2-hydroxy-1-methylethylamino)benzamide (68.1 mg) was obtained as colorless powders from 5-acetyl-N-(4-chloro-3-methoxybenzyl)-2-fluorobenzamide (100 mg) and (R)-2-amino-1-propanol (44.7 mg) in a manner similar to Example 1(1).

NMR (DMSO-d$_6$, δ): 1.14 (3H, d, J=7 Hz), 2.47 (3H, s), 3.38–3.50 (2H, m), 3.62–3.72 (1H, br), 3.85 (3H, s), 4.43 (2H, d, J=7 Hz), 4.91 (1H, t, J=7 Hz), 6.80 (1H, d, J=8 Hz), 6.91 (1H, dd, J=4, 8 Hz), 7.13 (1H, d, J=4 Hz), 7.38 (1H, d, J=8 Hz), 7.86 (1H, dd, J=4, 8 Hz), 8.25 (1H, d, J=4 Hz), 8.63 (1H, d, J=8 Hz), 9.17 (1H, br).

PREPARATION 153(1)

5-Chlorosulfonyl-2-fluorobenzoic acid (2 g) was dissolved in dichloromethane (20 mL) under nitrogen atmosphere and cooled to 0° C. tert-Butyl 1-piperazinecarboxylate (3.12 g) was added portionwise to the solution at 0° C. and stirred for 3 hours at ambient temperature. The organic solvent was evaporated in vacuo, and the residue was dissolved in 1N-sodium hydroxide solution. The aqueous solution was washed with diethyl ether and acidified with 1N-hydrochloric acid. The precipitates were collected by filtration and washed with water to give 5-[4-(tert-butoxycarbonyl)piperazin-1-ylsulfonyl]-2-fluorobenzoic acid (2.26 g) as a colorless solid substance.

mp. 203–204.5° C. NMR (DMSO-d$_6$, δ): 1.35 (9H, s), 2.84–3.01 (4H, m), 3.35–3.54 (4H, m), 7.62 (1H, dd, J=9.0, 8.5 Hz), 7.95–8.04 (1H, m), 8.14 (1H, dd, J=7.0, 2.5 Hz); Mass m/z: 387(M$^+$–1)

PREPARATION 153(2)

5-[4-(tert-Butoxycarbonyl)piperazin-1-ylsulfonyl]-N-(3,4-dimethoxybenzyl)-2-fluorobenzamide (1.34 g) was obtained as off-white amorphous substance from 5-[4-(tert-butoxycarbonyl)piperazin-1-ylsulfonyl]-2-fluorobenzoic acid (1.0 g) and 3,4-dimethoxybenzylamine (452 mg) in a manner similar to Preparation 1.

NMR (DMSO-d$_6$, δ): 1.34(9H, s), 2.85–2.94(4H, m), 3.36–3.44(4H, m), 3.73(3H, s), 3.74(3H, s), 4.42(2H, d, J=6.0 Hz), 6.86(1H, dd, J=8.0, 1.5 Hz), 6.92(1H, d, J=8.0 Hz), 6.96(1H, d, J=1.5 Hz), 7.60(1H, t, J=9.0 Hz), 7.85–7.92 (2H, m), 9.04(1H, t, J=6.0 Hz).

EXAMPLE 153(1)

5-[4-(tert-Butoxycarbonyl)piperazin-1-ylsulfonyl]-N-(3,4-dimethoxybenzyl)-2-(trans-4-hydroxycyclohexylamino)

benzamide (191.8 mg) was obtained as off-white solid substance from 5-[4-(tert-butoxycarbonyl)piperazin-1-ylsulfonyl]-N-(3,4-dimethoxybenzyl)-2-fluorobenzamid, (200 mg) and trans-4-aminocyclohexanol (129mg) in a manner similar to Example 1(1).

mp. 221–222° C. NMR (DMSO-d$_6$, δ): 1.13–1.41(4H, m), 1.34(9H, s), 1.76–1.86(2H, m), 1.90–2.01(2H, m), 2.77–2.88(4H, m), 3.30–3.54(6H, m), 3.72(3H, s), 3.73(3H, s), 4.36(2H, d, J=6.0 Hz), 4.60(1H, d, J=4.5 Hz), 6.83(1H, d, J=7.5 Hz), 6.89(1H, s), 6.93(2H, d, J=7.5 Hz), 7.52(1H, d, J=7.5 Hz), 7.91(1H, s), 8.50(1H, d, J=7.5 Hz), 9.15(1H, t, J=6.0 Hz) Mass m/z: 631(M$^+$–1).

EXAMPLE 153(2)

N-(3,4-Dimethoxybenzyl)-2-(trans-4-hydroxycyclohexylamino)-5-(piperazinosulfonyl) benzamide (88.3mg) was obtained as a pale yellow solid substance from 5-[4-(tert-butoxycarbonyl)piperazin-1-ylsulfonyl]-N-(3,4-dimethoxybenzyl)-2-(trans-4-hydroxycyclohexylamino)benzamide (125mg) in a manner similar to Example 77(2).

m.p. 108–110° C. NMR (DMSO-d$_6$, δ): 1.15–1.41(4H, m), 1.75–1.86(2H, m), 1.90–2.01(2H, m), 2.65–2.79(3H, m), 3.29–3.51(3H, m), 3.72(3H, s), 3.73(3H, s), 4.35(2H, d, J=6.0 Hz), 4.60(1H, d, J=4.5 Hz), 6.81(1H, dd, J=8.0, 1.0 Hz), 6.90(2H, d, J=8.0 Hz), 6.94(1H, d, J=1.0 Hz), 7.51(1H, dd, J=8.0, 1.0 Hz), 7.91(1H, d, J=1.0 Hz), 8.53(1H, d, J=7.0 Hz), 9.18(1H, t, J=6.0 Hz); Mass m/z: 533(M$^+$+1).

EXAMPLE 153(3)

To a mixture of N-(3-fluoro-4-methoxybenzyl)-2-(trans-4-hydroxycyclohexylamino)-5-nitrobenzamide (262 mg), benzoic acid (115 mg) and diethyl azodicarboxylate (164 mg) in anhydrous tetrahydrofuran (6 mL) was added triphenylphosphine (247 mg). After stirring for one day at ambient temperature, the mixture was evaporated in vacuo. The residue was purified by a silica gel column chromatography eluting with a mixture of hexane and ethyl acetate (4:1 to 2:1). Collection of an upper fraction gave 2-(3-cyclohexenylamino)-N-(3-fluoro-4-methoxybenzyl)-5-nitrobenzamide as yellow powders (40 mg).

m.p. 140° C. NMR (DMSO-d$_6$, δ): 1.61 (1H, m), 1.82–2.26 (4H, m), 2.45 (1H, m), 3.81 (3H, s), 3.85 (1H, m), 4.37 (2H, d, J=5 Hz), 5.64 (1H, br d, J=9 Hz), 5.73 (1H, br d, J=9 Hz), 6.94 (1H, d, J=9 Hz), 7.06–7.22 (3H, m), 8.12 (1H, dd, J=9, 3 Hz), 8.62 (1H, d, J=3 Hz), 9.19 (1H, d, J=8 Hz), 9.35 (1H, t, J=5 Hz); Mass m/z (ES) : 398. Collection of a lower fraction gave 2-(cis-4-benzoyloxycyclohexylamino)-N-(3-fluoro-4-methoxybenzyl)-5-nitrobenzamide as yellow powders (249 mg).

NMR (DMSO-d$_6$, δ): 1.60–1.78 (2H, m), 1.80–1.97 (6H, m), 3.75 (1H, m), 3.81 (3H, s), 4.40 (2H, d, J=6 Hz), 5.14 (1H, br), 6.97 (1H, d, J=10 Hz), 7.07–7.22 (2H, m), 7.45–7.60 (2H, m), 7.67 (1H, dd, J=7, 7 Hz), 8.01 (2x1H, d, J=7 Hz), 8.44 (1H, dd, J=10, 2 Hz), 8.64 (1H, d, J=2 Hz), 9.26 (1H, d, J=8 Hz), 9.39 (1H, t, J=6 Hz); Mass m/z (ES): 520.

PREPARATION 154

N-(4-Chloro-3-methoxybenzoyl)-5-cyano-2-fluorobenzamide (4.00 g) was obtained as colorless powders from 5-cyano-2-fluorobenzoic acid (4.57 g) and 4-chloro-3-methoxybenzylamine (150 mg) in a manner similar to Preparation 1.

NMR (DMSO-d$_6$, δ): 3.85(3H, s), 4.46(2H, d, J=7 Hz), 6.93(1H, dd, J=4, 8 Hz), 7.13(1H, d, J=4 Hz), 7.39(1H, d, J=8 Hz), 7.58(1H, t, J=8 Hz), 8.06(1H, m), 8.13(1H, dd, J=4, 8 Hz), 9.12(1H, br).

EXAMPLE 154

(R)-N-(4-Chloro-3-methoxybenzyl)-5-cyano-2-(2-hydroxy-1-methylethylamino)benzamide (153 mg) was obtained as colorless powders from N-(4-chloro-3-methoxybenzyl)-5-cyano-2-fluorobenzamide (150 mg) and (R)-2-amino-1-propanol (70.7 mg) in a manner similar to Example 1(1).

NMR (DMSO-d$_6$, δ): 1.12(3H, d, J=7 Hz), 3.42(2H, t, J=7 Hz), 3.60–3.74(1H, br), 3.85(3H, s), 4.41(2H, d, J=7 Hz), 4.93(1H, t, J=7 Hz), 6.84(1H, d, J=8 Hz), 6.92(1H, dd, J=4, 8 Hz), 7.12(1H, d, J=4 Hz), 7.37(1H, d, J=8 Hz), 7.61(1H, dd, J=4, 8 Hz), 8.06(1H, d, J=4 Hz), 8.69(1H, d, J=8 Hz), 9.07(1H, br); Mass m/z: 372.

What is claimed is:

1. A compound of the formula (I):

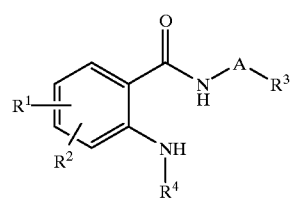

wherein

R$^1$ is hydrogen atom;

R$^2$ is nitro group, cyano group or a halo(lower)alkyl group;

R$^3$ is a phenyl group substituted with one or more substituent(s) selected from halogen, cyano and lower alkoxy;

A is a lower alkylene group;

R$^4$ is a group —CR$^6$R$^7$R$^8$ wherein
  R$^6$ and R$^7$ form, together with the carbon atom to which they are attached, a
cycloalkyl group optionally substituted with hydroxy, lower alkoxy or lower
alkanoylamino; and
  R$^8$ is hydrogen atom;

its pro-drug, and a salt thereof.

2. A compound of claim 1 which is

N-(3-chloro-4-methoxybenzyl)-2-(trans-4-hydroxycyclohexylamino)-5-nitrobenzamide, 2-(trans-acetamidocyclohexylamino)-N-(3,4-dimethoxybenzyl)-5-nitrobenzamide, N-(3,4-dimethoxybenzyl)-2-[(trans-4-formamidocyclohexyl)amino]-5-nitrobenzamide, or N-(4-ethoxy-3-methoxybenzyl)-2-(trans-4-formamidocyclohexylamino)-5-nitrobenzamide, or a salt thereof.

3. A process for preparing a compound of the formula:

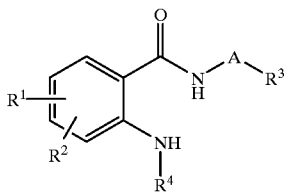
(I)

wherein $R^1$ is hydrogen atom;

$R^2$ is nitro group, cyano group or a halo(lower)alkyl group;

$R^3$ is a phenyl group substituted with one or more substituent(s) selected from halogen, cyano and lower alkoxy;

A is a lower alkylene group;

$R^4$ is a group —$CR^6R^7R^8$ wherein
$R^6$ and $R^7$ form, together with the carbon atom to which they are attached, a cycloalkyl group optionally substituted with hydroxy, lower alkoxy or lower alkanoylamino; and
$R^8$ is hydrogen atom;

and a salt thereof, which comprises (1) reacting a compound of the formula (II):

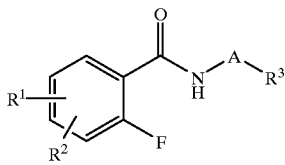
(II)

or its salt, with a compound of (III)

(III)

or its salt, wherein $R^1$, $R^2$, $R^3$, $R^4$ and A are each as defined above, or (2) reacting a compound of the formula (IV):

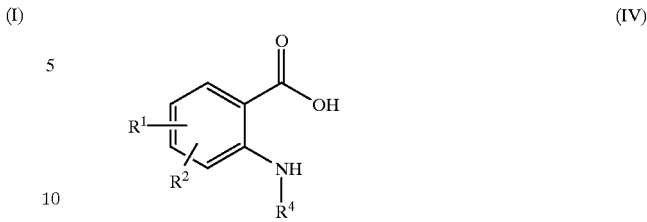
(IV)

or its salt, with a compound of the formula (V):
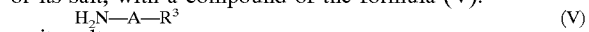
(V)
or its salt,
wherein $R^1$, $R^2$, $R^3$, $R^4$ and A are each as defined above, or
(3) subjecting a compound of the formula (VI):

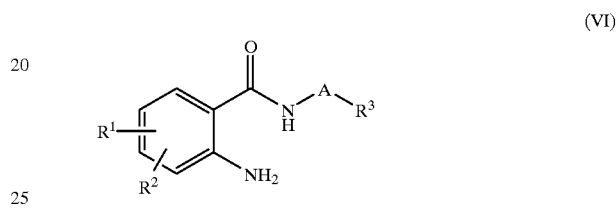
(VI)

or its salt, to reductive alkylation with a compound of the formula (VII):

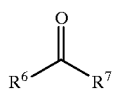
(VII)

or its salt,
wherein $R^1$, $R^2$, $R^3$, $R^6$, $R^7$ and A are each as defined above.

4. A pharmaceutical composition which comprises, as an active ingredient, a compound of claim 1 or a pharmaceutically acceptable salt thereof in admixture with a pharmaceutically acceptable carrier.

5. A pharmaceutical composition comprising a compound of claim 1 as an active ingredient, in association with a pharmaceutically acceptable, substantially non-toxic carrier or excipient.

6. A method for the treatment and/or prevention of angina, hypertension, pulmonary hypertension, congestive heart failure, glomerular diseases, renal tubulo-intestitinal diseases, renal failure, atherosclerosis, conditions of reduced blood vessel patency, peripheral vascular disease, stroke, bronchitis, asthma, allergic rhinitis, urticaria, glaucoma, diseases characterized by disorders of gut motility, erectile dysfunction, female sexual dysfunction, impotence, diabetic complications, micturition disorder, or incontinence or storage of urine disorder, by administering a compound of claim 1.

* * * * *